US012331320B2

(12) United States Patent
Ye et al.

(10) Patent No.: US 12,331,320 B2
(45) Date of Patent: Jun. 17, 2025

(54) GENOME EDITED CANCER CELL VACCINES

(71) Applicant: The Research Foundation for the State University of new York, Binghamton, NY (US)

(72) Inventors: Kaiming Ye, Vestal, NY (US); Sha Jin, Vestal, NY (US); Subhadra Jayaraman Rukmini, Binghamton, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 937 days.

(21) Appl. No.: 16/596,829

(22) Filed: Oct. 9, 2019

(65) Prior Publication Data

US 2020/0113986 A1 Apr. 16, 2020

Related U.S. Application Data

(60) Provisional application No. 62/743,801, filed on Oct. 10, 2018.

(51) Int. Cl.
| | |
|---|---|
| *C12N 5/09* | (2010.01) |
| *A61K 40/22* | (2025.01) |
| *A61K 40/35* | (2025.01) |
| *A61K 40/42* | (2025.01) |
| *C12N 5/10* | (2006.01) |
| *C12N 15/63* | (2006.01) |
| *A61K 39/00* | (2006.01) |

(52) U.S. Cl.
CPC ............ *C12N 5/0693* (2013.01); *A61K 40/22* (2025.01); *A61K 40/35* (2025.01); *A61K 40/4201* (2025.01); *C12N 5/10* (2013.01); *C12N 15/63* (2013.01); *A61K 2039/5152* (2013.01); *C12N 2502/99* (2013.01)

(58) Field of Classification Search
CPC ........ C12N 5/0693; C12N 5/10; C12N 15/63; C12N 2502/99; A61K 40/22; A61K 40/35; A61K 2039/5152
USPC ...................... 435/325, 455, 375; 424/93.21
See application file for complete search history.

(56) References Cited

U.S. PATENT DOCUMENTS

| | | | |
|---|---|---|---|
| 5,152,017 A | 10/1992 | Jaeger | |
| 5,616,471 A | 4/1997 | Yuspa | |
| 5,631,237 A | 5/1997 | Dzau et al. | |
| 5,709,854 A | 1/1998 | Griffith-Cima et al. | |
| 5,756,291 A | 5/1998 | Griffin et al. | |
| 5,859,312 A | 1/1999 | Littman et al. | |
| 6,129,761 A | 10/2000 | Hubbell | |
| 6,309,635 B1 | 10/2001 | Ingber et al. | |
| 6,340,461 B1 | 1/2002 | Terman | |
| 6,344,441 B1 | 2/2002 | Bihain et al. | |
| 6,372,494 B1 | 4/2002 | Naughton et al. | |
| 6,413,735 B1 | 7/2002 | Lau | |
| 6,673,908 B1 | 1/2004 | Stanton, Jr. | |
| 6,686,179 B2 | 2/2004 | Fleer et al. | |
| 6,759,047 B1 | 7/2004 | Kalluri | |
| 6,790,606 B1 | 9/2004 | Lau | |
| 6,805,869 B2 | 10/2004 | Guo | |
| 6,905,688 B2 | 6/2005 | Rosen et al. | |
| 6,905,827 B2 | 6/2005 | Wohlgemuth et al. | |
| 6,926,898 B2 | 8/2005 | Rosen et al. | |
| 6,946,134 B1 | 9/2005 | Rosen et al. | |
| 6,946,444 B2 | 9/2005 | Bihain et al. | |
| 6,962,974 B1 | 11/2005 | Kalluri | |
| 6,972,322 B2 | 12/2005 | Fleer et al. | |
| 6,974,667 B2 | 12/2005 | Horne et al. | |
| 6,987,006 B2 | 1/2006 | Fleer et al. | |
| 6,989,365 B2 | 1/2006 | Fleer et al. | |
| 6,994,857 B2 | 2/2006 | Rosen et al. | |
| 7,005,276 B1 | 2/2006 | Flegel et al. | |
| 7,026,121 B1 | 4/2006 | Wohlgemuth et al. | |
| 7,041,478 B2 | 5/2006 | Fleer et al. | |
| 7,045,318 B2 | 5/2006 | Ballance | |
| 7,056,701 B2 | 6/2006 | Fleer et al. | |
| 7,064,185 B2 | 6/2006 | Lau | |

(Continued)

OTHER PUBLICATIONS

Meng et al. (2012) Molecular Ther., vol. 20(5), 1046-1055.*
Kleinovink et al. (2017) Oncoimmunology, vol. 6(4), e1294299, pp. 1-7; doi:10.1080/212402X.2017.1294299.*
Maples et al. (Winter 2009/2010) Bioprocessing Journal, vol. 8(4), 4-14.*
Quezada et al. (2006) J. Clin. Invest., vol. 116(7), 1935-1945.*
Liang, Xudong (2015) ProQuest Dissertations and Theses, 2 pages, abstract only.*
Liu et al. (2018) Cell Reports, vol. 24, 2101-2111.*

(Continued)

*Primary Examiner* — Anne Marie S Wehbe
(74) *Attorney, Agent, or Firm* — Hoffberg & Associates; Steven M. Hoffberg

(57) ABSTRACT

A cancer vaccine technology is provided which knocks out expression of cell surface immune checkpoint proteins, to facilitate their processing by immune cells, and optionally by knocking-in the expression of cytokines to boost immune response. Non-replicating tumor cells lacking cell surface CD47 are highly effective immunizing agents against subcutaneous mouse melanoma. Whole-cell vaccines inhibited tumor growth, and immunophenotyping showed a dramatic increase in activated effector cell subsets and M1-type macrophages aided by a significant reduction in the tumor-associated macrophage and myeloid derived suppressor cell compartments. A remarkable downregulation of cell surface CD47 was observed in the tumors that did escape after vaccination with genetically modified cells, suggesting the intricate involvement of CD47 in a prophylactic situation. An effective vaccination strategy to increase tumor-specific immune response in solid tumors is provided to improve the outcome of cancer immunotherapy.

15 Claims, 32 Drawing Sheets

Specification includes a Sequence Listing.

(56) References Cited

U.S. PATENT DOCUMENTS

| | | |
|---|---|---|
| 7,081,345 B1 | 7/2006 | Roecklin et al. |
| 7,081,354 B2 | 7/2006 | Fleer et al. |
| 7,094,577 B2 | 8/2006 | Fleer et al. |
| 7,118,746 B1 | 10/2006 | Naughton et al. |
| 7,141,363 B2 | 11/2006 | Poznansky et al. |
| 7,141,547 B2 | 11/2006 | Rosen et al. |
| 7,189,507 B2 | 3/2007 | Mack et al. |
| 7,208,313 B2 | 4/2007 | McCart et al. |
| 7,220,722 B2 | 5/2007 | Bihain et al. |
| 7,232,683 B2 | 6/2007 | Lau |
| 7,235,358 B2 | 6/2007 | Wohlgemuth et al. |
| 7,238,667 B2 | 7/2007 | Rosen et al. |
| 7,244,578 B2 | 7/2007 | Hammond et al. |
| 7,250,496 B2 | 7/2007 | Bentwich |
| 7,252,949 B2 | 8/2007 | Flegel et al. |
| 7,282,556 B2 | 10/2007 | Parkos |
| 7,371,734 B2 | 5/2008 | Phillips et al. |
| 7,378,423 B2 | 5/2008 | Kawasaki et al. |
| 7,387,779 B2 | 6/2008 | Kalluri |
| 7,408,041 B2 | 8/2008 | Bowdish et al. |
| 7,410,779 B2 | 8/2008 | Fleer et al. |
| 7,411,052 B2 | 8/2008 | Tang |
| 7,415,358 B2 | 8/2008 | Mendrick et al. |
| 7,426,441 B2 | 9/2008 | Mendrick et al. |
| 7,427,665 B2 | 9/2008 | Bowdish et al. |
| 7,435,410 B2 | 10/2008 | Fleer et al. |
| 7,435,412 B2 | 10/2008 | Bowdish et al. |
| 7,482,013 B2 | 1/2009 | Ballance et al. |
| 7,498,171 B2 | 3/2009 | Hariri et al. |
| 7,507,413 B2 | 3/2009 | Rosen et al. |
| 7,507,414 B2 | 3/2009 | Rosen et al. |
| 7,510,843 B2 | 3/2009 | Roecklin et al. |
| 7,514,229 B2 | 4/2009 | Jamieson et al. |
| 7,521,424 B2 | 4/2009 | Rosen et al. |
| 7,521,540 B2 | 4/2009 | Lau et al. |
| 7,531,300 B2 | 5/2009 | Nakamura et al. |
| 7,550,432 B2 | 6/2009 | Ballance |
| 7,553,629 B2 | 6/2009 | Flegel et al. |
| 7,588,767 B2 | 9/2009 | Szalay et al. |
| 7,588,771 B2 | 9/2009 | Szalay et al. |
| 7,592,010 B2 | 9/2009 | Rosen et al. |
| 7,592,426 B2 | 9/2009 | Ebel et al. |
| 7,595,159 B2 | 9/2009 | Scherzer et al. |
| 7,598,353 B2 | 10/2009 | Bowdish et al. |
| 7,601,355 B2 | 10/2009 | Howard et al. |
| 7,615,372 B2 | 11/2009 | Nicolaides et al. |
| 7,622,108 B2 | 11/2009 | Collins et al. |
| 7,632,924 B2 | 12/2009 | Cho et al. |
| 7,645,575 B2 | 1/2010 | Wohlgemuth et al. |
| 7,662,398 B2 | 2/2010 | Szalay et al. |
| 7,666,596 B2 | 2/2010 | Halloran |
| 7,691,569 B2 | 4/2010 | Wohlgemuth et al. |
| 7,709,256 B2 | 5/2010 | Warren et al. |
| 7,709,257 B2 | 5/2010 | Tew et al. |
| 7,709,616 B2 | 5/2010 | Bentwich et al. |
| 7,714,110 B2 | 5/2010 | Bowdish et al. |
| 7,754,221 B2 | 7/2010 | Szalay et al. |
| 7,771,999 B2 | 8/2010 | Warren et al. |
| 7,775,469 B2 | 8/2010 | Poznansky et al. |
| 7,777,008 B2 | 8/2010 | Ponath et al. |
| 7,781,212 B2 | 8/2010 | Rock et al. |
| 7,785,806 B2 | 8/2010 | Warren et al. |
| 7,785,883 B2 | 8/2010 | Warren et al. |
| 7,786,270 B2 | 8/2010 | Johnson et al. |
| 7,794,715 B2 | 9/2010 | Utku |
| 7,807,150 B2 | 10/2010 | Griffith et al. |
| 7,807,382 B2 | 10/2010 | Zhou et al. |
| 7,825,099 B2 | 11/2010 | Feinstein |
| 7,829,336 B2 | 11/2010 | Fuchs et al. |
| 7,846,445 B2 | 12/2010 | Schellenberger et al. |
| 7,847,079 B2 | 12/2010 | Rosen et al. |
| 7,855,074 B2 | 12/2010 | Warren et al. |
| 7,855,279 B2 | 12/2010 | Schellenberger et al. |
| 7,863,418 B2 | 1/2011 | Utku et al. |
| 7,888,050 B2 | 2/2011 | Reagan et al. |
| 7,892,556 B2 | 2/2011 | Freyberg et al. |
| 7,915,000 B2 | 3/2011 | Bowdish et al. |
| 7,931,901 B2 | 4/2011 | Utku et al. |
| 7,935,338 B2 | 5/2011 | Fanger et al. |
| 7,939,083 B2 | 5/2011 | Dey et al. |
| 7,939,263 B2 | 5/2011 | Clarke et al. |
| 7,939,267 B2 | 5/2011 | Moore et al. |
| 7,960,512 B2 | 6/2011 | Stavenhagen et al. |
| 7,993,642 B2 | 8/2011 | Tsunoda et al. |
| 7,998,460 B2 | 8/2011 | Monje et al. |
| 8,003,385 B2 | 8/2011 | Sukumar et al. |
| 8,003,387 B2 | 8/2011 | Sukumar et al. |
| 8,003,774 B2 | 8/2011 | Stavenhagen et al. |
| 8,008,073 B2 | 8/2011 | Tsunoda et al. |
| 8,014,957 B2 | 9/2011 | Radich et al. |
| 8,021,662 B2 | 9/2011 | Szalay et al. |
| 8,030,070 B2 | 10/2011 | Sanchez-Schmitz et al. |
| 8,034,903 B2 | 10/2011 | Tsuchiya et al. |
| 8,044,178 B2 | 10/2011 | Boghaert et al. |
| 8,044,180 B2 | 10/2011 | Koenig et al. |
| 8,044,193 B2 | 10/2011 | Nakamura et al. |
| 8,062,889 B2 | 11/2011 | Warren et al. |
| 8,067,187 B2 | 11/2011 | Gebbink et al. |
| 8,071,373 B2 | 12/2011 | Warren et al. |
| 8,071,539 B2 | 12/2011 | Rosen et al. |
| 8,075,884 B2 | 12/2011 | Bowdish et al. |
| 8,080,416 B2 | 12/2011 | Warren et al. |
| 8,114,403 B2 | 2/2012 | Bowdish et al. |
| 8,114,617 B2 | 2/2012 | Reagan et al. |
| 8,114,832 B2 | 2/2012 | Gebbink et al. |
| 8,119,403 B2 | 2/2012 | Warren et al. |
| 8,124,083 B2 | 2/2012 | Grasso et al. |
| 8,129,340 B2 | 3/2012 | Kroemer et al. |
| 8,133,982 B2 | 3/2012 | Johnson et al. |
| 8,138,147 B2 | 3/2012 | Naughton et al. |
| 8,142,791 B2 | 3/2012 | Schirrmacher et al. |
| 8,142,994 B2 | 3/2012 | Moorhouse et al. |
| 8,148,106 B2 | 4/2012 | Fung et al. |
| 8,158,360 B2 | 4/2012 | Heise et al. |
| 8,158,385 B2 | 4/2012 | Ozaki et al. |
| 8,187,593 B2 | 5/2012 | Koenig et al. |
| 8,187,877 B2 | 5/2012 | Bowdish et al. |
| 8,188,232 B1 | 5/2012 | Murphy et al. |
| 8,192,737 B2 | 6/2012 | Stavenhagen et al. |
| 8,193,318 B2 | 6/2012 | Koenig et al. |
| 8,206,710 B2 | 6/2012 | Ebel et al. |
| 8,206,907 B2 | 6/2012 | Milstein et al. |
| 8,211,439 B2 | 7/2012 | Rosen et al. |
| 8,216,574 B2 | 7/2012 | Stavenhagen et al. |
| 8,216,579 B2 | 7/2012 | Johnson et al. |
| 8,217,147 B2 | 7/2012 | Stavenhagen et al. |
| 8,221,769 B2 | 7/2012 | Szalay et al. |
| 8,236,313 B2 | 8/2012 | Isenberg et al. |
| 8,247,226 B2 | 8/2012 | Sukumar et al. |
| 8,252,739 B2 | 8/2012 | Rosen et al. |
| 8,263,344 B2 | 9/2012 | Kroemer et al. |
| 8,277,812 B2 | 10/2012 | Iannacone et al. |
| 8,288,159 B2 | 10/2012 | Warren et al. |
| 8,298,823 B2 | 10/2012 | Warren et al. |
| 8,298,824 B2 | 10/2012 | Warren et al. |
| 8,318,492 B2 | 11/2012 | Choo et al. |
| 8,323,959 B2 | 12/2012 | Szalay et al. |
| 8,329,868 B2 | 12/2012 | Fung et al. |
| 8,343,497 B2 | 1/2013 | Shi et al. |
| 8,343,498 B2 | 1/2013 | Alexis et al. |
| 8,361,485 B2 | 1/2013 | Naughton et al. |
| 8,361,736 B2 | 1/2013 | Majeti et al. |
| 8,377,448 B2 | 2/2013 | Smith et al. |
| 8,377,902 B2 | 2/2013 | Lai et al. |
| 8,389,691 B2 | 3/2013 | Nicolaides et al. |
| 8,404,654 B2 | 3/2013 | Feinstein |
| 8,444,972 B2 | 5/2013 | Rock et al. |
| 8,470,815 B2 | 6/2013 | Saulnier Sholler et al. |
| 8,476,231 B2 | 7/2013 | Naughton et al. |
| 8,481,271 B2 | 7/2013 | Galon et al. |
| 8,481,703 B2 | 7/2013 | Ebel et al. |
| 8,491,913 B2 | 7/2013 | Offner et al. |
| 8,492,328 B2 | 7/2013 | Huang et al. |
| 8,492,530 B2 | 7/2013 | Schellenberger et al. |

(56) References Cited

U.S. PATENT DOCUMENTS

| | | |
|---|---|---|
| 8,506,947 B2 | 8/2013 | McCart et al. |
| 8,507,434 B2 | 8/2013 | Popel et al. |
| 8,513,189 B2 | 8/2013 | Rosen et al. |
| 8,524,237 B2 | 9/2013 | Nicolaides et al. |
| 8,524,656 B2 | 9/2013 | Galipeau et al. |
| 8,530,627 B2 | 9/2013 | Koenig et al. |
| 8,541,033 B2 | 9/2013 | Ito et al. |
| 8,541,185 B2 | 9/2013 | Oved et al. |
| 8,546,541 B2 | 10/2013 | Murphy et al. |
| 8,557,241 B2 | 10/2013 | Sigal et al. |
| 8,557,788 B2 | 10/2013 | Isenberg et al. |
| 8,562,997 B2 | 10/2013 | Jaiswal et al. |
| 8,562,998 B2 | 10/2013 | Shi et al. |
| 8,586,039 B2 | 11/2013 | Tsuchiya et al. |
| 8,591,905 B2 | 11/2013 | von Andrian et al. |
| 8,628,762 B2 | 1/2014 | Blander et al. |
| 8,629,151 B2 | 1/2014 | Zepp et al. |
| 8,637,028 B2 | 1/2014 | Alexis et al. |
| 8,647,837 B2 | 2/2014 | Mahmood et al. |
| 8,652,466 B2 | 2/2014 | Stavenhagen et al. |
| 8,658,173 B2 | 2/2014 | Ebel et al. |
| 8,668,926 B1 | 3/2014 | Mousa et al. |
| 8,669,105 B2 | 3/2014 | Sukumar et al. |
| 8,691,780 B2 | 4/2014 | Lih et al. |
| 8,697,071 B2 | 4/2014 | Stavenhagen et al. |
| 8,697,371 B2 | 4/2014 | Warren et al. |
| 8,709,415 B2 | 4/2014 | Bowdish et al. |
| 8,709,429 B2 | 4/2014 | Majeti et al. |
| 8,716,465 B2 | 5/2014 | Rossi et al. |
| 8,722,402 B2 | 5/2014 | Warren et al. |
| 8,728,456 B2 | 5/2014 | Sands et al. |
| 8,728,476 B2 | 5/2014 | van den Berg |
| 8,758,750 B2 | 6/2014 | Weissman et al. |
| 8,759,495 B2 | 6/2014 | Boghaert et al. |
| 8,765,120 B2 | 7/2014 | Chancellor et al. |
| 8,778,339 B2 | 7/2014 | Tuaillon et al. |
| 8,784,808 B2 | 7/2014 | Johnson et al. |
| 8,784,836 B2 | 7/2014 | Szalay et al. |
| 8,785,599 B2 | 7/2014 | Johnson et al. |
| 8,790,895 B2 | 7/2014 | Fiedler et al. |
| 8,791,238 B2 | 7/2014 | Fiedler et al. |
| 8,802,091 B2 | 8/2014 | Johnson et al. |
| 8,802,093 B2 | 8/2014 | Johnson et al. |
| 8,802,240 B2 | 8/2014 | Davis et al. |
| 8,802,438 B2 | 8/2014 | Rossi et al. |
| 8,835,398 B2 | 9/2014 | Harats et al. |
| 8,835,443 B2 | 9/2014 | Kawasaki et al. |
| 8,840,885 B2 | 9/2014 | Bowdish et al. |
| 8,840,889 B2 | 9/2014 | Chen |
| 8,853,382 B2 | 10/2014 | Hammarstrom et al. |
| 8,862,448 B2 | 10/2014 | Holmes et al. |
| 8,865,672 B2 | 10/2014 | Isenberg et al. |
| 8,871,219 B2 | 10/2014 | Heeney et al. |
| 8,883,506 B2 | 11/2014 | Rossi et al. |
| 8,883,980 B2 | 11/2014 | Umana et al. |
| 8,889,411 B2 | 11/2014 | Hariri et al. |
| 8,895,000 B2 | 11/2014 | Zhou et al. |
| 8,906,381 B2 | 12/2014 | Iannacone et al. |
| 8,906,607 B2 | 12/2014 | Duchateau et al. |
| 8,920,776 B2 | 12/2014 | Gaiger et al. |
| 8,932,583 B2 | 1/2015 | Mooney et al. |
| 8,932,595 B2 | 1/2015 | Iannacone et al. |
| 8,933,197 B2 | 1/2015 | Stemmer et al. |
| 8,945,543 B2 | 2/2015 | Igawa et al. |
| 8,946,387 B2 | 2/2015 | Koenig et al. |
| 8,951,517 B2 | 2/2015 | Stavenhagen et al. |
| 8,951,527 B2 | 2/2015 | Isenberg et al. |
| 8,951,737 B2 | 2/2015 | Bander |
| 8,962,319 B2 | 2/2015 | Warren et al. |
| 8,962,804 B2 | 2/2015 | Williams et al. |
| 8,968,730 B2 | 3/2015 | Koenig et al. |
| 8,969,289 B2 | 3/2015 | Gosselin et al. |
| 8,980,864 B2 | 3/2015 | Hoge et al. |
| 8,986,684 B2 | 3/2015 | Wang |
| 8,993,517 B2 | 3/2015 | Rosen et al. |
| 8,999,328 B2 | 4/2015 | Bowdish et al. |
| 8,999,380 B2 | 4/2015 | Bancel et al. |
| 8,999,654 B2 | 4/2015 | Gaitanaris et al. |
| 9,000,133 B2 | 4/2015 | Bowdish et al. |
| 9,005,613 B2 | 4/2015 | Liu et al. |
| 9,006,254 B2 | 4/2015 | Zepp et al. |
| 9,012,399 B2 | 4/2015 | Cao et al. |
| 9,017,693 B2 | 4/2015 | Freyberg et al. |
| 9,018,358 B2 | 4/2015 | Schwarz et al. |
| 9,028,815 B2 | 5/2015 | Stavenhagen et al. |
| 9,045,541 B2 | 6/2015 | Eckelman et al. |
| 9,045,562 B2 | 6/2015 | Murphy et al. |
| 9,050,279 B2 | 6/2015 | Offner et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,096,877 B2 | 8/2015 | Johnson et al. |
| 9,107,886 B2 | 8/2015 | Chakraborty et al. |
| 9,114,113 B2 | 8/2015 | Chakraborty et al. |
| 9,115,197 B2 | 8/2015 | Ebel et al. |
| 9,115,388 B2 | 8/2015 | Beg et al. |
| 9,127,292 B2 | 9/2015 | Murphy et al. |
| 9,132,210 B2 | 9/2015 | Mooney et al. |
| 9,133,239 B2 | 9/2015 | Cao et al. |
| 9,144,614 B2 | 9/2015 | Nicolaides et al. |
| 9,144,690 B2 | 9/2015 | McDaniel |
| 9,149,506 B2 | 10/2015 | Chakraborty et al. |
| 9,150,656 B2 | 10/2015 | Johnson et al. |
| 9,150,661 B2 | 10/2015 | Bowdish et al. |
| 9,151,760 B2 | 10/2015 | Weissman et al. |
| 9,156,897 B2 | 10/2015 | Alvarez et al. |
| 9,175,083 B2 | 11/2015 | Cho et al. |
| 9,181,319 B2 | 11/2015 | Schrum et al. |
| 9,186,372 B2 | 11/2015 | de Fougerolles et al. |
| 9,187,544 B2 | 11/2015 | Popel et al. |
| 9,192,651 B2 | 11/2015 | Chakraborty et al. |
| 9,193,794 B2 | 11/2015 | Lin et al. |
| 9,193,955 B2 | 11/2015 | Majeti et al. |
| 9,193,977 B2 | 11/2015 | Murphy et al. |
| 9,198,949 B2 | 12/2015 | Susin et al. |
| 9,201,063 B2 | 12/2015 | Sood et al. |
| 9,205,148 B2 | 12/2015 | Langermann et al. |
| 9,216,205 B2 | 12/2015 | Chakraborty et al. |
| 9,220,714 B2 | 12/2015 | Saulnier Sholler et al. |
| 9,220,755 B2 | 12/2015 | Chakraborty et al. |
| 9,220,788 B2 | 12/2015 | Davis et al. |
| 9,220,792 B2 | 12/2015 | Chakraborty et al. |
| 9,221,891 B2 | 12/2015 | Bancel et al. |
| 9,221,896 B2 | 12/2015 | Rosen et al. |
| 9,221,908 B2 | 12/2015 | Frazier et al. |
| 9,233,072 B2 | 1/2016 | Alexis et al. |
| 9,233,141 B2 | 1/2016 | Chakraborty et al. |
| 9,233,154 B2 | 1/2016 | Blander et al. |
| 9,234,896 B2 | 1/2016 | Klock et al. |
| 9,238,084 B2 | 1/2016 | Liu et al. |
| 9,241,994 B2 | 1/2016 | Igawa |
| 9,243,069 B2 | 1/2016 | Johnson et al. |
| 9,249,229 B2 | 2/2016 | Bowdish et al. |
| 9,254,311 B2 | 2/2016 | Bancel et al. |
| 9,255,129 B2 | 2/2016 | Chakraborty et al. |
| 9,271,996 B2 | 3/2016 | de Fougerolles et al. |
| 9,279,019 B2 | 3/2016 | Dimitrov et al. |
| 9,283,287 B2 | 3/2016 | Chakraborty et al. |
| 9,289,395 B2 | 3/2016 | Davis et al. |
| 9,295,689 B2 | 3/2016 | de Fougerolles et al. |
| 9,296,801 B2 | 3/2016 | Alvarez et al. |
| 9,296,809 B2 | 3/2016 | Rosen et al. |
| 9,296,820 B2 | 3/2016 | Umana et al. |
| 9,297,005 B2 | 3/2016 | Huebsch et al. |
| 9,301,993 B2 | 4/2016 | Chakraborty et al. |
| 9,303,079 B2 | 4/2016 | Chakraborty et al. |
| 9,308,280 B2 | 4/2016 | Shi et al. |
| 9,309,510 B2 | 4/2016 | La Porte et al. |
| 9,315,824 B2 | 4/2016 | Kuroiwa et al. |
| 9,320,813 B2 | 4/2016 | Peyman |
| 9,328,346 B2 | 5/2016 | Lee et al. |
| 9,334,328 B2 | 5/2016 | Schrum et al. |
| 9,334,329 B2 | 5/2016 | Lin et al. |

(56) References Cited

U.S. PATENT DOCUMENTS

| | | |
|---|---|---|
| 9,339,519 B2 | 5/2016 | Ayares |
| 9,340,584 B2 | 5/2016 | Wolfe et al. |
| 9,352,004 B2 | 5/2016 | Chancellor et al. |
| 9,352,037 B2 | 5/2016 | van den Berg |
| 9,358,282 B2 | 6/2016 | Cobbold et al. |
| 9,370,558 B2 | 6/2016 | Ali et al. |
| 9,381,235 B2 | 7/2016 | Sands et al. |
| 9,382,285 B2 | 7/2016 | Chan et al. |
| 9,382,320 B2 | 7/2016 | Liu et al. |
| 9,393,396 B2 | 7/2016 | Peyman |
| 9,394,365 B1 | 7/2016 | Eisenbach-Schwartz et al. |
| 9,399,679 B2 | 7/2016 | Utku |
| 9,399,682 B2 | 7/2016 | Jaiswal et al. |
| 9,402,377 B2 | 8/2016 | Flavell et al. |
| 9,402,916 B2 | 8/2016 | Cobbold et al. |
| 9,428,535 B2 | 8/2016 | de Fougerolles et al. |
| 9,428,553 B2 | 8/2016 | Williams et al. |
| 9,439,859 B2 | 9/2016 | Alexis et al. |
| 9,441,049 B2 | 9/2016 | Johnson et al. |
| 9,446,107 B2 | 9/2016 | Mooney et al. |
| 9,447,164 B2 | 9/2016 | Schrum et al. |
| 9,452,228 B2 | 9/2016 | Liu et al. |
| 9,458,486 B2 | 10/2016 | Naughton et al. |
| 9,460,263 B2 | 10/2016 | Holmes et al. |
| 9,462,794 B2 | 10/2016 | Murphy et al. |
| 9,463,217 B1 | 10/2016 | Colin Aronovicz et al. |
| 9,464,124 B2 | 10/2016 | Bancel et al. |
| 9,469,692 B2 | 10/2016 | Johnson et al. |
| 9,474,717 B2 | 10/2016 | von Andrian et al. |
| 9,486,512 B2 | 11/2016 | Kim et al. |
| 9,487,587 B2 | 11/2016 | Koenig |
| 9,492,499 B2 | 11/2016 | Jaynes et al. |
| 9,492,534 B2 | 11/2016 | Szalay et al. |
| 9,492,536 B2 | 11/2016 | Offner et al. |
| 9,492,566 B2 | 11/2016 | Goldenberg et al. |
| 9,493,569 B2 | 11/2016 | Igawa et al. |
| 9,493,575 B2 | 11/2016 | Jaiswal et al. |
| 9,498,536 B2 | 11/2016 | Mousa et al. |
| 9,504,236 B2 | 11/2016 | Bradley et al. |
| 9,505,842 B2 | 11/2016 | Zhou et al. |
| 9,512,225 B2 | 12/2016 | Eisenbach-Schwartz et al. |
| 9,512,227 B2 | 12/2016 | Eisenbach-Schwartz et al. |
| 9,517,276 B2 | 12/2016 | Lowman et al. |
| 9,518,116 B2 | 12/2016 | Frazier et al. |
| 9,518,117 B2 | 12/2016 | Frazier et al. |
| 9,522,195 B2 | 12/2016 | Grasso et al. |
| 9,522,944 B2 | 12/2016 | Rapraeger et al. |
| 9,526,702 B2 | 12/2016 | von Andrian et al. |
| 9,527,901 B2 | 12/2016 | Jing |
| 9,533,047 B2 | 1/2017 | de Fougerolles et al. |
| 9,534,052 B2 | 1/2017 | Eisenbach-Schwartz et al. |
| 9,539,210 B2 | 1/2017 | von Andrian et al. |
| 9,539,245 B2 | 1/2017 | Peters |
| 9,539,309 B2 | 1/2017 | Cao et al. |
| 9,540,424 B2 | 1/2017 | Gosselin et al. |
| 9,546,206 B2 | 1/2017 | Ring et al. |
| 9,562,073 B2 | 2/2017 | Moore et al. |
| 9,562,087 B2 | 2/2017 | Ring et al. |
| 9,566,250 B2 | 2/2017 | Mahmood et al. |
| 9,572,897 B2 | 2/2017 | Bancel et al. |
| 9,574,014 B2 | 2/2017 | Williams et al. |
| 9,574,211 B2 | 2/2017 | Gregory et al. |
| 9,579,300 B2 | 2/2017 | Mousa et al. |
| 9,585,920 B2 | 3/2017 | Kovarik et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,598,492 B2 | 3/2017 | Dimitrov et al. |
| 9,603,878 B2 | 3/2017 | Berry et al. |
| 9,603,894 B2 | 3/2017 | Cao et al. |
| 9,605,076 B2 | 3/2017 | Jaiswal et al. |
| 9,610,328 B2 | 4/2017 | Mooney et al. |
| 9,611,329 B2 | 4/2017 | Jaiswal et al. |
| 9,611,458 B2 | 4/2017 | Konno et al. |
| 9,624,276 B2 | 4/2017 | Young et al. |
| 9,624,297 B2 | 4/2017 | Grasso et al. |
| 9,624,305 B2 | 4/2017 | Jaiswal et al. |
| 9,625,444 B2 | 4/2017 | Warren et al. |
| 9,629,877 B2 | 4/2017 | Cooper et al. |
| 9,639,660 B2 | 5/2017 | Shin et al. |
| 9,644,005 B2 | 5/2017 | Qian et al. |
| 9,644,180 B2 | 5/2017 | Kahvejian et al. |
| 9,650,440 B2 | 5/2017 | Grasso et al. |
| 9,650,441 B2 | 5/2017 | Grosveld et al. |
| 9,650,445 B2 | 5/2017 | Cobbold et al. |
| 9,655,352 B2 | 5/2017 | Murphy et al. |
| 9,657,105 B2 | 5/2017 | Forman et al. |
| 9,657,295 B2 | 5/2017 | Schrum et al. |
| 9,663,575 B2 | 5/2017 | Eckelman et al. |
| 9,669,108 B2 | 6/2017 | Williams et al. |
| 9,670,205 B2 | 6/2017 | Aktoudianakis et al. |
| 9,670,269 B2 | 6/2017 | Igawa et al. |
| 9,670,281 B2 | 6/2017 | Lim et al. |
| 9,675,561 B2 | 6/2017 | Bencherif et al. |
| 9,675,668 B2 | 6/2017 | Bancel et al. |
| 9,676,856 B2 | 6/2017 | Chen |
| 9,677,125 B2 | 6/2017 | Sood et al. |
| 9,682,934 B2 | 6/2017 | Stafford et al. |
| 9,693,954 B2 | 7/2017 | Mooney et al. |
| 9,694,084 B2 | 7/2017 | Bradner et al. |
| 9,700,027 B2 | 7/2017 | Murphy et al. |
| 9,701,758 B2 | 7/2017 | Cooper et al. |
| 9,701,965 B2 | 7/2017 | Schrum et al. |
| 9,708,333 B2 | 7/2017 | Li et al. |
| 9,708,408 B2 | 7/2017 | Stavenhagen et al. |
| 9,714,295 B2 | 7/2017 | Johnson et al. |
| 9,714,296 B2 | 7/2017 | Johnson et al. |
| 9,717,694 B2 | 8/2017 | Green et al. |
| 9,726,668 B2 | 8/2017 | Oved et al. |
| 9,726,676 B2 | 8/2017 | Grabe et al. |
| 9,730,967 B2 | 8/2017 | Kovarik et al. |
| 9,737,480 B2 | 8/2017 | Lu et al. |
| 9,737,599 B2 | 8/2017 | Tuaillon et al. |
| 9,738,646 B2 | 8/2017 | Brown et al. |
| 9,738,724 B2 | 8/2017 | Thanos et al. |
| 9,745,367 B2 | 8/2017 | Bansal |
| 9,750,709 B2 | 9/2017 | Mousa et al. |
| 9,750,814 B2 | 9/2017 | Procko et al. |
| 9,750,816 B2 | 9/2017 | Bradner et al. |
| 9,757,196 B2 | 9/2017 | Moss et al. |
| 9,764,039 B2 | 9/2017 | Thanos et al. |
| 9,764,145 B2 | 9/2017 | Callas et al. |
| 9,765,143 B2 | 9/2017 | Jaiswal et al. |
| 9,770,512 B2 | 9/2017 | Bradner et al. |
| 9,770,517 B2 | 9/2017 | Govindan et al. |
| 9,770,535 B2 | 9/2017 | Mooney et al. |
| 9,771,428 B2 | 9/2017 | Weiskopf et al. |
| 9,775,332 B2 | 10/2017 | Kuroiwa et al. |
| 9,777,061 B2 | 10/2017 | Ebersbach et al. |
| 9,777,066 B2 | 10/2017 | Igawa |
| 9,782,462 B2 | 10/2017 | Bancel et al. |
| 9,783,593 B2 | 10/2017 | Bradley et al. |
| 9,783,618 B2 | 10/2017 | Friedrich et al. |
| 9,788,534 B2 | 10/2017 | Bradley et al. |
| 9,789,171 B2 | 10/2017 | Poznansky et al. |
| 9,790,275 B2 | 10/2017 | Van Den Berg |
| 9,790,490 B2 | 10/2017 | Zhang et al. |
| 9,790,503 B2 | 10/2017 | Zeng |
| 9,796,781 B2 | 10/2017 | Majeti et al. |
| 9,796,783 B2 | 10/2017 | Ågerstam et al. |
| 9,803,016 B2 | 10/2017 | Grosveld et al. |
| 9,803,177 B2 | 10/2017 | Rossi et al. |
| 9,804,160 B2 | 10/2017 | Haura |
| 9,809,581 B2 | 11/2017 | Chen et al. |
| 9,814,760 B2 | 11/2017 | Bancel et al. |
| 9,815,901 B2 | 11/2017 | Brogdon et al. |
| 9,816,080 B2 | 11/2017 | Lu et al. |
| 9,816,094 B2 | 11/2017 | Lee et al. |
| 9,820,476 B2 | 11/2017 | Flavell et al. |
| 9,821,045 B2 | 11/2017 | Ali et al. |
| 9,821,068 B2 | 11/2017 | Bradner et al. |
| 9,822,180 B2 | 11/2017 | Cobbold et al. |
| 9,827,329 B2 | 11/2017 | Li |
| 9,827,332 B2 | 11/2017 | Bancel et al. |

(56) References Cited

U.S. PATENT DOCUMENTS

| | | |
|---|---|---|
| 9,828,416 B2 | 11/2017 | Bancel et al. |
| 9,834,545 B2 | 12/2017 | Chen et al. |
| 9,834,608 B2 | 12/2017 | Lim et al. |
| 9,834,787 B2 | 12/2017 | Gregory et al. |
| 9,834,790 B1 | 12/2017 | Pauza et al. |
| 9,834,791 B2 | 12/2017 | Zhang et al. |
| 9,839,208 B2 | 12/2017 | Flavell et al. |
| 9,839,614 B2 | 12/2017 | Mousa et al. |
| 9,839,687 B2 | 12/2017 | Zhao |
| 9,840,493 B2 | 12/2017 | Yang et al. |
| 9,840,503 B2 | 12/2017 | Sun et al. |
| 9,845,345 B2 | 12/2017 | Ring et al. |
| 9,849,092 B2 | 12/2017 | Peyman |
| 9,850,483 B2 | 12/2017 | Clarke et al. |
| 9,856,314 B2 | 1/2018 | Lowman et al. |
| 9,856,318 B2 | 1/2018 | Eisenbach-Schwartz et al. |
| 9,856,479 B2 | 1/2018 | Lee et al. |
| 9,856,497 B2 | 1/2018 | Qi et al. |
| 9,862,705 B2 | 1/2018 | Jia et al. |
| 9,862,927 B2 | 1/2018 | Banchereau et al. |
| 9,872,900 B2 | 1/2018 | Ciaramella et al. |
| 9,873,734 B2 | 1/2018 | Fung et al. |
| 9,873,747 B2 | 1/2018 | Tykocinski |
| 9,878,056 B2 | 1/2018 | Bancel et al. |
| 9,884,112 B2 | 2/2018 | Zepp et al. |
| 9,884,813 B1 | 2/2018 | Martinez et al. |
| 9,884,893 B2 | 2/2018 | Glanville |
| 9,888,673 B2 | 2/2018 | Hering et al. |
| 9,888,956 B2 | 2/2018 | Model et al. |
| 9,889,141 B2 | 2/2018 | Yen et al. |
| 9,889,164 B2 | 2/2018 | Falb et al. |
| 9,894,888 B2 | 2/2018 | Garcia et al. |
| 9,895,189 B2 | 2/2018 | Pearson |
| 9,895,451 B2 | 2/2018 | Saltzman et al. |
| 9,896,508 B2 | 2/2018 | Johnson et al. |
| 9,896,516 B2 | 2/2018 | Bradley et al. |
| 9,901,082 B2 | 2/2018 | Flavell et al. |
| 9,901,083 B2 | 2/2018 | Murphy et al. |
| 9,902,771 B2 | 2/2018 | Boghaert et al. |
| 9,902,970 B2 | 2/2018 | Kuroiwa et al. |
| 9,914,759 B2 | 3/2018 | Tavernier et al. |
| 9,914,774 B2 | 3/2018 | de Sauvage et al. |
| 9,914,938 B2 | 3/2018 | Pauza et al. |
| 9,920,122 B2 | 3/2018 | van den Berg |
| 9,920,295 B2 | 3/2018 | Discher et al. |
| 9,920,317 B2 | 3/2018 | Lee et al. |
| 9,924,705 B2 | 3/2018 | Liang et al. |
| 9,925,183 B2 | 3/2018 | May |
| 9,925,247 B2 | 3/2018 | Liu et al. |
| 9,925,277 B2 | 3/2018 | Almarsson et al. |
| 9,932,591 B2 | 4/2018 | Lee et al. |
| 9,937,233 B2 | 4/2018 | Schrum et al. |
| 9,937,249 B2 | 4/2018 | Kim et al. |
| 9,938,331 B2 | 4/2018 | Schellenberger et al. |
| 9,938,345 B2 | 4/2018 | Papadopoulos et al. |
| 9,938,357 B2 | 4/2018 | Bradley et al. |
| 9,938,358 B2 | 4/2018 | Bradley et al. |
| 9,939,443 B2 | 4/2018 | Spetzler et al. |
| 9,944,647 B2 | 4/2018 | He et al. |
| 9,950,068 B2 | 4/2018 | De Fougerolles et al. |
| 9,951,065 B2 | 4/2018 | Bartlett et al. |
| 9,958,448 B2 | 5/2018 | Halbert et al. |
| 9,963,716 B2 | 5/2018 | Bradley et al. |
| 9,969,789 B2 | 5/2018 | Uger et al. |
| 9,974,774 B2 | 5/2018 | Garner et al. |
| 9,981,975 B2 | 5/2018 | Li et al. |
| 9,982,047 B2 | 5/2018 | Eisenbach-Schwartz et al. |
| 9,982,048 B2 | 5/2018 | Eisenbach-Schwartz et al. |
| 9,982,049 B2 | 5/2018 | Eisenbach-Schwartz et al. |
| 9,982,050 B2 | 5/2018 | Eisenbach-Schwartz et al. |
| 9,982,051 B2 | 5/2018 | Eisenbach-Schwartz et al. |
| 9,982,057 B2 | 5/2018 | Schreiber |
| 9,986,724 B2 | 6/2018 | Flavell et al. |
| 9,987,500 B2 | 6/2018 | Papadopoulos et al. |
| 9,988,408 B2 | 6/2018 | Zhao |
| 9,988,448 B2 | 6/2018 | Schwarz et al. |
| 9,988,452 B2 | 6/2018 | Freeman et al. |
| 9,993,460 B2 | 6/2018 | Garner et al. |
| 9,993,563 B2 | 6/2018 | Ziv |
| 9,994,527 B2 | 6/2018 | Stafford et al. |
| 9,994,821 B2 | 6/2018 | Keller et al. |
| 2001/0026937 A1 | 10/2001 | Punnonen et al. |
| 2002/0006397 A1 | 1/2002 | Roberts et al. |
| 2002/0037279 A1 | 3/2002 | Vandenburgh |
| 2002/0039786 A1 | 4/2002 | Reid et al. |
| 2002/0102278 A1 | 8/2002 | Guo |
| 2002/0142981 A1 | 10/2002 | Horne et al. |
| 2002/0150986 A1 | 10/2002 | Lau |
| 2002/0151498 A1 | 10/2002 | Bihain et al. |
| 2002/0165154 A1 | 11/2002 | Bihain et al. |
| 2002/0177551 A1 | 11/2002 | Terman |
| 2002/0182188 A1 | 12/2002 | Reid et al. |
| 2003/0026803 A1 | 2/2003 | Barclay |
| 2003/0031681 A1 | 2/2003 | McCart et al. |
| 2003/0032034 A1 | 2/2003 | Tang |
| 2003/0064053 A1 | 4/2003 | Liu et al. |
| 2003/0124614 A1 | 7/2003 | Utku et al. |
| 2003/0129202 A1 | 7/2003 | Trepo et al. |
| 2003/0138432 A1 | 7/2003 | Glazier |
| 2003/0144494 A1 | 7/2003 | Algate et al. |
| 2003/0148316 A1 | 8/2003 | Lipford et al. |
| 2003/0157113 A1 | 8/2003 | Terman |
| 2003/0162230 A1 | 8/2003 | Reagan et al. |
| 2003/0202977 A1 | 10/2003 | Amin et al. |
| 2003/0228570 A1 | 12/2003 | Yat Wah Tom et al. |
| 2003/0235561 A1 | 12/2003 | Vandenburgh et al. |
| 2003/0235909 A1 | 12/2003 | Hariri et al. |
| 2004/0002124 A1 | 1/2004 | Lau et al. |
| 2004/0005563 A1 | 1/2004 | Mack et al. |
| 2004/0009479 A1 | 1/2004 | Wohlgemuth et al. |
| 2004/0010119 A1 | 1/2004 | Guo et al. |
| 2004/0029114 A1 | 2/2004 | Mack et al. |
| 2004/0033493 A1 | 2/2004 | Tchernev et al. |
| 2004/0043010 A1 | 3/2004 | Vandenburgh |
| 2004/0047858 A1 | 3/2004 | Blumberg et al. |
| 2004/0058883 A1 | 3/2004 | Phillips et al. |
| 2004/0072160 A1 | 4/2004 | Mendrick et al. |
| 2004/0076955 A1 | 4/2004 | Mack et al. |
| 2004/0077601 A1 | 4/2004 | Adams et al. |
| 2004/0106120 A1 | 6/2004 | Tazi-Ahnini et al. |
| 2004/0110227 A1 | 6/2004 | Levanon et al. |
| 2004/0142885 A1 | 7/2004 | Paul et al. |
| 2004/0147731 A1 | 7/2004 | Parkos |
| 2004/0214783 A1 | 10/2004 | Terman |
| 2005/0005316 A1 | 1/2005 | Lau |
| 2005/0031643 A1 | 2/2005 | Szalay et al. |
| 2005/0069549 A1 | 3/2005 | Herman |
| 2005/0084490 A1 | 4/2005 | Adams et al. |
| 2005/0112141 A1 | 5/2005 | Terman |
| 2005/0118164 A1 | 6/2005 | Herman |
| 2005/0118715 A1 | 6/2005 | Hariri et al. |
| 2005/0123522 A1 | 6/2005 | Punnonen et al. |
| 2005/0136066 A1 | 6/2005 | Guo |
| 2005/0142539 A1 | 6/2005 | Herman |
| 2005/0142587 A1 | 6/2005 | Zlot et al. |
| 2005/0148072 A1 | 7/2005 | Reid et al. |
| 2005/0169914 A1 | 8/2005 | Colgan et al. |
| 2005/0181375 A1 | 8/2005 | Aziz et al. |
| 2005/0220789 A1 | 10/2005 | Utku et al. |
| 2005/0221435 A1 | 10/2005 | Acres et al. |
| 2005/0255114 A1 | 11/2005 | Labat et al. |
| 2005/0271659 A1 | 12/2005 | Utku et al. |
| 2005/0282177 A1 | 12/2005 | Seto et al. |
| 2006/0003322 A1 | 1/2006 | Bentwich |
| 2006/0014768 A1 | 1/2006 | Kawasaki et al. |
| 2006/0019256 A1 | 1/2006 | Clarke et al. |
| 2006/0040392 A1 | 2/2006 | Collins et al. |
| 2006/0051370 A1 | 3/2006 | Szalay et al. |
| 2006/0051803 A1 | 3/2006 | Wohlgemuth et al. |
| 2006/0063156 A1 | 3/2006 | Willman et al. |
| 2006/0073591 A1 | 4/2006 | Abitorabi et al. |
| 2006/0074034 A1 | 4/2006 | Collins et al. |
| 2006/0078540 A1 | 4/2006 | Warren et al. |
| 2006/0078900 A1 | 4/2006 | Mendrick et al. |

(56) References Cited

U.S. PATENT DOCUMENTS

| | | |
|---|---|---|
| 2006/0084055 A1 | 4/2006 | Gaiger et al. |
| 2006/0084167 A1 | 4/2006 | Cohenford et al. |
| 2006/0088522 A1 | 4/2006 | Boghaert et al. |
| 2006/0088820 A1 | 4/2006 | Perron et al. |
| 2006/0088836 A1 | 4/2006 | Wohlgemuth et al. |
| 2006/0104987 A1 | 5/2006 | Flegel et al. |
| 2006/0111312 A1 | 5/2006 | Eshleman et al. |
| 2006/0122132 A1 | 6/2006 | Touw et al. |
| 2006/0134109 A1 | 6/2006 | Gaitanaris et al. |
| 2006/0134122 A1 | 6/2006 | Rapraeger et al. |
| 2006/0134664 A1 | 6/2006 | Scherzer et al. |
| 2006/0149049 A1 | 7/2006 | Tang |
| 2006/0153860 A1 | 7/2006 | Cho et al. |
| 2006/0165684 A1 | 7/2006 | Utku |
| 2006/0171988 A1 | 8/2006 | Hilf et al. |
| 2006/0188508 A1 | 8/2006 | Cohen et al. |
| 2006/0199204 A1 | 9/2006 | Dix et al. |
| 2006/0199231 A1 | 9/2006 | Moore et al. |
| 2006/0222588 A1 | 10/2006 | Sandberg et al. |
| 2006/0223121 A1 | 10/2006 | Roecklin et al. |
| 2006/0239910 A1 | 10/2006 | Nicolaides et al. |
| 2006/0239911 A1 | 10/2006 | Nicolaides et al. |
| 2006/0241067 A1 | 10/2006 | Varner et al. |
| 2006/0251646 A1 | 11/2006 | Utku |
| 2006/0257903 A1 | 11/2006 | Akil et al. |
| 2006/0257965 A1 | 11/2006 | Lau |
| 2006/0263783 A1 | 11/2006 | Podhajcer et al. |
| 2006/0263803 A1 | 11/2006 | Tang |
| 2006/0263813 A1 | 11/2006 | Rosenberg et al. |
| 2006/0269949 A1 | 11/2006 | Halloran |
| 2006/0292143 A1 | 12/2006 | Utku et al. |
| 2006/0292683 A1 | 12/2006 | Gebbink et al. |
| 2006/0293708 A1 | 12/2006 | Voss |
| 2007/0015206 A1 | 1/2007 | Gebbink et al. |
| 2007/0025981 A1 | 2/2007 | Szalay et al. |
| 2007/0031890 A1 | 2/2007 | Wohlgemuth et al. |
| 2007/0041904 A1 | 2/2007 | Jiang et al. |
| 2007/0041981 A1 | 2/2007 | Howard et al. |
| 2007/0071745 A1 | 3/2007 | Umana et al. |
| 2007/0077232 A1 | 4/2007 | Naughton et al. |
| 2007/0099209 A1 | 5/2007 | Clarke et al. |
| 2007/0105133 A1 | 5/2007 | Clarke et al. |
| 2007/0111238 A1 | 5/2007 | Jamieson et al. |
| 2007/0134657 A1 | 6/2007 | Poznansky et al. |
| 2007/0134690 A1 | 6/2007 | Pascual et al. |
| 2007/0135393 A1 | 6/2007 | Monje et al. |
| 2007/0154458 A1 | 7/2007 | McCart et al. |
| 2007/0154931 A1 | 7/2007 | Radich et al. |
| 2007/0161587 A1 | 7/2007 | Collins et al. |
| 2007/0190078 A1 | 8/2007 | Mills et al. |
| 2007/0202572 A1 | 8/2007 | Szalay et al. |
| 2007/0209082 A1 | 9/2007 | Lih et al. |
| 2007/0212727 A1 | 9/2007 | Szalay et al. |
| 2007/0219125 A1 | 9/2007 | Cojocaru et al. |
| 2007/0231333 A1 | 10/2007 | Boghaert et al. |
| 2007/0243177 A1 | 10/2007 | Newgard et al. |
| 2007/0269432 A1 | 11/2007 | Nakamura et al. |
| 2008/0020979 A1 | 1/2008 | Rapraeger et al. |
| 2008/0026980 A1 | 1/2008 | Utku et al. |
| 2008/0039341 A1 | 2/2008 | Schellenberger et al. |
| 2008/0047026 A1 | 2/2008 | Fuchs et al. |
| 2008/0050374 A1 | 2/2008 | Cho et al. |
| 2008/0051565 A1 | 2/2008 | Tang |
| 2008/0057508 A1 | 3/2008 | Flegel et al. |
| 2008/0076715 A1 | 3/2008 | Tang |
| 2008/0081038 A1 | 4/2008 | Cho et al. |
| 2008/0085277 A1 | 4/2008 | Cho et al. |
| 2008/0102054 A1 | 5/2008 | Faustman |
| 2008/0108583 A1 | 5/2008 | Feinstein |
| 2008/0118529 A1 | 5/2008 | Gebbink et al. |
| 2008/0131431 A1 | 6/2008 | Smith et al. |
| 2008/0207488 A1 | 8/2008 | Gebbink et al. |
| 2008/0213839 A1 | 9/2008 | Tang |
| 2008/0214452 A1 | 9/2008 | Obeid |
| 2008/0227712 A1 | 9/2008 | Tang |
| 2008/0249009 A1 | 10/2008 | Bihain et al. |
| 2008/0249606 A1 | 10/2008 | Gebbink et al. |
| 2008/0260744 A1 | 10/2008 | Gaitanaris et al. |
| 2008/0268453 A1 | 10/2008 | Seto et al. |
| 2008/0274091 A1 | 11/2008 | Slepushkin et al. |
| 2008/0286808 A1 | 11/2008 | Schellenberger et al. |
| 2008/0292546 A1 | 11/2008 | Clarke et al. |
| 2008/0292615 A1 | 11/2008 | Tazi-Ahnini et al. |
| 2008/0305965 A1 | 12/2008 | Moorhouse et al. |
| 2008/0306004 A1 | 12/2008 | Tang |
| 2008/0312228 A1 | 12/2008 | Kawasaki et al. |
| 2009/0004134 A1 | 1/2009 | Obeid |
| 2009/0004172 A1 | 1/2009 | Obeid |
| 2009/0004178 A1 | 1/2009 | Obeid |
| 2009/0004211 A1 | 1/2009 | Obeid |
| 2009/0004678 A1 | 1/2009 | Obeid |
| 2009/0005302 A1 | 1/2009 | Obeid |
| 2009/0005305 A1 | 1/2009 | Obeid |
| 2009/0010908 A1 | 1/2009 | Gow et al. |
| 2009/0010952 A1 | 1/2009 | Obeid |
| 2009/0041825 A1 | 2/2009 | Kotov et al. |
| 2009/0048159 A1 | 2/2009 | Obeid |
| 2009/0048266 A1 | 2/2009 | Heise et al. |
| 2009/0075877 A1 | 3/2009 | Tang |
| 2009/0081228 A1 | 3/2009 | Lau et al. |
| 2009/0092582 A1 | 4/2009 | Bogin et al. |
| 2009/0099031 A1 | 4/2009 | Stemmer et al. |
| 2009/0104195 A1 | 4/2009 | Herman |
| 2009/0104628 A1 | 4/2009 | Reagan et al. |
| 2009/0123503 A1 | 5/2009 | Naughton et al. |
| 2009/0136917 A1 | 5/2009 | Szalay et al. |
| 2009/0155254 A1 | 6/2009 | Gebbink et al. |
| 2009/0156786 A1 | 6/2009 | Zlot et al. |
| 2009/0163434 A1 | 6/2009 | Bader et al. |
| 2009/0175827 A1 | 7/2009 | Byrom et al. |
| 2009/0178153 A1 | 7/2009 | Gaitanaris et al. |
| 2009/0181863 A1 | 7/2009 | Milstein et al. |
| 2009/0186073 A1 | 7/2009 | Yamazaki et al. |
| 2009/0191202 A1 | 7/2009 | Jamieson et al. |
| 2009/0191548 A1 | 7/2009 | Berlin et al. |
| 2009/0192102 A1 | 7/2009 | Bader et al. |
| 2009/0203588 A1 | 8/2009 | Willman et al. |
| 2009/0215053 A1 | 8/2009 | Galon et al. |
| 2009/0226406 A1 | 9/2009 | Hariri et al. |
| 2009/0227025 A1 | 9/2009 | Nichols et al. |
| 2009/0227533 A1 | 9/2009 | Bader et al. |
| 2009/0232893 A1 | 9/2009 | Bader et al. |
| 2009/0258002 A1 | 10/2009 | Barrett et al. |
| 2009/0280124 A1 | 11/2009 | Labat et al. |
| 2009/0280135 A1 | 11/2009 | Offner et al. |
| 2009/0286856 A1 | 11/2009 | Nakamura et al. |
| 2009/0324594 A1 | 12/2009 | Nicolaides et al. |
| 2010/0008946 A1 | 1/2010 | Szalay et al. |
| 2010/0015126 A1 | 1/2010 | Gebbink et al. |
| 2010/0015653 A1 | 1/2010 | Kroemer et al. |
| 2010/0016235 A1 | 1/2010 | Kroemer et al. |
| 2010/0021454 A1 | 1/2010 | Nicolaides et al. |
| 2010/0021483 A1 | 1/2010 | Boghaert et al. |
| 2010/0029746 A1 | 2/2010 | Feinstein |
| 2010/0041875 A1 | 2/2010 | Dey et al. |
| 2010/0047276 A1 | 2/2010 | Heeney et al. |
| 2010/0062007 A1 | 3/2010 | Schirrmacher et al. |
| 2010/0062016 A1 | 3/2010 | Szalay et al. |
| 2010/0068147 A1 | 3/2010 | Hibberd et al. |
| 2010/0092425 A1 | 4/2010 | von Andrian et al. |
| 2010/0092467 A1 | 4/2010 | Isenberg et al. |
| 2010/0092989 A1 | 4/2010 | Wohlgemuth et al. |
| 2010/0093556 A1 | 4/2010 | Clarke et al. |
| 2010/0104582 A1 | 4/2010 | Vignery et al. |
| 2010/0105054 A1 | 4/2010 | Wong et al. |
| 2010/0105066 A1 | 4/2010 | Halloran |
| 2010/0112568 A1 | 5/2010 | Achiron et al. |
| 2010/0120043 A1 | 5/2010 | Sood et al. |
| 2010/0129392 A1 | 5/2010 | Shi et al. |
| 2010/0129439 A1 | 5/2010 | Alexis et al. |
| 2010/0137149 A1 | 6/2010 | Shin et al. |
| 2010/0143372 A1 | 6/2010 | Yao et al. |
| 2010/0173024 A1 | 7/2010 | McDaniel |
| 2010/0173382 A1 | 7/2010 | Boghaert et al. |

(56) References Cited

U.S. PATENT DOCUMENTS

| | | |
|---|---|---|
| 2010/0183727 A1 | 7/2010 | Iannacone et al. |
| 2010/0184032 A1 | 7/2010 | Georgantas et al. |
| 2010/0189682 A1 | 7/2010 | Schellenberger et al. |
| 2010/0196426 A1 | 8/2010 | Skog et al. |
| 2010/0197015 A1 | 8/2010 | Reid et al. |
| 2010/0203010 A1 | 8/2010 | Hariharan et al. |
| 2010/0233199 A1 | 9/2010 | Silva et al. |
| 2010/0233251 A1 | 9/2010 | Von Andrian et al. |
| 2010/0233808 A1 | 9/2010 | Reid et al. |
| 2010/0239579 A1 | 9/2010 | Smith et al. |
| 2010/0240613 A1 | 9/2010 | Kawasaki et al. |
| 2010/0240732 A1 | 9/2010 | Gilboa |
| 2010/0247562 A1 | 9/2010 | Gong et al. |
| 2010/0254981 A1 | 10/2010 | Sigal et al. |
| 2010/0260706 A1 | 10/2010 | Bogin et al. |
| 2010/0261172 A1 | 10/2010 | Yao et al. |
| 2010/0261190 A1 | 10/2010 | Zlot et al. |
| 2010/0267648 A1 | 10/2010 | Tang |
| 2010/0272824 A1 | 10/2010 | Lupton et al. |
| 2010/0273258 A1 | 10/2010 | Lannutti et al. |
| 2010/0273667 A1 | 10/2010 | Kotov et al. |
| 2010/0292155 A1 | 11/2010 | Tang |
| 2010/0303850 A1 | 12/2010 | Lipford et al. |
| 2010/0305003 A1 | 12/2010 | Tang |
| 2010/0306863 A1 | 12/2010 | Colonna et al. |
| 2010/0310534 A1 | 12/2010 | Oved et al. |
| 2010/0330046 A1 | 12/2010 | Comer et al. |
| 2011/0003704 A1 | 1/2011 | Skog et al. |
| 2011/0008382 A1 | 1/2011 | Burrows et al. |
| 2011/0014119 A1 | 1/2011 | Jaiswal et al. |
| 2011/0015090 A1 | 1/2011 | Majeti et al. |
| 2011/0016543 A1 | 1/2011 | Weinstein et al. |
| 2011/0020388 A1 | 1/2011 | Zepp et al. |
| 2011/0023143 A1 | 1/2011 | Weinstein et al. |
| 2011/0027217 A1 | 2/2011 | Zepp et al. |
| 2011/0027235 A1 | 2/2011 | Gregory et al. |
| 2011/0028395 A1 | 2/2011 | Popel et al. |
| 2011/0030072 A1 | 2/2011 | Weinstein et al. |
| 2011/0038841 A1 | 2/2011 | Ayares |
| 2011/0038870 A1 | 2/2011 | van den Berg |
| 2011/0053157 A1 | 3/2011 | Skog et al. |
| 2011/0059901 A1 | 3/2011 | Terman |
| 2011/0060120 A1 | 3/2011 | Obeid |
| 2011/0070229 A1 | 3/2011 | Simard |
| 2011/0070230 A1 | 3/2011 | Simard |
| 2011/0071054 A1 | 3/2011 | Simard |
| 2011/0071276 A1 | 3/2011 | Simard |
| 2011/0092381 A1 | 4/2011 | Sood et al. |
| 2011/0093249 A1 | 4/2011 | Holmes et al. |
| 2011/0124552 A1 | 5/2011 | Galipeau et al. |
| 2011/0129817 A1 | 6/2011 | Banchereau et al. |
| 2011/0135641 A1 | 6/2011 | Isenberg et al. |
| 2011/0142902 A1 | 6/2011 | Jell et al. |
| 2011/0151433 A1 | 6/2011 | Schellenberger et al. |
| 2011/0152115 A1 | 6/2011 | Staudt et al. |
| 2011/0165588 A1 | 7/2011 | Reagan et al. |
| 2011/0166199 A1 | 7/2011 | Lai et al. |
| 2011/0171687 A1 | 7/2011 | Schellenberger et al. |
| 2011/0182937 A1 | 7/2011 | Banchereau et al. |
| 2011/0183866 A1 | 7/2011 | Clarke et al. |
| 2011/0185439 A1 | 7/2011 | Gaitanaris et al. |
| 2011/0189181 A1 | 8/2011 | Utku et al. |
| 2011/0190157 A1 | 8/2011 | Kipps et al. |
| 2011/0196614 A1 | 8/2011 | Banchereau et al. |
| 2011/0206696 A1 | 8/2011 | Frazier et al. |
| 2011/0214189 A1 | 9/2011 | Gaitanaris et al. |
| 2011/0217308 A1 | 9/2011 | Offner et al. |
| 2011/0217715 A1 | 9/2011 | Wong et al. |
| 2011/0223201 A1 | 9/2011 | Lipford et al. |
| 2011/0224800 A1 | 9/2011 | Ludlow et al. |
| 2011/0230647 A1 | 9/2011 | Murphy et al. |
| 2011/0236401 A1 | 9/2011 | Murphy et al. |
| 2011/0250220 A1 | 10/2011 | Dey et al. |
| 2011/0251077 A1 | 10/2011 | Podhajcer et al. |
| 2011/0251108 A1 | 10/2011 | Tang |
| 2011/0262491 A1 | 10/2011 | Keegan et al. |
| 2011/0268804 A1 | 11/2011 | Shi et al. |
| 2011/0268805 A1 | 11/2011 | Alexis et al. |
| 2011/0275096 A1 | 11/2011 | Moore et al. |
| 2011/0287022 A1 | 11/2011 | Yao et al. |
| 2011/0288080 A1 | 11/2011 | Saulnier Sholler et al. |
| 2011/0300176 A1 | 12/2011 | Szalay et al. |
| 2011/0305663 A1 | 12/2011 | Gosselin et al. |
| 2012/0010090 A1 | 1/2012 | Nakamura et al. |
| 2012/0027808 A1 | 2/2012 | Iannacone |
| 2012/0039841 A1 | 2/2012 | Blander et al. |
| 2012/0046346 A1 | 2/2012 | Rossi et al. |
| 2012/0064600 A1 | 3/2012 | Boghaert et al. |
| 2012/0065086 A1 | 3/2012 | Benson |
| 2012/0072124 A1 | 3/2012 | Radich et al. |
| 2012/0087890 A1 | 4/2012 | Iannacone et al. |
| 2012/0094301 A1 | 4/2012 | Simard |
| 2012/0094395 A1 | 4/2012 | Simard |
| 2012/0114759 A1 | 5/2012 | Green et al. |
| 2012/0135426 A1 | 5/2012 | Reagan et al. |
| 2012/0135521 A1 | 5/2012 | Eshleman et al. |
| 2012/0149714 A1 | 6/2012 | Heise et al. |
| 2012/0164101 A1 | 6/2012 | Galipeau et al. |
| 2012/0171200 A1 | 7/2012 | Nicolaides et al. |
| 2012/0190730 A1 | 7/2012 | Michael |
| 2012/0192298 A1 | 7/2012 | Weinstein et al. |
| 2012/0207759 A1 | 8/2012 | Murphy et al. |
| 2012/0219559 A1 | 8/2012 | Chen |
| 2012/0220011 A1 | 8/2012 | Schellenberger et al. |
| 2012/0220484 A1 | 8/2012 | Halloran |
| 2012/0222140 A1 | 8/2012 | Kuroiwa et al. |
| 2012/0225073 A1 | 9/2012 | Weissman et al. |
| 2012/0230940 A1 | 9/2012 | Naughton et al. |
| 2012/0230947 A1 | 9/2012 | Schellenberger et al. |
| 2012/0233715 A1 | 9/2012 | Kuroiwa et al. |
| 2012/0237500 A1 | 9/2012 | Milstein et al. |
| 2012/0276010 A1 | 11/2012 | Szalay et al. |
| 2012/0282174 A1 | 11/2012 | Weissman et al. |
| 2012/0295285 A1 | 11/2012 | An et al. |
| 2012/0295956 A1 | 11/2012 | Isenberg et al. |
| 2012/0295957 A1 | 11/2012 | Isenberg et al. |
| 2012/0301400 A1 | 11/2012 | Williams et al. |
| 2012/0308484 A1 | 12/2012 | Szalay et al. |
| 2012/0315216 A1 | 12/2012 | Clarke et al. |
| 2012/0322864 A1 | 12/2012 | Rossi et al. |
| 2012/0322865 A1 | 12/2012 | Rossi et al. |
| 2012/0322986 A1 | 12/2012 | Murphy et al. |
| 2013/0011401 A1 | 1/2013 | Huber et al. |
| 2013/0011438 A1 | 1/2013 | Bartunkov et al. |
| 2013/0034847 A1 | 2/2013 | Kojic et al. |
| 2013/0039884 A1 | 2/2013 | Bogin et al. |
| 2013/0039925 A1 | 2/2013 | Bansal |
| 2013/0078242 A1 | 3/2013 | Nicolaides et al. |
| 2013/0116150 A1 | 5/2013 | Wilcox et al. |
| 2013/0123192 A1 | 5/2013 | Cao et al. |
| 2013/0129790 A1 | 5/2013 | Alexis et al. |
| 2013/0130317 A1 | 5/2013 | Ogawa et al. |
| 2013/0131194 A1 | 5/2013 | Skog et al. |
| 2013/0156795 A1 | 6/2013 | Iavarone et al. |
| 2013/0189741 A1 | 7/2013 | Meis et al. |
| 2013/0190385 A1 | 7/2013 | Duchateau et al. |
| 2013/0190387 A1 | 7/2013 | Feinstein |
| 2013/0203169 A1 | 8/2013 | Naughton et al. |
| 2013/0209398 A1 | 8/2013 | Naughton et al. |
| 2013/0209427 A1 | 8/2013 | Thangapazham et al. |
| 2013/0209471 A1 | 8/2013 | Schwarz et al. |
| 2013/0210076 A1 | 8/2013 | Naughton et al. |
| 2013/0210725 A1 | 8/2013 | Naughton et al. |
| 2013/0216506 A1 | 8/2013 | Discher et al. |
| 2013/0217069 A1 | 8/2013 | Naughton et al. |
| 2013/0217129 A1 | 8/2013 | Naughton et al. |
| 2013/0224188 A1 | 8/2013 | Eckelman et al. |
| 2013/0225435 A1 | 8/2013 | Clarke et al. |
| 2013/0230921 A1 | 9/2013 | Keller et al. |
| 2013/0236533 A1 | 9/2013 | von Andrian et al. |
| 2013/0244256 A1 | 9/2013 | Clarke et al. |
| 2013/0244326 A1 | 9/2013 | Majeti et al. |
| 2013/0247233 A1 | 9/2013 | Gaitanaris et al. |
| 2013/0252895 A1 | 9/2013 | Rapraeger et al. |

(56) References Cited

U.S. PATENT DOCUMENTS

| | | |
|---|---|---|
| 2013/0267684 A1 | 10/2013 | Konno et al. |
| 2013/0287729 A1 | 10/2013 | Keselowsky et al. |
| 2013/0287857 A1 | 10/2013 | von Andrian et al. |
| 2013/0296185 A1 | 11/2013 | Benson |
| 2013/0323254 A1 | 12/2013 | Utku |
| 2013/0323819 A1 | 12/2013 | Hammarstrom et al. |
| 2013/0330325 A1 | 12/2013 | Grabe et al. |
| 2013/0331383 A1 | 12/2013 | Saulnier Sholler et al. |
| 2013/0336925 A1 | 12/2013 | Alvarez et al. |
| 2013/0337066 A1 | 12/2013 | Zhang et al. |
| 2013/0337474 A1 | 12/2013 | Vyas et al. |
| 2013/0338067 A1 | 12/2013 | Alvarez et al. |
| 2013/0338089 A1 | 12/2013 | Chan et al. |
| 2013/0340105 A1 | 12/2013 | Flavell et al. |
| 2014/0017215 A1 | 1/2014 | Ayares |
| 2014/0023664 A1 | 1/2014 | Lowman et al. |
| 2014/0030344 A1 | 1/2014 | Zepp et al. |
| 2014/0037736 A1 | 2/2014 | Shi et al. |
| 2014/0038833 A1 | 2/2014 | Shin et al. |
| 2014/0044735 A1 | 2/2014 | Blanc-Brude et al. |
| 2014/0044738 A1 | 2/2014 | Langermann et al. |
| 2014/0045915 A1 | 2/2014 | Skog et al. |
| 2014/0046030 A1 | 2/2014 | Thanos et al. |
| 2014/0056936 A1 | 2/2014 | Offner et al. |
| 2014/0057257 A1 | 2/2014 | Galon et al. |
| 2014/0065169 A1 | 3/2014 | Jaiswal et al. |
| 2014/0066598 A1 | 3/2014 | Stafford et al. |
| 2014/0079836 A1 | 3/2014 | McDaniel |
| 2014/0080732 A1 | 3/2014 | Banchereau et al. |
| 2014/0086957 A1 | 3/2014 | Bartunkova et al. |
| 2014/0100164 A1 | 4/2014 | Popel et al. |
| 2014/0101786 A1 | 4/2014 | Sykes et al. |
| 2014/0113348 A1 | 4/2014 | Williams et al. |
| 2014/0113832 A1 | 4/2014 | Wolfe et al. |
| 2014/0120622 A1 | 5/2014 | Gregory et al. |
| 2014/0127269 A1 | 5/2014 | Masli |
| 2014/0127301 A1 | 5/2014 | Alexis et al. |
| 2014/0134662 A1 | 5/2014 | Flavell et al. |
| 2014/0140989 A1 | 5/2014 | Eckelman et al. |
| 2014/0141986 A1 | 5/2014 | Spetzler et al. |
| 2014/0148350 A1 | 5/2014 | Spetzler et al. |
| 2014/0161805 A1 | 6/2014 | Jamieson et al. |
| 2014/0161825 A1 | 6/2014 | Jaiswal et al. |
| 2014/0178400 A1 | 6/2014 | Blander et al. |
| 2014/0179770 A1 | 6/2014 | Zhang et al. |
| 2014/0193453 A1 | 7/2014 | Zepp et al. |
| 2014/0194319 A1 | 7/2014 | Skog et al. |
| 2014/0194613 A1 | 7/2014 | Skog et al. |
| 2014/0199308 A1 | 7/2014 | van den Berg |
| 2014/0242173 A1 | 8/2014 | Zepp et al. |
| 2014/0242699 A1 | 8/2014 | Zhang |
| 2014/0248273 A1 | 9/2014 | van Strijp et al. |
| 2014/0255313 A1 | 9/2014 | Vasiljeva et al. |
| 2014/0255369 A1 | 9/2014 | Turner et al. |
| 2014/0255431 A1 | 9/2014 | Majeti et al. |
| 2014/0256649 A1 | 9/2014 | Haura |
| 2014/0271582 A1 | 9/2014 | Forman et al. |
| 2014/0271641 A1 | 9/2014 | Lawler et al. |
| 2014/0275082 A1 | 9/2014 | Tao et al. |
| 2014/0286959 A1 | 9/2014 | Hegen et al. |
| 2014/0294891 A1 | 10/2014 | Szalay et al. |
| 2014/0296161 A1 | 10/2014 | Qian et al. |
| 2014/0302060 A1 | 10/2014 | Beg et al. |
| 2014/0303354 A1 | 10/2014 | Masternak et al. |
| 2014/0308302 A1 | 10/2014 | Boghaert et al. |
| 2014/0308746 A1 | 10/2014 | Rossi et al. |
| 2014/0314865 A1 | 10/2014 | von Andrian et al. |
| 2014/0315984 A1 | 10/2014 | Newgard et al. |
| 2014/0328825 A1 | 11/2014 | Meis et al. |
| 2014/0341978 A1* | 11/2014 | Kim .................. A61K 39/395 424/277.1 |
| 2014/0356326 A1 | 12/2014 | Schellenberger et al. |
| 2014/0363496 A1 | 12/2014 | Ghoroghchian |
| 2014/0369924 A1 | 12/2014 | Weissman et al. |
| 2014/0370012 A1 | 12/2014 | Block et al. |
| 2014/0377221 A1 | 12/2014 | Tufaro et al. |
| 2014/0377287 A1 | 12/2014 | Govindan et al. |
| 2015/0005477 A1 | 1/2015 | Lowman et al. |
| 2015/0017187 A1 | 1/2015 | Thanos et al. |
| 2015/0020223 A1 | 1/2015 | Zhang et al. |
| 2015/0030533 A1 | 1/2015 | Algate et al. |
| 2015/0030535 A1 | 1/2015 | Williams et al. |
| 2015/0030657 A1 | 1/2015 | Ludlow et al. |
| 2015/0037359 A1 | 2/2015 | Schellenberger et al. |
| 2015/0044222 A1 | 2/2015 | Yao et al. |
| 2015/0056636 A1 | 2/2015 | Garcia et al. |
| 2015/0065556 A1 | 3/2015 | Birsoy et al. |
| 2015/0072893 A1 | 3/2015 | Kampmann et al. |
| 2015/0073041 A1 | 3/2015 | Saltzman et al. |
| 2015/0079046 A1 | 3/2015 | Sinden et al. |
| 2015/0079088 A1 | 3/2015 | Lowman et al. |
| 2015/0087810 A1 | 3/2015 | Moore et al. |
| 2015/0089678 A1 | 3/2015 | Murphy et al. |
| 2015/0089679 A1 | 3/2015 | Murphy et al. |
| 2015/0094518 A1 | 4/2015 | Wu et al. |
| 2015/0100345 A1 | 4/2015 | Holmes et al. |
| 2015/0110806 A1 | 4/2015 | Nassif et al. |
| 2015/0110836 A1 | 4/2015 | Glanville |
| 2015/0126456 A1 | 5/2015 | Susin et al. |
| 2015/0132313 A1 | 5/2015 | Yao et al. |
| 2015/0140566 A1 | 5/2015 | Gros |
| 2015/0147276 A1 | 5/2015 | Ingber et al. |
| 2015/0147336 A1 | 5/2015 | Yao et al. |
| 2015/0150996 A1 | 6/2015 | Miller et al. |
| 2015/0152147 A1 | 6/2015 | Gosselin et al. |
| 2015/0152187 A1 | 6/2015 | Sun et al. |
| 2015/0152474 A1 | 6/2015 | Pawlowski et al. |
| 2015/0164955 A1 | 6/2015 | Sinden et al. |
| 2015/0167088 A1 | 6/2015 | Staudt et al. |
| 2015/0168405 A1 | 6/2015 | Kojic et al. |
| 2015/0175707 A1 | 6/2015 | De Jong et al. |
| 2015/0182588 A1 | 7/2015 | Kahvejian et al. |
| 2015/0183812 A1 | 7/2015 | Kawasaki et al. |
| 2015/0203579 A1 | 7/2015 | Papadopoulos et al. |
| 2015/0203580 A1 | 7/2015 | Papadopoulos et al. |
| 2015/0208622 A1 | 7/2015 | Flavell et al. |
| 2015/0209389 A1 | 7/2015 | Gothelf et al. |
| 2015/0211020 A1 | 7/2015 | Kuroiwa et al. |
| 2015/0218217 A1 | 8/2015 | Moore et al. |
| 2015/0232881 A1 | 8/2015 | Glucksmann et al. |
| 2015/0232883 A1 | 8/2015 | Dahlman et al. |
| 2015/0238604 A1 | 8/2015 | Eckelman et al. |
| 2015/0246073 A1 | 9/2015 | Basu et al. |
| 2015/0250896 A1 | 9/2015 | Zhao |
| 2015/0259431 A1 | 9/2015 | Stemmer et al. |
| 2015/0265725 A1 | 9/2015 | Peyman |
| 2015/0266942 A1 | 9/2015 | Tian |
| 2015/0266956 A1 | 9/2015 | Schwarz et al. |
| 2015/0268245 A1 | 9/2015 | Galon et al. |
| 2015/0274826 A1 | 10/2015 | Frazier et al. |
| 2015/0284416 A1 | 10/2015 | Zhao |
| 2015/0284445 A1 | 10/2015 | Jin et al. |
| 2015/0284688 A1 | 10/2015 | Archetti |
| 2015/0285802 A1 | 10/2015 | Polyak et al. |
| 2015/0291966 A1 | 10/2015 | Zhang et al. |
| 2015/0297745 A1 | 10/2015 | Cobbold et al. |
| 2015/0299197 A1 | 10/2015 | Tao et al. |
| 2015/0301055 A1 | 10/2015 | Spetzler |
| 2015/0301058 A1 | 10/2015 | Schettini et al. |
| 2015/0306212 A1 | 10/2015 | Kahvejian et al. |
| 2015/0314017 A1 | 11/2015 | Zhao |
| 2015/0315289 A1 | 11/2015 | Liu et al. |
| 2015/0320810 A1 | 11/2015 | Conrad et al. |
| 2015/0322155 A1 | 11/2015 | Zhao |
| 2015/0328300 A1 | 11/2015 | Zepp et al. |
| 2015/0329875 A1 | 11/2015 | Gregory et al. |
| 2015/0330997 A1 | 11/2015 | Paramithiotis et al. |
| 2015/0343055 A1 | 12/2015 | Offner et al. |
| 2015/0344584 A1 | 12/2015 | Umana et al. |
| 2015/0353642 A1 | 12/2015 | Tykocinski |
| 2015/0366897 A1 | 12/2015 | Stevanato et al. |
| 2015/0366988 A1 | 12/2015 | Goldenberg et al. |
| 2015/0368719 A1 | 12/2015 | Regev et al. |
| 2015/0374790 A1 | 12/2015 | Liu et al. |

(56) References Cited

U.S. PATENT DOCUMENTS

| | | |
|---|---|---|
| 2015/0376288 A1 | 12/2015 | Weiskopf et al. |
| 2015/0376296 A1 | 12/2015 | Fedorov et al. |
| 2016/0000886 A1 | 1/2016 | Parker et al. |
| 2016/0000909 A1 | 1/2016 | Eisenbach-Schwartz et al. |
| 2016/0002336 A1 | 1/2016 | Chen |
| 2016/0002597 A1 | 1/2016 | Sinden et al. |
| 2016/0003835 A1 | 1/2016 | Halbert et al. |
| 2016/0007893 A1 | 1/2016 | Roberts |
| 2016/0008374 A1 | 1/2016 | Geleziunas et al. |
| 2016/0008463 A1 | 1/2016 | Eisenbach-Schwartz et al. |
| 2016/0009813 A1 | 1/2016 | Themeli et al. |
| 2016/0009814 A1 | 1/2016 | Jaiswal et al. |
| 2016/0009815 A1 | 1/2016 | Jaiswal et al. |
| 2016/0022976 A1 | 1/2016 | Peyman |
| 2016/0024211 A1 | 1/2016 | Chen |
| 2016/0038467 A1 | 2/2016 | Peters |
| 2016/0038576 A1 | 2/2016 | Vasserot et al. |
| 2016/0038612 A1 | 2/2016 | Hoge et al. |
| 2016/0039903 A1 | 2/2016 | Ring et al. |
| 2016/0039908 A1 | 2/2016 | Susin et al. |
| 2016/0045532 A1 | 2/2016 | Roberts et al. |
| 2016/0045551 A1 | 2/2016 | Brentjens et al. |
| 2016/0046724 A1 | 2/2016 | Brogdon et al. |
| 2016/0047735 A1 | 2/2016 | Grisham et al. |
| 2016/0050896 A1 | 2/2016 | Murphy et al. |
| 2016/0051651 A1 | 2/2016 | Brogdon et al. |
| 2016/0052983 A1 | 2/2016 | Alvarez et al. |
| 2016/0052990 A1 | 2/2016 | Ring et al. |
| 2016/0053003 A1 | 2/2016 | Li et al. |
| 2016/0058793 A1 | 3/2016 | Terman |
| 2016/0058885 A1 | 3/2016 | Grasso et al. |
| 2016/0060342 A1 | 3/2016 | Majeti et al. |
| 2016/0060594 A1 | 3/2016 | Xian |
| 2016/0060707 A1 | 3/2016 | Goldenberg et al. |
| 2016/0060709 A1 | 3/2016 | Wilhelm et al. |
| 2016/0068596 A1 | 3/2016 | de Sauvage et al. |
| 2016/0068601 A1 | 3/2016 | Brogdon et al. |
| 2016/0069889 A1 | 3/2016 | Spetzler et al. |
| 2016/0083791 A1 | 3/2016 | Gillespie et al. |
| 2016/0089397 A1 | 3/2016 | Rossi et al. |
| 2016/0090603 A1 | 3/2016 | Carnes et al. |
| 2016/0096892 A1 | 4/2016 | Brogdon et al. |
| 2016/0097773 A1 | 4/2016 | Pasqual et al. |
| 2016/0101111 A1 | 4/2016 | Yen et al. |
| 2016/0101150 A1 | 4/2016 | Jaynes et al. |
| 2016/0108045 A1 | 4/2016 | Andres et al. |
| 2016/0108123 A1 | 4/2016 | Freeman et al. |
| 2016/0122707 A1 | 5/2016 | Swee et al. |
| 2016/0130348 A1 | 5/2016 | Langermann et al. |
| 2016/0130552 A1 | 5/2016 | Henco et al. |
| 2016/0130569 A1 | 5/2016 | Jarjour et al. |
| 2016/0139012 A1 | 5/2016 | D'Silva et al. |
| 2016/0143961 A1 | 5/2016 | Berry et al. |
| 2016/0144009 A1 | 5/2016 | Tseng et al. |
| 2016/0144026 A1 | 5/2016 | Lutteropp et al. |
| 2016/0153004 A1 | 6/2016 | Zhang et al. |
| 2016/0153005 A1 | 6/2016 | Zhang et al. |
| 2016/0153053 A1 | 6/2016 | Skog et al. |
| 2016/0157470 A1 | 6/2016 | Gurer et al. |
| 2016/0159905 A1 | 6/2016 | Abdiche et al. |
| 2016/0159920 A1 | 6/2016 | Wang et al. |
| 2016/0165861 A1 | 6/2016 | Hering et al. |
| 2016/0166546 A1 | 6/2016 | Garner et al. |
| 2016/0168242 A1 | 6/2016 | Hass et al. |
| 2016/0175308 A1 | 6/2016 | Giangreco |
| 2016/0175358 A1 | 6/2016 | Jakobovits et al. |
| 2016/0175462 A1 | 6/2016 | Zhang et al. |
| 2016/0176916 A1 | 6/2016 | Bradner et al. |
| 2016/0176948 A1 | 6/2016 | Lawler et al. |
| 2016/0176976 A1 | 6/2016 | Jaiswal et al. |
| 2016/0176978 A1 | 6/2016 | Jaiswal et al. |
| 2016/0185859 A1 | 6/2016 | Boghaert et al. |
| 2016/0186146 A1 | 6/2016 | Thomson et al. |
| 2016/0186150 A1 | 6/2016 | Deming et al. |
| 2016/0193252 A1 | 7/2016 | Hicks et al. |
| 2016/0193258 A1 | 7/2016 | Berry et al. |
| 2016/0193357 A1 | 7/2016 | Govindan et al. |
| 2016/0194368 A1 | 7/2016 | Hoge et al. |
| 2016/0194399 A1 | 7/2016 | Irving et al. |
| 2016/0194406 A1 | 7/2016 | Leeper et al. |
| 2016/0194625 A1 | 7/2016 | Hoge et al. |
| 2016/0199424 A1 | 7/2016 | Berry et al. |
| 2016/0200804 A1 | 7/2016 | Weinberger et al. |
| 2016/0200816 A1 | 7/2016 | Jaiswal et al. |
| 2016/0206566 A1 | 7/2016 | Lu et al. |
| 2016/0207949 A1 | 7/2016 | Zhao |
| 2016/0207987 A1 | 7/2016 | Bansal |
| 2016/0208243 A1 | 7/2016 | Zhang et al. |
| 2016/0215052 A1 | 7/2016 | Shipp et al. |
| 2016/0219845 A1 | 8/2016 | Gaitanaris et al. |
| 2016/0220537 A1 | 8/2016 | Garner et al. |
| 2016/0222097 A1 | 8/2016 | Isenberg et al. |
| 2016/0222121 A1 | 8/2016 | Johnson et al. |
| 2016/0235045 A1 | 8/2016 | Kuroiwa et al. |
| 2016/0235730 A1 | 8/2016 | Bradner et al. |
| 2016/0235731 A1 | 8/2016 | Bradner et al. |
| 2016/0235788 A1 | 8/2016 | Hicks et al. |
| 2016/0235792 A1 | 8/2016 | Berry et al. |
| 2016/0237132 A1 | 8/2016 | Alvarez et al. |
| 2016/0237400 A1 | 8/2016 | Xian |
| 2016/0237455 A1 | 8/2016 | Glucksmann et al. |
| 2016/0243221 A1 | 8/2016 | Hoge et al. |
| 2016/0243247 A1 | 8/2016 | Bradner et al. |
| 2016/0243259 A1 | 8/2016 | Almarsson et al. |
| 2016/0244501 A1 | 8/2016 | Ellsworth et al. |
| 2016/0244502 A1 | 8/2016 | Bolen et al. |
| 2016/0244522 A1 | 8/2016 | van den Berg |
| 2016/0244528 A1 | 8/2016 | Gray et al. |
| 2016/0244751 A1 | 8/2016 | Ilagan |
| 2016/0251336 A1 | 9/2016 | Yang et al. |
| 2016/0251435 A1 | 9/2016 | Eckelman et al. |
| 2016/0251477 A1 | 9/2016 | Cui et al. |
| 2016/0256448 A1 | 9/2016 | Bair et al. |
| 2016/0256458 A1 | 9/2016 | Bair et al. |
| 2016/0257751 A1 | 9/2016 | Swanson et al. |
| 2016/0257932 A1 | 9/2016 | Kahvejian et al. |
| 2016/0264665 A1 | 9/2016 | Lim et al. |
| 2016/0271188 A1 | 9/2016 | Berry et al. |
| 2016/0273046 A1 | 9/2016 | Xu et al. |
| 2016/0278350 A1 | 9/2016 | Ayares |
| 2016/0280753 A1 | 9/2016 | Schellenberger et al. |
| 2016/0282365 A1 | 9/2016 | Gaitanaris et al. |
| 2016/0283653 A1 | 9/2016 | Staudt et al. |
| 2016/0287670 A1 | 10/2016 | Van Den Brink et al. |
| 2016/0289229 A1 | 10/2016 | Aktoudianakis et al. |
| 2016/0289238 A1 | 10/2016 | He et al. |
| 2016/0289324 A1 | 10/2016 | Moore et al. |
| 2016/0289341 A1 | 10/2016 | Wu |
| 2016/0289343 A1 | 10/2016 | Wu |
| 2016/0297880 A1 | 10/2016 | Eisenbach-Schwartz et al. |
| 2016/0298082 A1 | 10/2016 | Henco et al. |
| 2016/0299146 A1 | 10/2016 | Garraway et al. |
| 2016/0303095 A1 | 10/2016 | Aguayo et al. |
| 2016/0304969 A1 | 10/2016 | Ayers et al. |
| 2016/0311903 A1 | 10/2016 | West et al. |
| 2016/0311905 A1 | 10/2016 | Eisenbach-Schwartz et al. |
| 2016/0311908 A1 | 10/2016 | Arena et al. |
| 2016/0311917 A1 | 10/2016 | Beatty et al. |
| 2016/0312295 A1 | 10/2016 | Ayers et al. |
| 2016/0312297 A1 | 10/2016 | Ayers et al. |
| 2016/0317647 A1 | 11/2016 | Ciaramella et al. |
| 2016/0319021 A1 | 11/2016 | Eisenbach-Schwartz et al. |
| 2016/0319256 A9 | 11/2016 | Deming et al. |
| 2016/0319361 A1 | 11/2016 | Spetzler et al. |
| 2016/0324897 A1 | 11/2016 | Ingber et al. |
| 2016/0324983 A1 | 11/2016 | Li |
| 2016/0326253 A1 | 11/2016 | Ueda et al. |
| 2016/0326261 A1 | 11/2016 | Spits et al. |
| 2016/0326263 A1 | 11/2016 | Bamdad et al. |
| 2016/0326585 A1 | 11/2016 | Gros |
| 2016/0326596 A1 | 11/2016 | Levine et al. |
| 2016/0331828 A1 | 11/2016 | Ciaramella et al. |
| 2016/0333008 A1 | 11/2016 | Sun et al. |
| 2016/0333009 A1 | 11/2016 | Bartlett et al. |

(56) References Cited

U.S. PATENT DOCUMENTS

| | | |
|---|---|---|
| 2016/0333114 A1 | 11/2016 | Williams et al. |
| 2016/0339064 A1 | 11/2016 | Kovarik et al. |
| 2016/0340397 A1 | 11/2016 | Ring et al. |
| 2016/0340407 A1 | 11/2016 | Hodi et al. |
| 2016/0340661 A1 | 11/2016 | Cong et al. |
| 2016/0340743 A1 | 11/2016 | Yen et al. |
| 2016/0345549 A1 | 12/2016 | Gurer et al. |
| 2016/0347857 A1 | 12/2016 | Liu et al. |
| 2016/0348073 A1 | 12/2016 | Meissner et al. |
| 2016/0354397 A1 | 12/2016 | Chan et al. |
| 2016/0355587 A1 | 12/2016 | West et al. |
| 2016/0355592 A1 | 12/2016 | Sagert et al. |
| 2016/0355599 A1 | 12/2016 | Sagert et al. |
| 2016/0355797 A1 | 12/2016 | Konermann et al. |
| 2016/0362464 A1 | 12/2016 | Ghosh |
| 2016/0362472 A1 | 12/2016 | Bitter et al. |
| 2016/0362678 A1 | 12/2016 | Skog et al. |
| 2016/0366862 A1 | 12/2016 | Flavell et al. |
| 2016/0367670 A1 | 12/2016 | Unger |
| 2016/0368994 A1 | 12/2016 | Kelley et al. |
| 2016/0369002 A1 | 12/2016 | Gauthier et al. |
| 2016/0369269 A1 | 12/2016 | Shen et al. |
| 2016/0374321 A1 | 12/2016 | Murphy et al. |
| 2016/0374949 A9 | 12/2016 | Green et al. |
| 2016/0375033 A1 | 12/2016 | Edgar et al. |
| 2016/0375148 A1 | 12/2016 | Li |
| 2016/0376333 A1 | 12/2016 | Procko et al. |
| 2016/0376663 A1 | 12/2016 | Brown |
| 2017/0000779 A1 | 1/2017 | Hariri et al. |
| 2017/0000869 A1 | 1/2017 | O'Connor |
| 2017/0002060 A1 | 1/2017 | Bolen et al. |
| 2017/0002068 A1 | 1/2017 | Yarden et al. |
| 2017/0002088 A1 | 1/2017 | Algate et al. |
| 2017/0007644 A1 | 1/2017 | Pai et al. |
| 2017/0007685 A1 | 1/2017 | Pasare et al. |
| 2017/0008891 A1 | 1/2017 | Tao et al. |
| 2017/0008951 A1 | 1/2017 | Block et al. |
| 2017/0009238 A1 | 1/2017 | Nyce et al. |
| 2017/0014527 A1 | 1/2017 | Goldenberg et al. |
| 2017/0020835 A1 | 1/2017 | Chang |
| 2017/0020926 A1 | 1/2017 | Mata-Fink et al. |
| 2017/0020956 A1 | 1/2017 | Jaynes et al. |
| 2017/0023548 A1 | 1/2017 | Nagata et al. |
| 2017/0027140 A1 | 2/2017 | Flavell et al. |
| 2017/0028079 A1 | 2/2017 | Li |
| 2017/0029418 A1 | 2/2017 | Kawasaki et al. |
| 2017/0029508 A1 | 2/2017 | Eisenbach-Schwartz et al. |
| 2017/0035808 A1 | 2/2017 | Jarvis et al. |
| 2017/0037431 A1 | 2/2017 | Lieber et al. |
| 2017/0038394 A1 | 2/2017 | Jarvis et al. |
| 2017/0038395 A1 | 2/2017 | Jarvis et al. |
| 2017/0044164 A1 | 2/2017 | Li et al. |
| 2017/0044258 A1 | 2/2017 | Van Den Berg |
| 2017/0044259 A1 | 2/2017 | Tipton et al. |
| 2017/0051358 A1 | 2/2017 | Bittinger et al. |
| 2017/0053091 A1 | 2/2017 | Holmes et al. |
| 2017/0055561 A1 | 3/2017 | Naughton et al. |
| 2017/0056347 A1 | 3/2017 | Glick et al. |
| 2017/0056470 A1 | 3/2017 | Rapraeger et al. |
| 2017/0057965 A1 | 3/2017 | Li et al. |
| 2017/0065636 A1 | 3/2017 | Moriarity et al. |
| 2017/0067021 A1 | 3/2017 | Moriarity et al. |
| 2017/0067065 A1 | 3/2017 | Falb et al. |
| 2017/0067875 A1 | 3/2017 | Laing et al. |
| 2017/0071918 A1 | 3/2017 | Ng Lui et al. |
| 2017/0071944 A1 | 3/2017 | Geleziunas et al. |
| 2017/0072067 A1 | 3/2017 | Lowman et al. |
| 2017/0072071 A1 | 3/2017 | Gros |
| 2017/0073414 A1 | 3/2017 | Weiskopf et al. |
| 2017/0073425 A1 | 3/2017 | Grasso et al. |
| 2017/0073664 A1 | 3/2017 | McCafferty et al. |
| 2017/0079916 A1 | 3/2017 | Khan et al. |
| 2017/0080029 A1 | 3/2017 | Reginald et al. |
| 2017/0081407 A1 | 3/2017 | Grosveld et al. |
| 2017/0088898 A1 | 3/2017 | Skog et al. |
| 2017/0095531 A1 | 4/2017 | Schreiber et al. |
| 2017/0095552 A1 | 4/2017 | Szalay et al. |
| 2017/0096671 A1 | 4/2017 | Morrisey |
| 2017/0100486 A1 | 4/2017 | Ziv |
| 2017/0101472 A1 | 4/2017 | Ullman et al. |
| 2017/0106068 A1 | 4/2017 | Bourinbaiar et al. |
| 2017/0107216 A1 | 4/2017 | Wu et al. |
| 2017/0107270 A1 | 4/2017 | Pons et al. |
| 2017/0107300 A1 | 4/2017 | Kuchroo et al. |
| 2017/0107536 A1 | 4/2017 | Zhang et al. |
| 2017/0107578 A1 | 4/2017 | Ramos et al. |
| 2017/0114413 A1 | 4/2017 | Hahn et al. |
| 2017/0115291 A1 | 4/2017 | Wong et al. |
| 2017/0119687 A1 | 5/2017 | Rotello et al. |
| 2017/0119820 A1 | 5/2017 | Moriarity et al. |
| 2017/0119930 A1 | 5/2017 | Evans et al. |
| 2017/0121310 A1 | 5/2017 | Jia et al. |
| 2017/0121409 A1 | 5/2017 | Verona et al. |
| 2017/0121771 A1 | 5/2017 | Yao et al. |
| 2017/0122853 A1 | 5/2017 | Kobayashi et al. |
| 2017/0128490 A1 | 5/2017 | Bauer et al. |
| 2017/0128505 A1 | 5/2017 | Ungerechts et al. |
| 2017/0130200 A1 | 5/2017 | Moriarity et al. |
| 2017/0130232 A1 | 5/2017 | Stampfer et al. |
| 2017/0130247 A1 | 5/2017 | Dowen et al. |
| 2017/0130271 A1 | 5/2017 | Wong |
| 2017/0136073 A1 | 5/2017 | Falb et al. |
| 2017/0137783 A1 | 5/2017 | Bedoya et al. |
| 2017/0137845 A1 | 5/2017 | Tan et al. |
| 2017/0137885 A1 | 5/2017 | Salomon et al. |
| 2017/0143830 A1 | 5/2017 | Wang et al. |
| 2017/0143845 A1 | 5/2017 | Zhao |
| 2017/0144996 A1 | 5/2017 | Chen et al. |
| 2017/0144997 A1 | 5/2017 | Chen et al. |
| 2017/0145025 A1 | 5/2017 | Li et al. |
| 2017/0145381 A1 | 5/2017 | Pai et al. |
| 2017/0145464 A1 | 5/2017 | Gosselin et al. |
| 2017/0151281 A1 | 6/2017 | Wagner et al. |
| 2017/0151282 A1 | 6/2017 | Discher et al. |
| 2017/0151339 A1 | 6/2017 | White et al. |
| 2017/0151346 A1 | 6/2017 | Zhao |
| 2017/0152274 A1 | 6/2017 | Zhao et al. |
| 2017/0152528 A1 | 6/2017 | Zhang |
| 2017/0157230 A1 | 6/2017 | O'Dwyer |
| 2017/0157262 A1 | 6/2017 | Zhao et al. |
| 2017/0158749 A1 | 6/2017 | Cooper et al. |
| 2017/0165298 A1 | 6/2017 | Jarvis et al. |
| 2017/0165375 A1 | 6/2017 | Ashley et al. |
| 2017/0166903 A1 | 6/2017 | Zhang et al. |
| 2017/0173001 A1 | 6/2017 | May |
| 2017/0173085 A1 | 6/2017 | Kovarik et al. |
| 2017/0173109 A1 | 6/2017 | Watnick |
| 2017/0173128 A1 | 6/2017 | Hoge et al. |
| 2017/0173168 A1 | 6/2017 | Zhao |
| 2017/0173176 A1 | 6/2017 | Zhao |
| 2017/0174671 A1 | 6/2017 | Wu et al. |
| 2017/0174679 A1 | 6/2017 | Lajkiewicz et al. |
| 2017/0174713 A1 | 6/2017 | Du et al. |
| 2017/0174748 A1 | 6/2017 | Mitchell et al. |
| 2017/0174779 A1 | 6/2017 | Varghese et al. |
| 2017/0174781 A1 | 6/2017 | Brownstein |
| 2017/0174790 A1 | 6/2017 | Armstrong et al. |
| 2017/0175128 A1 | 6/2017 | Welstead et al. |
| 2017/0182096 A1 | 6/2017 | Holt et al. |
| 2017/0183420 A1 | 6/2017 | Gregory et al. |
| 2017/0184565 A1 | 6/2017 | Roberts et al. |
| 2017/0184604 A1 | 6/2017 | Lee et al. |
| 2017/0188555 A1 | 7/2017 | Gaitanaris et al. |
| 2017/0190776 A1 | 7/2017 | Jaiswal et al. |
| 2017/0191034 A1 | 7/2017 | Wang et al. |
| 2017/0191055 A1 | 7/2017 | Short et al. |
| 2017/0191128 A1 | 7/2017 | Salomon et al. |
| 2017/0196818 A1 | 7/2017 | Shin et al. |
| 2017/0196966 A1 | 7/2017 | Henderson |
| 2017/0198038 A1 | 7/2017 | Gauthier et al. |
| 2017/0198051 A1 | 7/2017 | Eckelman et al. |
| 2017/0198302 A1 | 7/2017 | Feng et al. |
| 2017/0198308 A1 | 7/2017 | Qi et al. |
| 2017/0199193 A1 | 7/2017 | Filvaroff et al. |

(56) References Cited

U.S. PATENT DOCUMENTS

| | | |
|---|---|---|
| 2017/0202914 A1 | 7/2017 | Blankenberg |
| 2017/0202975 A1 | 7/2017 | Zhao |
| 2017/0202979 A1 | 7/2017 | Chakraborty et al. |
| 2017/0204139 A1 | 7/2017 | Moore et al. |
| 2017/0204152 A1 | 7/2017 | Nelson et al. |
| 2017/0204181 A1 | 7/2017 | Grosveld |
| 2017/0204407 A1 | 7/2017 | Gilbert et al. |
| 2017/0204422 A1 | 7/2017 | Nelson et al. |
| 2017/0209492 A1 | 7/2017 | June et al. |
| 2017/0209595 A1 | 7/2017 | Zhao |
| 2017/0209864 A1 | 7/2017 | Grisham et al. |
| 2017/0210788 A1 | 7/2017 | Huang et al. |
| 2017/0210802 A1 | 7/2017 | Gauthier et al. |
| 2017/0210803 A1 | 7/2017 | Willingham et al. |
| 2017/0210811 A1 | 7/2017 | Wong et al. |
| 2017/0210812 A1 | 7/2017 | Wong et al. |
| 2017/0211055 A1 | 7/2017 | Brogdon et al. |
| 2017/0216353 A1 | 8/2017 | Nuccitelli et al. |
| 2017/0218086 A1 | 8/2017 | Kim et al. |
| 2017/0224734 A1 | 8/2017 | Chapman et al. |
| 2017/0224737 A1 | 8/2017 | Shizuru et al. |
| 2017/0224814 A1 | 8/2017 | Chang |
| 2017/0224837 A1 | 8/2017 | Chang et al. |
| 2017/0226217 A1 | 8/2017 | Ellmark et al. |
| 2017/0226223 A1 | 8/2017 | Williams et al. |
| 2017/0226507 A1 | 8/2017 | Chan et al. |
| 2017/0233451 A1 | 8/2017 | Ring et al. |
| 2017/0233474 A1 | 8/2017 | Lim et al. |
| 2017/0233808 A1 | 8/2017 | Haining et al. |
| 2017/0240613 A1 | 8/2017 | Zhu et al. |
| 2017/0240634 A1 | 8/2017 | Eisenbach-Schwartz et al. |
| 2017/0240637 A1 | 8/2017 | Cheung et al. |
| 2017/0240639 A1 | 8/2017 | Kumar et al. |
| 2017/0247464 A1 | 8/2017 | Poirier et al. |
| 2017/0247685 A1 | 8/2017 | Short |
| 2017/0248603 A1 | 8/2017 | Hodi et al. |
| 2017/0252379 A1 | 9/2017 | Law et al. |
| 2017/0252396 A1 | 9/2017 | Rudloff et al. |
| 2017/0253933 A1 | 9/2017 | Wang |
| 2017/0258882 A1 | 9/2017 | De Vries et al. |
| 2017/0260137 A1 | 9/2017 | Stafford et al. |
| 2017/0260245 A1 | 9/2017 | Faustman et al. |
| 2017/0260268 A1 | 9/2017 | Beatty et al. |
| 2017/0260277 A1 | 9/2017 | Forman et al. |
| 2017/0260763 A1 | 9/2017 | Fortin et al. |
| 2017/0265442 A1 | 9/2017 | Murphy et al. |
| 2017/0267637 A1 | 9/2017 | Stafford et al. |
| 2017/0269093 A1 | 9/2017 | Gertler et al. |
| 2017/0274014 A1 | 9/2017 | Brogdon et al. |
| 2017/0275290 A1 | 9/2017 | Li et al. |
| 2017/0275364 A1 | 9/2017 | Van Den Berg |
| 2017/0281627 A1 | 10/2017 | Aktoudianakis et al. |
| 2017/0281684 A1 | 10/2017 | Basu et al. |
| 2017/0281791 A1 | 10/2017 | Govindan et al. |
| 2017/0281795 A1 | 10/2017 | Geall et al. |
| 2017/0283497 A1 | 10/2017 | Schiffer-Mannioui |
| 2017/0283807 A1 | 10/2017 | Mounir et al. |
| 2017/0290858 A1 | 10/2017 | Zhao et al. |
| 2017/0290899 A1 | 10/2017 | Bartňkova et al. |
| 2017/0290923 A1 | 10/2017 | Li et al. |
| 2017/0291945 A1 | 10/2017 | Leeper et al. |
| 2017/0291958 A1 | 10/2017 | Dai et al. |
| 2017/0296623 A1 | 10/2017 | Juillerat et al. |
| 2017/0296663 A1 | 10/2017 | Zhao et al. |
| 2017/0306038 A1 | 10/2017 | Brogdon et al. |
| 2017/0306303 A1 | 10/2017 | Taunton et al. |
| 2017/0306416 A1 | 10/2017 | Bedoya et al. |
| 2017/0313707 A1 | 11/2017 | Andres et al. |
| 2017/0313781 A1 | 11/2017 | Govindan et al. |
| 2017/0313978 A1 | 11/2017 | Wang et al. |
| 2017/0314075 A1 | 11/2017 | Skog et al. |
| 2017/0320875 A1 | 11/2017 | Li et al. |
| 2017/0320945 A1 | 11/2017 | Jaiswal et al. |
| 2017/0321194 A1 | 11/2017 | Budge et al. |
| 2017/0321220 A1 | 11/2017 | Douglas et al. |
| 2017/0321443 A1 | 11/2017 | Biffiger et al. |
| 2017/0326093 A1 | 11/2017 | McCormick et al. |
| 2017/0326179 A1 | 11/2017 | Mukherjee |
| 2017/0327567 A1 | 11/2017 | Skokos et al. |
| 2017/0327577 A1 | 11/2017 | Wang et al. |
| 2017/0327590 A1 | 11/2017 | Lowy et al. |
| 2017/0334967 A1 | 11/2017 | Siegel et al. |
| 2017/0335281 A1 | 11/2017 | Loew et al. |
| 2017/0335331 A1 | 11/2017 | Zhao et al. |
| 2017/0335344 A1 | 11/2017 | Pauza et al. |
| 2017/0340724 A1 | 11/2017 | Ciaramella et al. |
| 2017/0340725 A1 | 11/2017 | Ciaramella et al. |
| 2017/0342060 A1 | 11/2017 | Lu et al. |
| 2017/0342068 A1 | 11/2017 | Aktoudianakis et al. |
| 2017/0342119 A1 | 11/2017 | Liu et al. |
| 2017/0342380 A1 | 11/2017 | Petratos et al. |
| 2017/0342390 A1 | 11/2017 | Wissing et al. |
| 2017/0343552 A1 | 11/2017 | Hodi et al. |
| 2017/0343554 A1 | 11/2017 | Sullivan et al. |
| 2017/0348234 A1 | 12/2017 | McDevitt et al. |
| 2017/0348390 A1 | 12/2017 | Wong et al. |
| 2017/0348391 A1 | 12/2017 | Koreth et al. |
| 2017/0348415 A1 | 12/2017 | Hoge et al. |
| 2017/0348429 A1 | 12/2017 | Reilly et al. |
| 2017/0349433 A1 | 12/2017 | Lipford et al. |
| 2017/0349658 A1 | 12/2017 | Micklem et al. |
| 2017/0349874 A1 | 12/2017 | Jaques et al. |
| 2017/0349950 A1 | 12/2017 | Regev et al. |
| 2017/0350879 A1 | 12/2017 | Chen et al. |
| 2017/0355767 A1 | 12/2017 | Engelberts et al. |
| 2017/0355773 A1 | 12/2017 | Schreiber et al. |
| 2017/0355774 A1 | 12/2017 | Delfino et al. |
| 2017/0355958 A1 | 12/2017 | Sankaran |
| 2017/0356022 A1 | 12/2017 | Khan et al. |
| 2017/0356903 A1 | 12/2017 | Domenyuk et al. |
| 2017/0360706 A1 | 12/2017 | Ghoroghchian |
| 2017/0360836 A1 | 12/2017 | Novik et al. |
| 2017/0360873 A1 | 12/2017 | Blencowe et al. |
| 2017/0360932 A1 | 12/2017 | Parry |
| 2017/0360959 A1 | 12/2017 | Saltzman et al. |
| 2017/0360963 A1 | 12/2017 | Haining et al. |
| 2017/0361126 A1 | 12/2017 | Ghoroghchian |
| 2017/0362253 A1 | 12/2017 | Xiao et al. |
| 2017/0362302 A1 | 12/2017 | Susin et al. |
| 2017/0362329 A1 | 12/2017 | Schreiber |
| 2017/0362332 A1 | 12/2017 | Weiskopf et al. |
| 2017/0362334 A1 | 12/2017 | Thanos et al. |
| 2017/0362582 A1 | 12/2017 | Chen et al. |
| 2017/0362593 A1 | 12/2017 | Maiorano |
| 2017/0362605 A1 | 12/2017 | Chakraborty |
| 2017/0368169 A1 | 12/2017 | Loew et al. |
| 2017/0369572 A1 | 12/2017 | Sato et al. |
| 2017/0369573 A1 | 12/2017 | Gauthier |
| 2017/0369828 A1 | 12/2017 | Mietzner et al. |
| 2017/0369843 A1 | 12/2017 | Kahvejian et al. |
| 2018/0000865 A1 | 1/2018 | Weissman et al. |
| 2018/0000914 A1 | 1/2018 | Valton et al. |
| 2018/0002422 A1 | 1/2018 | Freeman et al. |
| 2018/0008694 A1 | 1/2018 | Ciaramella et al. |
| 2018/0009779 A1 | 1/2018 | Bradner et al. |
| 2018/0009815 A1 | 1/2018 | Li et al. |
| 2018/0009816 A1 | 1/2018 | Buesking et al. |
| 2018/0009893 A1 | 1/2018 | Eisenbach-Schwartz et al. |
| 2018/0009895 A1 | 1/2018 | Smith et al. |
| 2018/0010082 A1 | 1/2018 | Jaques et al. |
| 2018/0010179 A1 | 1/2018 | Hansen et al. |
| 2018/0015137 A1 | 1/2018 | de Keizer |
| 2018/0015153 A1 | 1/2018 | Tang et al. |
| 2018/0016260 A1 | 1/2018 | Yu et al. |
| 2018/0016344 A1 | 1/2018 | Moore et al. |
| 2018/0016352 A1 | 1/2018 | Thurecht et al. |
| 2018/0020647 A1 | 1/2018 | Flavell et al. |
| 2018/0021429 A1 | 1/2018 | Kudo et al. |
| 2018/0021448 A9 | 1/2018 | Zhao et al. |
| 2018/0022781 A1 | 1/2018 | Bridier-Nahmias et al. |
| 2018/0022806 A1 | 1/2018 | Majeti et al. |
| 2018/0022813 A1 | 1/2018 | Lazar et al. |
| 2018/0028455 A1 | 2/2018 | Green et al. |
| 2018/0028645 A1 | 2/2018 | Ciaramella et al. |

(56) References Cited

U.S. PATENT DOCUMENTS

| | | |
|---|---|---|
| 2018/0028651 A1 | 2/2018 | Leeper et al. |
| 2018/0028686 A1 | 2/2018 | Brinker et al. |
| 2018/0030137 A1 | 2/2018 | Van Eenennaam et al. |
| 2018/0030142 A1 | 2/2018 | Majeti et al. |
| 2018/0030148 A1 | 2/2018 | Algate et al. |
| 2018/0030411 A1 | 2/2018 | Kahvejian et al. |
| 2018/0030515 A1 | 2/2018 | Regev et al. |
| 2018/0036289 A1 | 2/2018 | Gonzalez Buenrostro et al. |
| 2018/0036425 A1 | 2/2018 | Thanos et al. |
| 2018/0037652 A1 | 2/2018 | Liu et al. |
| 2018/0037861 A1 | 2/2018 | Wilkins |
| 2018/0037898 A1 | 2/2018 | Ring et al. |
| 2018/0038865 A1 | 2/2018 | Leung et al. |
| 2018/0042905 A1 | 2/2018 | Aguayo et al. |
| 2018/0044404 A1 | 2/2018 | Oda et al. |
| 2018/0044423 A1 | 2/2018 | Ebersbach et al. |
| 2018/0044424 A1 | 2/2018 | June et al. |
| 2018/0044662 A1 | 2/2018 | Platt et al. |
| 2018/0049413 A1 | 2/2018 | Flavell et al. |
| 2018/0049984 A1 | 2/2018 | Brinker et al. |
| 2018/0051081 A1 | 2/2018 | Frazier et al. |
| 2018/0051335 A9 | 2/2018 | Skog et al. |
| 2018/0051347 A1 | 2/2018 | Ribas et al. |
| 2018/0052176 A1 | 2/2018 | Holt et al. |
| 2018/0055891 A1 | 3/2018 | Zhao |
| 2018/0057486 A1 | 3/2018 | Wu et al. |
| 2018/0057594 A1 | 3/2018 | Evnin |
| 2018/0057598 A1 | 3/2018 | Lazar et al. |
| 2018/0064425 A1 | 3/2018 | Sanyal |
| 2018/0064745 A1 | 3/2018 | Katibah et al. |
| 2018/0064787 A1 | 3/2018 | Schreiber et al. |
| 2018/0065938 A1 | 3/2018 | Chin et al. |
| 2018/0066262 A1 | 3/2018 | Domenyuk et al. |
| 2018/0066285 A1 | 3/2018 | Ojala et al. |
| 2018/0068057 A1 | 3/2018 | Shin et al. |
| 2018/0070564 A1 | 3/2018 | Sykes |
| 2018/0071344 A1 | 3/2018 | Berry et al. |
| 2018/0072718 A1 | 3/2018 | Liu et al. |
| 2018/0072719 A1 | 3/2018 | Ye et al. |
| 2018/0072720 A1 | 3/2018 | Vechorkin et al. |
| 2018/0072740 A1 | 3/2018 | Beck et al. |
| 2018/0072741 A1 | 3/2018 | Vechorkin et al. |
| 2018/0072743 A1 | 3/2018 | Beck et al. |
| 2018/0078624 A1 | 3/2018 | Zhou et al. |
| 2018/0079812 A1 | 3/2018 | Lim et al. |
| 2018/0080087 A1 | 3/2018 | Bacus et al. |
| 2018/0085434 A1 | 3/2018 | Evans et al. |
| 2018/0085447 A1 | 3/2018 | Chaudhuri et al. |
| 2018/0085465 A1 | 3/2018 | Bradner et al. |
| 2018/0086734 A1 | 3/2018 | Yang et al. |
| 2018/0086755 A1 | 3/2018 | Chin et al. |
| 2018/0086829 A1 | 3/2018 | Zhang et al. |
| 2018/0092338 A1 | 4/2018 | Hering et al. |
| 2018/0092937 A1 | 4/2018 | Oost et al. |
| 2018/0092968 A1 | 4/2018 | Albelda |
| 2018/0092973 A1 | 4/2018 | Kaplan |
| 2018/0094231 A1 | 4/2018 | Mietzner et al. |
| 2018/0094244 A1 | 4/2018 | Novik et al. |
| 2018/0098972 A1 | 4/2018 | Goldfeld et al. |
| 2018/0100026 A1 | 4/2018 | Kim et al. |
| 2018/0100201 A1 | 4/2018 | Garraway et al. |
| 2018/0100860 A1 | 4/2018 | Hennig |
| 2018/0104187 A1 | 4/2018 | Liu et al. |
| 2018/0105591 A1 | 4/2018 | Grosveld et al. |
| 2018/0105592 A1 | 4/2018 | Eisenbach-Schwartz et al. |
| 2018/0105600 A1 | 4/2018 | Pons et al. |
| 2018/0110772 A1 | 4/2018 | Govindan et al. |
| 2018/0110831 A1 | 4/2018 | Brinker et al. |
| 2018/0110847 A1 | 4/2018 | Wagner et al. |
| 2018/0110874 A1 | 4/2018 | Li |
| 2018/0111997 A1 | 4/2018 | Eisenbach-Schwartz et al. |
| 2018/0111998 A1 | 4/2018 | Eisenbach-Schwartz et al. |
| 2018/0111999 A1 | 4/2018 | Eisenbach-Schwartz et al. |
| 2018/0112213 A1 | 4/2018 | Welstead et al. |
| 2018/0117117 A1 | 5/2018 | Choi et al. |
| 2018/0117150 A1 | 5/2018 | O'Dwyer et al. |
| 2018/0118826 A1 | 5/2018 | Eisenbach-Schwartz et al. |
| 2018/0118834 A1 | 5/2018 | Brogdon et al. |
| 2018/0119101 A1 | 5/2018 | Kahvejian et al. |
| 2018/0119107 A1 | 5/2018 | Neal et al. |
| 2018/0119118 A1 | 5/2018 | Lu et al. |
| 2018/0125892 A1 | 5/2018 | Brannetti et al. |
| 2018/0125935 A1 | 5/2018 | Schreiber et al. |
| 2018/0125988 A1 | 5/2018 | Yang et al. |
| 2018/0126001 A1 | 5/2018 | Malecki et al. |
| 2018/0126003 A1 | 5/2018 | Hoerr |
| 2018/0126014 A1 | 5/2018 | Zhou et al. |
| 2018/0127499 A1 | 5/2018 | Wilson et al. |
| 2018/0127509 A1 | 5/2018 | Armstrong |
| 2018/0127748 A1 | 5/2018 | Whetstine |
| 2018/0127783 A1 | 5/2018 | Zhang et al. |
| 2018/0133296 A1 | 5/2018 | Barrett et al. |
| 2018/0134684 A1 | 5/2018 | Bradner et al. |
| 2018/0135012 A1 | 5/2018 | Mata-Fink et al. |
| 2018/0135020 A1 | 5/2018 | Zhao |
| 2018/0139941 A1 | 5/2018 | Murphy et al. |
| 2018/0140602 A1 | 5/2018 | Angst et al. |
| 2018/0140698 A1 | 5/2018 | Clube et al. |
| 2018/0141934 A1 | 5/2018 | Chen et al. |
| 2018/0141939 A1 | 5/2018 | Lapina et al. |
| 2018/0141986 A1 | 5/2018 | Tian et al. |
| 2018/0142018 A1 | 5/2018 | Fischer |
| 2018/0142019 A1 | 5/2018 | Manning et al. |
| 2018/0142035 A1 | 5/2018 | Lobb et al. |
| 2018/0142257 A1 | 5/2018 | Pauza et al. |
| 2018/0142258 A1 | 5/2018 | Pauza et al. |
| 2018/0147257 A1 | 5/2018 | Corey et al. |
| 2018/0148503 A1 | 5/2018 | Scheinberg et al. |
| 2018/0148512 A1 | 5/2018 | Tykocinski |
| 2018/0148514 A1 | 5/2018 | Williams |
| 2018/0148790 A1 | 5/2018 | Ayers et al. |
| 2018/0153796 A1 | 6/2018 | Lin et al. |
| 2018/0153821 A1 | 6/2018 | Zhang et al. |
| 2018/0153884 A1 | 6/2018 | Qin et al. |
| 2018/0153937 A1 | 6/2018 | Nuccitelli et al. |
| 2018/0153942 A1 | 6/2018 | Giacalone et al. |
| 2018/0153975 A1 | 6/2018 | Fritsch et al. |
| 2018/0153978 A1 | 6/2018 | Pasare et al. |
| 2018/0153984 A1 | 6/2018 | Ernst et al. |
| 2018/0153989 A1 | 6/2018 | Kahvejian et al. |
| 2018/0155405 A1 | 6/2018 | Ring et al. |
| 2018/0155424 A1 | 6/2018 | Van Den Berg |
| 2018/0155716 A1 | 6/2018 | Zhang et al. |
| 2018/0155717 A1 | 6/2018 | Valamehr et al. |
| 2018/0156798 A1 | 6/2018 | Haura |
| 2018/0156800 A1 | 6/2018 | Lin et al. |
| 2018/0156807 A1 | 6/2018 | Placantonakis et al. |
| 2018/0160662 A1 | 6/2018 | Garcia et al. |
| 2018/0161300 A1 | 6/2018 | Erez et al. |
| 2018/0161307 A1 | 6/2018 | Du et al. |
| 2018/0161349 A1 | 6/2018 | Makkouk et al. |
| 2018/0161371 A1 | 6/2018 | O'Dwyer |
| 2018/0162903 A1 | 6/2018 | Pease et al. |
| 2018/0162937 A1 | 6/2018 | Boghaert et al. |
| 2018/0162939 A1 | 6/2018 | Ma et al. |
| 2018/0162940 A1 | 6/2018 | Willuda et al. |
| 2018/0163178 A1 | 6/2018 | Schneider et al. |
| 2018/0163197 A1 | 6/2018 | Brummelkamp et al. |
| 2018/0163210 A1 | 6/2018 | Simons et al. |
| 2018/0163882 A1 | 6/2018 | Mietzner |
| 2018/0168488 A1 | 6/2018 | Jones et al. |
| 2018/0168489 A1 | 6/2018 | Jones et al. |
| 2018/0168490 A1 | 6/2018 | Jones et al. |
| 2018/0169027 A1 | 6/2018 | Zhang et al. |
| 2018/0169091 A1 | 6/2018 | May |
| 2018/0169097 A1 | 6/2018 | Hammerman et al. |
| 2018/0169153 A1 | 6/2018 | Berry et al. |
| 2018/0169154 A1 | 6/2018 | Falb et al. |
| 2018/0169230 A1 | 6/2018 | Adams et al. |
| 2018/0170907 A1 | 6/2018 | Jia et al. |
| 2018/0170916 A1 | 6/2018 | Chen et al. |
| 2018/0171014 A1 | 6/2018 | Manning et al. |
| 2018/0171028 A1 | 6/2018 | Chatterjee et al. |
| 2018/0171337 A1 | 6/2018 | O'Neill et al. |

(56) References Cited

U.S. PATENT DOCUMENTS

| | | |
|---|---|---|
| 2018/0177784 A1 | 6/2018 | Wu et al. |
| 2018/0177827 A1 | 6/2018 | Turner et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0179221 A1 | 6/2018 | Sampson et al. |
| 2018/0179492 A1 | 6/2018 | Xian |
| 2018/0179494 A1 | 6/2018 | Muffat et al. |
| 2018/0179590 A1 | 6/2018 | Belgrader et al. |
| 2018/0179591 A1 | 6/2018 | Belgrader et al. |
| 2018/0179601 A1 | 6/2018 | Alexandrov et al. |
| 2018/0184630 A1 | 7/2018 | Joseph |
| 2018/0185351 A1 | 7/2018 | Goldenberg et al. |
| 2018/0185668 A1 | 7/2018 | Papadopoulos et al. |
| 2018/0185844 A1 | 7/2018 | Kerns et al. |
| 2018/0186878 A1 | 7/2018 | Rosenthal |
| 2018/0186882 A1 | 7/2018 | Freeman et al. |
| 2018/0186883 A1 | 7/2018 | Papadopoulos et al. |
| 2018/0187149 A1 | 7/2018 | Ma et al. |
| 2018/0187153 A1 | 7/2018 | Kahvejian et al. |
| 2018/0187154 A1 | 7/2018 | Kahvejian et al. |
| 2018/0192623 A1 | 7/2018 | Jishage et al. |
| 2018/0193479 A1 | 7/2018 | Williams et al. |
| 2018/0194831 A1 | 7/2018 | De Lorenzo et al. |
| 2018/0200366 A1 | 7/2018 | Wong et al. |
| 2018/0200378 A1 | 7/2018 | Bennett et al. |
| 2018/0201661 A1 | 7/2018 | O'Dwyer |
| 2018/0201677 A1 | 7/2018 | Grosveld et al. |
| 2018/0201901 A1 | 7/2018 | Duchateau et al. |
| 2018/0207267 A1 | 7/2018 | Schurpf et al. |
| 2018/0207273 A1 | 7/2018 | Dranoff et al. |
| 2018/0208636 A1 | 7/2018 | Lim et al. |
| 2018/0208659 A1 | 7/2018 | Fang et al. |
| 2018/0208897 A1 | 7/2018 | Kahvejian et al. |
| 2018/0208903 A1 | 7/2018 | Kotton et al. |
| 2018/0208943 A1 | 7/2018 | Schmidt |
| 2018/0209983 A1 | 7/2018 | Lafleur |
| 2018/0211447 A1 | 7/2018 | Spayd |
| 2018/0214524 A1 | 8/2018 | Weissman et al. |
| 2018/0214566 A1 | 8/2018 | Dodgson et al. |
| 2018/0214579 A1 | 8/2018 | Almarsson et al. |
| 2018/0216067 A1 | 8/2018 | Kahvejian et al. |
| 2018/0216073 A1 | 8/2018 | Reginald et al. |
| 2018/0216078 A1 | 8/2018 | Rossi et al. |
| 2018/0216162 A1 | 8/2018 | Belhocine et al. |
| 2018/0217131 A1 | 8/2018 | Yu |
| 2018/0221362 A1 | 8/2018 | Ghosh et al. |
| 2018/0221381 A1 | 8/2018 | Yen et al. |
| 2018/0221508 A1 | 8/2018 | Kadiyala et al. |
| 2018/0222944 A1 | 8/2018 | Glanville |
| 2018/0222982 A1 | 8/2018 | Dranoff et al. |
| 2018/0223256 A1 | 8/2018 | Kim |
| 2018/0224432 A1 | 8/2018 | Kerns et al. |
| 2018/0228786 A1 | 8/2018 | Sokolsky et al. |
| 2018/0228881 A1 | 8/2018 | Barreira Da Silva et al. |
| 2018/0228926 A1 | 8/2018 | Kelly et al. |
| 2018/0229241 A1 | 8/2018 | Bishop et al. |
| 2018/0230417 A1 | 8/2018 | Kerns et al. |
| 2018/0235894 A1 | 8/2018 | Gu et al. |
| 2018/0235897 A1 | 8/2018 | Gong et al. |
| 2018/0238884 A1 | 8/2018 | Bass et al. |
| 2018/0243311 A1 | 8/2018 | Lee et al. |
| 2018/0243341 A1 | 8/2018 | June et al. |
| 2018/0243426 A1 | 8/2018 | Ziv |
| 2018/0243444 A1 | 8/2018 | Pozuelo Rubio et al. |
| 2018/0244627 A1 | 8/2018 | Pan et al. |
| 2018/0244738 A1 | 8/2018 | Peng et al. |
| 2018/0244748 A1 | 8/2018 | Gill et al. |
| 2018/0246099 A1 | 8/2018 | Kotton et al. |
| 2018/0249688 A1 | 9/2018 | Ayares et al. |
| 2018/0249689 A1 | 9/2018 | Gurer et al. |
| 2018/0250339 A1 | 9/2018 | Gill et al. |
| 2018/0250395 A1 | 9/2018 | Pietsch et al. |
| 2018/0250405 A1 | 9/2018 | Biel et al. |
| 2018/0250418 A1 | 9/2018 | Afar et al. |
| 2018/0251460 A1 | 9/2018 | Aktoudianakis et al. |
| 2018/0251464 A1 | 9/2018 | Shi |
| 2018/0251521 A1 | 9/2018 | Lafleur et al. |
| 2018/0251533 A1 | 9/2018 | Hedrick et al. |
| 2018/0251558 A1 | 9/2018 | Maute et al. |
| 2018/0251563 A1 | 9/2018 | Lafleur et al. |
| 2018/0252727 A1 | 9/2018 | Garfall et al. |
| 2018/0256549 A1 | 9/2018 | Garner et al. |
| 2018/0256572 A1 | 9/2018 | Yates |
| 2018/0256624 A1 | 9/2018 | Pauza et al. |
| 2018/0256709 A1 | 9/2018 | Zepp et al. |
| 2018/0256742 A1 | 9/2018 | Poznansky |
| 2018/0256747 A1 | 9/2018 | Hawthorne et al. |
| 2018/0258149 A1 | 9/2018 | Motz et al. |
| 2018/0258158 A1 | 9/2018 | Krystek, Jr. et al. |
| 2018/0258186 A1 | 9/2018 | Bamdad et al. |
| 2018/0258411 A1 | 9/2018 | Kadiyala et al. |
| 2018/0258422 A1 | 9/2018 | Johnson et al. |
| 2018/0258484 A1 | 9/2018 | Gros |
| 2018/0263985 A1 | 9/2018 | Geleziunas et al. |
| 2018/0264094 A1 | 9/2018 | Lisziewicz et al. |
| 2018/0264095 A1 | 9/2018 | Lisziewicz et al. |
| 2018/0264186 A1 | 9/2018 | Van Bruggen et al. |
| 2018/0265530 A1 | 9/2018 | Lai et al. |
| 2018/0265847 A1 | 9/2018 | Kahvejian et al. |
| 2018/0267043 A1 | 9/2018 | Lopez-Girona et al. |
| 2018/0267516 A1 | 9/2018 | Fister et al. |
| 2018/0271795 A1 | 9/2018 | Martini et al. |
| 2018/0271870 A1 | 9/2018 | Khleif et al. |
| 2018/0271891 A1 | 9/2018 | Garraway et al. |
| 2018/0271910 A1 | 9/2018 | Mata-Fink et al. |
| 2018/0271970 A1 | 9/2018 | Ciaramella et al. |
| 2018/0271975 A1 | 9/2018 | Ciaramella et al. |
| 2018/0271992 A1 | 9/2018 | Cardillo et al. |
| 2018/0273519 A1 | 9/2018 | Wu et al. |
| 2018/0273531 A1 | 9/2018 | Kawasaki et al. |
| 2018/0273578 A1 | 9/2018 | Oost et al. |
| 2018/0273903 A1 | 9/2018 | Zhang et al. |
| 2018/0273948 A1 | 9/2018 | Kadiyala et al. |
| 2018/0273980 A1 | 9/2018 | Qi et al. |
| 2018/0274043 A1 | 9/2018 | Yu |
| 2018/0275143 A1 | 9/2018 | Wilcox et al. |
| 2018/0280451 A9 | 10/2018 | Falb et al. |
| 2018/0280502 A1 | 10/2018 | Lutteropp et al. |
| 2018/0280532 A1 | 10/2018 | Goldenberg |
| 2018/0280539 A1 | 10/2018 | Debs et al. |
| 2018/0282693 A1 | 10/2018 | June et al. |
| 2018/0282726 A1 | 10/2018 | Bertram et al. |
| 2018/0282803 A1 | 10/2018 | Belgrader et al. |
| 2018/0282808 A1 | 10/2018 | Milla et al. |

OTHER PUBLICATIONS

Ain, Qurrat Ul, Jee Young Chung, and Yong-Hee Kim. "Current and future delivery systems for engineered nucleases: ZFN, TALEN and RGEN." Journal of Controlled Release 205 (2015): 120-127.

Akhter, A., M.A. Gavrilin, L. Frantz, S. Washington, C. Ditty, D. Limoli, C. Day, A. Sarkar, C. Newland, J. Butchar, C.B. Marsh, M.D. Wewers, S. Tridandapani, T.D. Kanneganti, A.O. Amer, Caspase-7 activation by the Nlrc4/Ipaf inflammasome restricts Legionella pneumophila infection. PLoS Pathog. 5 (2009) e1000361.

Alvey, Cory, and Dennis E. Discher. "Engineering macrophages to eat cancer: from "marker of self" CD47 and phagocytosis to differentiation." Journal of leukocyte biology 102, No. 1 (2017): 31-40.

Anderson, A.C., N. Joller, and V.K. Kuchroo, Lag-3, Tim-3, and TIGIT: Co-inhibitory Receptors with Specialized Functions in Immune Regulation. Immunity, 2016. 44(5): p. 989-1004.

Ankarcrona, M., J.M. Dypbukt, E. Bonfoco, B. Zhivotovsky, S. Orrenius, S.A. Lipton, P. Nicotera, Glutamate-induced neuronal death: a succession of necrosis or apoptosis depending on mitochondrial function. Neuron 15 (1995) 961-973.

Baglole, Carolyn J., Denise M. Ray, Steven H. Bernstein, Steven E. Feldon, Terry J. Smith, Patricia J. Sime, and Richard P. Phipps.

(56) References Cited

OTHER PUBLICATIONS

"More than structural cells, fibroblasts create and orchestrate the tumor microenvironment." Immunological investigations 35, No. 3-4 (2006): 297-325.

Balachandran, S., E. Thomas, G.N. Barber, A FADD-dependent innate immune mechanism in mammalian cells. Nature 432 (2004) 401-405.

Barclay A.N. and Van den Berg T.K. 2014. The interaction between signal regulatory protein alpha (SIRP-α) and CD47: structure, function, and therapeutic target. Annu Rev Immunol. 32:25-50.

Bell, B.D., S. Leverrier, B.M. Weist, R.H. Newton, A.F. Arechiga, K.A. Luhrs, N.S. Morrissette, C.M. Walsh, FADD and caspase-8 control the outcome of autophagic signaling in proliferating T cells. Proc. Natl. Acad. Sci. U.S.A. 105 (2008) 16677-16682.

Benencia, F., et al., Dendritic cells the tumor microenvironment and the challenges for an effective antitumor vaccination. J Biomed Biotechnol, 2012. 2012: p. 425476.

Bergsbaken, T., S.L. Fink, B.T. Cookson, Pyroptosis: host cell death and inflammation. Nat. Rev. Microbiol. 7 (2009) 99-109.

Berry, D.L., E.H. Baehrecke, Growth arrest and autophagy are required for salivary gland cell degradation in *Drosophila*. Cell 131 (2007) 1137-1148.

Brennan, M.A., B.T. Cookson, *Salmonella* induces macrophage death by caspase-1-dependent necrosis. Mol. Microbiol. 38 (2000) 31-40.

Brightwell, R. M., K. S. Grzankowski, S. Lele, K. Eng, M. Arshad, H. Chen, and K. Odunsi. "The CD47 "don't eat me signal" is highly expressed in human ovarian cancer." Gynecologic oncology 143, No. 2 (2016): 393-397.

Bronte, V., et al., Recommendations for myeloid-derived suppressor cell nomenclature and characterization standards. Nat Commun, 2016. 7: p. 12150.

Bullock, T.N., TNF-receptor superfamily agonists as molecular adjuvants for cancer vaccines. Curr Opin Immunol, 2017. 47: p. 70-77.

Cannon, Martin J., and Timothy J. O'Brien. "Cellular immunotherapy for ovarian cancer." Expert opinion on biological therapy 9, No. 6 (2009): 677-688.

Carucci, John A. "Understanding dendritic cells and their role in cutaneous carcinoma and cancer immunotherapy." Clinical and Developmental Immunology 2013 (2013).

Chamuleau, M.E., G.J. Ossenkoppele, and A.A. van de Loosdrecht, MHC class II molecules in tumour immunology: prognostic marker and target for immune modulation. Immunobiology, 2006. 211(6-8): p. 619-25.

Chan, F.K., J. Shisler, J.G. Bixby, M. Felices, L. Zheng, M. Appel, J. Orenstein, B. Moss, M.J. Lenardo, A role for tumor necrosis factor receptor-2 and receptor-interacting protein in programmed necrosis and antiviral responses. J. Biol. Chem. 278 (2003) 51613-51621.

Chao MP, Jaiswal S, Weissman-Tsukamoto R, Alizadeh AA, Gentles AJ, Volkmer J, et al. Calreticulin is the dominant pro-phagocytic signal on multiple human cancers and is counterbalanced by CD47. Sci Transl Med. 2010;2:63-94.

Chao, M.P., I.L. Weissman, and R. Majeti, The CD47-SIRP-α pathway in cancer immune evasion and potential therapeutic implications. Curr Opin Immunol, 2012. 24(2): p. 225-32.

Chautan, M., G. Chazal, F. Cecconi, P. Gruss, P. Golstein, Interdigital cell death can occur through a necrotic and caspase-independent pathway. Curr. Biol. 9 (1999) 967-970.

Cheung, Alexander S., Sandeep T. Koshy, Alexander G. Stafford, Maartje MC Bastings, and David J. Mooney. "Adjuvant-Loaded Subcellular Vesicles Derived From Disrupted Cancer Cells for Cancer Vaccination." Small 12, No. 17 (2016): 2321-2333.

Chiang CL, Benencia F, Coukos G. Whole tumor antigen vaccines. Semin Immunol. 2010;22:132-43.

Cho, Y., S. Challa, D. Moquin, R. Genga, T.D. Ray, M. Guildford, F.K.-M. Chan, Phosphorylation-driven assembly of the RIP1-RIP3 complex regulates programmed necrosis and virus-induced inflammation. Cell 137 (2009) 1112-1123.

Choi P.S. and Meyerson M. 2014. Targeted genomic rearrangements using CRISPR/Cas technology. Nature Communications 5:3728. doi:10.1038/ncomms4728.

Cornelis, S., K. Kersse, N. Festjens, M. Lamkanfi, P. Vandenabeele, Inflammatory caspases: targets for novel therapies. Curr. Pharm. Des. 13 (2007) 367-385.

Curiel, Tyler J., et al. "Specific recruitment of regulatory T cells in ovarian carcinoma fosters immune privilege and predicts reduced survival." Nature medicine 10.9 (2004): 942-949. PubMed PMID: 15322536.

Curran, E., et al., STING Pathway Activation Stimulates Potent Immunity against Acute Myeloid Leukemia. Cell Rep, 2016. 15(11): p. 2357-66.

Curran, Emily, Leticia Corrales, and Justin Kline. "Targeting the innate immune system as immunotherapy for acute myeloid leukemia." Frontiers in oncology 5 (2015): 83.

Danial, Nika N., and Stanley J. Korsmeyer. "Cell death: critical control points." Cell 116, No. 2 (2004): 205-219.

De Gruijl TD, van den Eertwegh AJ, Pinedo HM, Scheper RJ. Whole-cell cancer vaccination: from autologous to allogeneic tumor- and dendritic cell-based vaccines. Cancer Immunol Immunother. 2008;57:1569-1577.

Degterev, A., J. Hitomi, M. Germscheid, I.L. Ch'en, O. Korkina, X. Teng, D. Abbott, G.D. Cuny, C. Yuan, G. Wagner, S.M. Hedrick, S.A. Gerber, A. Lugovskoy, J. Yuan, Identification of RIP1 kinase as a specific cellular target of necrostatins. Nat. Chem. Biol. 4 (2008) 313-321.

Degterev, A., Z. Huang, M. Boyce, Y. Li, P. Jagtap, N. Mizushima, G.D. Cuny, T.J. Mitchison, M.A. Moskowitz, J. Yuan, Chemical inhibitor of nonapoptotic cell death with therapeutic potential for ischemic brain injury. Nat. Chem. Biol. 1 (2005) 112-119.

Dhodapkar, Madhav V., and Kavita M. Dhodapkar. "Vaccines targeting cancer stem cells: are they within reach?." Cancer journal (Sudbury, Mass.) 17, No. 5 (2011): 397.

Dranoff, G., et al., Vaccination with irradiated tumor cells engineered to secrete murine granulocyte-macrophage colony-stimulating factor stimulates potent, specific, and long-lasting anti-tumor immunity. Proc Natl Acad Sci U S A, 1993. 90(8): p. 3539-43.

Dudek, A.M., et al., Immature, Semi-Mature, and Fully Mature Dendritic Cells: Toward a DC-Cancer Cells Interface That Augments Anticancer Immunity. Front Immunol, 2013. 4: p. 438.

Dunn, G.P., L.J. Old, and R.D. Schreiber, The immunobiology of cancer immunosurveillance and immunoediting. Immunity, 2004. 21(2): p. 137-48.

Dunn, Gavin P., et al. "Cancer immunoediting: from immunosurveillance to tumor escape." Nature immunology 3.11 (2002): 991-998. PubMed PMID: 12407406.

Duprez, L., E. Wirawan, T. Vanden Berghe, P. Vandenabeele, "Major cell death pathways at a glance", Microbes Infect., 11 (2009), pp. 1050-1062.

Earls JK, Jin S, Ye K. Mechanobiology of human pluripotent stem cells. Tissue Eng Part B Rev. 2013;19:420-30.

Eder, C., Mechanisms of interleukin-1beta release. Immunobiology (2009).

Eggermont, Alexander MM. "Cancer Immunotherapy 2017 (Paris, France). Progress and challenges."

Elliott, L.A., et al., Human Tumor-Infiltrating Myeloid Cells: Phenotypic and Functional Diversity. Front Immunol, 2017. 8: p. 86.

Elmore, Susan. "Apoptosis: a review of programmed cell death." Toxicologic pathology 35, No. 4 (2007): 495-516.

Espert, L., M. Denizot, M. Grimaldi, V. Robert-Hebmann, B. Gay, M. Varbanov, P. Codogno, M. Biard-Piechaczyk, Autophagy is involved in T cell death after binding of HIV-1 envelope proteins to CXCR4. J. Clin. Invest. 116 (2006) 2161-2172.

Eyileten, Ceren, Kinga Majchrzak, Zofia Pilch, Katarzyna Tonecka, Joanna Mucha, Bartlomiej Taciak, Katarzyna Ulewicz et al. "Immune cells in cancer therapy and drug delivery." Mediators of inflammation 2016 (2016).

Fadok, V.A., D.L. Bratton, L. Guthrie, P.M. Henson, Differential effects of apoptotic versus lysed cells on macrophage production of cytokines: role of proteases. J. Immunol. 166 (2001) 6847-6854.

Faherty, C.S., A.T. Maurelli, Staying alive: bacterial inhibition of apoptosis during infection. Trends Microbiol. 16 (2008) 173-180.

(56) References Cited

OTHER PUBLICATIONS

Fang, Ronnie H., Che-Ming J. Hu, Brian T. Luk, Weiwei Gao, Jonathan A. Copp, Yiyin Tai, Derek E. O'Connor, and Liangfang Zhang. "Cancer cell membrane-coated nanoparticles for anticancer vaccination and drug delivery." Nano letters 14, No. 4 (2014): 2181-2188.
Feng, Mingye, James Y. Chen, Rachel Weissman-Tsukamoto, Jens-Peter Volkmer, Po Yi Ho, Kelly M. McKenna, Samuel Cheshier et al. "Macrophages eat cancer cells using their own calreticulin as a guide: roles of TLR and Btk." Proceedings of the National Academy of Sciences 112, No. 7 (2015): 2145-2150.
Feng, S., Y. Yang, Y. Mei, L. Ma, D.E. Zhu, N. Hoti, M. Castanares, M. Wu, Cleavage of RIP3 inactivates its caspase-independent apoptosis pathway by removal of kinase domain. Cell. Signal. 19 (2007) 2056-2067.
Fernandes-Alnemri, T., J.W. Yu, P. Datta, J. Wu, E.S. Alnemri, AIM2 activates the inflammasome and cell death in response to cytoplasmic DNA. Nature 458 (2009) 509-513.
Festjens, N., T. Vanden Berghe, P. Vandenabeele, Necrosis, a well-orchestrated form of cell demise: signalling cascades, important mediators and concomitant immune response. Biochim. Biophys. Acta 1757 (2006) 1371-1387.
Festjens, N., T. Vanden Berghe, S. Cornelis, P. Vandenabeele, RIP1, a kinase on the crossroads of a cell's decision to live or die. Cell Death Differ. 14 (2007) 400-410.
Fink, S.L., B.T. Cookson, Caspase-1-dependent pore formation during pyroptosis leads to osmotic lysis of infected host macrophages. Cell Microbiol 8 (2006) 1812-1825.
Finn, Olivera J. "Cancer immunology." New England Journal of Medicine 358, No. 25 (2008): 2704-2715.
Fong, Lawrence, Yafei Hou, Alberto Rivas, Claudia Benike, Alan Yuen, George A. Fisher, Mark M. Davis, and Edgar G. Engleman. "Altered peptide ligand vaccination with Flt3 ligand expanded dendritic cells for tumor immunotherapy." Proceedings of the National Academy of Sciences 98, No. 15 (2001): 8809-8814.
Fuentes-Prior, P., G.S. Salvesen, The protein structures that shape caspase activity, specificity, activation and inhibition. Biochem. J. 384 (2004) 201-232.
Gaj, Thomas, Charles A. Gersbach, and Carlos F. Barbas III. "ZFN, TALEN, and CRISPR/Cas-based methods for genome engineering." Trends in biotechnology 31, No. 7 (2013): 397-405.
Galluzzi, L, M.C. Maiuri, I. Vitale, H. Zischka, M. Castedo, L. Zitvogel, G. Kroemer, Cell death modalities: classification and pathophysiological implications. Cell Death Differ. 14 (2007) 1237-1243.
Galluzzi, L., C. Brenner, E. Morselli, Z. Touat, G. Kroemer, Viral control of mitochondrial apoptosis. PLoS Pathog. 4 (2008) e1000018.
Galon, Jérôme, Denis Franchimont, Naoki Hiroi, Gregory Frey, Antje Boettner, Monika Ehrhart-Bornstein, John J. O'Shea, George P. Chrousos, And Stefan R. Bornstein. "Gene profiling reveals unknown enhancing and suppressive actions of glucocorticoids on immune cells." The FASEB journal 16, No. 1 (2002): 61-71.
Gameiro, Sofia R., Momodou L. Jammed, Max M. Wattenberg, Kwong Y. Tsang, Soldano Ferrone, and James W. Hodge. "Radiation-induced immunogenic modulation of tumor enhances antigen processing and calreticulin exposure, resulting in enhanced T-cell killing." Oncotarget 5, No. 2 (2014): 403.
Gao, Lu, Kexin Chen, Qi Gao, Xiaodan Wang, Jian Sun, Yong-Guang Yang, "CD47 deficiency in tumor stroma promotes tumor progression by enhancing angiogenesis", Oncotarget. 2017; 8:22406-22413. doi.org/10.18632/oncotarget.9899 (Jun. 7, 2016).
Garg, Abhishek D., Sanne Elsen, Dmitri V. Krysko, Peter Vandenabeele, Peter de Witte, and Patrizia Agostinis. "Resistance to anticancer vaccination effect is controlled by a cancer cell-autonomous phenotype that disrupts immunogenic phagocytic removal." Oncotarget 6, No. 29 (2015): 26841.
Geller, L.T., et al., Potential role of intratumor bacteria in mediating tumor resistance to the chemotherapeutic drug gemcitabine. Science, 2017. 357(6356): p. 1156-1160.

Gopalakrishnan, V., et al., Gut microbiome modulates response to anti-PD-1 immunotherapy in melanoma patients. Science, 2018. 359(6371): p. 97-103.
Gregoire, M., C. Ligeza-Poisson, N. Juge-Morineau, and R. Spisek. "Anti-cancer therapy using dendritic cells and apoptotic tumour cells: pre-clinical data in human mesothelioma and acute myeloid leukaemia." Vaccine 21, No. 7-8 (2003): 791-794.
Guillerey, C., N.D. Huntington, and M.J. Smyth, Targeting natural killer cells in cancer immunotherapy. Nat Immunol, 2016. 17(9): p. 1025-36.
Gul, N., et al., Macrophages eliminate circulating tumor cells after monoclonal antibody therapy. J Clin Invest, 2014. 124(2): p. 812-23.
Haining, W. Nicholas. "Abstract SY40-01: In vivo genetic screens for genes that modulate tumor immunity." (2018): SY40-01.
Halestrap, A.P., C.P. Connern, E.J. Griffiths, P.M. Kerr, Cyclosporin A binding to mitochondrial cyclophilin inhibits the permeability transition pore and protects hearts from ischaemia/reperfusion injury. Mol. Cell. Biochem. 174 (1997) 167-172.
Hannani, Dalil, Antonella Sistigu, Oliver Kepp, Lorenzo Galluzzi, Guido Kroemer, and Laurence Zitvogel. "Prerequisites for the antitumor vaccine-like effect of chemotherapy and radiotherapy." The Cancer Journal 17, No. 5 (2011): 351-358.
Hayday, A., F. Kyle, O. Nussbaumer, D. Enting, and M. L. Iannitto. "51: How T cells may distinguish stress from normality in an epithelium." European Journal of Cancer 50 (2014): S13.
He, S., L. Wang, L. Miao, T. Wang, F. Du, L. Zhao, X. Wang, Receptor interacting protein kinase-3 determines cellular necrotic response to TNF-alpha. Cell 137 (2009) 1100-1111.
He, X., et al., Antitumor efficacy induced by a B16F10 tumor cell vaccine treated with mitoxantrone alone or in combination with reserpine and verapamil in mice. Exp Ther Med, 2011. 2(5): p. 911-916.
Hellerstedt BA, Pienta KJ. The current state of hormonal therapy for prostate cancer. CA Cancer J Clin. 2002;52:154-79.
Helmy, Karim Y., Shyam A. Patel, George R. Nahas, and Pranela Rameshwar. "Cancer immunotherapy: accomplishments to date and future promise." Therapeutic delivery 4, No. 10 (2013): 1307-1320.
Herzog, Karl-Heinz, Miriam J. Chong, Manuela Kapsetaki, James I. Morgan, and Peter J. McKinnon. "Requirement for Atm in ionizing radiation-induced cell death in the developing central nervous system." Science 280, No. 5366 (1998): 1089-1091.
Hirohashi, Yoshihiko, Toshihiko Torigoe, Satoko Inoda, Akari Takahashi, Rena Morita, Satoshi Nishizawa, Yasuaki Tamura, Hiromu Suzuki, Minoru Toyota, and Noriyuki Sato. "Immune response against tumor antigens expressed on human cancer stem-like cells/tumor-initiating cells." Immunotherapy 2, No. 2 (2010): 201-211.
Holler, N., R. Zaru, O. Micheau, M. Thome, A. Attinger, S. Valitutti, J.L. Bodmer, P. Schneider, B. Seed, J. Tschopp, Fas triggers an alternative, caspase-8-independent cell death pathway using the kinase RIP as effector molecule. Nat. Immunol. 1 (2000) 489-495.
Inoda, Satoko, Yoshihiko Hirohashi, Toshihiko Torigoe, Rena Morita, Akari Takahashi, Hiroko Asanuma, Munehide Nakatsugawa et al. "Cytotoxic T lymphocytes efficiently recognize human colon cancer stem-like cells." The American journal of pathology 178, No. 4 (2011): 1805-1813.
Italiani, P. and D. Boraschi, From Monocytes to M1/M2 Macrophages: Phenotypical vs. Functional Differentiation. Front Immunol, 2014. 5: p. 514.
Jagtap, P., C. Szabo, Poly(ADP-ribose) polymerase and the therapeutic effects of its inhibitors. Nat. Rev. Drug Discov. 4 (2005) 421-440.
Jaiswal, Siddhartha, and Irving L. Weissman. "Hematopoietic stem and progenitor cells and the inflammatory response." Annals of the New York Academy of Sciences 1174, No. 1 (2009): 118-121.
Jayaraman, Subhadra, "Cancer and the Immune System: Deciphering the Relationship" (Mar. 14, 2017), blog.addgene.org/cancer-and-the-immune-system-deciphering-the-relationship.
Jin S, Ellis E, Veetil JV, Yao H, Ye K. Visualization of human immunodeficiency virus protease inhibition using a novel Forster resonance energy transfer molecular probe. Biotechnol Prog. 2011;27:1107-14.

(56) References Cited

OTHER PUBLICATIONS

Jin S, Veetil JV, Garrett JR, Ye K. Construction of a panel of glucose indicator proteins for continuous glucose monitoring. Biosens Bioelectron. 2011;26:3427-31.

Jin S, Yao H, Krisanarungson P, Haukas A, Ye K. Porous membrane substrates offer better niches to enhance the Wnt signaling and promote human embryonic stem cell growth and differentiation. Tissue Eng Part A. 2012;18:1419-30.

Jin, Sha, Huantong Yao, Jennifer L. Weber, Zara K. Melkoumian, and Kaiming Ye. "A synthetic, xeno-free peptide surface for expansion and directed differentiation of human induced pluripotent stem cells." PloS one 7, No. 11 (2012): e50880; Sha, Jin, Huantong Yao, Jennifer L. Weber, Zara K. Melkoumian, and Kaiming Ye. "Correction: A Synthetic, Xeno-Free Peptide Surface for Expansion and Directed Differentiation of Human Induced Pluripotent Stem Cells." PLoS One 8, No. 2 (2013).

Jin S, Ye K. Targeted drug delivery for breast cancer treatment. Recent Pat Anticancer Drug Discov. 2013;8:143-53.

Johnston, J.B., J.W. Barrett, S.H. Nazarian, M. Goodwin, D. Ricciuto, G. Wang, G. McFadden, A poxvirus-encoded pyrin domain protein interacts with ASC-1 to inhibit host inflammatory and apoptotic responses to infection. Immunity 23 (2005) 587-598.

Jones, K. R., L. W. Elmore, C. Jackson-Cook, G. Demasters, L. F. Povirk, S. E. Holt, and D. A. Gewirtz. "p53-Dependent accelerated senescence induced by ionizing radiation in breast tumour cells." International journal of radiation biology 81, No. 6 (2005): 445-458.

Joyce, Johanna A., and Douglas T. Fearon. "T cell exclusion, immune privilege, and the tumor microenvironment." Science348, No. 6230 (2015): 74-80.

Jung, C.H., C.B. Jun, S.H. Ro, Y.M. Kim, N.M. Otto, J. Cao, M. Kundu, D.H. Kim, ULK-Atg13-FIP200 complexes mediate mTOR signaling to the autophagy machinery. Mol. Biol. Cell 20 (2009) 1992-2003.

Kalai, M., G. Van Loo, T. Vanden Berghe, A. Meeus, W. Burm, X. Saelens, P. Vandenabeele, Tipping the balance between necrosis and apoptosis in human and murine cells treated with interferon and dsRNA. Cell Death Differ. 9 (2002) 981-994.

Kazemi, Tohid, Vahid Younesi, Farhad Jadidi-Niaragh, and Mehdi Yousefi. "Immunotherapeutic approaches for cancer therapy: an updated review." Artificial cells, nanomedicine, and biotechnology 44, No. 3 (2016): 769-779.

Keirsse, J., et al., Exploiting tumor-associated dendritic cell heterogeneity for novel cancer therapies. J Leukoc Biol, 2017. 102(2): p. 317-324.

Kennedy MK, Glaccum M, Brown SN, Butz EA, Viney JL, Embers M et al. Reversible defects in natural killer and memory CD8 T cell lineages in interleukin 15-deficient mice. J Exp Med 2000; 191: 771-780.

Kenneth C. Valkenburg and Bart O. Williams. 2011. Mouse models of prostate cancer. Prostate Cancer vol. 2011.

Kershaw MH and Smyth MJ. 2013. Making macrophages eat cancers. Immunology. Science. 341(6141):41-2.

Kershaw, Michael H., and Mark J. Smyth. "Making Macrophages Eat Cancer." Science 341, No. 6141 (2013): 41-42.

Kim, M.J., et al., Association of CD47 with natural killer cell-mediated cytotoxicity of head-and-neck squamous cell carcinoma lines. Tumour Biol, 2008. 29(1): p. 28-34.

Kleeff, Jorg, Murray Korc, Minoti Apte, Carlo La Vecchia, Colin D. Johnson, Andrew V. Biankin, Rachel E. Neale et al. "Pancreatic cancer." Nature reviews Disease primers 2 (2016): 16022.

Koh, Eunee, Yoosoo Yang, and In-San Kim, "Exosome-SIRP-α, a CD47 blockade increases cancer cell phagocytosis", ISEV2017 OT1.05 (May 15, 2017), www.rug.nl/research/portal/files/51552775/Abstract_Book_ISEV2017.pdf.

Koike, M., M. Shibata, M. Tadakoshi, K. Gotoh, M. Komatsu, S. Waguri, N. Kawahara, K. Kuida, S. Nagata, E. Kominami, K. Tanaka, Y. Uchiyama, Inhibition of autophagy prevents hippocampal pyramidal neuron death after hypoxic-ischemic injury. Am. J. Pathol. 172 (2008) 454-469.

Kooreman, N.G., et al., Autologous iPSC-Based Vaccines Elicit Anti-tumor Responses In Vivo. Cell Stem Cell, 2018. 22(4): p. 501-513 e7.

Kosta, A., C. Roisin-Bouffay, M.F. Luciani, G.P. Otto, R.H. Kessin, P. Golstein, Autophagy gene disruption reveals a non-vacuolar cell death pathway in Dictyostelium. J. Biol. Chem. 279 (2004) 48404-48409.

Kroemer, G., et al., Immunogenic cell death in cancer therapy. Annu Rev Immunol, 2013. 31: p. 51-72.

Kroemer, G., L. Galluzzi, C. Brenner, Mitochondrial membrane permeabilization in cell death. Physiol. Rev. 87 (2007) 99-163.

Kroemer, Guido, Laura Senovilla, Lorenzo Galluzzi, Fabrice André, and Laurence Zitvogel. "Natural and therapy-induced immunosurveillance in breast cancer." Nature medicine 21, No. 10 (2015): 1128.

Kroemer, Guido, Lorenzo Galluzzi, Oliver Kepp, and Laurence Zitvogel. "Immunogenic cell death in cancer therapy." Annual review of immunology 31 (2013): 51-72.

Kruger, C., T.F. Greten, and F. Korangy, Immune based therapies in cancer. Histol Histopathol, 2007. 22(6): p. 687-96.

Krysko, D.V., G. Brouckaert, M. Kalai, P. Vandenabeele, K. D'Herde, Mechanisms of internalization of apoptotic and necrotic L929 cells by a macrophage cell line studied by electron microscopy. J. Morphol. 258 (2003) 336-345.

Krysko, D.V., P. Vandenabeele, From regulation of dying cell engulfment to development of anti-cancer therapy. Cell Death Differ. 15 (2008) 29-38.

Kumai, T., et al., Cancer immunotherapy: moving forward with peptide T cell vaccines. Curr Opin Immunol, 2017. 47: p. 57-63.

Kumar, V., et al., The Nature of Myeloid-Derived Suppressor Cells in the Tumor Microenvironment. Trends Immunol, 2016. 37(3): p. 208-220.

Labbe, K., M. Saleh, Cell death in the host response to infection. Cell Death Differ. 15 (2008) 1339-1349.

LaCasse, E.C., D.J. Mahoney, H.H. Cheung, S. Plenchette, S. Baird, R.G. Korneluk, IAP-targeted therapies for cancer. Oncogene 27 (2008) 6252-6275.

Lamkanfi, M., T.D. Kanneganti, P. Van Damme, T. Vanden Berghe, I. Vanoverberghe, J. Vandekerckhove, P. Vandenabeele, K. Gevaert, G. Nunez, Targeted peptidecentric proteomics reveals caspase-7 as a substrate of the caspase-1 inflammasomes. Mol. Cell Proteomics 7 (2008) 2350-2363.

Lane-Reticker, Sarah K., Robert T. Manguso, and W. Nicholas Haining. "Pooled in vivo screens for cancer immunotherapy target discovery." (2018): 167-170.

Laporte, C., A. Kosta, G. Klein, L. Aubry, D. Lam, E. Tresse, M.F. Luciani, P. Golstein, A necrotic cell death model in a protist. Cell Death Differ. 14 (2007) 266-274.

Lara-Tejero, M., F.S. Sutterwala, Y. Ogura, E.P. Grant, J. Bertin, A.J. Coyle, R.A. Flavell, J.E. Galan, Role of the caspase-1 inflammasome in *Salmonella typhimurium* pathogenesis. J. Exp. Med. 203 (2006) 1407-1412.

Lau, Cia-Hin, and Yousin Suh. "In vivo genome editing in animals using AAV-CRISPR system: applications to translational research of human disease." F1000Research 6 (2017).

Lavender, Kerry J., Wendy W. Pang, Ronald J. Messer, Amanda K. Duley, Brent Race, Katie Phillips, Dana Scott et al. "BLT-humanized C57BL/6 Rag2-/-γc-/-CD47-/-mice are resistant to GVHD and develop B and T cell immunity to HIV infection." Blood (2013): blood-2013.

Lee, C.Y., E.H. Baehrecke, Steroid regulation of autophagic programmed cell death during development. Development 128 (2001) 1443-1455.

Lee, Daniel W., et al. "T cells expressing CD19 chimeric antigen receptors for acute lymphoblastic leukaemia in children and young adults: a phase 1 dose-escalation trial." The Lancet 385.9967 (2015): 517-528. PubMed PMID: 25319501.

Lee, S. and K. Margolin, Tumor-infiltrating lymphocytes in melanoma. Curr Oncol Rep, 2012. 14(5): p. 468-74.

Lehmann, B., et al., Tumor location determines tissue-specific recruitment of tumor-associated macrophages and antibody-dependent immunotherapy response. Sci Immunol, 2017. 2(7).

Li, P., H. Allen, S. Banerjee, S. Franklin, L. Herzog, C. Johnston, J. McDowell, M. Paskind, L. Rodman, J. Salfeld, et al., Mice deficient

(56) References Cited

OTHER PUBLICATIONS in IL-1 beta-converting enzyme are defective in production of mature IL-1 beta and resistant to endotoxic shock. Cell 80 (1995) 401-411.
Li, T., et al., Antitumor Activity of cGAMP via Stimulation of cGAS-cGAMP-STING-IRF3 Mediated Innate Immune Response. Sci Rep, 2016. 6: p. 19049.
Li, Ting, Bo Liu, Martin H. Spalding, Donald P. Weeks, and Bing Yang. "High-efficiency TALEN-based gene editing produces disease-resistant rice." Nature biotechnology 30, No. 5 (2012): 390.
Liang, Puping, Yanwen Xu, Xiya Zhang, Chenhui Ding, Rui Huang, Zhen Zhang, Jie Lv et al. "CRISPR/Cas9-mediated gene editing in human tripronuclear zygotes." Protein & cell 6, No. 5 (2015): 363-372.
Liang, Xudong. "Development of a novel breast cancer vaccine." PhD diss., State University of New York at Binghamton, 2015.
Lim, S.Y., S.M. Davidson, M.M. Mocanu, D.M. Yellon, C.C. Smith, The cardioprotective effect of necrostatin requires the cyclophilin-D component of the mitochondrial permeability transition pore. Cardiovasc Drugs Ther. 21 (2007) 467-469.
Lin, Y., A. Devin, Y. Rodriguez, Z.G. Liu, Cleavage of the death domain kinase RIP by caspase-8 prompts TNF-induced apoptosis. Genes Dev. 13 (1999) 2514-2526.
Lin, Y., S. Choksi, H.M. Shen, Q.F. Yang, G.M. Hur, Y.S. Kim, J.H. Tran, S.A. Nedospasov, Z.G. Liu, Tumor necrosis factor-induced nonapoptotic cell death requires receptor-interacting protein-mediated cellular reactive oxygen species accumulation. J. Biol. Chem. 279 (2004) 10822-10828.
Liu, Xiaojuan, Yang Pu, Kyle Cron, Liufu Deng, Justin Kline, William A. Frazier, Hairong Xu, Hua Peng, Yang-Xin Fu, and Meng Michelle Xu. "CD47 blockade triggers T cell-mediated destruction of immunogenic tumors." Nature medicine 21, No. 10 (2015): 1209.
Locher, Clara, Rosa Conforti, Laetitia Aymeric, Yuting Ma, Takahiro Yamazaki, Sylvie Rusakiewicz, Antoine Tesnière et al. "Desirable cell death during anticancer chemotherapy." Annals of the New York Academy of Sciences 1209, No. 1 (2010): 99-108.
Lombardo, Angelo, Pietro Genovese, Christian M. Beausejour, Silvia Colleoni, Ya-Li Lee, Kenneth A. Kim, Dale Ando et al. "Gene editing in human stem cells using zinc finger nucleases and integrase-defective lentiviral vector delivery." Nature biotechnology 25, No. 11 (2007): 1298.
Lowry, L.E. and W.A. Zehring, Potentiation of Natural Killer Cells for Cancer Immunotherapy: A Review of Literature. Front Immunol, 2017. 8: p. 1061.
Lum, J.J., D.E. Bauer, M. Kong, M.H. Harris, C. Li, T. Lindsten, C.B. Thompson, Growth factor regulation of autophagy and cell survival in the absence of apoptosis. Cell 120 (2005) 237-248.
Ma, Y., V. Temkin, H. Liu, R.M. Pope, NF-kappaB protects macrophages from lipopolysaccharide-induced cell death: the role of caspase 8 and receptor-interacting protein. J. Biol. Chem. 280 (2005) 41827-41834.
Ma, Yuting, Laetitia Aymeric, Clara Locher, Guido Kroemer, and Laurence Zitvogel. "The dendritic cell-tumor cross-talk in cancer." Current opinion in immunology 23, No. 1 (2011): 146-152.
Ma, Yuting, Oliver Kepp, François Ghiringhelli, Lionel Apetoh, Laetitia Aymeric, Clara Locher, Antoine Tesniere et al. "Chemotherapy and radiotherapy: cryptic anticancer vaccines." In Seminars in immunology, vol. 22, No. 3, pp. 113-124. Academic Press, 2010.
Mackall, Crystal L., Melinda S. Merchant, and Terry J. Fry. "Immune-based therapies for childhood cancer." Nature reviews Clinical oncology 11, No. 12 (2014): 693.
Maeng, H., M. Terabe, and J.A. Berzofsky, Cancer vaccines: translation from mice to human clinical trials. Curr Opin Immunol, 2018. 51: p. 111-122.
Maiuri, M.C., E. Zalckvar, A. Kimchi, G. Kroemer, Self-eating and self-killing: crosstalk between autophagy and apoptosis. Nat. Rev. Mol. Cell Biol. 8 (2007) 741-752.
Majeti, R., Chao, M.P., Alizadeh, A.A., Pang, W.W., Jaiswal, S., Gibbs, K.D. Jr, van Rooijen, N., and Weissman, I.L. 2009. CD47 is an adverse prognostic factor and therapeutic antibody target on human acute myeloid leukemia stem cells. Cell 138, 286-299.
Manguso, Robert T., Hans W. Pope, Margaret D. Zimmer, Flavian D. Brown, Kathleen B. Yates, Brian C. Miller, Natalie B. Collins et al. "In vivo CRISPR screening identifies Ptpn2 as a cancer immunotherapy target." Nature 547, No. 7664 (2017): 413.
Manguso, Robert T., Hans W. Pope, Margaret D. Zimmer, Flavian D. Brown, Kathleen B. Yates, Brian C. Miller, Natalie B. Collins et al. "In vivo CRISPR screening identifies Ptpn2 as a target for cancer immunotherapy." Cancer Research AACR (2017): Abstract 1019.
Marcucci, Fabrizio, Cristiano Rumio, Angelo Corti, "Tumor cell-associated immune checkpoint molecules—Drivers of malignancy and stemness", Biochimica et Biophysica Acta (BBA)—Reviews on Cancer, vol. 1868, Issue 2, Dec. 2017, pp. 571-583.
Marguet, D., M.F. Luciani, A. Moynault, P. Williamson, G. Chimini, Engulfment of apoptotic cells involves the redistribution of membrane phosphatidylserine on phagocyte and prey. Nat Cell Biol 1 (1999) 454-456.
Matsui, Y., H. Takagi, X. Qu, M. Abdellatif, H. Sakoda, T. Asano, B. Levine, J. Sadoshima, Distinct roles of autophagy in the heart during ischemia and reperfusion: roles of AMP-activated protein kinase and Beclin 1 in mediating autophagy. Circ. Res. 100 (2007) 914-922.
McCracken, Melissa N., Adriel C. Cha, and Irving L. Weissman. "Molecular pathways: activating T cells after cancer cell phagocytosis from blockade of CD47 "Don't eat me" signals." Clinical cancer research (2015): clincanres-2520.
McKenna, E., et al., Persistent DNA damage caused by low levels of mitomycin C induces irreversible cell senescence. Cell Cycle, 2012. 11(16): p. 3132-40.
Melssen, M. and C.L. Slingluff, Jr., Vaccines targeting helper T cells for cancer immunotherapy. Curr Opin Immunol, 2017. 47: p. 85-92.
Ménard, Cédric, François Martin, Lionel Apetoh, Florence Bouyer, and François Ghiringhelli. "Cancer chemotherapy: not only a direct cytotoxic effect, but also an adjuvant for antitumor immunity." Cancer Immunology, Immunotherapy 57, No. 11 (2008): 1579-1587.
Merad, M., et al., The dendritic cell lineage: ontogeny and function of dendritic cells and their subsets in the steady state and the inflamed setting. Annu Rev Immunol, 2013. 31: p. 563-604.
Merritt, Anita J., Terence D. Allen, Christopher S. Potten, and John A. Hickman. "Apoptosis in small intestinal epithelia from p53-null mice: evidence for a delayed, p53-independent G2/M-associated cell death after y-irradiation." Oncogene 14, No. 23 (1997): 2759.
Michallet, M.C., E. Meylan, M.A. Ermolaeva, J. Vazquez, M. Rebsamen, J. Curran, H. Poeck, M. Bscheider, G. Hartmann, M. Konig, U. Kalinke, M. Pasparakis, J. Tschopp, TRADD protein is an essential component of the RIG-like helicase antiviral pathway. Immunity 28 (2008) 651-661.
Mittal, Deepak, Matthew M. Gubin, Robert D. Schreiber, and Mark J. Smyth. "New insights into cancer immunoediting and its three component phases—elimination, equilibrium and escape." Current opinion in immunology 27 (2014): 16-25.
Mizushima, N., A. Kuma, Y. Kobayashi, A. Yamamoto, M. Matsubae, T. Takao, T. Natsume, Y. Ohsumi, T. Yoshimori, Mouse Apg16L, a novel WD-repeat protein, targets to the autophagic isolation membrane with the Apg12-Apg5 conjugate. J. Cell Sci. 116 (2003) 1679-1688.
Morris JC, et al. 2014. Vaccination with tumor cells expressing IL-15 and IL-15Rα inhibits murine breast and prostate cancer. Gene Therapy. 21: 393-401.
Movahedi, K., et al., Different tumor microenvironments contain functionally distinct subsets of macrophages derived from Ly6C(high) monocytes. Cancer Res, 2010. 70(14): p. 5728-39.
Munn, D.H. and V. Bronte, Immune suppressive mechanisms in the tumor microenvironment. Curr Opin Immunol, 2016. 39: p. 1-6.
Muranen, Taru, and Joan S. Brugge. "Moving Closer To Victory." In Cold Spring Harbor symposia on quantitative biology, vol. 81, pp. 281-288. Cold Spring Harbor Laboratory Press, 2016.
Muthna, Darina, Tomas Soukup, Jirina Vavrova, Jaroslav Mokry, Jana Cmielova, Benjamin Visek, Alena Jiroutova et al. "Irradiation of adult human dental pulp stem cells provokes activation of p53,

(56) References Cited

OTHER PUBLICATIONS cell cycle arrest, and senescence but not apoptosis." Stem cells and development 19, No. 12 (2010): 1855-1862.
Naiyer A. Rizvi, 2*† Matthew D. Hellmann, 1,2* Alexandra Snyder, 1,2,3* Pia Kvistborg,4, et al., Mutational landscape determines sensitivity to PD-1 blockade in non-small cell lung cancer. Cancer Immunology, 2015. vol. 34(8 Issue 6230): p. 124-128.
Nakagawa, T., S. Shimizu, T. Watanabe, O. Yamaguchi, K. Otsu, H. Yamagata, H. Inohara, T. Kubo, Y. Tsujimoto, Cyclophilin D-dependent mitochondrial permeability transition regulates some necrotic but not apoptotic cell death. Nature 434 (2005) 652-658.
Naujokat, Cord. "Monoclonal antibodies against human cancer stem cells." Immunotherapy 6, No. 3 (2014): 290-308.
Neagu, Martha R., Maria Carmela Speranza, Robert T. Manguso, Sean E. Lawler, Gordon J. Freeman, John Doench, Arlene H. Sharpe, and W. Nicholas Haining. "Immu-28. Defining Molecular Mechanisms Of Resistance To Glioblastoma (gbm) Immunity Using A Novel Crispr/cas9 In Vivo Loss-of-function Screening Platform." Neuro-oncology 19, No. suppl_6 (2017): vi118-vi118.
Neagu, Martha R., Robert T. Manguso, Hans Pope, Maria C. Speranza, Gordon J. Freeman, John Doench, Arlene H. Sharpe, and William Nicholas Haining. "Defining molecular mechanisms of resistance to glioblastoma immunity using a novel CRISPR/Cas9 in vivo loss-of-function screening platform." (2017): 417-417.
Neumar, R.W., Molecular mechanisms of ischemic neuronal injury. Ann. Emerg. Med. 36 (2000) 483-506.
Ngo, M., et al., Antibody Therapy Targeting CD47 and CD271 Effectively Suppresses Melanoma Metastasis in Patient-Derived Xenografts. Cell Rep, 2016. 16(6): p. 1701-1716.
Nilsson, A. and P.A. Oldenborg, CD47 promotes both phosphatidylserine-independent and phosphatidylserine-dependent phagocytosis of apoptotic murine thymocytes by non-activated macrophages. Biochem Biophys Res Commun, 2009. 387(1): p. 58-63.
Obeid, Michel, Antoine Tesniere, François Ghiringhelli, Gian Maria Fimia, Lionel Apetoh, Jean-Luc Perfettini, Maria Castedo et al. "Calreticulin exposure dictates the immunogenicity of cancer cell death." Nature medicine 13, No. 1 (2007): 54.
Oldenborg PA, Zhelznyak A, Fang YF, Lagenaur CF, Gresham HD, Lindberg FP. Role of CD47 as a marker of self on red blood cells. Science. 2000;288:2051-4.
Ostrand-Rosenberg, S. and P. Sinha, Myeloid-derived suppressor cells: linking inflammation and cancer. J Immunol, 2009. 182(8): p. 4499-506.
Ott, P.A., et al., An immunogenic personal neoantigen vaccine for patients with melanoma. Nature, 2017. 547(7662): p. 217-221.
Overwijk, W.W. and N.P. Restifo, B16 as a mouse model for human melanoma. Curr Protoc Immunol, 2001. Chapter 20: p. Unit 20 1.
Overwijk, W.W., Cancer vaccines in the era of checkpoint blockade: the magic is in the adjuvant. Curr Opin Immunol, 2017. 47: p. 103-109.
Pachynski, R.K., et al., Evaluation of Tumor-infiltrating Leukocyte Subsets in a Subcutaneous Tumor Model. J Vis Exp, 2015(98).
Palucka, Karolina, and Jacques Banchereau. "Cancer immunotherapy via dendritic cells." Nature Reviews Cancer 12.4 (2012): 265-277. PubMed PMID: 22437871. PubMed Central PMCID: PMC3433802.
Parajuli, N., et al., Infiltrating CD11b+CD11c+ cells have the potential to mediate inducible nitric oxide synthase-dependent cell death in mammary carcinomas of HER-2/neu transgenic mice. Int J Cancer, 2010. 126(4): p. 896-908.
Pattingre, S., A. Tassa, X. Qu, R. Garuti, X.H. Liang, N. Mizushima, M. Packer, M.D. Schneider, B. Levine, Bcl-2 antiapoptotic proteins inhibit Beclin 1-dependent autophagy. Cell 122 (2005) 927-939.
Pattingre, S., L. Espert, M. Biard-Piechaczyk, P. Codogno, Regulation of macroautophagy by mTOR and Beclin 1 complexes. Biochimie 90 (2008) 313-323.
Peinado, Héctor, Haiying Zhang, Irina R. Matei, Bruno Costa-Silva, Ayuko Hoshino, Goncalo Rodrigues, Bethan Psaila et al. "Premetastatic niches: organ-specific homes for metastases." Nature Reviews Cancer 17, No. 5 (2017): 302.
Penaloza, C., L. Lin, R.A. Lockshin, Z. Zakeri, Cell death in development: shaping the embryo. Histochem. Cell Biol. 126 (2006) 149-158.
Peter, M.E., P.H. Krammer, The CD95(APO-1/Fas) DISC and beyond. Cell Death Differ. 10 (2003) 26-35.
Pobezinskaya, Y.L., Y.S. Kim, S. Choksi, M.J. Morgan, T. Li, C. Liu, Z. Liu, The function of TRADD in signaling through tumor necrosis factor receptor 1 and TRIF-dependent toll-like receptors. Nat. Immunol. 9 (2008) 1047-1054.
Portt, Liam, Grant Norman, Caitlin Clapp, Matthew Greenwood, and Michael T. Greenwood. "Anti-apoptosis and cell survival: a review." Biochimica et Biophysica Acta (BBA)-Molecular Cell Research 1813, No. 1 (2011): 238-259. www.sciencedirect.com/science/article/pii/S0167488910002764.
Pulendran B, Dillon S, Joseph C, Curiel T, Banchereau J, Mohamadzadeh M. Dendritic cells generated in the presence of GM-CSF plus IL-15 prime potent CD8+ Tc1 responses in vivo. Eur J Immunol 2004; 34: 66-73.
Qu, X., Z. Zou, Q. Sun, K. Luby-Phelps, P. Cheng, R.N. Hogan, C. Gilpin, B. Levine, Autophagy gene-dependent clearance of apoptotic cells during embryonic development. Cell 128 (2007) 931-946.
Reed, John C. "Bcl-2 and the regulation of programmed cell death." The Journal of cell biology 124, No. 1-2 (1994): 1-6.
Richards, D.M., J. Hettinger, and M. Feuerer, Monocytes and macrophages in cancer: development and functions. Cancer Microenviron, 2013. 6(2): p. 179-91.
Riedl, S.J., G.S. Salvesen, The apoptosome: signalling platform of cell death. Nat. Rev. Mol. Cell Biol. 8 (2007) 405-413.
Roh, D.S., et al., DNA cross-linking, double-strand breaks, and apoptosis in corneal endothelial cells after a single exposure to mitomycin C. Invest Ophthalmol Vis Sci, 2008. 49(11): p. 4837-43.
Roisin-Bouffay, C., M.F. Luciani, G. Klein, J.P. Levraud, M. Adam, P. Golstein, Developmental cell death in dictyostelium does not require paracaspase. J. Biol. Chem. 279 (2004) 11489-11494.
Roy, A., et al., Increased efficiency of gamma-irradiated versus mitomycin C-treated feeder cells for the expansion of normal human cells in long-term cultures. J Hematother Stem Cell Res, 2001. 10(6): p. 873-80.
Sahin, U., et al., Personalized RNA mutanome vaccines mobilize poly-specific therapeutic immunity against cancer. Nature, 2017. 547(7662): p. 222-226.
Sallets, Adrienne, Sophie Robinson, Adel Kardosh, and Ronald Levy. "Enhancing immunotherapy of STING agonist for lymphoma in preclinical models." Blood advances 2, No. 17 (2018): 2230-2241.
Salvesen, G.S., S.J. Riedl, Caspase mechanisms. Adv. Exp. Med. Biol. 615 (2008) 13-23.
Sarkar, A., M.W. Hall, M. Exline, J. Hart, N. Knatz, N.T. Gatson, M.D. Wewers, Caspase-1 regulates *Escherichia coli* sepsis and splenic B cell apoptosis independently of interleukin-1beta and interleukin-18. Am. J. Respir. Crit. Care Med. 174 (2006) 1003-1010.
Saxena, Mansi, Sreekumar Balan, Vladimir Roudko, and Nina Bhardwaj. "Towards superior dendritic-cell vaccines for cancer therapy." Nat. Biomed. Eng. 2 (2018): 341-346.
Scarlatti, F., R. Granata, A.J. Meijer, P. Codogno, Does autophagy have a license to kill mammalian cells? Cell Death Differ. 16 (2009) 12-20.
Scarlett, U.K., et al., Ovarian cancer progression is controlled by phenotypic changes in dendritic cells. J Exp Med, 2012. 209(3): p. 495-506.
Schanne, F. A., Agnes B. Kane, Ellora E. Young, and John L. Farber. "Calcium dependence of toxic cell death: a final common pathway." Science 206, No. 4419 (1979): 700-702.
Scheffer, S.R., et al., Apoptotic, but not necrotic, tumor cell vaccines induce a potent immune response in vivo. Int J Cancer, 2003. 103(2): p. 205-11.
Schroder, K., D.A. Muruve, J. Tschopp, Innate immunity: cytoplasmic DNA sensing by the AIM2 inflammasome. Curr. Biol. 19 (2009) R262-265.
Scott, Andrew M., Jedd D. Wolchok, and Lloyd J. Old. "Antibody therapy of cancer." Nature Reviews Cancer 12.4 (2012): 278-287. PubMed PMID: 22437872.

(56) References Cited

OTHER PUBLICATIONS

Shao, W., G. Yeretssian, K. Doiron, S.N. Hussain, M. Saleh, The caspase-1 digestome identifies the glycolysis pathway as a target during infection and septic shock. J. Biol. Chem. 282 (2007) 36321-36329.
Sharma, Padmanee, Siwen Hu-Lieskovan, Jennifer A. Wargo, and Antoni Ribas. "Primary, adaptive, and acquired resistance to cancer immunotherapy." Cell 168, No. 4 (2017): 707-723.
Shen, Bin, Jun Zhang, Hongya Wu, Jianying Wang, Ke Ma, Zheng Li, Xueguang Zhang, Pumin Zhang, and Xingxu Huang. "Generation of gene-modified mice via Cas9/RNA-mediated gene targeting." Cell research 23, No. 5 (2013): 720.
Shiao, Stephen L., A. Preethi Ganesan, Hope S. Rugo, and Lisa M. Coussens. "Immune microenvironments in solid tumors: new targets for therapy." Genes & development 25, No. 24 (2011): 2559-2572.
Sick, E., et al., CD47 update: a multifaceted actor in the tumour microenvironment of potential therapeutic interest. Br J Pharmacol, 2012. 167(7): p. 1415-30.
Smyth, Mark J., Shin Foong Ngiow, Antoni Ribas, and Michele WL Teng. "Combination cancer immunotherapies tailored to the tumour microenvironment." Nature reviews Clinical oncology 13, No. 3 (2016): 143.
Sockolosky, J.T., et al., Durable antitumor responses to CD47 blockade require adaptive immune stimulation. Proc Natl Acad Sci U S A, 2016. 113(19): p. E2646-54.
Sofia R. Gameiro, J.A.C., Jack P. Higgins, David Apelian, James W. Hodge, Exploitation of differential homeostatic proliferation of T-cell subsets following chemotherapy to enhance the efficacy of vaccine-mediated antitumor responses. Cancer Immunol Immunother, 2011.
Sofia R. Gameiro1, M.L.J., Max M. Wattenberg1, Kwong Y. Tsang1, and a.J.W.H. Soldano Ferrone, Radiation-induced immunogenic modulation of tumor enhances antigen processing and calreticulin exposure, resulting in enhanced T-cell killing. Oncotarget, 2013. 5.
Sokolowska, O. and D. Nowis, STING Signaling in Cancer Cells: Important or Not? Arch Immunol Ther Exp (Warsz), 2018. 66(2): p. 125-132.
Song, Jun, Dongshan Yang, Jie Xu, Tianqing Zhu, Y. Eugene Chen, and Jifeng Zhang. "RS-1 enhances CRISPR/Cas9-and TALEN-mediated knock-in efficiency." Nature communications 7 (2016): 10548.
Soto-Pantoja, D.R., et al., CD47 in the tumor microenvironment limits cooperation between antitumor T-cell immunity and radiotherapy. Cancer Res, 2014. 74(23): p. 6771-83.
Stanton, S.E. and M.L. Disis, Designing vaccines to prevent breast cancer recurrence or invasive disease. Immunotherapy, 2015. 7(2): p. 69-72.
Steinman, Ralph M., and Madhav Dhodapkar. "Active immunization against cancer with dendritic cells: the near future." International journal of cancer 94, No. 4 (2001): 459-473.
Strozyk, Elwira, and Dagmar Kulms. "The role of AKT/mTOR pathway in stress response to UV-irradiation: implication in skin carcinogenesis by regulation of apoptosis, autophagy and senescence." International journal of molecular sciences 14, No. 8 (2013): 15260-15285.
Suzuki, Yasuyuki, Yuzuru Imai, Hiroshi Nakayama, Kazuko Takahashi, Koji Takio, and Ryosuke Takahashi. "A serine protease, HtrA2, is released from the mitochondria and interacts with XIAP, inducing cell death." Molecular cell 8, No. 3 (2001): 613-621.
Syn, Nicholas L., Lingzhi Wang, Edward Kai-Hua Chow, Chwee Teck Lim, and Boon-Cher Goh. "Exosomes in cancer nanomedicine and immunotherapy: prospects and challenges." Trends in biotechnology 35, No. 7 (2017): 665-676.
Tebas, Pablo, David Stein, Winson W. Tang, Ian Frank, Shelley Q. Wang, Gary Lee, S. Kaye Spratt et al. "Gene editing of CCR5 in autologous CD4 T cells of persons infected with HIV." New England Journal of Medicine 370, No. 10 (2014): 901-910.
Terness, P., et al., Mitomycin C-treated dendritic cells inactivate autoreactive T cells: toward the development of a tolerogenic vaccine in autoimmune diseases. Proc Natl Acad Sci U S A, 2008. 105(47): p. 18442-7.
Thibodeaux, Suzanne R., and Tyler J. Curiel. "Immune therapy for ovarian cancer: promise and pitfalls." International reviews of immunology 30, No. 2-3 (2011): 102-119.
Thyss, Raphael, Virginie Virolle, Véronique Imbert, Jean-François Peyron, Daniel Aberdam, and Thierry Virolle. "NF-κB/Egr-1/Gadd45 are sequentially activated upon UVB irradiation to mediate epidermal cell death." The EMBO journal 24, No. 1 (2005): 128-137.
Tran Janco, J.M., et al., Tumor-infiltrating dendritic cells in cancer pathogenesis. J Immunol, 2015. 194(7): p. 2985-91.
Tseng, Diane, Jens-Peter Volkmer, Stephen B. Willingham, Humberto Contreras-Trujillo, John W. Fathman, Nathaniel B. Fernhoff, Jun Seita et al. "Anti-CD47 antibody-mediated phagocytosis of cancer by macrophages primes an effective antitumor T-cell response." Proceedings of the National Academy of Sciences 110, No. 27 (2013): 11103-11108.
Turnis, Meghan E., and Cliona M. Rooney. "Enhancement of dendritic cells as vaccines for cancer." Immunotherapy 2, No. 6 (2010): 847-862.
Valkenburg KC, Williams BO. Mouse models of prostate cancer. Prostate Cancer. 2011;2011:895238.
Van Noorden, C.J., The history of Z-VAD-FMK, a tool for understanding the significance of caspase inhibition. Acta Histochem. 103 (2001) 241-251.
Vanden Berghe, T., M. Kalai, G. Denecker, A. Meeus, X. Saelens, P. Vandenabeele, Necrosis is associated with IL-6 production but apoptosis is not. Cell. Signal. 18 (2006) 328-335.
Vandenabeele, P., T. Vanden Berghe, N. Festjens, Caspase inhibitors promote alternative cell death pathways 2006. Sci. STKE (2006) e44.
Vanlangenakker, N., T.V. Berghe, D.V. Krysko, N. Festjens, P. Vandenabeele, Molecular mechanisms and pathophysiology of necrotic cell death. Curr Mol Med 8 (2008) 207-220.
Veetil JV, Jin S, Ye K. A glucose sensor protein for continuous glucose monitoring. Biosens Bioelectron. 2010;26:1650-5.
Veetil JV, Jin S, Ye K. Fluorescence lifetime imaging microscopy of intracellular glucose dynamics. J Diabetes Sci Technol. 2012;6:1276-85.
Vermeer, Daniel W., William C. Spanos, Paola D. Vermeer, Annie M. Bruns, Kimberly M. Lee, and John H. Lee. "Radiation-induced loss of cell surface CD47 enhances immune-mediated clearance of human papillomavirus-positive cancer." International journal of cancer 133, No. 1 (2013): 120-129.
Villanueva, M. Teresa. "Cancer immunotherapy: Searching in the immune checkpoint black box." Nature Reviews Drug Discovery 16, No. 9 (2017): 599.
Vinay, Dass S., et al. "Immune evasion in cancer: Mechanistic basis and therapeutic strategies." Seminars in cancer biology. vol. 35, p. S185-S198. Academic Press, 2015. PubMed PMID: 25818339.
Voisine, Richard, Louis-P. Vézina, and Claude Willemot. "Induction of senescence-like deterioration of microsomal membranes from cauliflower by free radicals generated during gamma irradiation." Plant physiology 97, No. 2 (1991): 545-550.
Volkmer, A. K., S. B. Willingham, S. R. Tseng, P. Y. Ho, J. P. Volkmer, B. I. Sikic, R. Majeti, and I. L. Weissman. "50: Proffered Paper: Overcoming immune evasion in ovarian and breast cancer with anti-CD47 antibody blockade: A novel class of immune therapy." European Journal of Cancer 50 (2014): S13.
Von Roemeling, Christina, Wen Jiang, Charles K. Chan, Irving L. Weissman, and Betty YS Kim. "Breaking down the barriers to precision cancer nanomedicine." Trends in biotechnology 35, No. 2 (2017): 159-171.
Waldman, Todd, Yonggang Zhang, Larry Dillehay, Jian Yu, Kenneth Kinzler, Bert Vogelstein, and Jerry Williams. "Cell-cycle arrest versus cell death in cancer therapy." Nature medicine 3, No. 9 (1997): 1034.

(56) References Cited

OTHER PUBLICATIONS

Wang Y, Xu Z, Guo S, Zhang L, Sharma A, Robertson GP, et al. Intravenous delivery of siRNA targeting CD47 effectively inhibits melanoma tumor growth and lung metastasis. Mol Ther. 2013;21:1919-29.
Wang, L., F. Du, X. Wang, TNF-alpha induces two distinct caspase-8 activation pathways. Cell 133 (2008) 693-703.
Wei, Chuanxian, Jiyong Liu, Zhongsheng Yu, Bo Zhang, Guanjun Gao, and Renjie Jiao. "TALEN or Cas9-rapid, efficient and specific choices for genome modifications." Journal of Genetics and Genomics 40, No. 6 (2013): 281-289.
Wei, Y., S. Pattingre, S. Sinha, M. Bassik, B. Levine, JNK1-mediated phosphorylation of Bcl-2 regulates starvation-induced autophagy. Mol. Cells 30 (2008) 678-688.
Weiner, George J. "Building better monoclonal antibody-based therapeutics." Nature Reviews Cancer 15.6 (2015): 361-370. PubMed PMID: 25998715. PubMed Central PMCID: PMC4491443.
Weiskopf K, Ring AM, Ho CC, Volkmer JP, Levin AM, Volkmer AK, et al. Engineered SIRPα variants as immunotherapeutic adjuvants to anticancer antibodies. Science. 2013;341:88-91.
Weiskopf, K., et al., CD47-blocking immunotherapies stimulate macrophage-mediated destruction of small-cell lung cancer. J Clin Invest, 2016. 126(7): p. 2610-20.
Weiskopf, K., et al., Engineered SIRP-α variants as immunotherapeutic adjuvants to anticancer antibodies. Science, 2013. 341(6141): p. 88-91.
Weiskopf, Kipp. "Cancer immunotherapy targeting the CD47/SIRP-α axis." European Journal of Cancer 76 (2017): 100-109.
Wherry, E.J. and M. Kurachi, Molecular and cellular insights into T cell exhaustion. Nat Rev Immunol, 2015. 15(8): p. 486-99.
Wiemann, S., A. Bott, I. Keklikoglou, C. Giacomelli, A. Balwierz, S. Uhlmann, H. Mannsperger, U. Korf, and C. Breunig. "53: miRNA-protein interaction networks in cancer." European Journal of Cancer 50 (2014): S13.
Willingham, S.B., D.T. Bergstralh, W. O'Connor, A.C. Morrison, D.J. Taxman, J.A. Duncan, S. Barnoy, M.M. Venkatesan, R.A. Flavell, M. Deshmukh, H.M. Hoffman, J.P. Ting, Microbial pathogen-induced necrotic cell death mediated by the inflammasome components CIAS1/cryopyrin/NLRP3 and ASC. Cell Host Microbe. 2 (2007) 147-159.
Willingham, Stephen B., Jens-Peter Volkmer, Andrew J. Gentles, Debashis Sahoo, Piero Dalerba, Siddhartha S. Mitra, Jian Wang et al. "The CD47-signal regulatory protein alpha (SIRP-α) interaction is a therapeutic target for human solid tumors." Proceedings of the National Academy of Sciences 109, No. 17 (2012): 6662-6667.
Wilson, N.S., V. Dixit, A. Ashkenazi, Death receptor signal transducers: nodes of coordination in immune signaling networks. Nat. Immunol. 10 (2009) 348-355.
Wilt TJ, MacDonald R, Rutks I, Shamliyan TA, Taylor BC, Kane RL. Systematic review: comparative effectiveness and harms of treatments for clinically localized prostate cancer. Ann Intern Med. 2008; 148:435-48.
Wlaschek, Meinhard, Wenjian Ma, Pidder Jansen-Dürr, and Karin Scharffetter-Kochanek. "Photoaging as a consequence of natural and therapeutic ultraviolet irradiation—studies on PUVA-induced senescence-like growth arrest of human dermal fibroblasts." Experimental gerontology 38, No. 11-12 (2003): 1265-1270.
Wong, Karrie K., WeiWei Aileen Li, David J. Mooney, and Glenn Dranoff. "Advances in therapeutic cancer vaccines." In Advances in immunology, vol. 130, pp. 191-249. Academic Press, 2016.
Wu, Y.T. H.L. Tan, Q. Huang, Y.S. Kim, N. Pan, W.Y. Ong, Z.G. Liu, C. N. Ong, H.M. Shen, Autophagy plays a protective role during zVAD-induced necrotic cell death. Autophagy 4 (2008) 457-466.
Wyllie, Andrew H. "Cell death." In Cytology and Cell Physiology (Fourth Edition), pp. 755-785. 1987.
Xie, Yu-Qing, Lixia Wei, and Li Tang. "Immunoengineering with biomaterials for enhanced cancer immunotherapy." Wiley Interdisciplinary Reviews: Nanomedicine and Nanobiotechnology (2018): e1506.
Xie, Z., D.J. Klionsky, Autophagosome formation: core machinery and adaptations. Nat. Cell Biol. 9 (2007) 1102-1109.
Xu, Y., S. Huang, Z.G. Liu, J. Han, Poly(ADP-ribose) polymerase-1 signaling to mitochondria in necrotic cell death requires RIP1/TRAF2-mediated JNK1 activation. J. Biol. Chem. 281 (2006) 8788-8795.
Xu, Zhenghong, Yuhua Wang, Lu Zhang, and Leaf Huang. "Nanoparticle-delivered transforming growth factor-β siRNA enhances vaccination against advanced melanoma by modifying tumor microenvironment." ACS nano 8, No. 4 (2014): 3636-3645.
Yamashima, T., Y. Kohda, K. Tsuchiya, T. Ueno, J. Yamashita, T. Yoshioka, E. Kominami, Inhibition of ischaemic hippocampal neuronal death in primates with cathepsin B inhibitor CA-074: a novel strategy for neuroprotection based on 'calpain-cathepsin hypothesis'. Eur. J. Neurosci. 10 (1998) 1723-1733.
Yarchoan, Mark, Burles A. Johnson III, Eric R. Lutz, Daniel A. Laheru, and Elizabeth M. Jaffee. "Targeting neoantigens to augment antitumour immunity." Nature Reviews Cancer 17, No. 4 (2017): 209.
Yi, J.S., M.A. Cox, and A.J. Zajac, T-cell exhaustion: characteristics, causes and conversion. Immunology, 2010. 129(4): p. 474-81.
Yinuo Li, S.L., Ying Xu, Chunping Qiu, Chengjuan Jin, Yuqiong Wang, Zhaojian Liu, Beihua Kong, Overexpression of CD47 predicts poor prognosis and promotes cancer cell invasion in high-grade serous ovarian carcinoma. Am J Transl Res, 2017.
Yong, Seok-Beom, Jee Young Chung, Yoonsung Song, and Yong-Hee Kim. "Recent challenges and advances in genetically-engineered cell therapy." Journal of Pharmaceutical Investigation (2018): 1-10.
You, Benshuai, Wenrong Xu, and Bin Zhang. "Engineering exosomes: a new direction for anticancer treatment." American journal of cancer research 8, No. 8 (2018): 1332.
Youle, R.J., A. Strasser, The BCL-2 protein family: opposing activities that mediate cell death. Nat. Rev. Mol. Cell Biol. 9 (2008) 47-59.
Yu, Guang-Tao, Lin-Lin Bu, Cong-Fa Huang, Wen-Feng Zhang, Wan-Jun Chen, J. Silvio Gutkind, Ashok B. Kulkarni, and Zhi-Jun Sun. "PD-1 blockade attenuates immunosuppressive myeloid cells due to inhibition of CD47/SIRP-α axis in HPV negative head and neck squamous cell carcinoma." Oncotarget 6, No. 39 (2015): 42067.
Yu, L., A. Alva, H. Su, P. Dutt, E. Freundt, S. Welsh, E.H. Baehrecke, M. J. Lenardo, Regulation of an ATG7-beclin 1 program of autophagic cell death by caspase-8. Science 304 (2004) 1500-1502.
Yu, L., F. Wan, S. Dutta, S. Welsh, Z. Liu, E. Freundt, E.H. Baehrecke, M. Lenardo, Autophagic programmed cell death by selective catalase degradation. Proc. Natl. Acad. Sci. U.S.A. 103 (2006) 4952-4957.
Zampetti-Bosseler, F., and David Scott. "Cell death, chromosome damage and mitotic delay in normal human, ataxia telangiectasia and retinoblastoma fibroblasts after X-irradiation." International Journal of Radiation Biology and Related Studies in Physics, Chemistry and Medicine 39, No. 5 (1981): 547-558.
Zanke, Brent W., Kimberly Boudreau, Elizabeth Rubie, Elaine Winnett, Lee Anne Tibbles, Leonard Zon, John Kyriakis, Fei-Fei Liu, and James R. Woodgett. "The stress-activated protein kinase pathway mediates cell death following injury induced by cis-platinum, UV irradiation or heat." Current Biology 6, No. 5 (1996): 606-613.
Zhang, D.W., J. Shao, J. Lin, N. Zhang, B.J. Lu, S.C. Lin, M.Q. Dong, J. Han, RIP3, an energy metabolism regulator that switches TNF-induced cell death from apoptosis to necrosis. Science (2009).
Zhang, H., et al., Antitumor efficacy of CD137 ligation is maximized by the use of a CD137 single-chain Fv-expressing whole-cell tumor vaccine compared with CD137-specific monoclonal antibody infusion. Mol Cancer Ther, 2006. 5(1): p. 149-55.
Zhang, M., et al., Anti-CD47 Treatment Stimulates Phagocytosis of Glioblastoma by M1 and M2 Polarized Macrophages and Promotes M1 Polarized Macrophages In Vivo. PLoS One, 2016. 11(4): p. e0153550.
Zhao, H., et al., CD47 Promotes Tumor Invasion and Metastasis in Non-small Cell Lung Cancer. Sci Rep, 2016. 6: p. 29719.

(56) References Cited

OTHER PUBLICATIONS

Zheng, Yuanhong, Guifang Yin, Vanminh Le, Anle Zhang, Siyu Chen, Xin Liang, and Jianwen Liu. "Photodynamic-therapy activates immune response by disrupting immunity homeostasis of tumor cells, which generates vaccine for cancer therapy." International journal of biological sciences 12, No. 1 (2016): 120.
Zhu Y, Dong Z, Wejinya UC, Jin S, Ye K. Determination of mechanical properties of soft tissue scaffolds by atomic force microscopy nanoindentation. J Biomech. 2011;44:2356-61.

* cited by examiner

GENOME EDITED CANCER CELL VACCINES

CROSS REFERENCE TO RELATED APPLICATIONS

The present application is a non-provisional of, and claims benefit of priority under 35 U.S.C. § 119(e) from U.S. Provisional Patent Application No. 62/743,404, filed Oct. 10, 2018, the entirety of which is expressly incorporated herein by reference.

FIELD OF THE INVENTION

The present invention relates to the field of cancer vaccines and immunotherapy, and more particularly to cellular vaccines.

BACKGROUND OF THE INVENTION

Each reference cited herein is expressly incorporated herein by reference for all purposes.

Harnessing the body's immune system and "teaching" it to fight against cancerous outgrowth has been one of the most rewarding endeavors in cancer therapy (Vinay et al. 2015; Kruger et al. 2007). Cancer cells possess a plethora of immune evasion mechanisms in reaction to specific immune responses. They efficiently modulate expression of cell surface and secretory proteins in response to chemical stress, cytokines, or initial attacks by the immune system (Vinay et al. 2015; Zhang et al. 2016). Tumors evolve based on immune responses, and the specific interactions between them orchestrates the outcome of tumor escape or rejection (Dunn et al. 2004).

One of the most studied immune checkpoint mechanisms in cancer is the CD47-SIRP-α interaction (Zhang et al. 2016; Chao et al. 2012; Sick et al., 2012). CD47, a ubiquitous cell-surface antigen, is reported to act as a marker of self and by corollary, a "don't eat me" signal. It binds to the signal recognition protein alpha (SIRP-α), presents primarily on macrophages that form the first line of defense in the innate immune system, and renders the cell unrecognizable (Chao et al. 2012). This interaction curbs macrophage-mediated phagocytosis and hampers the downstream antigen presentation and tumor cell lysis mechanisms. Tumor cells have been shown to overexpress CD47 on their cell surface as a defense mechanism to blindside the host's immune defense systems (Yinuo et al. 2017; Zhao et al. 2016).

CD47 has been primarily targeted for developing immune checkpoint blockade therapies. For instance, the blocking of CD47-SIRP-α interaction using anti-CD47 antibodies, anti-SIRP-α antibodies Alvey et al. 2017; Weiskopf et al. 2013), or nanobodies (Zhang et al. 2016; Gul et al. 2014; Liu et al. 2015), has shown delayed tumor progression by engaging the myeloid arm of the immune system. These studies have been precedents for combination therapy with CD47 using monoclonal antibodies, engineered SIRP-α variants, and other fusion proteins (Weiskopf et al. 2013; Gul et al. 2014; Sockolosky et al. 2016; Tseng et al. 2013; Weiskopf et al. 2016). A multitude of monoclonal antibodies against CD47 have been developed as anti-tumor agents (Weiskopf et al. 2013; Gul et al. 2014; Sockolosky et al. 2016; Weiskopf et al. 2016). Depletion of CD47 expression on cancer cells using either siRNA (Yinuo et al. 2017; Zhao et al. 2016) or genetic editing (Sockolosky et al. 2016) has also been explored. The genetic ablation of CD47 from cancer cells has proven effective in slowing down tumor growth and enhancing phagocytosis by macrophages (Alvey et al. 2017; Weiskopf et al 2016). Other immune checkpoint molecules have also been studied. (Marcucci et al. 2017; en.wikipedia.org/wiki/Immune_checkpoint, expressly incorporated herein by reference in its entirety, including cited references).

Vaccination is a powerful tool for generating a tumor-specific response to by exposing tumors to the immune system (Ngo et al. 2016). Vaccine formulations can range from mRNA mutanomes (He et al. 2011, tumor-associated neoantigen peptide cocktails (Dranoff et al. 1993), yeast-based tumor-associated antigen production (Stanton et al. 2015), or tumor cell lysates containing immune system stimulants (Sahin et al. 2017; Ott et al. 2017). Whole-cell vaccines have been as widely researched as the monoclonal antibodies but have not been explored in such depth for specific immune target proteins (Sofia et al. 2011; Maeng et al. 2018; Kumai et al. 2017). Providing the immune system with non-replicating tumor cells circumvents the need to perform tumor-associated antigen profiling, protein purification, viral packaging, and a multitude of other preparation regimes (Maeng et al. 2018; de Gruijl et al. 2008). With respect to whole-cell vaccines, one of the most important things to consider is a method that will allow for efficient uptake of whole cells by the first responders—the infiltrating neutrophils and monocytes.

Vaccination with an appropriate immune-system stimulation regime, would be an alternative or additional method, in addition to surgery, chemotherapy, radio therapy, thermotherapy, etc., to treat cancer, because it takes advantage of the immune system to seek and destroy cancer cells. Whole tumor cells are an ideal source of tumor-associated antigens (TAAs) for vaccination development, because the whole cancer cells have a diverse panel of TAAs (either known or unknown) which elicits $CD8^+$ and $CD4^+$ T-cell responses (Chiang et al. 2010; de Gruijl et al. 2008). Vaccination with irradiated tumor cells has been studied in various animal models as early as the 1970s, and whole-tumor cell vaccines have shown great potentials in inducing immune responses and in improving patient survival (de Gruijl et al. 2008).

Immune cells are supposed to recognize TAAs and destroy cancer cells, because they constantly search and destroy foreign invaders. Cells that lack CD47 are frequently cleared out efficiently by the macrophages in the body. However, cancer cells frequently escape immune attack because they express CD47 on their surface (LaCasse et al. 2008). CD47 is present on the surface of both normal cells and all tested cancer cells; particularly, it is overexpressed on the cancer cells. Increased CD47 expression on cancer cells imply worse prognosis. In cancer cells, CD47 functions by initially binding to its receptor, SIRP-α (also known as CD172a and SHPS-1), which is expressed on the surface of macrophages. The binding of CD47 to SIRP-α inhibits phagocytosis of cancer cells by the macrophages. Therefore, CD47 acts as a "don't-eat-me" signal to enable cancer cells to escape immune-surveillance (See FIGS. 1A and 1B) (LaCasse et al. 2008; Peter et al. 2003).

Previous research has shown that both anti-CD47 antibody and anti-CD47 siRNA enable phagocytosis by macrophages and subsequently inhibit tumor growth (Wilson et al. 2009; Wang et al. 2008; Penazola et al. 2006). Although both methods show efficacy, both methods have their weaknesses. Because of ubiquitous expression of CD47, particularly on hematopoietic cells, anti-CD47 antibody and anti-CD47 siRNA could raise safety concerns. Although anti-CD47 antibodies show relative selectivity on cancer cells because of calreticulin (a pro-phagocytic signal that is highly expressed on the surface of several human cancers, but is minimally expressed on most normal cells) (Elmore et al. 2007), anti-CD47 antibodies can still cause adverse side effects and their large size can hinder their tumor penetration. According Krysko et al. 2008, CD47-deficient erythrocytes infused into wild-type mice were found to be cleared within 24 hours. In contrast, normal red blood cells survive for 60-80 days in mice.

Radiation induces DNA damage, which can lead to cellular reproductive incompetence, senescence, and especially at higher doses, cell death. While death by an apoptosis pathway may occur in portions of a highly irradiated cell population, it is not the exclusive mode of cell death, and portions of the cell population may undergo death mediated by a necrosis pathway. Sublethal irradiation at sufficient dose can result in permanent cell cycle arrest in the G2 phase and by stress-induced premature senescence. (Marcucci et al. 2017; Zanke et al. 1996; Merritt et al. 1997; Zampetti-Bosseler et al. 1981; Herzog et al. 1998; Suzuki et al. 2001; Wyllie et al. 1987; Thyss et al. 2005; Danial et al. 2004; Waldman et al. 1997; Schanne, et al. 1979; Reed et6 al. 1994; Galluzzi et al. 1997; Strozyk et al. 2013; Voisine et al. 1991; Wlaschek et al. 2003; Jones et al. 2005; Muthna et al. 2010).

Apoptosis (Type I programmed cell death) is a form of programmed cell death that occurs in multicellular organisms. Biochemical events lead to characteristic cell changes (morphology) and death. These changes include blebbing, cell shrinkage, nuclear fragmentation, chromatin condensation, chromosomal DNA fragmentation, and global mRNA decay. (en.wikipedia.org/wiki/Apoptosis; Elmore 2007) Apoptotic cell death is a genetically programmed mechanism(s) that allows the cell to commit suicide. The extrinsic and intrinsic pathways represent the two major well-studied apoptotic processes. The extrinsic pathway is mediated by a sub-group of Tumor Necrosis Factor receptors (TNFR) superfamily that includes TNFR, Fas and TRAIL. Activation of these so-called death receptors leads to the recruitment and activation of initiator caspases such as caspases 8 and 10. The process involves the formation and activation of complexes such as the death inducing signaling complex (DISC). This leads to the activation of an effector caspase, typically caspase 3. The active caspase 3 is responsible for the cleavage of a number of so-called death substrates that lead to the well-known characteristic hallmarks of an apoptotic cell including DNA fragmentation, nuclear fragmentation, membrane blebbing and other morphological and biochemical changes. More recent evidence suggests even greater complexity and diversity in the extrinsic pathways that also involves the cross-activation of other apoptotic pathways such as the intrinsic apoptotic as well as necrotic sub-pathways. (Pertt et al. 2011; Duprez et al. 2009)

Other pathways to cell death include necrotic cell death, autophagic cell death, and pyroptosis.

Necrotic cell death. For a long time, necrosis has been considered an accidental and uncontrolled form of cell death lacking underlying signaling events. This might be true for cell death resulting from severe physical damage, such as hyperthermia or detergent-induced cytolysis. However, accumulating evidence supports the existence of caspase-independent cell death pathways that can function even in a strictly regulated developmental context, such as interdigital cell death (Chautan et al. 1999). Necrotic cell death is characterized by cytoplasmic and organelle swelling, followed by the loss of cell membrane integrity and release of the cellular contents into the surrounding extracellular space.

TNFR1 stimulation leads to the activation of RIP1, which induces a pro-survival pathway by activating transcription factors, e.g., NF-kB and AP-1. RIP1 interacts with RIP3, and both are crucial initiators of death receptor-induced necrotic signaling. A wide range of necrotic mediators are activated RIP1 kinase activity, such as ROS, calcium, calpains, cathepsins, phospholipases, NO and ceramide. The same mediators can be activated by DNA damage or by triggering of TLR-3, TLR-4 and Nalp-3.

In most cell lines, death receptor ligands activate apoptosis rather than necrosis as the default cell death pathway. However, if caspase activation in this pathway is hampered, necrotic cell death might ensue instead, acting as a kind of back-up cell death pathway. zVAD-fmk is frequently used as a potent inhibitor of caspases, but off-target effects can also contribute to caspase-independent cell death. For example, zVAD-fmk binds and blocks the adenine nucleotide translocator (ANT), inhibits other proteases such as cathepsins, and generates the highly toxic fluoroacetate, due to metabolic conversion of the fluoromethylketone group (Vandenabeele et al. 2006; Van Noorden 2001). FADD remains a crucial adaptor protein in Fas and TRAIL-R-induced necrosis, but the importance of FADD in TNF-induced necrosis is controversial (Lin et al. 2004; Holler et al. 2000). It was demonstrated in the TRADD knockout mouse, that TRADD is essential for TNF-induced necrosis in MEF cells (Pobezinskaya et al. 2008). RIP1 is a crucial initiator of death receptor-mediated necrosis (Festjens et al. 2007) and the term necroptosis was introduced to designate programmed necrosis that depends on RIP1 (Degterev et al. 2005). The kinase activity of RIP1 is dispensable for the activation of NF-kB and MAPKs, but is required for necroptosis (Holler et al. 2000; Degterev et al. 2005; Chan et al. 2003). Necrostatin-1 (Nec-1) was identified as a small molecule inhibitor of necroptosis (Degterev et al. 2005), and more recently, the RIP1 kinase activity was found to be the target of Nec-1 (Degterev et al. 2008). Furthermore, recent studies identified RIP3 as a crucial upstream activating kinase that regulates RIP1-dependent necroptosis (Zhang et al. 2009; Cho et al. 2009; He et al. 2009). TNF treatment induced the formation of a RIP1-RIP3 pro-necrotic complex and the kinase activity of both RIP1 and RIP3 was crucial for stable complex formation and subsequent induction of necrosis. During death receptor-induced apoptosis, RIP1 and RIP3 are cleaved by caspase-8, which suppresses their anti-apoptotic and/or pro-necrotic properties (Lin et al. 1999; Feng et al. 2007).

Besides death receptor-mediated necrosis, triggering of pathogen recognition receptors (PRRs) can also lead to necrotic cell death. Receptors of this family include the transmembrane toll-like receptors (TLRs), the cytosolic NOD-like receptors (NLRs) and the RIG-I-like receptors (RLRs). They all recognize pathogen-associated molecular patterns (PAMPs) found in bacteria or viruses, such as LPS, flagellin and double-stranded RNA (dsRNA), and stimulation of these receptors leads to the activation of innate immunity and/or cell death. In Jurkat cells and L929 cells, the recognition of synthetic dsRNA by TLR3 induces necrotic cell death, which was suggested to be RIP1-dependent (Kalai et al. 2002). TLR4 is expressed on macrophages and monocytes and is critical for the recognition of LPS from Gram-negative bacteria. Impeding caspase-8 activation switches TLR4-induced cell death from apoptosis to RIP1-dependent necrosis (Ma et al. 2005). Pathogen-induced activation of NLRs results most commonly in caspase-1-dependent cell death or pyroptosis (see below). However, a recent report showed that the NLR member Nalp-3 mediates necrotic cell death of macrophages infected with *Shigella flexneri* at high multiplicity of infection (Willingham et al. 2007). RLR-induced activation of NF-kB and production of type I interferons are both dependent on FADD, RIP1 and TRADD (Balachandran to al. 2004; Michallet et al. 2008). Whether these proteins are also involved in RLR-induced cell death is unknown.

Extensive DNA damage causes hyperactivation of poly-(ADP-ribose) polymerase-1 (PARP-1) and leads to necrotic cell death (Jagtap et al. 2005). When DNA damage is moderate, PARP-1 participates in DNA repair processes. However, excessive PARP-1 activation causes depletion of NAD+ by catalyzing the hydrolysis of NAD+ into nicotinamide and poly(ADP-ribose) (PAR), leading to ATP depletion, irreversible cellular energy failure, and necrotic cell death. PARP-1-mediated cell death requires the activation of RIP1 and TRAF2 (Xu et al. 2006). Many mediators are involved in the execution phase of necrotic cell death, including reactive oxygen species (ROS), calcium ($Ca^{2+}$), calpains, cathepsins, phospholipases, and ceramide (Vanlangenakker et AL. 2008). Oxidative stress leads to damage of cellular macromolecules, including DNA, proteins, and lipids. As discussed earlier, excessive DNA damage results in hyperactivation of PARP-1 and necrotic cell death. Modification of proteins by ROS leads to loss of the normal functions of proteins and enhances their susceptibility to proteolytic degradation. Other targets of ROS are the polyunsaturated fatty acid residues in the membrane phospholipids, which are extremely sensitive to oxidation. In mitochondria, lipid peroxidation affects vital mitochondrial functions. In addition, it destabilizes the plasma membrane and intracellular membranes of endoplasmic reticulum and lysosomes, leading to intracellular leakage of $Ca^{2+}$ and lysosomal proteases, respectively. Among the different ROS, hydrogen peroxide ($H_2O_2$) plays a particularly important role because it diffuses freely across cellular membranes and can interact with iron in the Fenton reaction (Vanlangenakker et al. 2008). This reaction is favored in the lysosomes, because they are rich in free iron and do not contain $H_2O_2$-detoxifying enzymes. The resulting highly reactive hydroxyl radicals are among the most potent inducers of lipid peroxidation.

$Ca^{2+}$ overload of mitochondria causes mitochondrial permeability transition (MPT) by the opening of large nonselective pores (the so called mitochondrial permeability transition pores, MPTPs) connecting the cytosol with the mitochondrial matrix (Kroemer et al. 2007). MPT is accompanied by mitochondrial inner membrane depolarization, uncoupling of oxidative phosphorylation, matrix swelling, and outer mitochondrial membrane rupture (Kroemer et al. 2007). If most mitochondria of the cell are disrupted, and glycolytic sources of ATP are inadequate, the cell becomes profoundly ATP-depleted. Cyclophilin D (CypD) might have an important role in MPT, as inhibition of CypD renders cells resistant to MPT, and CypD-deficient mice are more resistant to ischemic injury than wild type mice (Halestrap et al. 1997; Nakagawa et al. 2005). Besides affecting mitochondrial respiration, $Ca^{2+}$ overload can activate phospholipases, proteases and neuronal nitric oxide synthase (nNOS), all of which contribute to the execution phase of necrotic cell death. For example, calpains are activated by elevated $Ca^{2+}$ levels, which then cleave the $Na^+/Ca^{2+}$ antiporter in the plasma membrane, resulting in a sustained $Ca^{2+}$ overload. Strong activation of calpains may also contribute to the release of cathepsins in the cytosol by causing lysosomal membrane permeabilization, as proposed in the "calpaine-cathepsin" hypothesis by Yamashima and colleagues (Yamashima et al. 1998).

Necrotic cell death participates in activation-induced cell death (AICD) of T lymphocytes, which is an important mechanism for reducing T cell numbers after an immune response (Holler et al. 2000). Necrotic cell death is always observed together with apoptosis or in the presence of caspase inhibitors, suggesting that it functions as a back-up mechanism and is never the sole cell death pathway. Necrotic cell death is often associated with pathological conditions. Necrosis has been observed during ischemia/reperfusion (I/R), which can lead to injury of organs, including heart, brain, liver, kidney, and intestine (Neumar 2000). Necrotic cell death also contributes to excitotoxicity, which may be involved in stroke, traumatic brain injury, and neurodegenerative disorders (Ankarcrona et al. 1995). More specifically, using Nec-1, it was shown that RIP1-dependent necrotic cell death or necroptosis contributes to a wide range of pathological cell death events, such as ischemic brain injury (Degterev et al. 2005) and myocardial infarction (Lim et al. 2007). Furthermore, $RIP3^{-/-}$ mice failed to initiate vaccinia virus-induced tissue necrosis and inflammation, resulting in much more viral replication and mortality (Cho et al. 2009). Several other reports also illustrate the occurrence of necrotic cell death during infection by other pathogens, such as *Shigella*, HIV-1, West Nile virus, and Coxsackievirus B (Vanlangenakker et al. 2008). In addition, patients carrying a disease-associated mutation in Nalp-3 show excessive necrotic-like cell death with features similar to the *Shigella flexneri*-induced Nalp-3-dependent necrosis (Willingham et al. 2007).

In contrast to apoptosis, the recognition and uptake of necrotic cells by macropinocytosis is slower, less efficient and occurs only after the loss of plasma membrane integrity (Krysko et al. 2003). As a result, necrotic cells initiate a proinflammatory response by the passive release of DAMPs (danger/damage-associated molecular patterns) (Fadok et al. 2001). In addition, necrotic cells actively secrete inflammatory cytokines due to the activation of NF-kB and MAPKs (Vanden Berghe et al. 2006).

Autophagy is an evolutionarily conserved catabolic pathway that allows eukaryotes to degrade and recycle cellular components. Proteins and organelles are sequestered in specialized double-membrane vesicles, designated autophagosomes, which are typical of autophagic cells. Basal levels of autophagy ensure the maintenance of intracellular homeostasis, but in addition, many studies have revealed its diverse functions in important cellular processes, such as cellular stress, differentiation, development, longevity and immune defense. Although a pro-survival role for autophagy is well-established, frequently debated is whether or not autophagy has a causative role in cell death. The presence of autophagic vacuoles in dying cells has led to the introduction of autophagic cell death, although autophagy often accompanies rather than causes cell death. It is plausible though that massive autophagic activity could result in cellular demise. In addition, several interconnections exist between autophagy and apoptotic or necrotic cell death (Maiuri et al. 2007).

Pyroptosis is form of regulated cell death with morphological and biochemical properties distinct from necrosis and apoptosis (Labbe et al. 2008). Pyroptosis has been described in monocytes, macrophages and dendritic cells infected with a range of microbial pathogens, such as *Salmonella*, *Francisella* and *Legionella*, and is uniquely dependent on caspase-1 (Bergsbaken et al. 2009). In addition, non-infectious stimuli, such as DAMPs, can induce pyroptosis in non-macrophage cells.

Caspase-1, previously known as Interleukin-1 (IL-1b) Converting Enzyme (ICE), was the first mammalian caspase to be identified. As a member of the inflammatory caspases, it is not involved in apoptotic cell death (Li et al. 1995), and the apoptotic caspases usually do not contribute to pyroptosis (Lamkanfi et al. 2008). Caspase-1 is present in the cytosol as an inactive zymogen. In analogy to activation of caspase-9 in the apoptosome, caspase-1 is activated in a complex called the inflammasome. This molecular platform includes NLR family members that recruit caspase-1 through adaptor molecules, such as ASC/Pycard and is formed through homotypic interactions between these inflammasome components. Four inflammasomes have been characterized and named after their NLR (Nalp-1, Nalp-3 and Ipaf) or HIN-200 protein (AIM2) (Bergsbaken et al. 2009; Schroder et al. 2009). Assembly of the inflammasome occurs when NLRs are triggered by intracellular bacterial, viral or host danger signals. For example, Nalp-1 recognizes cytosolic delivery of Bacillus anthracis lethal toxin, Ipaf recognizes cytosolic flagellin, and Nalp-3 responds to multiple DAMPs and PAMPs (Bergsbaken et al. 2009) (FIG. 4). Most NLRs consist of three distinct domains: an N-terminal CARD domain or pyrin effector domain (PYD), a central nucleotide binding and oligomerization domain (NACHT), and several C-terminal leucine-rich repeats (LRRs). In addition, Nalp-1 has a C-terminal extension that harbors a CARD domain. In contrast to human Nalp-1, the mouse orthologue Nalp-1b does not contain an N-terminal PYD domain. Upon stimulation, NLRs undergo oligomerization through homotypic NACHT domain interactions. Subsequently, the NLRs associate with the adaptor protein ASC through homotypic PYD interactions. In addition, Nalp-3 associates with the adaptor Cardinal in its inflammasome. These adaptor molecules then recruit caspase-1 through CARDe CARD interactions, resulting in its oligomerization and proximity-induced activation. Recently, the AIM2 inflammasome was identified (Schroder et al. 2009). Through its HIN domain, AIM2 can directly bind to dsDNA, resulting in the activation of caspase-1 and maturation of pro-IL-1b. The source of the cytoplasmic dsDNA appears unimportant for AIM2 activation because viral, bacterial, mammalian and synthetic dsDNA could all activate caspase-1 (Schroder et al. 2009). Double stranded DNA-dependent cell death depends on AIM2, ASC and caspase-1 and shows features of pyroptosis (Fernandes et al. 2009).

Active caspase-1 is the central executor of pyroptotic cell death and acts mainly by inducing the formation of discretely sized ion-permeable pores in the plasma membrane (Fink et al. 20096). The resulting osmotic pressure leads to water influx, cell swelling and ultimately cell lysis. Furthermore, caspase-1 activation initiates an inflammatory response by the cleavage of the proinflammatory cytokines pro-IL-1b and pro-IL-18, which are released by the cell upon their activation (Eder 2009). However, this inflammatory response is not required for the execution of cell death (Sarkar et al. 2006). Although caspase-1 activation is inherently associated with an inflammatory response, it is still unclear whether it is inevitably linked to pyroptotic cell death. Cells dying by pyroptosis have biochemical and morphological features of both apoptotic and necrotic cells (Bergsbaken et al, 2009). Pyroptotic cells lose their mitochondrial membrane potential and plasma membrane integrity and release their cytoplasmic contents into the extracellular milieu. As in apoptosis, pyroptotic cells undergo DNA fragmentation and nuclear condensation. However, this caspase-1-dependent nuclease-mediated cleavage of DNA does not exhibit the oligonucleosomal fragmentation pattern characteristic of apoptosis (Bennan et al. 2000). In addition, the DNA damage and concomitant PARP-1 activation associated with pyroptotic cell death are not required for cell lysis to occur (Fink et al. 2006). Because of its dependence on caspase-1 activity, pyroptosis is associated with the initiation of a proinflammatory response, which is further amplified by the release of the cytoplasmic content upon cell lysis. Since NLR-mediated activation of caspase-1 affects several cellular pathways, it is difficult to distinguish the precise role of caspase-1 in the cell death process itself.

There are a number of genome editing systems available. These include ZFNs (Zinc Finger Nucleases); TALENs (Transcription Activator Like Effector Nucleases); and CRISPR (Clustered Regularly Interspaced Short Palindromic Repeats). In addition, recombinant Adeno-Associated Virus (MV) and transposons can also be employed. Further, RNAi may also be employed to reduce gene function. These techniques are known in the art.

See, en.wikipedia.org/wiki/Genome_editing, Tebas et al. 2014; Lombardo et al. 2007; Li et al. 2012; Liang et al. 2015; Gaj et al. 2013; Ain et al. 2015; Song et al. 2016; Wei et al. 2013; Shen et al. 2013).

Acronyms:

| | |
|---|---|
| CD—Cluster of Differentiation | MMC—Mitomycin C |
| SIRP—Signal regulatory protein | NK—Natural Killer |
| TME—Tumor microenvironment | DC—Dendritic cell |
| TDLN—Tumor-draining lymph node | CTL—Cytotoxic T cell |
| | TAM—Tumor-associated macrophage |
| APC—Antigen presenting cell | MDSC—Myeloid-derived suppressor cell |
| PBS—Phosphate buffered saline | |
| PCR—polymerase chain reaction | PMN—Polymorphonuclear |
| CFSE—Carboxyfluorescein | BMDM—Bone marrow-derived macrophage |
| GM-CSF—Granulocyte macrophage colony stimulating factor | MHC—Major histocompatibility complex |
| TM—Tumor-associated antigen | STING—Stimulator of interferon genes |

SUMMARY OF THE INVENTION

The present technology provides a system and method for the treatment of tumors with replicatively inactivated tumor cells as vaccines by silencing their immune checkpoint proteins such as CD47, PD-L1, etc. through genetic modification such as CRISP/cas 9 genome editing. The modified tumor cells become immune checkpoint deficient; thereby eliciting a strong immunogenicity after being introduced into the body. CD47-depleted tumor cells inactivated appropriately would be processed effectively by immune cells such as circulating macrophages and cause the body to trigger an anti-tumor immune response. Related work is discussed in: Gao et al. 2016; Koh et al. 2017; Jayaraman, 2017.

Types of tumors that might be addressed by the present technology include: solid immunogenic (or "hot") tumors including melanoma, bladder cancer, head and neck cancers, kidney cancer, liver cancer, and non-small cell lung cancer; and non-immunogenic tumors (or "cold") including ovarian, prostate, pancreatic cancer, etc.

Among other differences from prior work, it was not previously appreciated that in order to provoke a suitable immune response for an efficacious vaccine, the cells should not be treated in such a manner that causes apoptosis, e.g., Mitomycin C. See FIG. 17. On the other hand, inactivation is generally required for safe administration to humans, since the cells have pathogenic potential. This finding is consistent with the hypothesis that a live cell vaccine is preferred over cellular components.

One feature of the present technology is that it does not rely on identification and selective processing of cancer-associated antigens, and rather employs a patient's own neoplasia (or in some cases, a prototype neoplasia) to define the antigenic determinants. Likewise, it does not require qualification of proposed vaccine antigens with respect to cross reactivity, and rather relies on the normal immune mechanisms of the host organism to avoid unchecked autoimmune responses. Thus, present cancer vaccine technology does not rely on the prerequisite of comprehensive knowledge of all cancer associated neo-antigens. It utilizes information from syngeneic tumor cells themselves, making the system precise and personalized.

While melanoma was used as a model system to prove the concept, the technology can be used, in principle, to treat any cancer, in particular metastatic cancers.

Another feature is that, while the cells are being processed, additional genetic engineering may be performed, for example causing the cells to express cytokines that boost immune responses, to display additional antigens that enhance the immune response, and/or to suppress multiple immune checkpoint blockades such as CD47 and PD-L1 simultaneously to facilitate the processing of vaccines by multiple types of immune cells, leading to the enhancement of immune response.

The immunogenicity of the developed cancer vaccines can be further enhanced by co-expressing cytokines, such as GM-CSF, that stimulate maturation and activation of immune cells including macrophages, T cells, natural killer cells, dendritic cells, etc. The genes encoding cytokines such as GM-CSF are integrated into the genome of tumor cells through genomic knocking in. The immune checkpoint deficient tumor cells such as $CD47^{-/-}$ tumor cells are maintained in an in vitro culture, and then used as a prophylactic measure to prevent relapse and metastasis of the original cancer, or as a treatment for an active localized tumor.

The current embodiment has been tested on the syngeneic mouse melanoma model. In this embodiment, irradiated and non-replicating (but non-apoptotic) melanoma cells lacking surface expression of CD47 have been formulated as vaccines to prevent subcutaneous melanoma growth upon a tumor challenge.

Traditional vaccines which employ normal tumor cells could escape the antigen-presenting cells, such as macrophages, because of their normally present surface CD47, and thus the TAAs could not be efficiently presented to immune cells. Removal of CD47 could create an opportunity for immune cells such as the macrophages to recognize and present the TAAs from the cancer cell vaccine and create strong immune responses to kill the cancer cells.

Because introduction of live cancer cells into the human body could cause safety concerns, the modified cancer cells are preferably inactivated and rendered non-replicating, for example, exposed to gamma irradiation in a sufficient amount to ensure that the cells are replication-incompetent. Additionally, because the absence of CD47 on the vaccine cell surface, the cancer cells could be rapidly engulfed by macrophages, eliciting an immune response in the body. Other treatments may be available to modify the cells without causing apoptosis or immediate cell death.

It has been found that apoptosis, or treatments of the cells which lead to apoptosis, are suboptimal, and that metabolic processes within the cancer cells, and/or an intact cellular membrane appears to be important for the correct immune response.

CD47 is a potent target for creating genome edited whole-cell cancer vaccines. Mice vaccinated with irradiated $CD47^{-/-}$ 3BD9 cells were successfully immunized against a tumor challenge. 40% of mice are tumor free for 70-days post tumor challenge, and 33% of mice are tumor free for 90-days post tumor challenge.

Immunity is due to significant increase in mature antigen presenting cells (macrophages and dendritic cells), and activated effector cells ($CD8^+$ and $CD4^+$ T cells). Vaccination with $CD47^{-/-}$ 3BD9 cells regulates and maintains homogenous levels of tumor infiltrating lymphocytes throughout the tumor growth phase.

Therapies to increase macrophage specific cytokines (GM-CSF), reduce regulatory T cells, and avoid T cell exhaustion (PD-L1, PD1, CTLA-4, LAG-3) can be effective combination therapies with the $CD47^{-/-}$ whole-cell vaccine regime.

Therefore, the present technology provides a composition and a method for preparation thereof comprising inactivated cultured tumor cells which present antigens characteristic of a specific tumor type, such as melanoma, is deficient in CD47 expression. The composition is prepared by gene editing cells of a live cell culture, expanding the cell culture, and then inactivating them, such as with gamma irradiation, or another method of deactivating the cells without causing apoptosis. The inactivated tumor cells are then administered to the patient, optionally with an adjuvant, in a known manner.

The vaccination strategy is therefore to deplete the CD47 protein from cancer cell surface by editing the cd47 gene using the CRISPR-Cas9 technology to switch off the "don't-eat-me" signal from cancer cells, hence permitting the macrophages to engulf the vaccine cells, i.e. the $CD47^{-/-}$ melanoma cells, and present TAAs to $CD8^+$ and $CD4^+$ T-cells to generate an immune response to inhibit tumor growth or to eliminate tumors.

The present technology fully harnesses the immune systems to recognize the TAAs and subsequently to eliminate cancer cells. Cancer cells could easily escape from the immune systems because of their surface protein CD47, and after CD47 is deleted from the vaccine cancer cells, the roadblock for immune recognition and antigen presenting could be removed.

The present invention therefore provides whole-cell tumor vaccines, preferably of an autologous nature, that have been genetically modified to knockout the expression of cell surface CD47, a molecule tumor cells overexpress to evade attack by macrophages in the immune system. When rendered non-replicating, these cells act as an effective immunizing agent and elicit a strong anti-tumor immune response to a current tumor, or the future relapse or metastasis of the same type of tumor.

CD47 was identified as a target for the genetically modified whole-cell vaccines, based on its status as one of the foremost immune evasion markers overexpressed by the tumor cells. As macrophages form the first line of defense by the myeloid arm of the immune system, it is imperative for the tumor cells to be susceptible to attack and engulfment (phagocytosis) by the macrophages in order to elicit an amplified tumor-specific immune response comprising of effector cytotoxic cells. (FIGS. 1A and 1B)

For the proof of concept study of the vaccines, the syngeneic mouse melanoma (B16F10) model was used. They were tested in female C57BL/6 mice for efficacy and tumor growth studies. The biology of CD47 in C57BL/6 mice is believed to be reasonably predictive of human response, and that of many other species.

The CRISPR/Cas9 system was utilized to deplete CD47 expression. Briefly, single guide-RNAs, 20 bp long, were designed in silico with 100% sequence complementarity to a target region of the cd47 gene. The guides were introduced into melanoma B16F10 cells along with the Cas9 endonuclease as a ribonucleoprotein (RNP) complex. Coding exons were edited to create a frameshift mutation in the cd47 gene, leading to the knockout of the CD47 expression on the tumor cell surface. CD47 knockout was confirmed by DNA sequencing, flow cytometry, and immunofluorescence microscopy.

An inactivation technique that renders the genetically modified cells non-replicating, but at the same time non-apoptotic, provides an effective vaccine for use. It was surprisingly found that inactivating the cells using the chemical alkylating agent Mitomycin-C (MMC), masked the involvement of the target protein, CD47. In other words, MMC-treated inactive melanoma cells had some effect as anti-tumor vaccines, but the depletion of cell surface CD47 did not enhance this effect. However, when inactivated by gamma irradiation, the effect of CD47 was clearly seen, a 1.5-fold increase in comparison with $CD47^{+/+}$ inactivated whole-cell vaccines, see FIG. 17.

Since the deletion of CD47 and its subsequent effects have been tested as proof of concept for melanoma, this system is expected to be especially effective on solid tumors that are capable of creating neo-vasculature around themselves. The experiments reveal of the involvement of the PD-1/PD-L1 pathway proteins, and the presence of myeloid derived cells that are usually present in hypoxic conditions. The following are the categories of tumors based on immune infiltration:

a. "Hot" inflamed tumors: High mutational burden, T-cell infiltration, and elevated expression of PD-1 and PD-L1 proteins, like non-small cell lung cancer, liver cancer, bladder cancer, melanoma, head and neck cancer, etc.

b. "Warm" semi-inflamed tumors: Moderate mutational burden, peripheral presence of T-cells. PD-1 and PD-L1 proteins may or may not be expressed depending on the type of cancer. Examples: ovarian cancer, kidney cancer, some brain tumors, some lung cancers.

c. "Cold" non-inflamed tumors: Very few mutations, no T-cell infiltration, and virtually no PD-1 and PD-L1 proteins. Examples: ER+ breast and prostate cancers, pancreatic cancer, glioblastoma.

The $CD47^{-/-}$ whole-cell tumor vaccines according to the present technology would work on the "hot" and "warm" categories. They may also find use in the "cold" category, and also in tumors which are uncharacterized or which are heterogeneous and include regions or metastases of various types. As noted in the art, the irradiated tumor cells are antigenic, regardless of the $CD47^-$ mutation, and therefore the cells may have activity both specifically because of the CD47 knockout and for other reasons.

Further, it is noted that the vaccine operates to stimulate immune cells systemically, and not necessarily in proximity to a tumor. Inactivated such as irradiated $CD47^{-/-}$ (null) autologous cancer cells can serve as immunotherapy vaccines to eliminate (kill) and prevent the cancer recurrence after treatment. Further, the irradiated or otherwise inactivated cells may also be used as a heterologous vaccine. For example, if a patient has an aggressive tumor that has a likely future mutation with poor prognosis, a vaccine may be prepared from cells of a different patient that have already mutated, and thus induce immunity before the patient's own cells undergo the changes. This may also be used as a preventive vaccine in patients with high risk, but before neoplasia is found.

The genetic engineering of the cells is not limited to CD47 knockout and, for example, the same cells may have their genome edited with a knock-in of an immune-stimulatory adjuvant, such as GM-CSF, which enhances the efficacy of the inactivated $CD47^{-/-}$ autologous cancer vaccines. Further, other knock-outs or knock-ins may be provided, such as a PD-L1 knock-out.

The dual knock-out of CD47 and PD-L1 and knock-in GM-CSF tumor cells can be developed into immune checkpoint-free tumor organoids for in vitro training and generating tumor-responsive T cells by coculturing these tumor organoids with peripheral blood lymphocytes. The trained tumor responsive T cells can then be transplanted into patients to eliminate tumors, or to provide a reservoir of immunity against future tumors.

The efficacy of the $CD47^{-/-}$ vaccines can be further enhanced through cancer combination therapy by combining the vaccination with antibody therapy such as PD-L1 antibody therapy. Normally, the PD-L1 expresses at a low level. The expression of PD-L1 is usually upregulated under the stress such as production of IFN-γ or GM-CSF. The introduction of $CD47^{-/-}$ cancer vaccine as disclosed herein will induce the production of IFN-γ, upregulating PD-L1 expression on tumor cells. Therefore, the efficacy of $0D47^{-/-}$ vaccines can be considerably enhanced if anti PD-L1 antibodies are used along with vaccines, enabling more tumor-specific T cells to attack and kill tumor cells. PD-L1 antibody treatment has been successful, but being limited to very few tumors. The combination treatment with vaccine and PD-L1 antibody therapy will maximize the immunotherapy by targeting two immune checkpoints simultaneously.

It is therefore an object to provide a vaccine against a neoantigen, comprising a nucleated live cell expressing the neoantigen, which is genetically engineered to block expression of at least one immunosuppressive cell product, and which is nonapoptotic and replicatively incompetent.

It is also an object to provide a method of producing a vaccine against a neoantigen, and the vaccine per se, comprising: obtaining a nucleated live cell expressing the neoantigen; genetically engineering the live cell to block expression of at least one immunosuppressive cell product; and modifying the live cell to render it non-apoptotic and replicatively incompetent.

It is also an object to provide a method for preparing whole-cell vaccine, and the vaccine itself, comprising: isolating a live cell which expresses at least one tumor-associated antigen; genetically editing the live cell to suppress the presentation of cell surface CD47; and modifying the live cell to ensure that it remains alive but is incapable of proliferating in vivo in a patient.

It is a further object to provide a method of treating a disease, comprising: obtaining a biopsy sample from a patient comprising a cell type; genetically editing a cell of the cell type to knockout the expression of CD47; culturing the genetically edited cell to expand the culture; rendering cells of the expanded culture replication nonapoptotic and incompetent; and administering the nonapoptotic replication incompetent cells to the patient, to thereby induce an immune response in the patient to the cell type.

A further object provides a vaccine, comprising a mitosis-arrested and/or senescent cell expressing a target antigen, being genetically edited to reduce expression of a checkpoint molecule.

It is also an object to provide a vaccine, comprising genetically edited cells which express tumor-associated antigens, and do not express cell surface CD47, the genetically edited cells being incapable of proliferating in vivo in a patient and being nonapoptotic.

The method may further comprise administering the vaccine to an animal or human. The animal or human may be the same or different from a source of the cell. The method may further comprise obtaining the administering the live cell from a human suffering from a neoplasia, wherein the live cell is a neoplastic cell, and readministering the modified live cell to the human. The cell may be of an immunogenic or non-immunogenic tumor cell type. The cell type may be selected from the group consisting of melanoma, bladder cancer, head and neck cancers, kidney cancer, liver cancer, and non-small cell lung cancer. The cell type may be selected from the group consisting of ovarian, prostate, and pancreatic cancer. The cell type may be selected from the group consisting of non-small cell lung cancer, liver cancer, bladder cancer, melanoma, and head and neck cancer. The cell type may be a neoplastic cell having an elevated, or normal, or reduced expression of PD-1 and PD-L1 proteins with respect to normal cells from the same organ.

The at least one immunosuppressive cell product may comprise CD47 and/or PD-L1. The vaccine may be administered in conjunction (i.e., prior, concurrently, or subsequently) to a therapy targeting cells that express PD-1, CTLA-4 and/or LAG-3, e.g., monoclonal antibodies. The live nucleated cell may be further genetically engineered to express an immunostimulant. The immunostimulant may be a cytokine, such as GM-CSF. The cells may also produce a protease inhibitor, e.g., a serpin, that acts on the cell's own products or on factors produced by immune cells with which it interacts. Preferably, the protease inhibitor targets a regulatory pathway. The cells may also produce a protease, e.g., a serpin, that acts on proteins in its environment. For example, the protease can target immunosuppressive factors, or itself act in an immunostimulatory capacity. The protease may be a regulatory protein, e.g., which acts on a specific substrate, as part of a regulatory cascade, or a more generic degradative enzyme. The protease and/or protease inhibitor (s) may act to enhance the immune response to the vaccine, and/or reduce immunosuppressive effects of the tumor cell independent of CD47.

The cells may be genetically edited with CRISPR, e.g., CRISPR-Cas9, ZFN, TALEN, rAAV, transposons, or the like. The cell may express an RNAi, which reduces expression of the immune checkpoint molecule. The live nucleated cell may be genetically engineered to include at least one restriction endonuclease recognition site, a nuclease, and/or a guide RNA (gRNA).

The cell may be derived from a neoplastic cell, e.g., a melanoma cell. The cell may be rendered nonapoptotic and replicatively incompetent and/or senescent by irradiation, e.g., gamma irradiation.

The method may further comprise administering the vaccine to a human or animal, wherein the vaccine is an autologous vaccine derived from nucleated live cells of the same human or animal to which it is administered or a heterologous vaccine derived from nucleated live cells of a different human or animal to which it is administered.

The cell may be edited to knockout the expression of antigens specific to the human or animal from which it is derived, and/or to produce expression of antigens specific to the human or animal to which it is administered.

It is also an object to provide an ex vivo method of training immune cells to respond to cancer cells, comprising interacting cancer cells which express a neoantigen, with immune cells (myeloid cells), under conditions of depleted expression of their immune checkpoint blockades, to therefore train T-cells to recognize the neoantigen with reduced suppression by cellular "don't eat me" signals. The cancer cells may be obtained from a patient having a cancer, and the trained T-cells may be infused back into the patient. It is also an object to provide a method of training T-cells to target cancer cells expressing a neoantigen, comprising: extracting cancer cells expressing the neoantigen from a host; modifying the cancer cells expressing the neoantigen; and training T-cells to cause T-cell activation toward the cancer cells expressing the neoantigen, wherein at least one of the cancer cells and the T-cells are modified to eliminate SIRP-α binding to CD47, PD-L1 binding to PD-1, etc. The cancer cells may be derived from the same host or a different host. Likewise, activated T-cells may be infused back into the host, or a different host. Preferably, heterologously activated T-cells are genetically modified to prevent graft vs. host disease or host vs. graft disease.

Another object provides a method of training T-cells to target cancer cells expressing a neoantigen, comprising: providing cancer cells expressing the neoantigen; extracting T cells from a host; modifying at least one of the cancer cells and the T cells to increase immune recognition of the cancer cells by the T cells; and contacting the cancer cells with the T cells, to cause activation of the T-cells toward the cancer cells. The modifying may reduce at least one of SIRP-α binding of CD47 and a PD-L1 binding to PD-1, and the cancer cells may be provided during the contacting as organoids expressing the neoantigen comprising only replication-incompetent cells.

The cancer cells may be processed to form an organoid and used for immune training as described above. The cancer cells may be processed to render them nonapoptotic and replicatively incompetent, such as by irradiation. For example, organoids may be irradiated after reaching a desired stage of maturation. The cancer cells may be genetically edited to include a conditional lethal gene, wherein after training of the immune cells, the cancer cells are killed by triggering of the conditional lethality caused by the gene. The cancer cells may be further edited to alter expression of cytokines, and other immunostimulatory and/or immunosuppressive factors, in a manner to enhance training of immune cells to produce activated T cells. An organoid may be formed including the neoplastic cells, as well as other cells, e.g., fibroblasts, which may be normally differentiated or stem cells from the same host, or a different host. The organoid may be cultured to provide a plurality of cell types within the organoid, including cells which express the neoantigen. In some cases, the organoid emulates the source tumor, but in other cases, it may emulate an environment of a metastasis. In still other cases, it may emulate a privileged biological compartment or immune organ. Such immune checkpoint blockades depleted organoids can also be used as an in vitro model for determining the underlying mechanisms of vaccination.

The activated T-cells may then be reinfused into the host, to provide a therapy for the cancer.

The cancer cells expressing the neoantigen, and/or the entire organoid, may be are further modified to render them nonapoptotic and replicatively incompetent, for example by irradiation. The cancer cells may also be genetically edited to include a lethal susceptibility, and a condition which triggers the lethal susceptibility applied after training, to thereby kill the cancer cells and ensure that live cancer cells are not implanted into a host along with the trained T-cells.

Cell separation technology such as FACS (fluorescence-activated cell sorting) and/or MACS (magnetic-activated cell sorting) may also be used to selected trained T cells to ensure infusing only the activated T-cells into the host. (Lavender et al. 2013; Baglole et al. 2006; Kleeff et al. 2016; Kroemer et al. 2013; Peinado et al. 2017; Tseng et al. 2013; Fong et al. 2001; Mittal et al. 2014; Liu et al. 2015; Galon et al. 2002).

U.S. Patent Nos. and U.S. Published Patent Application Nos: U.S. Pat. Nos. 5,616,471; 5,631,237; 5,709,854; 5,756,291; 5,859,312; 6,129,761; 6,309,635; 6,340,461; 6,344,441; 6,372,494; 6,413,735; 6,673,908; 6,686,179; 6,759,047; 6,790,606; 6,805,869; 6,905,688; 6,905,827; 6,926,898; 6,946,134; 6,946,444; 6,962,974; 6,972,322; 6,974,667; 6,987,006; 6,989,365; 6,994,857; 7,005,276; 7,026,121; 7,041,478; 7,045,318; 7,056,701; 7,064,185; 7,081,345; 7,081,354; 7,094,577; 7,118,746; 7,141,363; 7,141,547; 7,189,507; 7,208,313; 7,220,722; 7,232,683; 7,235,358; 7,238,667; 7,244,578; 7,250,496; 7,252,949; 7,282,556; 7,371,734; 7,378,423; 7,387,779; 7,408,041; 7,410,779; 7,411,052; 7,415,358; 7,426,441; 7,427,665; 7,435,410; 7,435,412; 7,482,013; 7,498,171; 7,507,413; 7,507,414; 7,510,843; 7,514,229; 7,521,424; 7,521,540; 7,531,300; 7,550,432; 7,553,629; 7,588,767; 7,588,771; 7,592,010; 7,592,426; 7,595,159; 7,598,353; 7,601,355; 7,615,372; 7,622,108; 7,632,924; 7,645,575; 7,662,398; 7,666,596; 7,691,569; 7,709,256; 7,709,257; 7,709,616; 7,714,110; 7,754,221; 7,771,999; 7,775,469; 7,777,008; 7,781,212; 7,785,806; 7,785,883; 7,786,270; 7,794,715; 7,807,150; 7,807,382; 7,825,099; 7,829,336; 7,846,445; 7,847,079; 7,855,074; 7,855,279; 7,863,418; 7,888,050; 7,892,556; 7,915,000; 7,931,901; 7,935,338; 7,939,083; 7,939,263; 7,939,267; 7,960,512; 7,993,642; 7,998,460; 8,003,385; 8,003,387; 8,003,774; 8,008,073; 8,014,957; 8,021,662; 8,030,070; 8,034,903; 8,044,178; 8,044,180; 8,044,193; 8,062,889; 8,067,187; 8,071,373; 8,071,539; 8,075,884; 8,080,416; 8,114,403; 8,114,617; 8,114,832; 8,119,403; 8,124,083; 8,129,340; 8,133,982; 8,138,147; 8,142,791; 8,142,994; 8,148,106; 8,158,360; 8,158,385; 8,187,593; 8,187,877; 8,188,232; 8,192,737; 8,193,318; 8,206,710; 8,206,907; 8,211,439; 8,216,574; 8,216,579; 8,217,147; 8,221,769; 8,236,313; 8,247,226; 8,252,739; 8,263,344; 8,277,812; 8,288,159; 8,298,823; 8,298,824; 8,318,492; 8,323,959; 8,329,868; 8,343,497; 8,343,498; 8,361,485; 8,361,736; 8,377,448; 8,377,902; 8,389,691; 8,404,654; 8,444,972; 8,470,815; 8,476,231; 8,481,271; 8,481,703; 8,491,913; 8,492,328; 8,492,530; 8,506,947; 8,507,434; 8,513,189; 8,524,237; 8,524,656; 8,530,627; 8,541,033; 8,541,185; 8,546,541; 8,557,241; 8,557,788; 8,562,997; 8,562,998; 8,586,039; 8,591,905; 8,628,762; 8,629,151; 8,637,028; 8,647,837; 8,652,466; 8,658,173; 8,668,926; 8,669,105; 8,691,780; 8,697,071; 8,697,371; 8,709,415; 8,709,429; 8,716,465; 8,722,402; 8,728,456; 8,728,476; 8,758,750; 8,759,495; 8,765,120; 8,778,339; 8,784,808; 8,784,836; 8,785,599; 8,790,895; 8,791,238; 8,802,091; 8,802,093; 8,802,240; 8,802,438; 8,835,398; 8,835,443; 8,840,885; 8,840,889; 8,853,382; 8,862,448; 8,865,672; 8,871,219; 8,883,506; 8,883,980; 8,889,411; 8,895,000; 8,906,381; 8,906,607; 8,920,776; 8,932,583; 8,932,595; 8,933,197; 8,945,543; 8,946,387; 8,951,517; 8,951,527; 8,951,737; 8,962,319; 8,962,804; 8,968,730; 8,969,289; 8,980,864; 8,986,684; 8,993,517; 8,999,328; 8,999,380; 8,999,654; 9,000,133; 9,005,613; 9,006,254; 9,012,399; 9,017,693; 9,018,358; 9,028,815; 9,045,541; 9,045,562; 9,050,279; 9,050,297; 9,061,059; 9,089,604; 9,095,552; 9,096,877; 9,107,886; 9,114,113; 9,115,197; 9,115,388; 9,127,292; 9,132,210; 9,133,239; 9,144,614; 9,144,690; 9,149,506; 9,150,656; 9,150,661; 9,151,760; 9,156,897; 9,175,083; 9,181,319; 9,186,372; 9,187,544; 9,192,651; 9,193,794; 9,193,955; 9,193,977; 9,198,949; 9,201,063; 9,205,148; 9,216,205; 9,220,714; 9,220,755; 9,220,788; 9,220,792; 9,221,891; 9,221,896; 9,221,908; 9,233,072; 9,233,141; 9,233,154; 9,234,896; 9,238,084; 9,241,994; 9,243,069; 9,249,229; 9,254,311; 9,255,129; 9,271,996; 9,279,019; 9,283,287; 9,289,395; 9,295,689; 9,296,801; 9,296,809; 9,296,820; 9,297,005; 9,301,993; 9,303,079; 9,308,280; 9,309,510; 9,315,824; 9,320,813; 9,328,346; 9,334,328; 9,334,329; 9,339,519; 9,340,584; 9,352,004; 9,352,037; 9,358,282; 9,370,558; 9,381,235; 9,382,285; 9,382,320; 9,393,396; 9,394,365; 9,399,679; 9,399,682; 9,402,377; 9,402,916; 9,428,535; 9,428,553; 9,439,859; 9,441,049; 9,446,107; 9,447,164; 9,452,228; 9,458,486; 9,460,263; 9,462,794; 9,463,217; 9,464,124; 9,469,692; 9,474,717; 9,486,512; 9,487,587; 9,492,499; 9,492,534; 9,492,536; 9,492,566; 9,493,569; 9,493,575; 9,498,536; 9,504,236; 9,505,842; 9,512,225; 9,512,227; 9,517,276; 9,518,116; 9,518,117; 9,522,195; 9,522,944; 9,526,702; 9,527,901; 9,533,047; 9,534,052; 9,539,210; 9,539,245; 9,539,309; 9,540,424; 9,546,206; 9,562,073; 9,562,087; 9,566,250; 9,572,897; 9,574,014; 9,574,211; 9,579,300; 9,585,920; 9,587,003; 9,597,357; 9,597,380; 9,598,492; 9,603,878; 9,603,894; 9,605,076; 9,610,328; 9,611,329; 9,611,458; 9,624,276; 9,624,297; 9,624,305; 9,625,444; 9,629,877; 9,639,660; 9,644,005; 9,644,180; 9,650,440; 9,650,441; 9,650,445; 9,655,352; 9,657,105; 9,657,295; 9,663,575; 9,669,108; 9,670,205; 9,670,269; 9,670,281; 9,675,561; 9,675,668; 9,676,856; 9,677,125; 9,682,934; 9,693,954; 9,694,084; 9,700,027; 9,701,758; 9,701,965; 9,708,333; 9,708,408; 9,714,295; 9,714,296; 9,717,694; 9,726,668; 9,726,676; 9,730,967; 9,737,480; 9,737,599; 9,738,646; 9,738,724; 9,745,367; 9,750,709; 9,750,814; 9,750,816; 9,757,196; 9,764,039; 9,764,145; 9,765,143; 9,770,512; 9,770,517; 9,770,535; 9,771,428; 9,775,332; 9,777,061; 9,777,066; 9,782,462; 9,783,593; 9,783,618; 9,788,534; 9,789,171; 9,790,275; 9,790,490; 9,790,503; 9,796,781; 9,796,783; 9,803,016; 9,803,177; 9,804,160; 9,809,581; 9,814,760; 9,815,901; 9,816,080; 9,816,094; 9,820,476; 9,821,045; 9,821,068; 9,822,180; 9,827,329; 9,827,332; 9,828,416; 9,834,545; 9,834,608; 9,834,787; 9,834,790; 9,834,791; 9,839,208; 9,839,614; 9,839,687; 9,840,493; 9,840,503; 9,845,345; 9,849,092; 9,850,483; 9,856,314; 9,856,318; 9,856,479; 9,856,497; 9,862,705; 9,862,927; 9,872,900; 9,873,734; 9,873,747; 9,878,056; 9,884,112; 9,884,813; 9,884,893; 9,888,673; 9,888,956; 9,889,141; 9,889,164; 9,894,888; 9,895,189; 9,895,451; 9,896,508; 9,896,516; 9,901,082; 9,901,083; 9,902,771; 9,902,970; 9,914,759; 9,914,774; 9,914,938; 9,920,122; 9,920,295; 9,920,317; 9,924,705; 9,925,183; 9,925,247; 9,925,277; 9,932,591; 9,937,233; 9,937,249; 9,938,331; 9,938,345; 9,938,357; 9,938,358; 9,939,443; 9,944,647; 9,950,068; 9,951,065; 9,958,448; 9,963,716; 9,969,789; 9,974,774; 9,981,975; 9,982,047; 9,982,048; 9,982,049; 9,982,050; 9,982,051; 9,982,057; 9,986,724; 9,987,500; 9,988,408; 9,988,448; 9,988,452; 9,993,460; 9,993,563; 9,994,527; 9,994,821; 10,000,746; 10,015,953; 10,016,480; 10,022,425; 10,022,436; 10,023,623; 10,023,840; 10,023,880; 10,035,855; 10,035,859; 10,035,860; 10,036,040; 10,045,947; 10,053,683; 10,053,694; 10,064,398; 10,064,925; 10,064,959; 10,077,442; 10,080,789; 10,081,680; 10,081,792; 10,081,798; 10,086,042; 10,087,257; 10,087,442; 20010026937; 20020006397; 20020037279; 20020039786; 20020102278; 20020142981; 20020150986; 20020151498; 20020165154; 20020177551; 20020182188; 20030026803; 20030031681; 20030032034; 20030064053;

20030124614; 20030129202; 20030138432; 20030144494; 20030148316; 20030157113; 20030162230; 20030202977; 20030228570; 20030235561; 20030235909; 20040002124; 20040005563; 20040009479; 20040010119; 20040029114; 20040033493; 20040043010; 20040047858; 20040058883; 20040072160; 20040076955; 20040077601; 20040106120; 20040110227; 20040142885; 20040147731; 20040214783; 20050005316; 20050031643; 20050069549; 20050084490; 20050112141; 20050118164; 20050118715; 20050123522; 20050136066; 20050142539; 20050142587; 20050148072; 20050169914; 20050181375; 20050220789; 20050221435; 20050255114; 20050271659; 20050282177; 20060003322; 20060014768; 20060019256; 20060040392; 20060051370; 20060051803; 20060063156; 20060073591; 20060074034; 20060078540; 20060078900; 20060084055; 20060084167; 20060088522; 20060088820; 20060088836; 20060104987; 20060111312; 20060122132; 20060134109; 20060134122; 20060134664; 20060149049; 20060153860; 20060165684; 20060171988; 20060188508; 20060199204; 20060199231; 20060222588; 20060223121; 20060239910; 20060239911; 20060241067; 20060251646; 20060257903; 20060257965; 20060263783; 20060263803; 20060263813; 20060269949; 20060292143; 20060292683; 20060293708; 20070015206; 20070025981; 20070031890; 20070041904; 20070041981; 20070071745; 20070077232; 20070099209; 20070105133; 20070111238; 20070134657; 20070134690; 20070135393; 20070154458; 20070154931; 20070161587; 20070190078; 20070202572; 20070209082; 20070212727; 20070219125; 20070231333; 20070243177; 20070269432; 20080020979; 20080026980; 20080039341; 20080047026; 20080050374; 20080051565; 20080057508; 20080076715; 20080081038; 20080085277; 20080102054; 20080108583; 20080118529; 20080131431; 20080207488; 20080213839; 20080214452; 20080227712; 20080249009; 20080249606; 20080260744; 20080268453; 20080274091; 20080286808; 20080292546; 20080292615; 20080305965; 20080306004; 20080312228; 20090004134; 20090004172; 20090004178; 20090004211; 20090004678; 20090005302; 20090005305; 20090010908; 20090010952; 20090041825; 20090048159; 20090048266; 20090075877; 20090081228; 20090092582; 20090099031; 20090104195; 20090104628; 20090123503; 20090136917; 20090155254; 20090156786; 20090163434; 20090175827; 20090178153; 20090181863; 20090186073; 20090191912; 20090191548; 20090192102; 20090203588; 20090215053; 20090226406; 20090227025; 20090227533; 20090232893; 20090258002; 20090280124; 20090280135; 20090286856; 20090324594; 20100008946; 20100015126; 20100015653; 20100016235; 20100021454; 20100021483; 20100029746; 20100041875; 20100047276; 20100062007; 20100062016; 20100068147; 20100092425; 20100092467; 20100092989; 20100093556; 20100104582; 20100105054; 20100105066; 20100112568; 20100120043; 20100129392; 20100129439; 20100137149; 20100143372; 20100173024; 20100173382; 20100183727; 20100184032; 20100189682; 20100196426; 20100197015; 20100203010; 20100233199; 20100233251; 20100233808; 20100239579; 20100240613; 20100240732; 20100247562; 20100254981; 20100260706; 20100261172; 20100261190; 20100267648; 20100272824; 20100273258; 20100273667; 20100292155; 20100303850; 20100305003; 20100306863; 20100310534; 20100330046; 20110003704; 20110008382; 20110014119; 20110015090; 20110016543; 20110020388; 20110023143; 20110027217; 20110027235; 20110028395; 20110030072; 20110038841; 20110038870; 20110053157; 20110059901; 20110060120; 20110070229; 20110070230; 20110071054; 20110071276; 20110092381; 20110093249; 20110124552; 20110129817; 20110135641; 20110142902; 20110151433; 20110152115; 20110165588; 20110166199; 20110171687; 20110182937; 20110183866; 20110185439; 20110189181; 20110190157; 20110196614; 20110206696; 20110214189; 20110217308; 20110217715; 20110223201; 20110224800; 20110230647; 20110236401; 20110250220; 20110251077; 20110251108; 20110262491; 20110268804; 20110268805; 20110275096; 20110287022; 20110288080; 20110300176; 20110305663; 20120010090; 20120027808; 20120039841; 20120046346; 20120064600; 20120065086; 20120072124; 20120087890; 20120094301; 20120094395; 20120114759; 20120135426; 20120135521; 20120149714; 20120164101; 20120171200; 20120190730; 20120192298; 20120207759; 20120219559; 20120220011; 20120220484; 20120222140; 20120225073; 20120230940; 20120230947; 20120233715; 20120237500; 20120276010; 20120282174; 20120295285; 20120295956; 20120295957; 20120301400; 20120308484; 20120315216; 20120322864; 20120322865; 20120322986; 20130011401; 20130011438; 20130034847; 20130039884; 20130039925; 20130078242; 20130116150; 20130123192; 20130129790; 20130130317; 20130131194; 20130156795; 20130189741; 20130190385; 20130190387; 20130203169; 20130209398; 20130209427; 20130209471; 20130210076; 20130210725; 20130216506; 20130217069; 20130217129; 20130224188; 20130225435; 20130230921; 20130236533; 20130244256; 20130244326; 20130247233; 20130252895; 20130267684; 20130287729; 20130287857; 20130296185; 20130323254; 20130323819; 20130330325; 20130331383; 20130336925; 20130337066; 20130337474; 20130338067; 20130338089; 20130340105; 20140017215; 20140023664; 20140030344; 20140037736; 20140038833; 20140044735; 20140044738; 20140045915; 20140046030; 20140056936; 20140057257; 20140065169; 20140066598; 20140079836; 20140080732; 20140086957; 20140100164; 20140101786; 20140113348; 20140113832; 20140120622; 20140127269; 20140127301; 20140134662; 20140140989; 20140141986; 20140148350; 20140161805; 20140161825; 20140178400; 20140179770; 20140193453; 20140194319; 20140194613; 20140199308; 20140242173; 20140242699; 20140248273; 20140255313; 20140255369; 20140255431; 20140256649; 20140271582; 20140271641; 20140275082; 20140286959; 20140294891; 20140296161; 20140302060; 20140303354; 20140308302; 20140308746; 20140314865; 20140315984; 20140328825; 20140356326; 20140363496; 20140369924; 20140370012; 20140377221; 20140377287; 20150005477; 20150017187; 20150020223; 20150030533; 20150030535; 20150030657; 20150037359; 20150044222; 20150056636; 20150065556; 20150072893; 20150073041; 20150079046; 20150079088; 20150087810; 20150089678; 20150089679; 20150094518; 20150100345; 20150110806; 20150110836; 20150126456; 20150132313; 20150140566; 20150147276; 20150147336; 20150150996; 20150152147; 20150152187; 20150152474; 20150164955; 20150167088; 20150168405; 20150175707; 20150182588; 20150183812; 20150203579; 20150203580; 20150208622; 20150209389; 20150211020; 20150218217; 20150232881; 20150232883; 20150238604; 20150246073; 20150250896; 20150259431; 20150265725; 20150266942; 20150266956; 20150268245; 20150274826; 20150284416; 20150284445; 20150284688; 20150285802; 20150291966; 20150297745; 20150299197; 20150301055; 20150301058; 20150306212; 20150314017; 20150315289; 20150320810; 20150322155; 20150328300; 20150329875; 20150330997; 20150343055; 20150344584; 20150353642; 20150366897; 20150366988; 20150368719; 20150374790; 20150376288; 20150376296; 20160000886; 20160000909; 20160002336; 20160002729; 20160003835; 20160007893; 20160008374; 20160008463; 20160009813; 20160009814; 20160009815; 20160022976; 20160024211; 20160038467; 20160038576; 20160038612;

20160039903; 20160039908; 20160045532; 20160045551; 20160046724; 20160047735; 20160050896; 20160051651; 20160052983; 20160052990; 20160053003; 20160058793; 20160058885; 20160060342; 20160060594; 20160060707; 20160060709; 20160068596; 20160068601; 20160069889; 20160083791; 20160089397; 20160090603; 20160096892; 20160097773; 20160101111; 20160101150; 20160108045; 20160108123; 20160122707; 20160130348; 20160130552; 20160130569; 20160139012; 20160143961; 20160144009; 20160144026; 20160153004; 20160153005; 20160153053; 20160157470; 20160159905; 20160159920; 20160165861; 20160166546; 20160168242; 20160175308; 20160175358; 20160175462; 20160176916; 20160176948; 20160176976; 20160176978; 20160185859; 20160186146; 20160186150; 20160193252; 20160193258; 20160193357; 20160194368; 20160194399; 20160194406; 20160194625; 20160199424; 20160200804; 20160200816; 20160206566; 20160207949; 20160207987; 20160208243; 20160215052; 20160219845; 20160220537; 20160222097; 20160222121; 20160235045; 20160235730; 20160235731; 20160235788; 20160235792; 20160237132; 20160237400; 20160237455; 20160243221; 20160243247; 20160243259; 20160244501; 20160244502; 20160244522; 20160244528; 20160244751; 20160245336; 20160251435; 20160251477; 20160256448; 20160256458; 20160257751; 20160257932; 20160264665; 20160271188; 20160273046; 20160278350; 20160280753; 20160282365; 20160283653; 20160287670; 20160289229; 20160289238; 20160289324; 20160289341; 20160289343; 20160297880; 20160298082; 20160299146; 20160303095; 20160304969; 20160311903; 20160311905; 20160311908; 20160311917; 20160312295; 20160312297; 20160317647; 20160319021; 20160319256; 20160319361; 20160324897; 20160324983; 20160326253; 20160326261; 20160326263; 20160326585; 20160326596; 20160331828; 20160333008; 20160333009; 20160333114; 20160339064; 20160340397; 20160340407; 20160340661; 20160340743; 20160345549; 20160347857; 20160348073; 20160354397; 20160355587; 20160355592; 20160355599; 20160355797; 20160362464; 20160362472; 20160362678; 20160366862; 20160367670; 20160368994; 20160369002; 20160369269; 20160374321; 20160374949; 20160375033; 20160375148; 20160376333; 20160376663; 20170000779; 20170000869; 20170002060; 20170002068; 20170002088; 20170007644; 20170007685; 20170008891; 20170008951; 20170009238; 20170014527; 20170020835; 20170020926; 20170020956; 20170023548; 20170027140; 20170028079; 20170029418; 20170029508; 20170035808; 20170037431; 20170038394; 20170038395; 20170044164; 20170044258; 20170044259; 20170051358; 20170053091; 20170055561; 20170056347; 20170056470; 20170057965; 20170065636; 20170067021; 20170067065; 20170067875; 20170071918; 20170071944; 20170072067; 20170072071; 20170073414; 20170073425; 20170073664; 20170079916; 20170080029; 20170081407; 20170088898; 20170095531; 20170095552; 20170096671; 20170100486; 20170101472; 20170106068; 20170107216; 20170107270; 20170107300; 20170107536; 20170107578; 20170114413; 20170115291; 20170119687; 20170119820; 20170119930; 20170121310; 20170121409; 20170121771; 20170122853; 20170128490; 20170128505; 20170130200; 20170130232; 20170130247; 20170130271; 20170136073; 20170137783; 20170137845; 20170137885; 20170143830; 20170143845; 20170144996; 20170144997; 20170145025; 20170145381; 20170145464; 20170151281; 20170151282; 20170151339; 20170151451; 20170152274; 20170152528; 20170157230; 20170157262; 20170158749; 20170165298; 20170165375; 20170166903; 20170173001; 20170173085; 20170173109; 20170173128; 20170173168; 20170173176; 20170174671; 20170174679; 20170174713; 20170174748; 20170174779; 20170174781; 20170174790; 20170175128; 20170182096; 20170183420; 20170184565; 20170184604; 20170188555; 20170190776; 20170191034; 20170191055; 20170191128; 20170196818; 20170196966; 20170198038; 20170198051; 20170198302; 20170198308; 20170199193; 20170202914; 20170202975; 20170202979; 20170204139; 20170204152; 20170204181; 20170204407; 20170204422; 20170209492; 20170209595; 20170209864; 20170210788; 20170210802; 20170210803; 20170210811; 20170210812; 20170211055; 20170216353; 20170218086; 20170224734; 20170224737; 20170224814; 20170224837; 20170226217; 20170226223; 20170226507; 20170233451; 20170233474; 20170233808; 20170240613; 20170240634; 20170240637; 20170240639; 20170247464; 20170247685; 20170248603; 20170252379; 20170252396; 20170253933; 20170258882; 20170260137; 20170260245; 20170260268; 20170260277; 20170260763; 20170265442; 20170267637; 20170269093; 20170274014; 20170275290; 20170275364; 20170281627; 20170281684; 20170281791; 20170281795; 20170283497; 20170283807; 20170290858; 20170290899; 20170290923; 20170291945; 20170291958; 20170296623; 20170296663; 20170306038; 20170306303; 20170306416; 20170313707; 20170313781; 20170313978; 20170314075; 20170320875; 20170320945; 20170321194; 20170321220; 20170321443; 20170326093; 20170326179; 20170327567; 20170327577; 20170327590; 20170334967; 20170335281; 20170335331; 20170335344; 20170340724; 20170340725; 20170342060; 20170342068; 20170342119; 20170342380; 20170342390; 20170343552; 20170343554; 20170348234; 20170348390; 20170348391; 20170348415; 20170348429; 20170349433; 20170349658; 20170349874; 20170349950; 20170350879; 20170355767; 20170355773; 20170355774; 20170355958; 20170356022; 20170356903; 20170360706; 20170360836; 20170360873; 20170360932; 20170360959; 20170360963; 20170361126; 20170362253; 20170362302; 20170362329; 20170362332; 20170362334; 20170362582; 20170362593; 20170362605; 20170368169; 20170369572; 20170369573; 20170369828; 20170369843; 20180000865; 20180000914; 20180002422; 20180008694; 20180009779; 20180009815; 20180009816; 20180009893; 20180009895; 20180010082; 20180010179; 20180015137; 20180015153; 20180016260; 20180016344; 20180016352; 20180020647; 20180021429; 20180021448; 20180022781; 20180022806; 20180022813; 20180028455; 20180028645; 20180028651; 20180028686; 20180030137; 20180030142; 20180030148; 20180030411; 20180030515; 20180036289; 20180036425; 20180037652; 20180037861; 20180037898; 20180038865; 20180042905; 20180044404; 20180044423; 20180044424; 20180044662; 20180049413; 20180049984; 20180051081; 20180051335; 20180051347; 20180052176; 20180055891; 20180057486; 20180057594; 20180057598; 20180064425; 20180064745; 20180064787; 20180065938; 20180066262; 20180066285; 20180068057; 20180070564; 20180071344; 20180072718; 20180072719; 20180072720; 20180072740; 20180072741; 20180072743; 20180078624; 20180079812; 20180080087; 20180085434; 20180085447; 20180085465; 20180086734; 20180086755; 20180086829; 20180092338; 20180092937; 20180092968; 20180092973; 20180094231; 20180094244; 20180098972; 20180100026; 20180100201; 20180100860; 20180104187; 20180105591; 20180105592; 20180105600; 20180110772; 20180110831; 20180110847; 20180110874; 20180111997; 20180111998; 20180111999; 20180112213; 20180117117; 20180117150; 20180118826; 20180118834; 20180119101; 20180119107; 20180119118; 20180125892; 20180125935; 20180125988; 20180126001; 20180126003; 20180126014; 20180127499; 20180127509; 20180127748; 20180127783; 20180133296;

20180134684; 20180135012; 20180135020; 20180139941; 20180140602; 20180140698; 20180141934; 20180141939; 20180141986; 20180142018; 20180142019; 20180142035; 20180142257; 20180142258; 20180147257; 20180148503; 20180148512; 20180148514; 20180148790; 20180153796; 20180153821; 20180153884; 20180153937; 20180153942; 20180153975; 20180153978; 20180153984; 20180153989; 20180155405; 20180155424; 20180155716; 20180155717; 20180156798; 20180156800; 20180156807; 20180160662; 20180161300; 20180161307; 20180161349; 20180161371; 20180162903; 20180162937; 20180162939; 20180162940; 20180163178; 20180163197; 20180163210; 20180163882; 20180168488; 20180168489; 20180168490; 20180169027; 20180169091; 20180169097; 20180169153; 20180169154; 20180169230; 20180170907; 20180170916; 20180171014; 20180171028; 20180171337; 20180177784; 20180177827; 20180177870; 20180179179; 20180179197; 20180179201; 20180179202; 20180179221; 20180179492; 20180179494; 20180179590; 20180179591; 20180179601; 20180184630; 20180185351; 20180185668; 20180185844; 20180186878; 20180186882; 20180186883; 20180187149; 20180187153; 20180187154; 20180192623; 20180193479; 20180194831; 20180200366; 20180200378; 20180201661; 20180201677; 20180201901; 20180207267; 20180207273; 20180208636; 20180208659; 20180208897; 20180208903; 20180208943; 20180209983; 20180211447; 20180214524; 20180214566; 20180214579; 20180216067; 20180216073; 20180216078; 20180216162; 20180217131; 20180221362; 20180221381; 20180221508; 20180222944; 20180222982; 20180223256; 20180224432; 20180228786; 20180228881; 20180228926; 20180229241; 20180230417; 20180235894; 20180235897; 20180238884; 20180243311; 20180243341; 20180243426; 20180243444; 20180244627; 20180244738; 20180244748; 20180246099; 20180249688; 20180249689; 20180250339; 20180250395; 20180250405; 20180250418; 20180251460; 20180251464; 20180251521; 20180251533; 20180251558; 20180251563; 20180252727; 20180256549; 20180256572; 20180256624; 20180256709; 20180256742; 20180256747; 20180258149; 20180258158; 20180258186; 20180258411; 20180258422; 20180258484; 20180263985; 20180264094; 20180264095; 20180264186; 20180265530; 20180265847; 20180267043; 20180267516; 20180271795; 20180271870; 20180271891; 20180271910; 20180271970; 20180271975; 20180271992; 20180273519; 20180273531; 20180273578; 20180273903; 20180273948; 20180273980; 20180274043; 20180275143; 20180280451; 20180280502; 20180280532; 20180280539; 20180282693; 20180282726; 20180282803; and 20180282808.

Ain, Qurrat U I, Jee Young Chung, and Yong-Hee Kim. "Current and future delivery systems for engineered nucleases: ZFN, TALEN and RGEN." Journal of Controlled Release 205 (2015): 120-127.

Akhter, A., M. A. Gavrilin, L. Frantz, S. Washington, C. Ditty, D. Limoli, C. Day, A. Sarkar, C. Newland, J. Butchar, C. B. Marsh, M. D. Wewers, S. Tridandapani, T. D. Kanneganti, A. O. Amer, Caspase-7 activation by the NIrc4/Ipaf inflammasome restricts Legionella pneumophila infection. PLoS Pathog. 5 (2009) e1000361.

Alvey, Cory, and Dennis E. Discher. "Engineering macrophages to eat cancer: from "marker of self" CD47 and phagocytosis to differentiation." Journal of leukocyte biology 102, no. 1 (2017): 31-40.

Anderson, A. C., N. Joller, and V. K. Kuchroo, *Lag-3, Tim-3, and TIGIT: Co-inhibitory Receptors with Specialized Functions in Immune Regulation*. Immunity, 2016. 44(5): p. 989-1004.

Ankarcrona, M., J. M. Dypbukt, E. Bonfoco, B. Zhivotovsky, S. Orrenius, S. A. Lipton, P. Nicotera, Glutamate-induced neuronal death: a succession of necrosis or apoptosis depending on mitochondrial function. Neuron 15 (1995) 961-973.

Baglole, Carolyn J., Denise M. Ray, Steven H. Bernstein, Steven E. Feldon, Terry J. Smith, Patricia J. Sime, and Richard P. Phipps. "More than structural cells, fibroblasts create and orchestrate the tumor microenvironment." Immunological investigations 35, no. 3-4 (2006): 297-325.

Balachandran, S., E. Thomas, G. N. Barber, A FADD-dependent innate immune mechanism in mammalian cells. Nature 432 (2004) 401-405.

Barclay A. N. and Van den Berg T. K. 2014. The interaction between signal regulatory protein alpha (SIRP-α) and CD47: structure, function, and therapeutic target. Annu Rev Immunol. 32:25-50.

Bell, B. D., S. Leverrier, B. M. Weist, R. H. Newton, A. F. Arechiga, K. A. Luhrs, N. S. Morrissette, C. M. Walsh, FADD and caspase-8 control the outcome of autophagic signaling in proliferating T cells. Proc. Natl. Acad. Sci. U.S.A. 105 (2008) 16677-16682.

Benencia, F., et al., *Dendritic cells the tumor microenvironment and the challenges for an effective antitumor vaccination*. J Biomed Biotechnol, 2012. 2012: p. 425476.

Bergsbaken, T., S. L. Fink, B. T. Cookson, Pyroptosis: host cell death and inflammation. Nat. Rev. Microbiol. 7 (2009) 99-109.

Berry, D. L., E. H. Baehrecke, Growth arrest and autophagy are required for salivary gland cell degradation in *Drosophila*. Cell 131 (2007) 1137-1148.

Brennan, M. A., B. T. Cookson, *Salmonella* induces macrophage death by caspase-1-dependent necrosis. Mol. Microbiol. 38 (2000) 31-40.

Brightwell, R. M., K. S. Grzankowski, S. Lele, K. Eng, M. Arshad, H. Chen, and K. Odunsi. "The CD47 "don't eat me signal" is highly expressed in human ovarian cancer." Gynecologic oncology 143, no. 2 (2016): 393-397.

Bronte, V., et al., *Recommendations for myeloid-derived suppressor cell nomenclature and characterization standards*. Nat Commun, 2016. 7: p. 12150.

Bullock, T. N., *TNF-receptor superfamily agonists as molecular adjuvants for cancer vaccines*. Curr Opin Immunol, 2017. 47: p. 70-77.

Cannon, Martin J., and Timothy J. O'Brien. "Cellular immunotherapy for ovarian cancer." Expert opinion on biological therapy 9, no. 6 (2009): 677-688.

Carucci, John A. "Understanding dendritic cells and their role in cutaneous carcinoma and cancer immunotherapy." Clinical and Developmental Immunology 2013 (2013).

Chamuleau, M. E., G. J. Ossenkoppele, and A. A. van de Loosdrecht, *MHC class II molecules in tumour immunology: prognostic marker and target for immune modulation*. Immunobiology, 2006. 211(6-8): p. 619-25.

Chan, F. K., J. Shisler, J. G. Bixby, M. Felices, L. Zheng, M. Appel, J. Orenstein, B. Moss, M. J. Lenardo, A role for tumor necrosis factor receptor-2 and receptor-interacting protein in programmed necrosis and antiviral responses. J. Biol. Chem. 278 (2003) 51613-51621.

Chao M P, Jaiswal S, Weissman-Tsukamoto R, Alizadeh A A, Gentles A J, Volkmer J, et al. Calreticulin is the dominant pro-phagocytic signal on multiple human cancers and is counterbalanced by CD47. Sci Transl Med. 2010; 2:63-94.

Chao, M. P., I. L. Weissman, and R. Majeti, *The CD47-SIRP-α pathway in cancer immune evasion and potential therapeutic implications*. Curr Opin Immunol, 2012. 24(2): p. 225-32.

Chautan, M., G. Chazal, F. Cecconi, P. Gruss, P. Golstein, Interdigital cell death can occur through a necrotic and caspase-independent pathway. Curr. Biol. 9 (1999) 967-970.

Cheung, Alexander S., Sandeep T. Koshy, Alexander G. Stafford, Maartje M C Bastings, and David J. Mooney. "Adjuvant-Loaded Subcellular Vesicles Derived From Disrupted Cancer Cells for Cancer Vaccination." Small 12, no. 17 (2016): 2321-2333.

Chiang C L, Benencia F, Coukos G. Whole tumor antigen vaccines. Semin Immunol. 2010; 22:132-43.

Cho, Y., S. Challa, D. Moquin, R. Genga, T. D. Ray, M. Guildford, F. K.-M. Chan, Phosphorylation-driven assembly of the RIP1-RIP3 complex regulates programmed necrosis and virus-induced inflammation. Cell 137 (2009) 1112-1123.

Choi P. S. and Meyerson M. 2014. Targeted genomic rearrangements using CRISPR/Cas technology. Nature Communications 5:3728. doi:10.1038/ncomms4728

Cornelis, S., K. Kersse, N. Festjens, M. Lamkanfi, P. Vandenabeele, Inflammatory caspases: targets for novel therapies. Curr. Pharm. Des. 13 (2007) 367-385.

Curiel, Tyler J., et al. "Specific recruitment of regulatory T cells in ovarian carcinoma fosters immune privilege and predicts reduced survival." Nature medicine 10.9 (2004): 942-949. PubMed PMID: 15322536.

Curran, E., et al., *STING Pathway Activation Stimulates Potent Immunity against Acute Myeloid Leukemia*. Cell Rep, 2016. 15(11): p. 2357-66.

Curran, Emily, Leticia Corrales, and Justin Kline. "Targeting the innate immune system as immunotherapy for acute myeloid leukemia." Frontiers in oncology 5 (2015): 83.

Danial, Nika N., and Stanley J. Korsmeyer. "Cell death: critical control points." Cell 116, no. 2 (2004): 205-219.

de Gruijl T D, van den Eertwegh A J, Pinedo H M, Scheper R J. Whole-cell cancer vaccination: from autologous to allogeneic tumor- and dendritic cell-based vaccines. Cancer Immunol Immunother. 2008; 57:1569-1577.

Degterev, A., J. Hitomi, M. Germscheid, I. L. Ch'en, O. Korkina, X. Teng, D. Abbott, G. D. Cuny, C. Yuan, G. Wagner, S. M. Hedrick, S. A. Gerber, A. Lugovskoy, J. Yuan, Identification of RIP1 kinase as a specific cellular target of necrostatins. Nat. Chem. Biol. 4 (2008) 313-321.

Degterev, A., Z. Huang, M. Boyce, Y. Li, P. Jagtap, N. Mizushima, G. D. Cuny, T. J. Mitchison, M. A. Moskowitz, J. Yuan, Chemical inhibitor of nonapoptotic cell death with therapeutic potential for ischemic brain injury. Nat. Chem. Biol. 1 (2005) 112-119.

Dhodapkar, Madhav V., and Kavita M. Dhodapkar. "Vaccines targeting cancer stem cells: are they within reach?." Cancer journal (Sudbury, Mass.) 17, no. 5 (2011): 397.

Dranoff, G., et al., *Vaccination with irradiated tumor cells engineered to secrete murine granulocyte-macrophage colony-stimulating factor stimulates potent, specific, and long-lasting anti-tumor immunity*. Proc Natl Acad Sci USA, 1993. 90(8): p. 3539-43.

Dudek, A. M., et al., *Immature, Semi-Mature, and Fully Mature Dendritic Cells: Toward a DC-Cancer Cells Interface That Augments Anticancer Immunity*. Front Immunol, 2013. 4: p. 438.

Dunn, G. P., L. J. Old, and R. D. Schreiber, *The immunobiology of cancer immunosurveillance and immunoediting*. Immunity, 2004. 21(2): p. 137-48.

Dunn, Gavin P., et al. "Cancer immunoediting: from immunosurveillance to tumor escape." Nature immunology 3.11 (2002): 991-998. PubMed PMID: 12407406.

Duprez, L., E. Wirawan, T. Vanden Berghe, P. Vandenabeele, "Major cell death pathways at a glance", Microbes Infect., 11 (2009), pp. 1050-1062.

Earls J K, Jin S, Ye K. Mechanobiology of human pluripotent stem cells. Tissue Eng Part B Rev. 2013; 19:420-30.

Eder, C., Mechanisms of interleukin-1beta release. Immunobiology (2009).

Eggermont, Alexander M M. "Cancer Immunotherapy 2017 (Paris, France). Progress and challenges."

Elliott, L. A., et al., *Human Tumor-Infiltrating Myeloid Cells: Phenotypic and Functional Diversity*. Front Immunol, 2017. 8: p. 86.

Elmore, Susan. "Apoptosis: a review of programmed cell death." Toxicologic pathology 35, no. 4 (2007): 495-516.

Espert, L., M. Denizot, M. Grimaldi, V. Robert-Hebmann, B. Gay, M. Varbanov, P. Codogno, M. Biard-Piechaczyk, Autophagy is involved in T cell death after binding of HIV-1 envelope proteins to CXCR4. J. Clin. Invest. 116 (2006) 2161-2172.

Eyileten, Ceren, Kinga Majchrzak, Zofia Pilch, Katarzyna Tonecka, Joanna Mucha, Bartlomiej Taciak, Katarzyna Ulewicz et al. "Immune cells in cancer therapy and drug delivery." Mediators of inflammation 2016 (2016).

Fadok, V. A., D. L. Bratton, L. Guthrie, P. M. Henson, Differential effects of apoptotic versus lysed cells on macrophage production of cytokines: role of proteases. J. Immunol. 166 (2001) 6847-6854.

Faherty, C. S., A. T. Maurelli, Staying alive: bacterial inhibition of apoptosis during infection. Trends Microbiol. 16 (2008) 173-180.

Fang, Ronnie H., Che-Ming J. Hu, Brian T. Luk, Weiwei Gao, Jonathan A. Copp, Yiyin Tai, Derek E. O'Connor, and Liangfang Zhang. "Cancer cell membrane-coated nanoparticles for anticancer vaccination and drug delivery." Nano letters 14, no. 4 (2014): 2181-2188.

Feng, Mingye, James Y. Chen, Rachel Weissman-Tsukamoto, Jens-Peter Volkmer, Po Yi Ho, Kelly M. McKenna, Samuel Cheshier et al. "Macrophages eat cancer cells using their own calreticulin as a guide: roles of TLR and Btk." Proceedings of the National Academy of Sciences 112, no. 7 (2015): 2145-2150.

Feng, S., Y. Yang, Y. Mei, L. Ma, D. E. Zhu, N. Hoti, M. Castanares, M. Wu, Cleavage of RIP3 inactivates its caspase-independent apoptosis pathway by removal of kinase domain. Cell. Signal. 19 (2007) 2056-2067.

Fernandes-Alnemri, T., J. W. Yu, P. Datta, J. Wu, E. S. Alnemri, AIM2 activates the inflammasome and cell death in response to cytoplasmic DNA. Nature 458 (2009) 509-513.

Festjens, N., T. Vanden Berghe, P. Vandenabeele, Necrosis, a well-orchestrated form of cell demise: signalling cascades, important mediators and concomitant immune response. Biochim. Biophys. Acta 1757 (2006) 1371-1387.

Festjens, N., T. Vanden Berghe, S. Cornelis, P. Vandenabeele, RIP1, a kinase on the crossroads of a cell's decision to live or die. Cell Death Differ. 14 (2007) 400-410.

Fink, S. L., B. T. Cookson, Caspase-1-dependent pore formation during pyroptosis leads to osmotic lysis of infected host macrophages. Cell Microbiol 8 (2006) 1812-1825.

Finn, Olivera J. "Cancer immunology." New England Journal of Medicine 358, no. 25 (2008): 2704-2715.

Fong, Lawrence, Yafei Hou, Alberto Rivas, Claudia Benike, Alan Yuen, George A. Fisher, Mark M. Davis, and Edgar G. Engleman. "Altered peptide ligand vaccination with Flt3 ligand expanded dendritic cells for tumor immunotherapy." Proceedings of the National Academy of Sciences 98, no. 15 (2001): 8809-8814.

Fuentes-Prior, P., G. S. Salvesen, The protein structures that shape caspase activity, specificity, activation and inhibition. Biochem. J. 384 (2004) 201-232.

Gaj, Thomas, Charles A. Gersbach, and Carlos F. Barbas III. "ZFN, TALEN, and CRISPR/Cas-based methods for genome engineering." Trends in biotechnology 31, no. 7 (2013): 397-405.

Galluzzi, L, M. C. Maiuri, I. Vitale, H. Zischka, M. Castedo, L. Zitvogel, G. Kroemer, Cell death modalities: classification and pathophysiological implications. Cell Death Differ. 14 (2007) 1237-1243.

Galluzzi, L., C. Brenner, E. Morselli, Z. Touat, G. Kroemer, Viral control of mitochondrial apoptosis. PLoS Pathog. 4 (2008) e1000018.

Galon, Je[]ôme, Denis Franchimont, Naoki Hiroi, Gregory Frey, Antje Boettner, Monika Ehrhart-Bornstein, John J. O'Shea, George P. Chrousos, And Stefan R. Bornstein. "Gene profiling reveals unknown enhancing and suppressive actions of glucocorticoids on immune cells." The FASEB journal 16, no. 1 (2002): 61-71.

Gameiro, Sofia R., Momodou L. Jammed, Max M. Wattenberg, Kwong Y. Tsang, Soldano Ferrone, and James W. Hodge. "Radiation-induced immunogenic modulation of tumor enhances antigen processing and calreticulin exposure, resulting in enhanced T-cell killing." Oncotarget 5, no. 2 (2014): 403.

Gao, Lu, Kexin Chen, Qi Gao, Xiaodan Wang, Jian Sun, Yong-Guang Yang, "CD47 deficiency in tumor stroma promotes tumor progression by enhancing angiogenesis", Oncotarget. 2017; 8:22406-22413. doi.org/10.18632/oncotarget.9899 (Jun. 7, 2016).

Garg, Abhishek D., Sanne Elsen, Dmitri V. Krysko, Peter Vandenabeele, Peter de Witte, and Patrizia Agostinis. "Resistance to anticancer vaccination effect is controlled by a cancer cell-autonomous phenotype that disrupts immunogenic phagocytic removal." Oncotarget 6, no. 29 (2015): 26841.

Geller, L. T., et al., *Potential role of intratumor bacteria in mediating tumor resistance to the chemotherapeutic drug gemcitabine*. Science, 2017. 357(6356): p. 1156-1160.

Gopalakrishnan, V., et al., *Gut microbiome modulates response to anti-PD-1 immunotherapy in melanoma patients*. Science, 2018. 359(6371): p. 97-103.

Gregoire, M., C. Ligeza-Poisson, N. Juge-Morineau, and R. Spisek. "Anti-cancer therapy using dendritic cells and apoptotic tumour cells: pre-clinical data in human mesothelioma and acute myeloid leukaemia." Vaccine 21, no. 7-8 (2003): 791-794.

Guillerey, C., N. D. Huntington, and M. J. Smyth, *Targeting natural killer cells in cancer immunotherapy*. Nat Immunol, 2016. 17(9): p. 1025-36.

Gul, N., et al., *Macrophages eliminate circulating tumor cells after monoclonal antibody therapy*. J Clin Invest, 2014. 124(2): p. 812-23.

Haining, W. Nicholas. "Abstract SY40-01: In vivo genetic screens for genes that modulate tumor immunity." (2018): SY40-01.

Halestrap, A. P., C. P. Connern, E. J. Griffiths, P. M. Kerr, Cyclosporin A binding to mitochondrial cyclophilin inhibits the permeability transition pore and protects hearts from ischaemia/reperfusion injury. Mol. Cell. Biochem. 174 (1997) 167-172.

Hannani, Dalil, Antonella Sistigu, Oliver Kepp, Lorenzo Galluzzi, Guido Kroemer, and Laurence Zitvogel. "Prerequisites for the antitumor vaccine-like effect of chemotherapy and radiotherapy." The Cancer Journal 17, no. 5 (2011): 351-358.

Hayday, A., F. Kyle, O. Nussbaumer, D. Enting, and M. L. Iannitto. "51: How T cells may distinguish stress from normality in an epithelium." European Journal of Cancer 50 (2014): S13.

He, S., L. Wang, L. Miao, T. Wang, F. Du, L. Zhao, X. Wang, Receptor interacting protein kinase-3 determines cellular necrotic response to TNF-alpha. Cell 137 (2009) 1100-1111.

He, X., et al., *Antitumor efficacy induced by a B16F10 tumor cell vaccine treated with mitoxantrone alone or in combination with reserpine and verapamil in mice*. Exp Ther Med, 2011. 2(5): p. 911-916.

Hellerstedt B A, Pienta K J. The current state of hormonal therapy for prostate cancer. CA Cancer J Clin. 2002; 52:154-79.

Helmy, Karim Y., Shyam A. Patel, George R. Nahas, and Pranela Rameshwar. "Cancer immunotherapy: accomplishments to date and future promise." Therapeutic delivery 4, no. 10 (2013): 1307-1320.

Herzog, Karl-Heinz, Miriam J. Chong, Manuela Kapsetaki, James I. Morgan, and Peter J. McKinnon. "Requirement for Atm in ionizing radiation-induced cell death in the developing central nervous system." Science 280, no. 5366 (1998): 1089-1091.

Hirohashi, Yoshihiko, Toshihiko Torigoe, Satoko Inoda, Akari Takahashi, Rena Morita, Satoshi Nishizawa, Yasuaki Tamura, Hiromu Suzuki, Minoru Toyota, and Noriyuki Sato. "Immune response against tumor antigens expressed on human cancer stem-like cells/tumor-initiating cells." Immunotherapy 2, no. 2 (2010): 201-211.

Holler, N., R. Zaru, O. Micheau, M. Thome, A. Attinger, S. Valitutti, J. L. Bodmer, P. Schneider, B. Seed, J. Tschopp, Fas triggers an alternative, caspase-8-independent cell death pathway using the kinase RIP as effector molecule. Nat. Immunol. 1 (2000) 489-495.

Inoda, Satoko, Yoshihiko Hirohashi, Toshihiko Torigoe, Rena Morita, Akari Takahashi, Hiroko Asanuma, Munehide Nakatsugawa et al. "Cytotoxic T lymphocytes efficiently recognize human colon cancer stem-like cells." The American journal of pathology 178, no. 4 (2011): 1805-1813.

Italiani, P. and D. Boraschi, *From Monocytes to M1/M2 Macrophages: Phenotypical vs. Functional Differentiation*. Front Immunol, 2014. 5: p. 514.

Jagtap, P., C. Szabo, Poly(ADP-ribose) polymerase and the therapeutic effects of its inhibitors. Nat. Rev. Drug Discov. 4 (2005) 421-440.

Jaiswal, Siddhartha, and Irving L. Weissman. "Hematopoietic stem and progenitor cells and the inflammatory response." Annals of the New York Academy of Sciences 1174, no. 1 (2009): 118-121.

Jayaraman, Subhadra, "Cancer and the Immune System: Deciphering the Relationship" (Mar. 14, 2017), blog.addgene.org/cancer-and-the-immune-system-deciphering-the-relationship.

Jin S, Ellis E, Veetil J V, Yao H, Ye K. Visualization of human immunodeficiency virus protease inhibition using a novel Forster resonance energy transfer molecular probe. Biotechnol Prog. 2011; 27:1107-14.

Jin S, Veetil J V, Garrett J R, Ye K. Construction of a panel of glucose indicator proteins for continuous glucose monitoring. Biosens Bioelectron. 2011; 26:3427-31.

Jin S, Yao H, Krisanarungson P, Haukas A, Ye K. Porous membrane substrates offer better niches to enhance the Wnt signaling and promote human embryonic stem cell growth and differentiation. Tissue Eng Part A. 2012; 18:1419-30.

Jin, Sha, Huantong Yao, Jennifer L. Weber, Zara K. Melkoumian, and Kaiming Ye. "A synthetic, xeno-free peptide surface for expansion and directed differentiation of human induced pluripotent stem cells." PloS one 7, no. 11 (2012): e50880; Sha, Jin, Huantong Yao, Jennifer L. Weber, Zara K. Melkoumian, and Kaiming Ye. "Correction: A Synthetic, Xeno-Free Peptide Surface for Expansion and Directed Differentiation of Human Induced Pluripotent Stem Cells." PLoS One 8, no. 2 (2013).

Jin S, Ye K. Targeted drug delivery for breast cancer treatment. Recent Pat Anticancer Drug Discov. 2013; 8:143-53.

Johnston, J. B., J. W. Barrett, S. H. Nazarian, M. Goodwin, D. Ricciuto, G. Wang, G. McFadden, A poxvirus-encoded pyrin domain protein interacts with ASC-1 to inhibit host inflammatory and apoptotic responses to infection. Immunity 23 (2005) 587-598.

Jones, K. R., L. W. Elmore, C. Jackson-Cook, G. Demasters, L. F. Povirk, S. E. Holt, and D. A. Gewirtz. "p53-Dependent accelerated senescence induced by ionizing radiation in breast tumour cells." International journal of radiation biology 81, no. 6 (2005): 445-458.

Joyce, Johanna A., and Douglas T. Fearon. "T cell exclusion, immune privilege, and the tumor microenvironment." Science 348, no. 6230 (2015): 74-80.

Jung, C. H., C. B. Jun, S. H. Ro, Y. M. Kim, N. M. Otto, J. Cao, M. Kundu, D. H. Kim, ULK-Atg13-FIP200 complexes mediate mTOR signaling to the autophagy machinery. Mol. Biol. Cell 20 (2009) 1992-2003.

Kalai, M., G. Van Loo, T. Vanden Berghe, A. Meeus, W. Burm, X. Saelens, P. Vandenabeele, Tipping the balance between necrosis and apoptosis in human and murine cells treated with interferon and dsRNA. Cell Death Differ. 9 (2002) 981-994.

Kazemi, Tohid, Vahid Younesi, Farhad Jadidi-Niaragh, and Mehdi Yousefi. "Immunotherapeutic approaches for cancer therapy: an updated review." Artificial cells, nanomedicine, and biotechnology 44, no. 3 (2016): 769-779.

Keirsse, J., et al., *Exploiting tumor-associated dendritic cell heterogeneity for novel cancer therapies*. J Leukoc Biol, 2017. 102(2): p. 317-324.

Kennedy M K, Glaccum M, Brown S N, Butz EA, Viney J L, Embers M et al. Reversible defects in natural killer and memory CD8 T cell lineages in interleukin 15-deficient mice. J Exp Med 2000; 191: 771-780.

Kenneth C. Valkenburg and Bart O. Williams. 2011. Mouse models of prostate cancer. Prostate Cancer Volume 2011, Kershaw M H and Smyth M J. 2013. Making macrophages eat cancers. Immunology. Science. 341(6141):41-2.

Kershaw, Michael H., and Mark J. Smyth. "Making Macrophages Eat Cancer." Science 341, no. 6141 (2013): 41-42.

Kim, M. J., et al., *Association of CD47 with natural killer cell-mediated cytotoxicity of head-and-neck squamous cell carcinoma lines*. Tumour Biol, 2008. 29(1): p. 28-34.

Kleeff, Jorg, Murray Korc, Minoti Apte, Carlo La Vecchia, Colin D. Johnson, Andrew V. Biankin, Rachel E. Neale et al. "Pancreatic cancer." Nature reviews Disease primers 2 (2016): 16022.

Koh, Eunee, Yoosoo Yang, and In-San Kim, "Exosome-SIRP-α, a CD47 blockade increases cancer cell phagocytosis", ISEV2017 OT1.05 (May 15, 2017), www.rug.nl/research/portal/files/51552775/Abstract_Book_ISEV2017.pdf.

Koike, M., M. Shibata, M. Tadakoshi, K. Gotoh, M. Komatsu, S. Waguri, N. Kawahara, K. Kuida, S. Nagata, E. Kominami, K. Tanaka, Y. Uchiyama, Inhibition of autophagy prevents hippocampal pyramidal neuron death after hypoxic-ischemic injury. Am. J. Pathol. 172 (2008) 454-469.

Kooreman, N. G., et al., *Autologous iPSC-Based Vaccines Elicit Anti-tumor Responses In Vivo*. Cell Stem Cell, 2018. 22(4): p. 501-513 e7.

Kosta, A., C. Roisin-Bouffay, M. F. Luciani, G. P. Otto, R. H. Kessin, P. Golstein, Autophagy gene disruption reveals a non-vacuolar cell death pathway in Dictyostelium. J. Biol. Chem. 279 (2004) 48404-48409.

Kroemer, G., et al., *Immunogenic cell death in cancer therapy*. Annu Rev Immunol, 2013. 31: p. 51-72.

Kroemer, G., L. Galluzzi, C. Brenner, Mitochondrial membrane permeabilization in cell death. Physiol. Rev. 87 (2007) 99-163.

Kroemer, Guido, Laura Senovilla, Lorenzo Galluzzi, Fabrice André, and Laurence Zitvogel. "Natural and therapy-induced immunosurveillance in breast cancer." Nature medicine 21, no. 10 (2015): 1128.

Kroemer, Guido, Lorenzo Galluzzi, Oliver Kepp, and Laurence Zitvogel. "Immunogenic cell death in cancer therapy." Annual review of immunology 31 (2013): 51-72.

Kruger, C., T. F. Greten, and F. Korangy, *Immune based therapies in cancer*. Histol Histopathol, 2007. 22(6): p. 687-96.

Krysko, D. V., G. Brouckaert, M. Kalai, P. Vandenabeele, K. D'Herde, Mechanisms of internalization of apoptotic and necrotic L929 cells by a macrophage cell line studied by electron microscopy. J. Morphol. 258 (2003) 336-345.

Krysko, D. V., P. Vandenabeele, From regulation of dying cell engulfment to development of anti-cancer therapy. Cell Death Differ. 15 (2008) 29-38.

Kumai, T., et al., *Cancer immunotherapy: moving forward with peptide T cell vaccines*. Curr Opin Immunol, 2017. 47: p. 57-63.

Kumar, V., et al., *The Nature of Myeloid-Derived Suppressor Cells in the Tumor Microenvironment*. Trends Immunol, 2016. 37(3): p. 208-220.

Labbe, K., M. Saleh, Cell death in the host response to infection. Cell Death Differ. 15 (2008) 1339-1349.

LaCasse, E. C., D. J. Mahoney, H. H. Cheung, S. Plenchette, S. Baird, R. G. Korneluk, IAP-targeted therapies for cancer. Oncogene 27 (2008) 6252-6275.

Lamkanfi, M., T. D. Kanneganti, P. Van Damme, T. Vanden Berghe, I. Vanoverberghe, J. Vandekerckhove, P. Vandenabeele, K. Gevaert, G. Nunez, Targeted peptidecentric proteomics reveals caspase-7 as a substrate of the caspase-1 inflammasomes. Mol. Cell Proteomics 7 (2008) 2350-2363.

Lane-Reticker, Sarah K., Robert T. Manguso, and W. Nicholas Haining. "Pooled in vivo screens for cancer immunotherapy target discovery." (2018): 167-170.

Laporte, C., A. Kosta, G. Klein, L. Aubry, D. Lam, E. Tresse, M.F. Luciani, P. Golstein, A necrotic cell death model in a protist. Cell Death Differ. 14 (2007) 266-274.

Lara-Tejero, M., F. S. Sutterwala, Y. Ogura, E. P. Grant, J. Bertin, A. J. Coyle, R. A. Flavell, J. E. Galan, Role of the caspase-1 inflammasome in *Salmonella typhimurium* pathogenesis. J. Exp. Med. 203 (2006) 1407-1412.

Lau, Cia-Hin, and Yousin Suh. "In vivo genome editing in animals using AAV-CRISPR system: applications to translational research of human disease." F1000Research 6 (2017).

Lavender, Kerry J., Wendy W. Pang, Ronald J. Messer, Amanda K. Duley, Brent Race, Katie Phillips, Dana Scott et al. "BLT-humanized C57BL/6 Rag2−/−γc−/−CD47−/−mice are resistant to GVHD and develop B and T cell immunity to HIV infection." Blood (2013): blood-2013.

Lee, C. Y., E. H. Baehrecke, Steroid regulation of autophagic programmed cell death during development. Development 128 (2001) 1443-1455.

Lee, Daniel W., et al. "T cells expressing CD19 chimeric antigen receptors for acute lymphoblastic leukaemia in children and young adults: a phase 1 dose-escalation trial." The Lancet 385.9967 (2015): 517-528. PubMed PMID: 25319501.

Lee, S. and K. Margolin, *Tumor-infiltrating lymphocytes in melanoma*. Curr Oncol Rep, 2012. 14(5): p. 468-74.

Lehmann, B., et al., *Tumor location determines tissue-specific recruitment of tumor-associated macrophages and antibody-dependent immunotherapy response*. Sci Immunol, 2017. 2(7).

Li, P., H. Allen, S. Banerjee, S. Franklin, L. Herzog, C. Johnston, J. McDowell, M. Paskind, L. Rodman, J. Salfeld, et al., Mice deficient in IL-1 beta-converting enzyme are defective in production of mature IL-1 beta and resistant to endotoxic shock. Cell 80 (1995) 401-411.

Li, T., et al., *Antitumor Activity of cGAMP via Stimulation of cGAS-cGAMP-STING-IRF3 Mediated Innate Immune Response*. Sci Rep, 2016. 6: p. 19049.

Li, Ting, Bo Liu, Martin H. Spalding, Donald P. Weeks, and Bing Yang. "High-efficiency TALEN-based gene editing produces disease-resistant rice." Nature biotechnology 30, no. 5 (2012): 390.

Liang, Puping, Yanwen Xu, Xiya Zhang, Chenhui Ding, Rui Huang, Zhen Zhang, Jie Lv et al. "CRISPR/Cas9-mediated gene editing in human tripronuclear zygotes." Protein & cell 6, no. 5 (2015): 363-372.

Liang, Xudong. "Development of a novel breast cancer vaccine." PhD diss., State University of New York at Binghamton, 2015.

Lim, S. Y., S. M. Davidson, M. M. Mocanu, D. M. Yellon, C. C. Smith, The cardioprotective effect of necrostatin requires the cyclophilin-D component of the mitochondrial permeability transition pore. Cardiovasc Drugs Ther. 21 (2007) 467-469.

Lin, Y., A. Devin, Y. Rodriguez, Z. G. Liu, Cleavage of the death domain kinase RIP by caspase-8 prompts TNF-induced apoptosis. Genes Dev. 13 (1999) 2514-2526.

Lin, Y., S. Choksi, H. M. Shen, Q. F. Yang, G. M. Hur, Y. S. Kim, J. H. Tran, S. A. Nedospasov, Z. G. Liu, Tumor necrosis factor-induced nonapoptotic cell death requires receptor-interacting protein-mediated cellular reactive oxygen species accumulation. J. Biol. Chem. 279 (2004) 10822-10828.

Liu, Xiaojuan, Yang Pu, Kyle Cron, Liufu Deng, Justin Kline, William A. Frazier, Hairong Xu, Hua Peng, Yang-Xin Fu, and Meng Michelle Xu. "CD47 blockade triggers T cell-mediated destruction of immunogenic tumors." Nature medicine 21, no. 10 (2015): 1209.

Locher, Clara, Rosa Conforti, Laetitia Aymeric, Yuting Ma, Takahiro Yamazaki, Sylvie Rusakiewicz, Antoine Tesnière et al. "Desirable cell death during anticancer chemotherapy." Annals of the New York Academy of Sciences 1209, no. 1 (2010): 99-108.

Lombardo, Angelo, Pietro Genovese, Christian M. Beausejour, Silvia Colleoni, Ya-Li Lee, Kenneth A. Kim, Dale Ando et al. "Gene editing in human stem cells using zinc finger nucleases and integrase-defective lentiviral vector delivery." Nature biotechnology 25, no. 11 (2007): 1298.

Lowry, L. E. and W. A. Zehring, *Potentiation of Natural Killer Cells for Cancer Immunotherapy: A Review of Literature*. Front Immunol, 2017. 8: p. 1061.

Lum, J. J., D. E. Bauer, M. Kong, M. H. Harris, C. Li, T. Lindsten, C. B. Thompson, Growth factor regulation of autophagy and cell survival in the absence of apoptosis. Cell 120 (2005) 237-248.

Ma, Y., V. Temkin, H. Liu, R. M. Pope, NF-kappaB protects macrophages from lipopolysaccharide-induced cell death: the role of caspase 8 and receptor-interacting protein. J. Biol. Chem. 280 (2005) 41827-41834.

Ma, Yuting, Laetitia Aymeric, Clara Locher, Guido Kroemer, and Laurence Zitvogel. "The dendritic cell-tumor cross-talk in cancer." Current opinion in immunology 23, no. 1 (2011): 146-152.

Ma, Yuting, Oliver Kepp, François Ghiringhelli, Lionel Apetoh, Laetitia Aymeric, Clara Locher, Antoine Tesniere et al. "Chemotherapy and radiotherapy: cryptic anticancer vaccines." In Seminars in immunology, vol. 22, no. 3, pp. 113-124. Academic Press, 2010.

Mackall, Crystal L., Melinda S. Merchant, and Terry J. Fry. "Immune-based therapies for childhood cancer." Nature reviews Clinical oncology 11, no. 12 (2014): 693.

Maeng, H., M. Terabe, and J. A. Berzofsky, *Cancer vaccines: translation from mice to human clinical trials*. Curr Opin Immunol, 2018. 51: p. 111-122.

Maiuri, M. C., E. Zalckvar, A. Kimchi, G. Kroemer, Self-eating and self-killing: crosstalk between autophagy and apoptosis. Nat. Rev. Mol. Cell Biol. 8 (2007) 741-752.

Majeti, R., Chao, M. P., Alizadeh, A. A., Pang, W. W., Jaiswal, S., Gibbs, K. D. Jr, van Rooijen, N., and Weissman, I. L. 2009. CD47 is an adverse prognostic factor and therapeutic antibody target on human acute myeloid leukemia stem cells. Cell 138, 286-299.

Manguso, Robert T., Hans W. Pope, Margaret D. Zimmer, Flavian D. Brown, Kathleen B. Yates, Brian C. Miller, Natalie B. Collins et al. "In vivo CRISPR screening identifies Ptpn2 as a cancer immunotherapy target." Nature 547, no. 7664 (2017): 413.

Manguso, Robert T., Hans W. Pope, Margaret D. Zimmer, Flavian D. Brown, Kathleen B. Yates, Brian C. Miller, Natalie B. Collins et al. "In vivo CRISPR screening identifies Ptpn2 as a target for cancer immunotherapy." Cancer Research AACR (2017): Abstract 1019.

Marcucci, Fabrizio, Cristiano Rumio, Angelo Corti, "Tumor cell-associated immune checkpoint molecules—Drivers of malignancy and stemness", Biochimica et Biophysica Acta (BBA)—Reviews on Cancer, Volume 1868, Issue 2, December 2017, Pages 571-583.

Marguet, D., M. F. Luciani, A. Moynault, P. Williamson, G. Chimini, Engulfment of apoptotic cells involves the redistribution of membrane phosphatidylserine on phagocyte and prey. Nat Cell Biol 1 (1999) 454-456.

Matsui, Y., H. Takagi, X. Qu, M. Abdellatif, H. Sakoda, T. Asano, B. Levine, J. Sadoshima, Distinct roles of autophagy in the heart during ischemia and reperfusion: roles of AMP-activated protein kinase and Beclin 1 in mediating autophagy. Circ. Res. 100 (2007) 914-922.

McCracken, Melissa N., Adriel C. Cha, and Irving L. Weissman. "Molecular pathways: activating T cells after cancer cell phagocytosis from blockade of CD47" Don't eat me" signals." Clinical cancer research (2015): clincanres-2520.

McKenna, E., et al., *Persistent DNA damage caused by low levels of mitomycin C induces irreversible cell senescence*. Cell Cycle, 2012. 11(16): p. 3132-40.

Melssen, M. and C. L. Slingluff, Jr., *Vaccines targeting helper T cells for cancer immunotherapy*. Curr Opin Immunol, 2017. 47: p. 85-92.

Ménard, Cédric, François Martin, Lionel Apetoh, Florence Bouyer, and François Ghiringhelli. "Cancer chemotherapy: not only a direct cytotoxic effect, but also an adjuvant for antitumor immunity." Cancer Immunology, Immunotherapy 57, no. 11 (2008): 1579-1587.

Merad, M., et al., *The dendritic cell lineage: ontogeny and function of dendritic cells and their subsets in the steady state and the inflamed setting*. Annu Rev Immunol, 2013. 31: p. 563-604.

Merritt, Anita J., Terence D. Allen, Christopher S. Potten, and John A. Hickman. "Apoptosis in small intestinal epithelia from p53-null mice: evidence for a delayed, p53-indepdendent G2/M-associated cell death after γ-irradiation." Oncogene 14, no. 23 (1997): 2759.

Michallet, M. C., E. Meylan, M. A. Ermolaeva, J. Vazquez, M. Rebsamen, J. Curran, H. Poeck, M. Bscheider, G. Hartmann, M. Konig, U. Kalinke, M. Pasparakis, J. Tschopp, TRADD protein is an essential component of the RIG-like helicase antiviral pathway. Immunity 28 (2008) 651-661.

Mittal, Deepak, Matthew M. Gubin, Robert D. Schreiber, and Mark J. Smyth. "New insights into cancer immunoediting and its three component phases—elimination, equilibrium and escape." Current opinion in immunology 27 (2014): 16-25.

Mizushima, N., A. Kuma, Y. Kobayashi, A. Yamamoto, M. Matsubae, T. Takao, T. Natsume, Y. Ohsumi, T. Yoshimori, Mouse Apg16L, a novel WD-repeat protein, targets to the autophagic isolation membrane with the Apg12-Apg5 conjugate. J. Cell Sci. 116 (2003) 1679-1688.

Morris J C, et al.2014. Vaccination with tumor cells expressing IL-15 and IL-15Rα inhibits murine breast and prostate cancer. Gene Therapy. 21: 393-401.

Movahedi, K., et al., *Different tumor microenvironments contain functionally distinct subsets of macrophages derived from Ly6C(high) monocytes*. Cancer Res, 2010. 70(14): p. 5728-39.

Munn, D. H. and V. Bronte, *Immune suppressive mechanisms in the tumor microenvironment*. Curr Opin Immunol, 2016. 39: p. 1-6.

Muranen, Taru, and Joan S. Brugge. "Moving Closer To Victory." In Cold Spring Harbor symposia on quantitative biology, vol. 81, pp. 281-288. Cold Spring Harbor Laboratory Press, 2016.

Muthna, Darina, Tomas Soukup, Jirina Vavrova, Jaroslav Mokry, Jana Cmielova, Benjamin Visek, Alena Jiroutova et al. "Irradiation of adult human dental pulp stem cells provokes activation of p53, cell cycle arrest, and senescence but not apoptosis." Stem cells and development 19, no. 12 (2010): 1855-1862.

Naiyer A. Rizvi, 2*† Matthew D. Hellmann,1,2* Alexandra Snyder,1,2,3* Pia Kvistborg,4, et al., *Mutational landscape determines sensitivity to PD-1 blockade in non-small cell lung cancer*. CANCER IMMUNOLOGY, 2015. VOL 34(8 ISSUE 6230): p. 124-128.

Nakagawa, T., S. Shimizu, T. Watanabe, O. Yamaguchi, K. Otsu, H. Yamagata, H. Inohara, T. Kubo, Y. Tsujimoto, Cyclophilin D-dependent mitochondrial permeability transition regulates some necrotic but not apoptotic cell death. Nature 434 (2005) 652-658.

Naujokat, Cord. "Monoclonal antibodies against human cancer stem cells." Immunotherapy 6, no. 3 (2014): 290-308.

Neagu, Martha R., Maria Carmela Speranza, Robert T. Manguso, Sean E. Lawler, Gordon J. Freeman, John Doench, Arlene H. Sharpe, and W. Nicholas Haining. "Immu-28. Defining Molecular Mechanisms Of Resistance To Glioblastoma (gbm) Immunity Using A Novel Crispr/cas9 In Vivo Loss-of-function Screening Platform." Neuro-oncology19, no. suppl_6 (2017): vi118-vi118.

Neagu, Martha R., Robert T. Manguso, Hans Pope, Maria C. Speranza, Gordon J. Freeman, John Doench, Arlene H. Sharpe, and William Nicholas Haining. "Defining molecular mechanisms of resistance to glioblastoma immunity using a novel CRISPR/Cas9 in vivo loss-of-function screening platform." (2017): 417-417.

Neumar, R. W., Molecular mechanisms of ischemic neuronal injury. Ann. Emerg. Med. 36 (2000) 483-506.

Ngo, M., et al., *Antibody Therapy Targeting CD47 and CD271 Effectively Suppresses Melanoma Metastasis in Patient-Derived Xenografts*. Cell Rep, 2016. 16(6): p. 1701-1716.

Nilsson, A. and P. A. Oldenborg, *CD47 promotes both phosphatidylserine-independent and phosphatidylserine-dependent phagocytosis of apoptotic murine thymocytes by non-activated macrophages*. Biochem Biophys Res Commun, 2009. 387(1): p. 58-63.

Obeid, Michel, Antoine Tesniere, François Ghiringhelli, Gian Maria Fimia, Lionel Apetoh, Jean-Luc Perfettini, Maria Castedo et al. "Calreticulin exposure dictates the immunogenicity of cancer cell death." Nature medicine 13, no. 1 (2007): 54.

Oldenborg P A, Zheleznyak A, Fang Y F, Lagenaur C F, Gresham H D, Lindberg F P. Role of CD47 as a marker of self on red blood cells. Science. 2000; 288:2051-4.

Ostrand-Rosenberg, S. and P. Sinha, *Myeloid-derived suppressor cells: linking inflammation and cancer*. J Immunol, 2009. 182(8): p. 4499-506.

Ott, P. A., et al., *An immunogenic personal neoantigen vaccine for patients with melanoma*. Nature, 2017. 547 (7662): p. 217-221.

Overwijk, W. W. and N. P. Restifo, *B16 as a mouse model for human melanoma*. Curr Protoc Immunol, 2001. Chapter 20: p. Unit 20 1.

Overwijk, W. W., *Cancer vaccines in the era of checkpoint blockade: the magic is in the adjuvant*. Curr Opin Immunol, 2017. 47: p. 103-109.

Pachynski, R. K., et al., *Evaluation of Tumor-infiltrating Leukocyte Subsets in a Subcutaneous Tumor Model*. J Vis Exp, 2015(98).

Palucka, Karolina, and Jacques Banchereau. "Cancer immunotherapy via dendritic cells." Nature Reviews Cancer 12.4 (2012): 265-277. PubMed PMID: 22437871. PubMed Central PMCID: PMC3433802.

Parajuli, N., et al., *Infiltrating CD11b+CD11c+ cells have the potential to mediate inducible nitric oxide synthase-dependent cell death in mammary carcinomas of HER-2/neu transgenic mice*. Int J Cancer, 2010. 126(4): p. 896-908.

Pattingre, S., A. Tassa, X. Qu, R. Garuti, X. H. Liang, N. Mizushima, M. Packer, M. D. Schneider, B. Levine, Bcl-2 antiapoptotic proteins inhibit Beclin 1-dependent autophagy. Cell 122 (2005) 927-939.

Pattingre, S., L. Espert, M. Biard-Piechaczyk, P. Codogno, Regulation of macroautophagy by mTOR and Beclin 1 complexes. Biochimie 90 (2008) 313-323.

Peinado, Héctor, Haiying Zhang, Irina R. Matei, Bruno Costa-Silva, Ayuko Hoshino, Goncalo Rodrigues, Bethan Psaila et al. "Pre-metastatic niches: organ-specific homes for metastases." Nature Reviews Cancer 17, no. 5 (2017): 302.

Penaloza, C., L. Lin, R. A. Lockshin, Z. Zakeri, Cell death in development: shaping the embryo. Histochem. Cell Biol. 126 (2006) 149-158.

Peter, M. E., P. H. Krammer, The CD95(APO-1/Fas) DISC and beyond. Cell Death Differ. 10 (2003) 26-35.

Pobezinskaya, Y. L., Y. S. Kim, S. Choksi, M. J. Morgan, T. Li, C. Liu, Z. Liu, The function of TRADD in signaling through tumor necrosis factor receptor 1 and TRIF-dependent toll-like receptors. Nat. Immunol. 9 (2008) 1047-1054.

Portt, Liam, Grant Norman, Caitlin Clapp, Matthew Greenwood, and Michael T. Greenwood. "Anti-apoptosis and cell survival: a review." Biochimica et Biophysica Acta (BBA)-Molecular Cell Research 1813, no. 1 (2011): 238-259. www.sciencedirect.com/science/article/pii/S0167488910002764

Pulendran B, Dillon S, Joseph C, Curiel T, Banchereau J, Mohamadzadeh M. Dendritic cells generated in the presence of GM-CSF plus IL-15 prime potent CD8+ Tc1 responses in vivo. Eur J Immunol 2004; 34: 66-73.

Qu, X., Z. Zou, Q. Sun, K. Luby-Phelps, P. Cheng, R. N. Hogan, C. Gilpin, B. Levine, Autophagy gene-dependent clearance of apoptotic cells during embryonic development. Cell 128 (2007) 931-946.

Reed, John C. "Bcl-2 and the regulation of programmed cell death." The Journal of cell biology 124, no. 1-2 (1994): 1-6.

Richards, D. M., J. Hettinger, and M. Feuerer, *Monocytes and macrophages in cancer: development and functions*. Cancer Microenviron, 2013. 6(2): p. 179-91.

Riedl, S. J., G. S. Salvesen, The apoptosome: signalling platform of cell death. Nat. Rev. Mol. Cell Biol. 8 (2007) 405-413.

Roh, D. S., et al., *DNA cross-linking, double-strand breaks, and apoptosis in corneal endothelial cells after a single exposure to mitomycin C*. Invest Ophthalmol Vis Sci, 2008. 49(11): p. 4837-43.

Roisin-Bouffay, C., M. F. Luciani, G. Klein, J. P. Levraud, M. Adam, P. Golstein, Developmental cell death in dictyostelium does not require paracaspase. J. Biol. Chem. 279 (2004) 11489-11494.

Roy, A., et al., *Increased efficiency of gamma-irradiated versus mitomycin C-treated feeder cells for the expansion of normal human cells in long-term cultures*. J Hematother Stem Cell Res, 2001. 10(6): p. 873-80.

Sahin, U., et al., *Personalized RNA mutanome vaccines mobilize poly-specific therapeutic immunity against cancer*. Nature, 2017. 547(7662): p. 222-226.

Sallets, Adrienne, Sophie Robinson, Adel Kardosh, and Ronald Levy. "Enhancing immunotherapy of STING agonist for lymphoma in preclinical models." Blood advances 2, no. 17 (2018): 2230-2241.

Salvesen, G. S., S. J. Riedl, Caspase mechanisms. Adv. Exp. Med. Biol. 615 (2008) 13-23.

Sarkar, A., M. W. Hall, M. Exline, J. Hart, N. Knatz, N. T. Gatson, M. D. Wewers, Caspase-1 regulates *Escherichia coli* sepsis and splenic B cell apoptosis independently of interleukin-1beta and interleukin-18. Am. J. Respir. Crit. Care Med. 174 (2006) 1003-1010.

Saxena, Mansi, Sreekumar Balan, Vladimir Roudko, and Nina Bhardwaj. "Towards superior dendritic-cell vaccines for cancer therapy." Nat. Biomed. Eng. 2 (2018): 341-346.

Scarlatti, F., R. Granata, A. J. Meijer, P. Codogno, Does autophagy have a license to kill mammalian cells? Cell Death Differ. 16 (2009) 12-20.

Scarlett, U. K., et al., *Ovarian cancer progression is controlled by phenotypic changes in dendritic cells*. J Exp Med, 2012. 209(3): p. 495-506.

Schanne, F. A., Agnes B. Kane, Ellora E. Young, and John L. Farber. "Calcium dependence of toxic cell death: a final common pathway." Science 206, no. 4419 (1979): 700-702.

Scheffer, S. R., et al., *Apoptotic, but not necrotic, tumor cell vaccines induce a potent immune response in vivo*. Int J Cancer, 2003. 103(2): p. 205-11.

Schroder, K., D. A. Muruve, J. Tschopp, Innate immunity: cytoplasmic DNA sensing by the AIM2 inflammasome. Curr. Biol. 19 (2009) R262-265.

Scott, Andrew M., Jedd D. Wolchok, and Lloyd J. Old. "Antibody therapy of cancer." Nature Reviews Cancer 12.4 (2012): 278-287. PubMed PMID: 22437872.

Shao, W., G. Yeretssian, K. Doiron, S. N. Hussain, M. Saleh, The caspase-1 digestome identifies the glycolysis pathway as a target during infection and septic shock. J. Biol. Chem. 282 (2007) 36321-36329.

Sharma, Padmanee, Siwen Hu-Lieskovan, Jennifer A. Wargo, and Antoni Ribas. "Primary, adaptive, and acquired resistance to cancer immunotherapy." Cell 168, no. 4 (2017): 707-723.

Shen, Bin, Jun Zhang, Hongya Wu, Jianying Wang, Ke Ma, Zheng Li, Xueguang Zhang, Pumin Zhang, and Xingxu Huang. "Generation of gene-modified mice via Cas9/RNA-mediated gene targeting." Cell research 23, no. 5 (2013): 720.

Shiao, Stephen L., A. Preethi Ganesan, Hope S. Rugo, and Lisa M. Coussens. "Immune microenvironments in solid tumors: new targets for therapy." Genes & development 25, no. 24 (2011): 2559-2572.

Sick, E., et al., *CD47 update: a multifaceted actor in the tumour microenvironment of potential therapeutic interest*. Br J Pharmacol, 2012. 167(7): p. 1415-30.

Smyth, Mark J., Shin Foong Ngiow, Antoni Ribas, and Michele W L Teng. "Combination cancer immunotherapies tailored to the tumour microenvironment." Nature reviews Clinical oncology 13, no. 3 (2016): 143.

Sockolosky, J. T., et al., *Durable antitumor responses to CD47 blockade require adaptive immune stimulation*. Proc Natl Acad Sci USA, 2016. 113(19): p. E2646-54.

Sofia R. Gameiro, J. A. C., Jack P. Higgins, David Apelian, James W. Hodge, *Exploitation of differential homeostatic proliferation of T-cell subsets following chemotherapy to enhance the efficacy of vaccine-mediated antitumor responses*. Cancer Immunol Immunother, 2011.

Sofia R. Gameiro1, M. L. J., Max M. Wattenberg1, Kwong Y. Tsang1, and a. J. W. H. Soldano Ferrone, *Radiation-induced immunogenic modulation of tumor enhances antigen processing and calreticulin exposure, resulting in enhanced T-cell killing*. Oncotarget, 2013. 5.

Sokolowska, O. and D. Nowis, STING Signaling in Cancer Cells: Important or Not? Arch Immunol Ther Exp (Warsz), 2018. 66(2): p. 125-132.

Song, Jun, Dongshan Yang, Jie Xu, Tianqing Zhu, Y. Eugene Chen, and Jifeng Zhang. "RS-1 enhances CRISPR/Cas9-and TALEN-mediated knock-in efficiency." Nature communications 7 (2016): 10548.

Soto-Pantoja, D. R., et al., *CD47 in the tumor microenvironment limits cooperation between antitumor T-cell immunity and radiotherapy*. Cancer Res, 2014. 74(23): p. 6771-83.

Stanton, S. E. and M. L. Disis, *Designing vaccines to prevent breast cancer recurrence or invasive disease*. Immunotherapy, 2015. 7(2): p. 69-72.

Steinman, Ralph M., and Madhav Dhodapkar. "Active immunization against cancer with dendritic cells: the near future." International journal of cancer 94, no. 4 (2001): 459-473.

Strozyk, Elwira, and Dagmar Kulms. "The role of AKT/mTOR pathway in stress response to UV-irradiation: implication in skin carcinogenesis by regulation of apoptosis, autophagy and senescence." International journal of molecular sciences 14, no. 8 (2013): 15260-15285.

Suzuki, Yasuyuki, Yuzuru Imai, Hiroshi Nakayama, Kazuko Takahashi, Koji Takio, and Ryosuke Takahashi. "A serine protease, HtrA2, is released from the mitochondria and interacts with XIAP, inducing cell death." Molecular cell 8, no. 3 (2001): 613-621.

Syn, Nicholas L., Lingzhi Wang, Edward Kai-Hua Chow, Chwee Teck Lim, and Boon-Cher Goh. "Exosomes in cancer nanomedicine and immunotherapy: prospects and challenges." Trends in biotechnology 35, no. 7 (2017): 665-676.

Tebas, Pablo, David Stein, Winson W. Tang, Ian Frank, Shelley Q. Wang, Gary Lee, S. Kaye Spratt et al. "Gene editing of CCR5 in autologous CD4 T cells of persons infected with HIV." New England Journal of Medicine 370, no. 10 (2014): 901-910.

Terness, P., et al., *Mitomycin C-treated dendritic cells inactivate autoreactive T cells: toward the development of a tolerogenic vaccine in autoimmune diseases*. Proc Natl Acad Sci USA, 2008. 105(47): p. 18442-7.

Thibodeaux, Suzanne R., and Tyler J. Curiel. "Immune therapy for ovarian cancer: promise and pitfalls." International reviews of immunology 30, no. 2-3 (2011): 102-119.

Thyss, Raphael, Virginie Virolle, Véronique Imbert, Jean-François Peyron, Daniel Aberdam, and Thierry Virolle. "NF-κB/Egr-1/Gadd45 are sequentially activated upon UVB irradiation to mediate epidermal cell death." The EMBO journal 24, no. 1 (2005): 128-137.

Tran Janco, J. M., et al., *Tumor-infiltrating dendritic cells in cancer pathogenesis*. J Immunol, 2015. 194(7): p. 2985-91.

Tseng, Diane, Jens-Peter Volkmer, Stephen B. Willingham, Humberto Contreras-Trujillo, John W. Fathman, Nathaniel B. Fernhoff, Jun Seita et al. "Anti-CD47 antibody-mediated phagocytosis of cancer by macrophages primes an effective antitumor T-cell response." Proceedings of the National Academy of Sciences 110, no. 27 (2013): 11103-11108.

Turnis, Meghan E., and Cliona M. Rooney. "Enhancement of dendritic cells as vaccines for cancer." Immunotherapy 2, no. 6 (2010): 847-862.

Valkenburg K C, Williams B O. Mouse models of prostate cancer. Prostate Cancer. 2011; 2011:895238.

Van Noorden, C. J., The history of Z-VAD-FMK, a tool for understanding the significance of caspase inhibition. Acta Histochem. 103 (2001) 241-251.

Vanden Berghe, T., M. Kalai, G. Denecker, A. Meeus, X. Saelens, P. Vandenabeele, Necrosis is associated with IL-6 production but apoptosis is not. Cell. Signal. 18 (2006) 328-335.

Vandenabeele, P., T. Vanden Berghe, N. Festjens, Caspase inhibitors promote alternative cell death pathways 2006. Sci. STKE (2006) e44.

Vanlangenakker, N., T. V. Berghe, D. V. Krysko, N. Festjens, P. Vandenabeele, Molecular mechanisms and pathophysiology of necrotic cell death. Curr Mol Med 8 (2008) 207-220.

Veetil J V, Jin S, Ye K. A glucose sensor protein for continuous glucose monitoring. Biosens Bioelectron. 2010; 26:1650-5.

Veetil J V, Jin S, Ye K. Fluorescence lifetime imaging microscopy of intracellular glucose dynamics. J Diabetes Sci Technol. 2012; 6:1276-85.

Vermeer, Daniel W., William C. Spanos, Paola D. Vermeer, Annie M. Bruns, Kimberly M. Lee, and John H. Lee. "Radiation-induced loss of cell surface CD47 enhances immune-mediated clearance of human papillomavirus-positive cancer." International journal of cancer 133, no. 1 (2013): 120-129.

Villanueva, M. Teresa. "Cancer immunotherapy: Searching in the immune checkpoint black box." Nature Reviews Drug Discovery 16, no. 9 (2017): 599.

Vinay, Dass S., et al. "Immune evasion in cancer: Mechanistic basis and therapeutic strategies." Seminars in cancer biology. Vol. 35, p. S185-S198. Academic Press, 2015. PubMed PMID: 25818339.

Voisine, Richard, Louis-P. Vezina, and Claude Willemot. "Induction of senescence-like deterioration of microsomal membranes from cauliflower by free radicals generated during gamma irradiation." Plant physiology 97, no. 2 (1991): 545-550.

Volkmer, A. K., S. B. Willingham, S. R. Tseng, P. Y. Ho, J. P. Volkmer, B. I. Sikic, R. Majeti, and I. L. Weissman. "50: Proffered Paper: Overcoming immune evasion in ovarian and breast cancer with anti-CD47 antibody blockade: A novel class of immune therapy." European Journal of Cancer 50 (2014): S13.

von Roemeling, Christina, Wen Jiang, Charles K. Chan, Irving L. Weissman, and Betty Y S Kim. "Breaking down the barriers to precision cancer nanomedicine." Trends in biotechnology35, no. 2 (2017): 159-171.

Waldman, Todd, Yonggang Zhang, Larry Dillehay, Jian Yu, Kenneth Kinzler, Bert Vogelstein, and Jerry Williams. "Cell-cycle arrest versus cell death in cancer therapy." Nature medicine 3, no. 9 (1997): 1034.

Wang Y, Xu Z, Guo S, Zhang L, Sharma A, Robertson G P, et al. Intravenous delivery of siRNA targeting CD47 effectively inhibits melanoma tumor growth and lung metastasis. Mol Ther. 2013; 21:1919-29.

Wang, L., F. Du, X. Wang, TNF-alpha induces two distinct caspase-8 activation pathways. Cell 133 (2008) 693-703.

Wei, Chuanxian, Jiyong Liu, Zhongsheng Yu, Bo Zhang, Guanjun Gao, and Renjie Jiao. "TALEN or Cas9-rapid, efficient and specific choices for genome modifications." Journal of Genetics and Genomics 40, no. 6 (2013): 281-289.

Wei, Y., S. Pattingre, S. Sinha, M. Bassik, B. Levine, JNK1-mediated phosphorylation of Bcl-2 regulates starvation-induced autophagy. Mol. Cells 30 (2008) 678-688.

Weiner, George J. "Building better monoclonal antibody-based therapeutics." Nature Reviews Cancer 15.6 (2015): 361-370. PubMed PMID: 25998715. PubMed Central PMCID: PMC4491443.

Weiskopf K, Ring A M, Ho C C, Volkmer J P, Levin A M, Volkmer A K, et al. Engineered SIRPα variants as immunotherapeutic adjuvants to anticancer antibodies. Science. 2013; 341:88-91.

Weiskopf, K., et al., *CD47-blocking immunotherapies stimulate macrophage-mediated destruction of small-cell lung cancer*. J Clin Invest, 2016. 126(7): p. 2610-20.

Weiskopf, K., et al., *Engineered SIRP-α variants as immunotherapeutic adjuvants to anticancer antibodies*. Science, 2013. 341(6141): p. 88-91.

Weiskopf, Kipp. "Cancer immunotherapy targeting the CD47/SIRP-α axis." European Journal of Cancer 76 (2017): 100-109.

Wherry, E. J. and M. Kurachi, *Molecular and cellular insights into T cell exhaustion*. Nat Rev Immunol, 2015. 15(8): p. 486-99.

Wiemann, S., A. Bott, I. Keklikoglou, C. Giacomelli, A. Balwierz, S. Uhlmann, H. Mannsperger, U. Korf, and C. Breunig. "53: miRNA-protein interaction networks in cancer." European Journal of Cancer 50 (2014): S13.

Willingham, S. B., D. T. Bergstralh, W. O'Connor, A. C. Morrison, D. J. Taxman, J. A. Duncan, S. Barnoy, M. M. Venkatesan, R. A. Flavell, M. Deshmukh, H. M. Hoffman, J. P. Ting, Microbial pathogen-induced necrotic cell death mediated by the inflammasome components CIAS1/cryopyrin/NLRP3 and ASC. Cell Host Microbe. 2 (2007) 147-159.

Willingham, Stephen B., Jens-Peter Volkmer, Andrew J. Gentles, Debashis Sahoo, Piero Dalerba, Siddhartha S. Mitra, Jian Wang et al. "The CD47-signal regulatory protein alpha (SIRP-α) interaction is a therapeutic target for human solid tumors." Proceedings of the National Academy of Sciences 109, no. 17 (2012): 6662-6667.

Wilson, N. S., V. Dixit, A. Ashkenazi, Death receptor signal transducers: nodes of coordination in immune signaling networks. Nat. Immunol. 10 (2009) 348-355.

Wilt T J, MacDonald R, Rutks I, Shamliyan T A, Taylor B C, Kane R L. Systematic review: comparative effectiveness and harms of treatments for clinically localized prostate cancer. Ann Intern Med. 2008; 148:435-48.

Wlaschek, Meinhard, Wenjian Ma, Pidder Jansen-Dürr, and Karin Scharffetter-Kochanek. "Photoaging as a consequence of natural and therapeutic ultraviolet irradiation—studies on PUVA-induced senescence-like growth arrest of human dermal fibroblasts." Experimental gerontology 38, no. 11-12 (2003): 1265-1270.

Wong, Karrie K., WeiWei Aileen Li, David J. Mooney, and Glenn Dranoff. "Advances in therapeutic cancer vaccines." In Advances in immunology, vol. 130, pp. 191-249. Academic Press, 2016.

Wu, Y. T. H. L. Tan, Q. Huang, Y. S. Kim, N. Pan, W. Y. Ong, Z. G. Liu, C. N. Ong, H. M. Shen, Autophagy plays a protective role during zVAD-induced necrotic cell death. Autophagy 4 (2008) 457-466.

Wyllie, Andrew H. "Cell death." In Cytology and Cell Physiology (Fourth Edition), pp. 755-785. 1987.

Xie, Yu-Qing, Lixia Wei, and Li Tang. "Immunoengineering with biomaterials for enhanced cancer immunotherapy." Wiley Interdisciplinary Reviews: Nanomedicine and Nanobiotechnology (2018): e1506.

Xie, Z., D. J. Klionsky, Autophagosome formation: core machinery and adaptations. Nat. Cell Biol. 9 (2007) 1102-1109.

Xu, Y., S. Huang, Z. G. Liu, J. Han, Poly(ADP-ribose) polymerase-1 signaling to mitochondria in necrotic cell death requires RIP1/TRAF2-mediated JNK1 activation. J. Biol. Chem. 281 (2006) 8788-8795.

Xu, Zhenhong, Yuhua Wang, Lu Zhang, and Leaf Huang. "Nanoparticle-delivered transforming growth factor-β siRNA enhances vaccination against advanced melanoma by modifying tumor microenvironment." ACS nano 8, no. 4 (2014): 3636-3645.

Yamashima, T., Y. Kohda, K. Tsuchiya, T. Ueno, J. Yamashita, T. Yoshioka, E. Kominami, Inhibition of ischaemic hippocampal neuronal death in primates with cathepsin B inhibitor CA-074: a novel strategy for neuroprotection based on 'calpain-cathepsin hypothesis'. Eur. J. Neurosci. 10 (1998) 1723-1733.

Yarchoan, Mark, Buries A. Johnson III, Eric R. Lutz, Daniel A. Laheru, and Elizabeth M. Jaffee. "Targeting neoantigens to augment antitumour immunity." Nature Reviews Cancer 17, no. 4 (2017): 209.

Yi, J. S., M. A. Cox, and A. J. Zajac, T-cell exhaustion: characteristics, causes and conversion. Immunology, 2010. 129(4): p. 474-81

Yinuo Li, S. L., Ying Xu, Chunping Qiu, Chengjuan Jin, Yuqiong Wang, Zhaojian Liu, Beihua Kong, *Overexpression of CD47 predicts poor prognosis and promotes cancer cell invasion in high-grade serous ovarian carcinoma*. Am J Transl Res, 2017.

Yong, Seok-Beom, Jee Young Chung, Yoonsung Song, and Yong-Hee Kim. "Recent challenges and advances in genetically-engineered cell therapy." Journal of Pharmaceutical Investigation (2018): 1-10.

You, Benshuai, Wenrong Xu, and Bin Zhang. "Engineering exosomes: a new direction for anticancer treatment." American journal of cancer research 8, no. 8 (2018): 1332.

Youle, R. J., A. Strasser, The BCL-2 protein family: opposing activities that mediate cell death. Nat. Rev. Mol. Cell Biol. 9 (2008) 47-59.

Yu, Guang-Tao, Lin-Lin Bu, Cong-Fa Huang, Wen-Feng Zhang, Wan-Jun Chen, J. Silvio Gutkind, Ashok B. Kulkarni, and Zhi-Jun Sun. "PD-1 blockade attenuates immunosuppressive myeloid cells due to inhibition of CD47/SIRP-α axis in HPV negative head and neck squamous cell carcinoma." Oncotarget 6, no. 39 (2015): 42067.

Yu, L., A. Alva, H. Su, P. Dutt, E. Freundt, S. Welsh, E. H. Baehrecke, M. J. Lenardo, Regulation of an ATG7-beclin 1 program of autophagic cell death by caspase-8. Science 304 (2004) 1500-1502.

Yu, L., F. Wan, S. Dutta, S. Welsh, Z. Liu, E. Freundt, E. H. Baehrecke, M. Lenardo, Autophagic programmed cell death by selective catalase degradation. Proc. Natl. Acad. Sci. U.S.A. 103 (2006) 4952-4957.

Zampetti-Bosseler, F., and David Scott. "Cell death, chromosome damage and mitotic delay in normal human, ataxia telangiectasia and retinoblastoma fibroblasts after X-irradiation." International Journal of Radiation Biology and Related Studies in Physics, Chemistry and Medicine 39, no. 5 (1981): 547-558.

Zanke, Brent W., Kimberly Boudreau, Elizabeth Rubie, Elaine Winnett, Lee Anne Tibbles, Leonard Zon, John Kyriakis, Fei-Fei Liu, and James R. Woodgett. "The stress-activated protein kinase pathway mediates cell death following injury induced by cis-platinum, UV irradiation or heat." Current Biology 6, no. 5 (1996): 606-613.

Zhang, D. W., J. Shao, J. Lin, N. Zhang, B. J. Lu, S. C. Lin, M. Q. Dong, J. Han, RIP3, an energy metabolism regulator that switches TNF-induced cell death from apoptosis to necrosis. Science (2009).

Zhang, H., et al., *Antitumor efficacy of CD137 ligation is maximized by the use of a CD137 single-chain Fv-expressing whole-cell tumor vaccine compared with CD137-specific monoclonal antibody infusion*. Mol Cancer Ther, 2006. 5(1): p. 149-55.

Zhang, M., et al., *Anti-CD47 Treatment Stimulates Phagocytosis of Glioblastoma by M1 and M2 Polarized Macrophages and Promotes M1 Polarized Macrophages In Vivo*. PLoS One, 2016. 11(4): p. e0153550.

Zhao, H., et al., *CD47 Promotes Tumor Invasion and Metastasis in Non-small Cell Lung Cancer.* Sci Rep, 2016. 6: p. 29719.

Zheng, Yuanhong, Guifang Yin, Vanminh Le, Anle Zhang, Siyu Chen, Xin Liang, and Jianwen Liu. "Photodynamic-therapy activates immune response by disrupting immunity homeostasis of tumor cells, which generates vaccine for cancer therapy." International journal of biological sciences 12, no. 1 (2016): 120.

Zhu Y, Dong Z, Wejinya U C, Jin S, Ye K. Determination of mechanical properties of soft tissue scaffolds by atomic force microscopy nanoindentation. J Biomech. 2011; 44:2356-61.

DETAILED DESCRIPTION OF THE PREFERRED EMBODIMENTS

Current cancer treatments are not satisfactory. On the other hand, the body immune system is designed to defend the body against pathogens and dangerous invaders including cancers. However, the body immune system fails to act on cancer cells. The increased expression of CD47 on tumor cells prevents them from being recognized by circulating immune cells such as macrophages. The use of anti-CD47 antibodies to block CD47 on tumor cells has proven effective. Nevertheless, this treatment represents some challenges including difficulty in penetrating antibodies into solid tumors. CD47 is expressed on the surface of many cells and is involved in a range of cellular processes such as apoptosis, proliferation, adhesion, and migration. Thus, the use of anti-CD47 antibodies can have some unpredictable side effects. The present technology utilizes whole-tumor cells as vaccines against cancer. According to a preferred embodiment, CD47-deficient cancer cells serve as both preventive and therapeutic vaccines to facilitate phagocytosis by macrophages, which then present tumor antigens to and activate immune cells such as cytotoxic CD8+ T cells. The activated CD8$^+$ T cells will attack and kill cancer cells on their own.

The technology harnesses the body immune system to eliminate cancer cells by creating CD47-deficient cancer cell vaccines. Cancer cells can easily escape from the immune system due to the expression of CD47 on their surface. The deletion of CD47 by genome editing enables their phagocytosis by macrophages that activate cytotoxic CD8$^+$ T cells. The activated CD8$^+$ T cells attack and kill cancer cells. The adaptive immune response is induced by either a standard cell line vaccine, or by using the patient's own tumor cells that have been genome-edited (to delete CD47) and inactivated by irradiation (to suppress their proliferation). Moreover, it is very powerful for treating metastatic cancer cells where none of current therapies is effective or eliminate recurrent cancer cells after solid tumors are surgically removed.

It is noted that in some cases, it is not the primary tumor which represents the ultimate target of the therapy. That is, in some cases, a tumor is benign or low grade, but is associated with a possible or even likely future change toward increased aggressiveness. Therefore, in such patients, a treatment may be provided that vaccinates the patient against the aggressively transformed cells.

To demonstrate the technology, i.e., the hypothesis of whether CD47 null tumor cells can be formulated into a vaccine eliciting a strong immune response of the host to eliminate cancers from the body, the cd47 gene from B16F10, a mouse melanoma cell line, was knocked out through CRISPR/Cas9 genome editing.

Figure 2A:
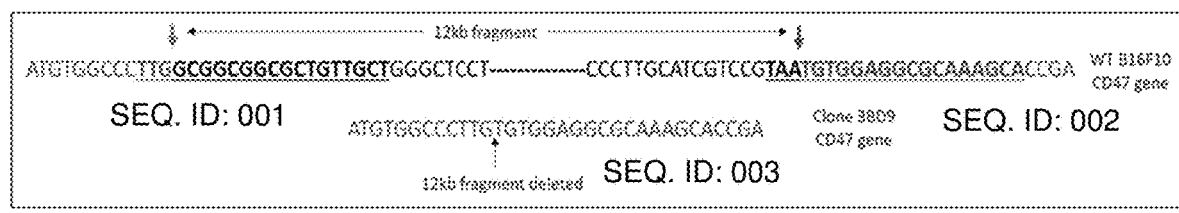
FIGS. 2A-2E show the knockout of the cd47 gene from the genome of B16F10 cells through CRISPR/Cas9 editing.
Figure 2B:
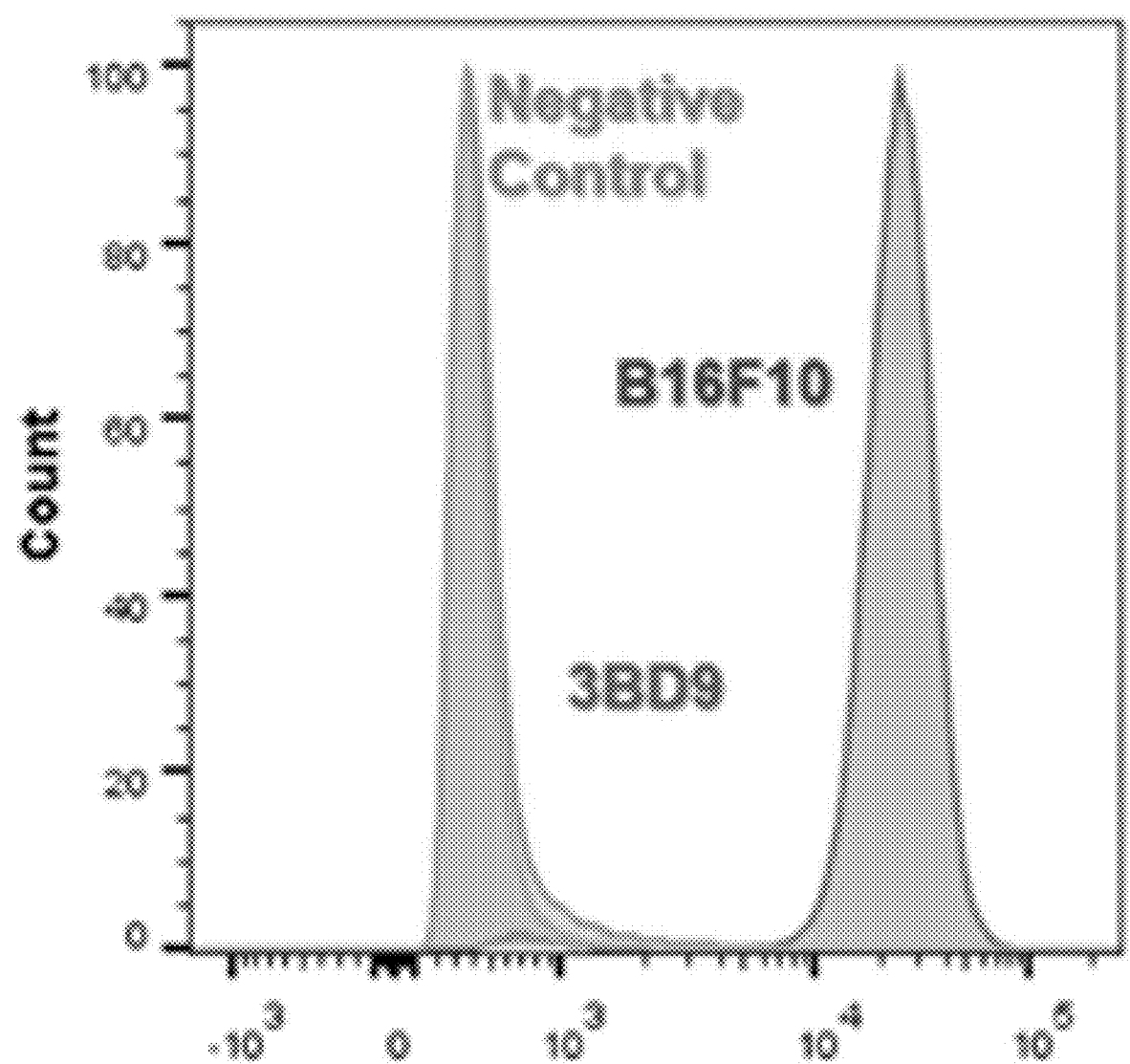
Figure 2C:
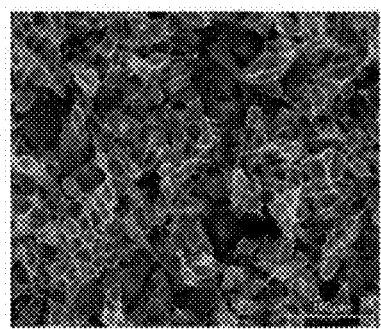
Figure 2D:
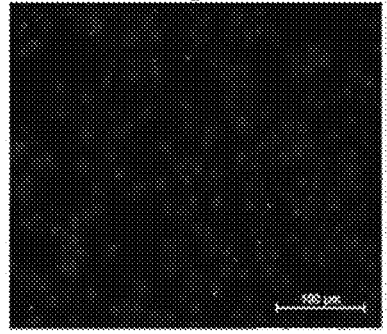
Figure 2E:
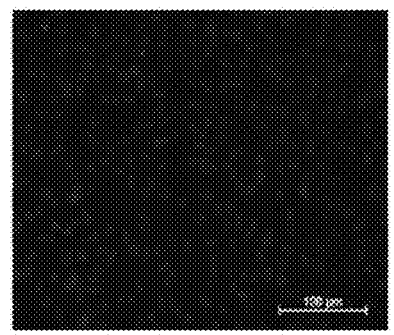

Two guide RNAs were designed that target the exons 1 and 2 of the cd47 gene (SEQ ID: 001, SEQ ID: 002). The guide RNAs were subcloned individually into an all-inclusive plasmid system, PX458 and co-transfected into B16F10 cells. Transfected cells were FACS sorted, and the resultant single cell clones were screened for bi-allelic CD47 knockout by PCR and DNA sequencing (Table 1). The resultant clone was named as 3BD9. The biallelic gene deletion was confirmed through DNA sequencing (FIG. 2A). The absence of CD47 expression on cell surface of 3BD9 was quantified through both flow cytometry (FIG. 2B) and immunofluorescence microscopy (FIGS. 2C-E). The CD47$^{-/-}$ 3BD9 cells were used in the subsequent experiments to ascertain their ability to elicit an immune response in the host.

FIGS. 2A-2E show the knockout of the cd47 gene from the genome of B16F10 cells by means of CRISPR/Cas9 editing. (FIG. 2A) DNA sequencing data showing the deletion of a 12 kb fragment from the cd47 gene (SEQ ID: 003). Underlined sequences represent the gRNA target regions, and bold arrows represent cut sites for Cas9. (FIG. 5B)

FACS histograms of rat anti-mouse CD47 antibody labeled unedited B16F10 cells (in red), the edited 3BD9 clone (in blue), and a negative control (3BD9 cells without primary antibody treatment) (in orange). Immunofluorescence microscopy was performed to detect the expression of CD47 (green) on the surface of B16F10 (FIG. 2C) and 3BD9 (FIG. 2D). (FIG. 2E), a negative control where the 3BD9 was labeled in the absence of the primary antibody. All cells were counterstained with DAPI (blue). Scale bar: 100 μm.

flow cytometry. The depleting or blocking of CD47 expression alone on the surface of melanoma cancer cells was found not to lead to a significant increase in their phagocytosis by BMDMs. However, the blocking of gp75 in $CD47^{-/-}$ 3BD9 cells with TA99 antibodies resulted in a considerable increase in phagocytosis, suggesting the combinatory effect of CD47 absence and the opsonizing effect of antibody (TA99). In this context, a similar enhancement of phagocytosis of 3BD9 was observed when cells are exposed

TABLE 1

Guide RNA and PCR primer sequences designed for CD47 knockout and screening

| ID | Sequence | Location/Function |
|---|---|---|
| | | CRISPR gRNA Sequences |
| Guide M1 | AACCGCCGCCGCGACAACGA SEQ ID: 004 | Exon 1, cd47 gene, used for RNP electroporation, and in PX458 plasmid for gene deletion |
| Guide M3 | TGCTTTGCGCCTCCACATTA SEQ ID: 005 | Exon 2, cd47 gene, used in PX458 plasmid for gene deletion |
| | | PCR Primers |
| MA-FP | AGCCAGAGGGAAGGAGTT SEQ ID: 006 | Forward primer, upstream of Guide M1 targeted cd47 gene |
| MC-RP | CCACTTGCCCAAGAAGAG SEQ ID: 007 | Reverse primer, downstream of Guide M3 targeted cd47 gene (with MA-FP, amplicon length: 12,986 bp in intact, and 473 bp in a deleted cd47 gene) |

Opsonizing Antibody Enhances Phagocytosis of $CD47^{-/-}$ B16 Cells (3BD9) by Bone Marrow-Derived Macrophages (BMDMs)

While CD47 depletion makes cells more susceptible to phagocytosis by macrophages, efficient phagocytosis requires the presence of an opsonizing antibody that engages the Fc receptors on macrophages. An in vitro phagocytosis assay was performed to determine whether phagocytosis of 3DB9 cells by BMDMs is enhanced in the presence of opsonizing antibody such as TA99, an antibody against glycoprotein 75 (gp75), a common melanoma tumor-associated antigen (Sockolosky et al. 2016). The expression of gp75 on the surface of the B16F10 and 3BD9 was determined by flow cytometry (FIG. 3). Presence of gp75 correlates with the ability of the TA99 antibody to block surface markers on tumor cells and act as an opsonizing agent for phagocytosis.

Figure 3A:
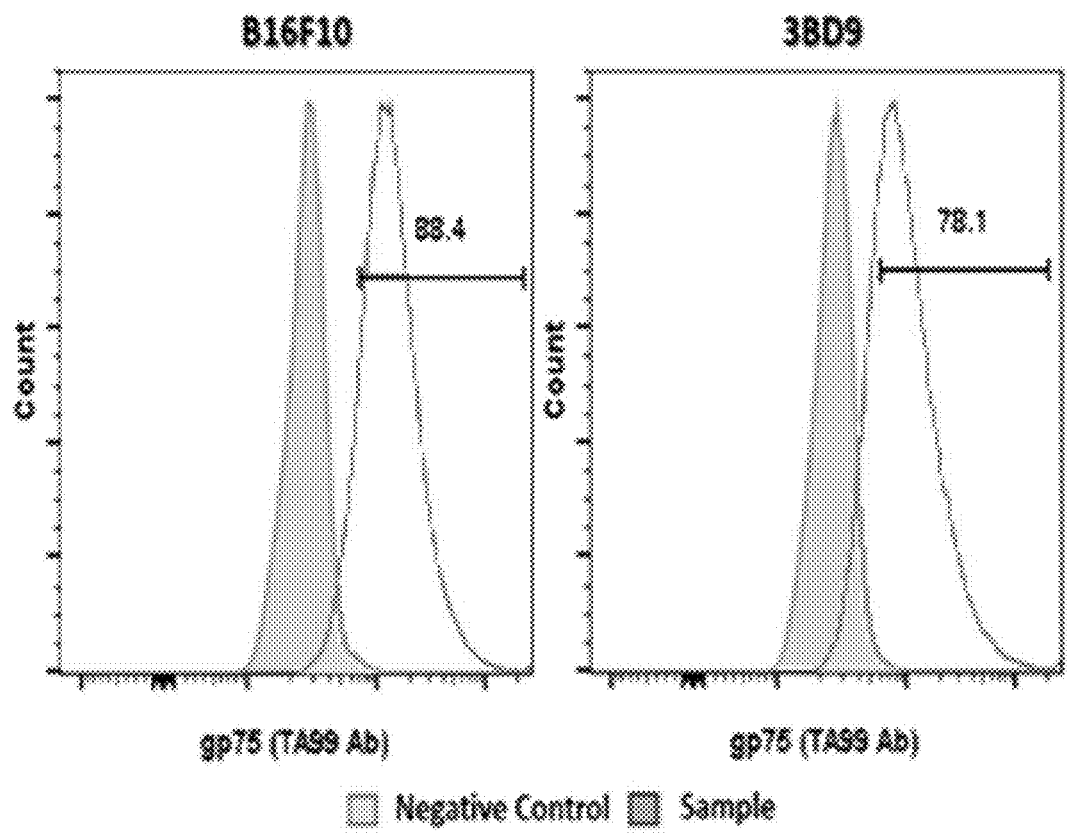
FIGS. 3A-3E show profiling of gp75 and CD47; and the effect of CD47 blockade, GM-CSF, and opsonizing antibodies on phagocytosis of CD47$^{-/-}$ 3BD9 by BMDMs
Figure 3B:
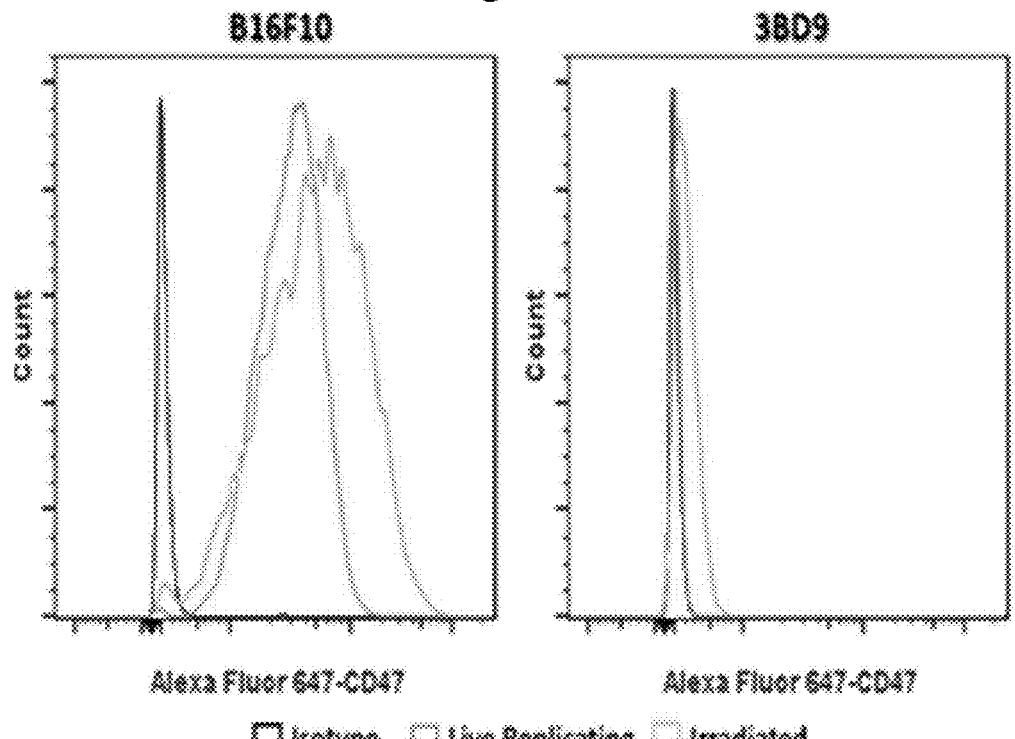
Figure 3C:
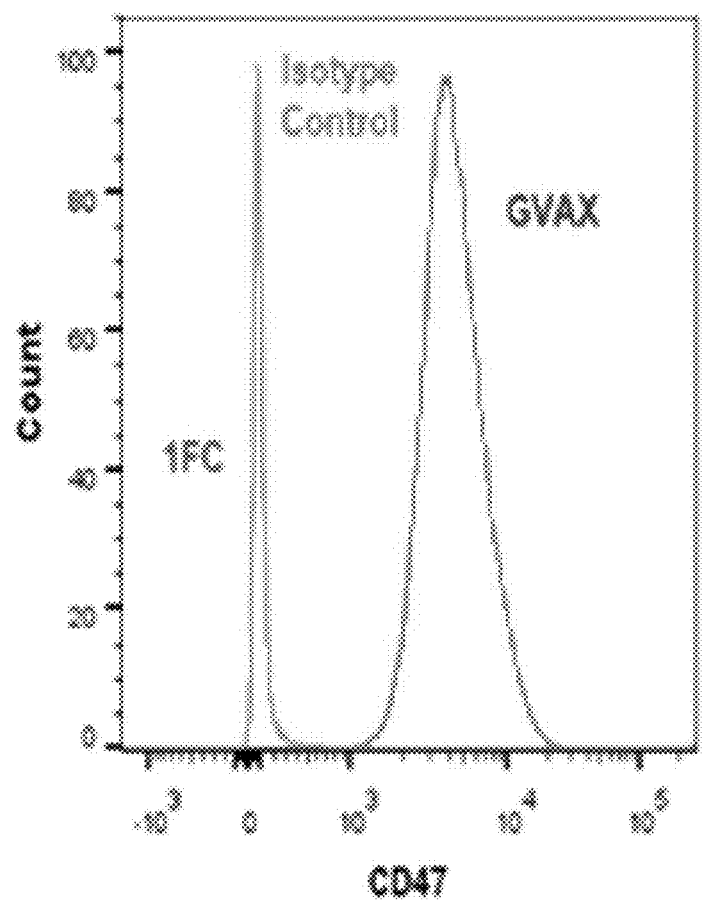

FIGS. 3A-3E show profiling of gp75 and CD47; and the effect of CD47 blockade, GM-CSF, and opsonizing antibodies on phagocytosis of $CD47^{-/-}$ 3BD9 by BMDMs. Flow cytometric analysis of cell surface gp75 expression on live B16F10 and 3BD9 cells (FIG. 3A), cell surface CD47 expression on irradiated B16F10 and 3BD9 cells (FIG. 3B), and cell surface CD47 expression on GVAX (red histogram) and 1FC ($CD47^{-/-}$ GVAX; blue histogram) cells with an isotype control (orange histogram) (FIG. 3C). (FIG. 3D) In vitro BMDM phagocytosis of the various types of melanoma cells under different conditions. $p<0.01$, *$p<0.001$ by one-way ANOVA using GraphPad Prism. (FIG. 3E) The trend shows increase in phagocytosis with the absence of CD47 and the presence of GM-CSF and the TA99 antibody. Data are expressed as mean±SEM.

Figure 3D:
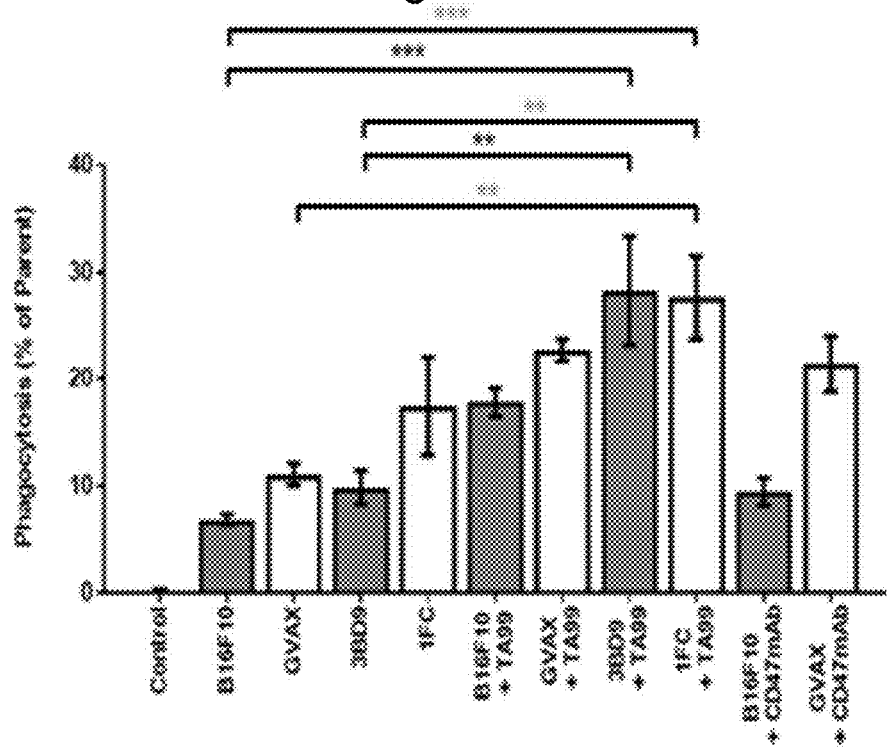
Figure 3E:
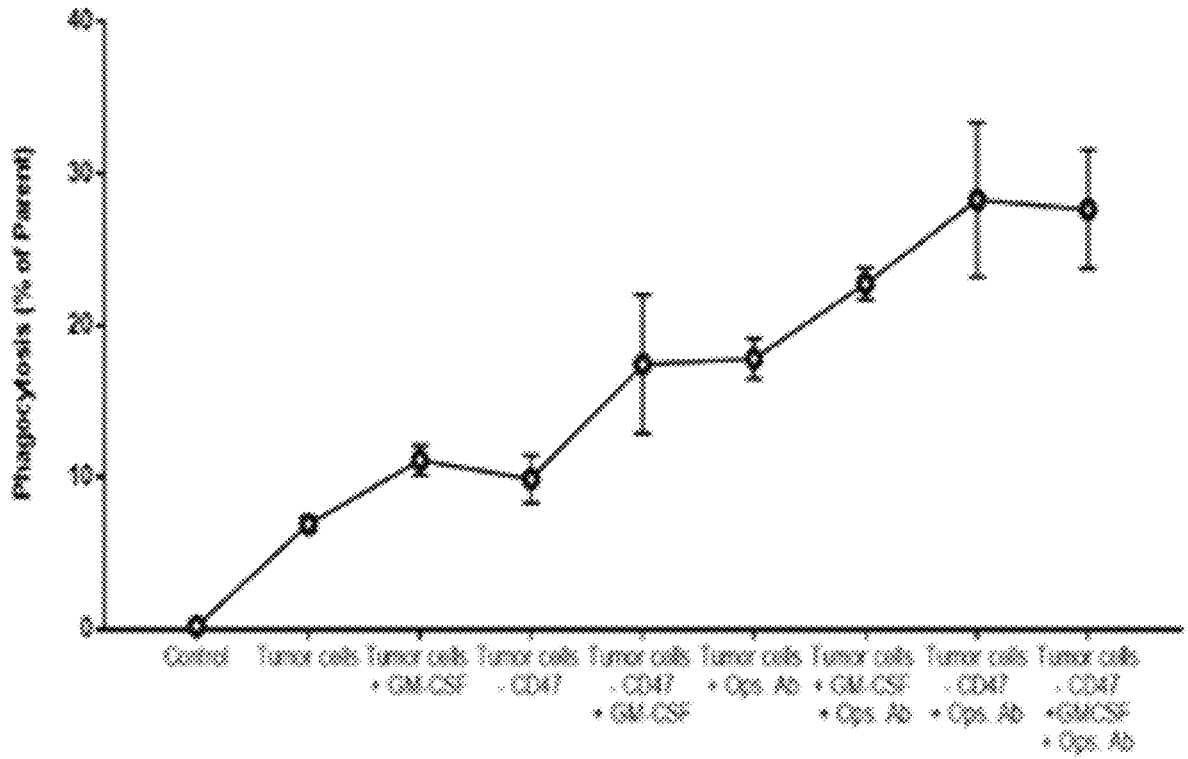
Figure 4A:
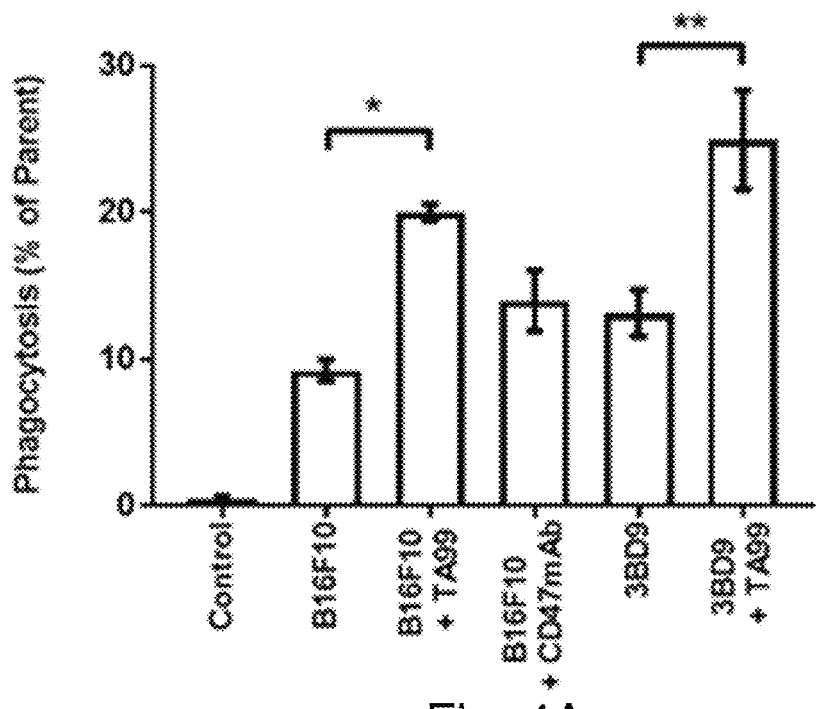
FIGS. 4A-4E show in vitro phagocytosis of 3BD9 and B16F10 by BMDMs and in vivo tumor growth after implanting live B16F10 and 3BD9 in mice.
Figure 4B:
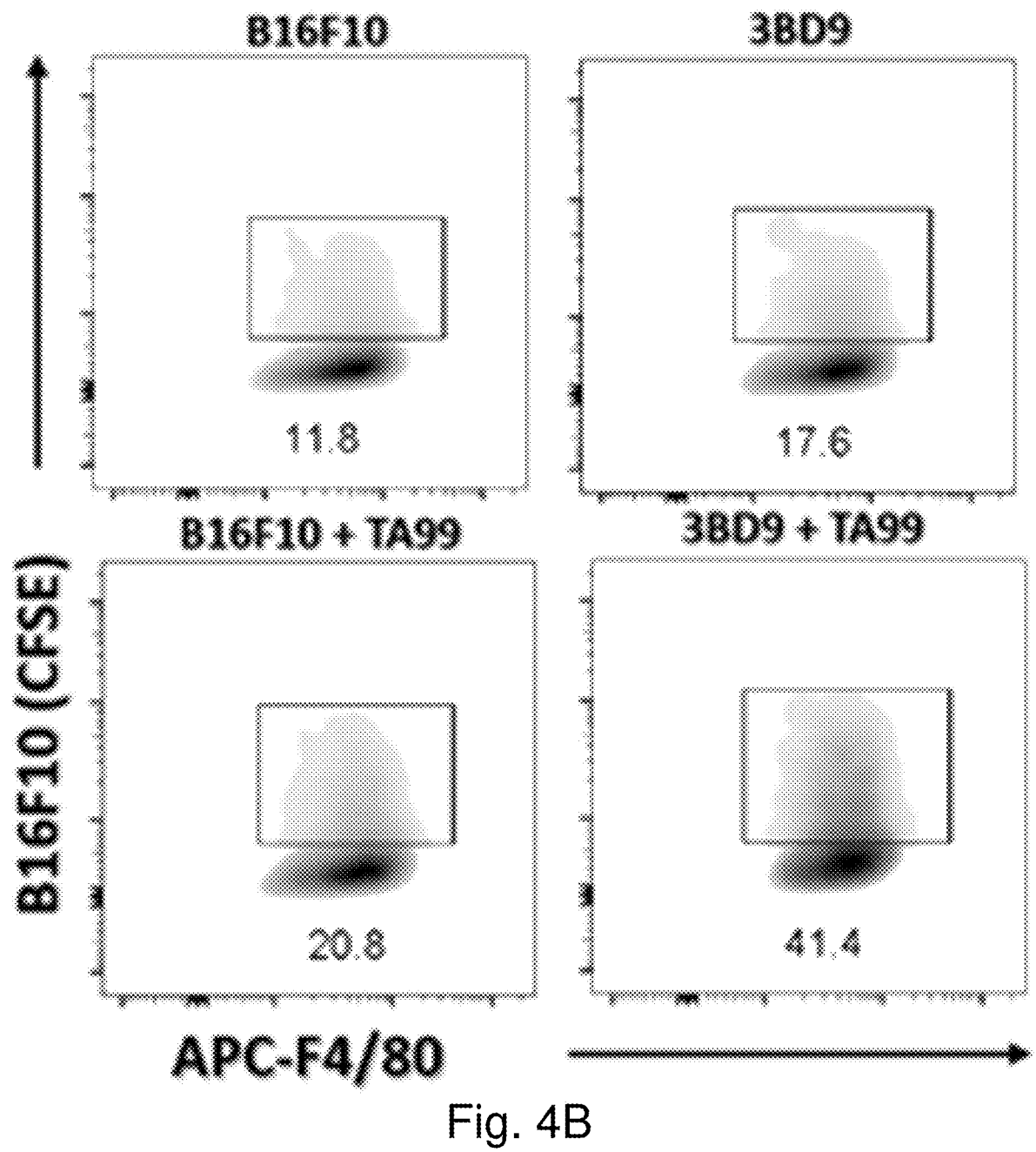

The efficiency of phagocytosis of 3BD9 and B16F10 by BMDMs is shown in FIGS. 4A-B. BMDMs were co-incubated with CFSE-labeled tumor cells in the presence of different opsonizing antibodies, and phagocytosis was analyzed as a percentage of $F4/80^+$ and $CFSE^+$ macrophages by to a macrophage activating cytokine such as the granulocyte macrophage colony stimulating factor (GM-CSF) (FIG. 3E). The phagocytosis efficiency of CD47 depleted melanoma cancer cells by BMDMs is increased when the cells are exposed to GM-CSF. It also does not appear that the exposure of CD47 depleted cells to both TA99 and GM-CSF can further improve their phagocytosis by BMDMs (FIG. 3C-E).

FIGS. 4A-4E show in vitro phagocytosis of 3BD9 and B16F10 by BMDMs and in vivo tumor growth after implanting live B16F10 and 3BD9 in mice. (FIG. 4A) BMDM phagocytosis of B16F10 cells treated with various opsonizing antibodies—purified anti-CD47 (clone miap301), or anti-gp75 antibodies (TA99). These antibody-dependent conditions were tested alongside un-opsonized conditions with only B16F10 and $CD47^{-/-}$ B16 (3BD9) cells. The data shown are the mean (n=3) and the error bars indicate the standard error. *$p<0.05$, $p<0.01$, one-way ANOVA. (FIG. 4B) Flow cytometric analysis of APC-F4/80 and CFSE dual labeled macrophages, depicting the percentage of phagocytosis in each condition. (FIG. 4C) Tumor growth in mice after implanting B16F10 or 3BD9. Points indicate tumor measurements from individual mice (n=8). Data shown are the combination of two independently performed experiments. *$p<0.001$, unpaired t test. Error bars indicate standard errors. (FIG. 4D) Survival rate of mice implanted with B16F10 and 3BD9. **$p<0.01$, Mantel-Cox test. (FIG. 4E) Tumor growth rate after challenge (second tumor implantation with live B16F10 cells) for two mice that were tumor-free for 60 days after initial 3BD9 implantation. $p=0.003$ by linear regression analysis. All statistical analyses were performed using GraphPad Prism.

These together appear to show that the phagocytosis of melanoma cancer cells is correlated to (i) the blockade of CD47-SIRP-α binding, (ii) the engagement of the Fc receptors on macrophages, and (iii) the presence of enhancing cytokines. Translated in vivo, this observation implies that the antigen presenting compartment must be aided by the effector compartment for efficient anti-tumor activity.

CD47 Ablation Delays Melanoma Tumor Growth Significantly In Vivo

Figure 4C:
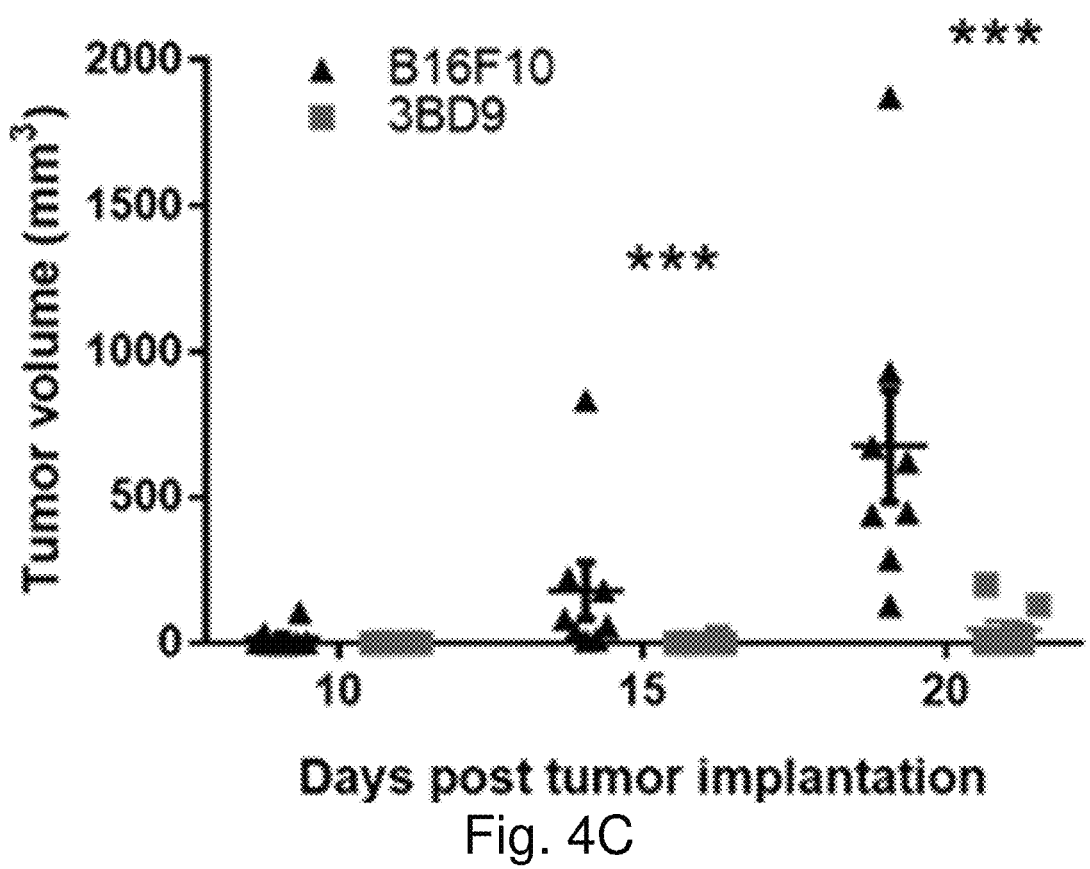
Figure 4D:
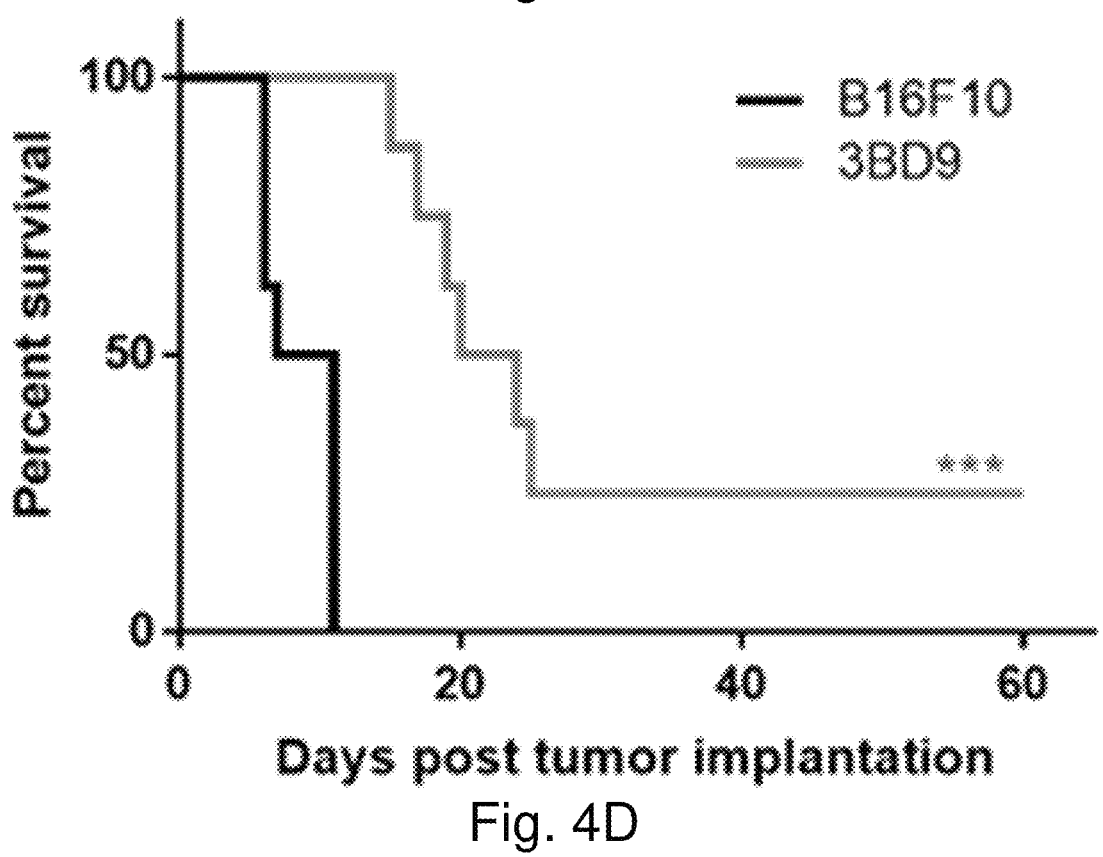
Figure 4E:
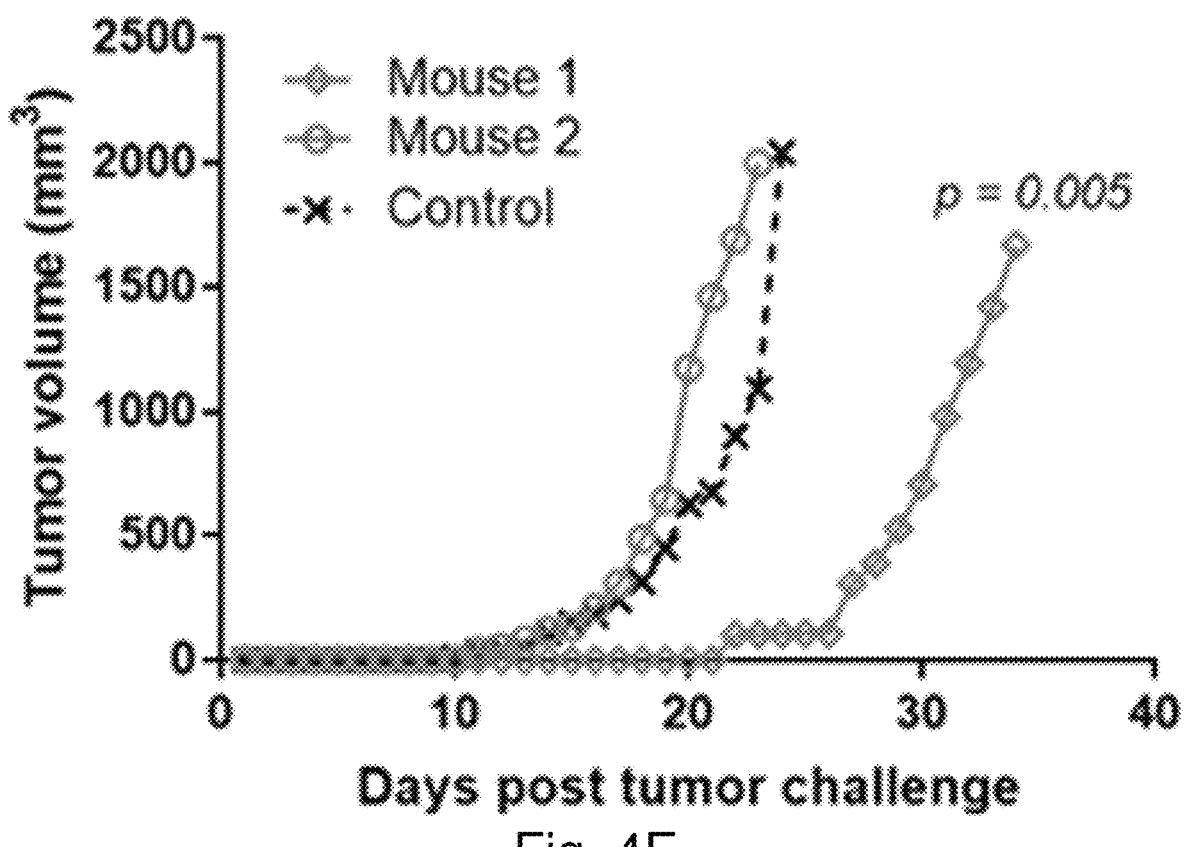
Figure 19A:
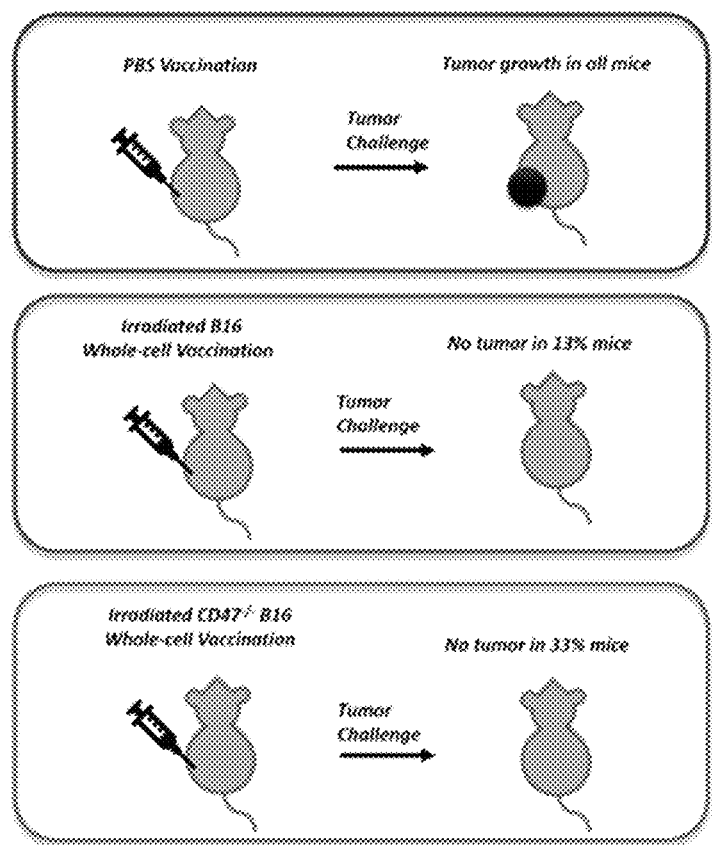
FIGS. 19A and 19B show schematic drawings of a vaccination procedure and tumor responses.
Figure 19B:
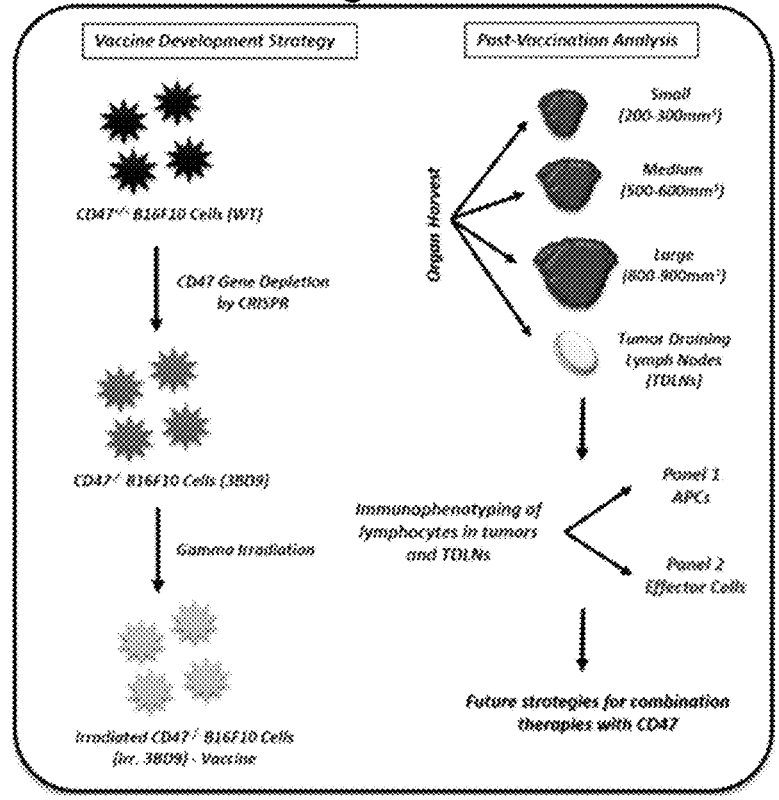

To determine whether CD47 ablated melanoma cells can elicit a strong immune response, tumor development was examined by implanting CD47$^{-/-}$ 3BD9 cells in syngeneic immunocompetent C57BL/6 mice (Weiskopf et al. 2016). For the mice that developed tumors, growth was delayed by at least 10 days in comparison with the mice implanted with CD47$^{+/-}$ B16F10. (FIG. 4C). Two of the eight mice (25% of mice) implanted with 3BD9 cells did not develop a tumor up to 60-days post implantation (FIG. 4D). To determine whether the tumor-free mice implanted with CD47$^{-/-}$ 3BD9 developed an immune memory against melanoma, a second tumor implantation was performed on Day 61. Interestingly, one mouse (50% of mice challenged) showed significantly delayed tumor growth—by about 20 days—in comparison to a control B16F10 implant mouse not previously injected with 3BD9 (FIG. 4E). These experiments were very critical, unveiling the possible elicitation of an immune response by CD47$^{-/-}$ tumor cells. Therefore, it appears that CD47$^{-/-}$ tumor cells are feasible to use as vaccines against melanoma. A procedure and its results are shown schematically in FIGS. 19A and 19B.

To characterize the immune activity in tumors that do not express CD47, an additional cohort of 15 mice per group that received B16F10 implants, and 3BD9 implants subcutaneously, were used. Examining immune organs of 3BD9 engrafted mice, enlarged spleens and lymph nodes were discovered (data not shown), indicating significant immune cell expansion after implantation. To further confirm the elicitation of an immune response by CD47$^{-/-}$ 3BD9, lymphocyte immuno-phenotyping was performed in the tumor microenvironment (TME) and in the tumor-draining lymph nodes (TDLNs) through multicolor flow cytometric analysis. Table 2 lists three panels of antibodies used for immuno-phenotyping: Panel T1 was used for phenotyping the antigen presenting compartment and the tumor cell phenotypes in the tumor microenvironment; Panel SL1 was used for phenotyping the antigen presenting compartment in the TDLNs; and Panel P2 was used for phenotyping the effector cell populations (T cells and NK cells) in both the TME and the TDLNs.

Figure 5A:
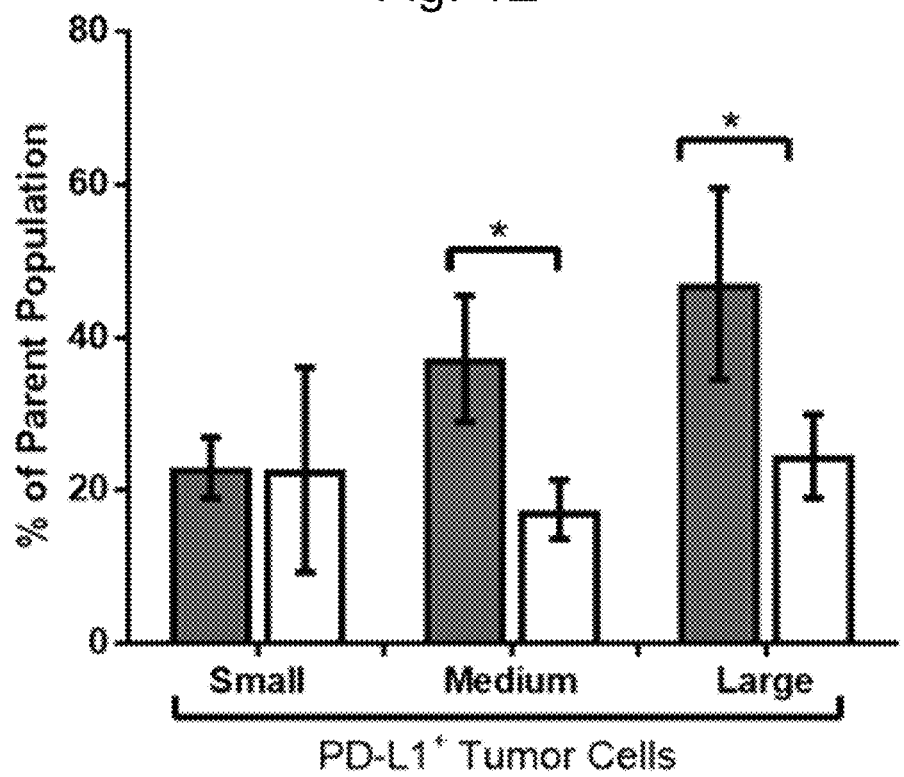
FIGS. 5A-5C show alterations in the tumor microenvironment in mice implanted with CD47$^{-/-}$ melanoma cells.
Figure 5B:
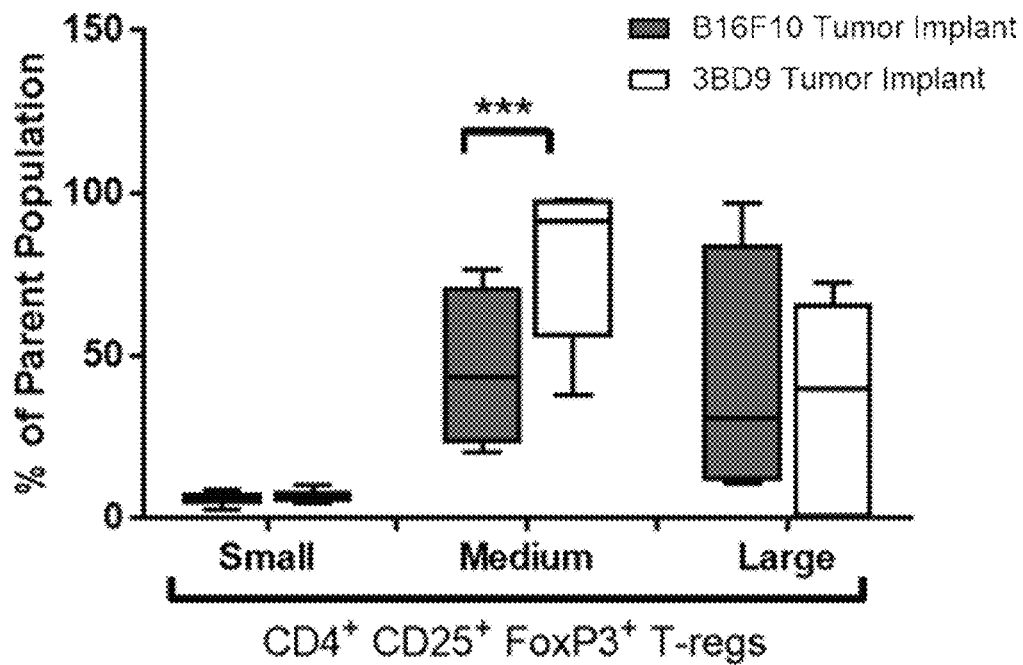
Figure 5C:
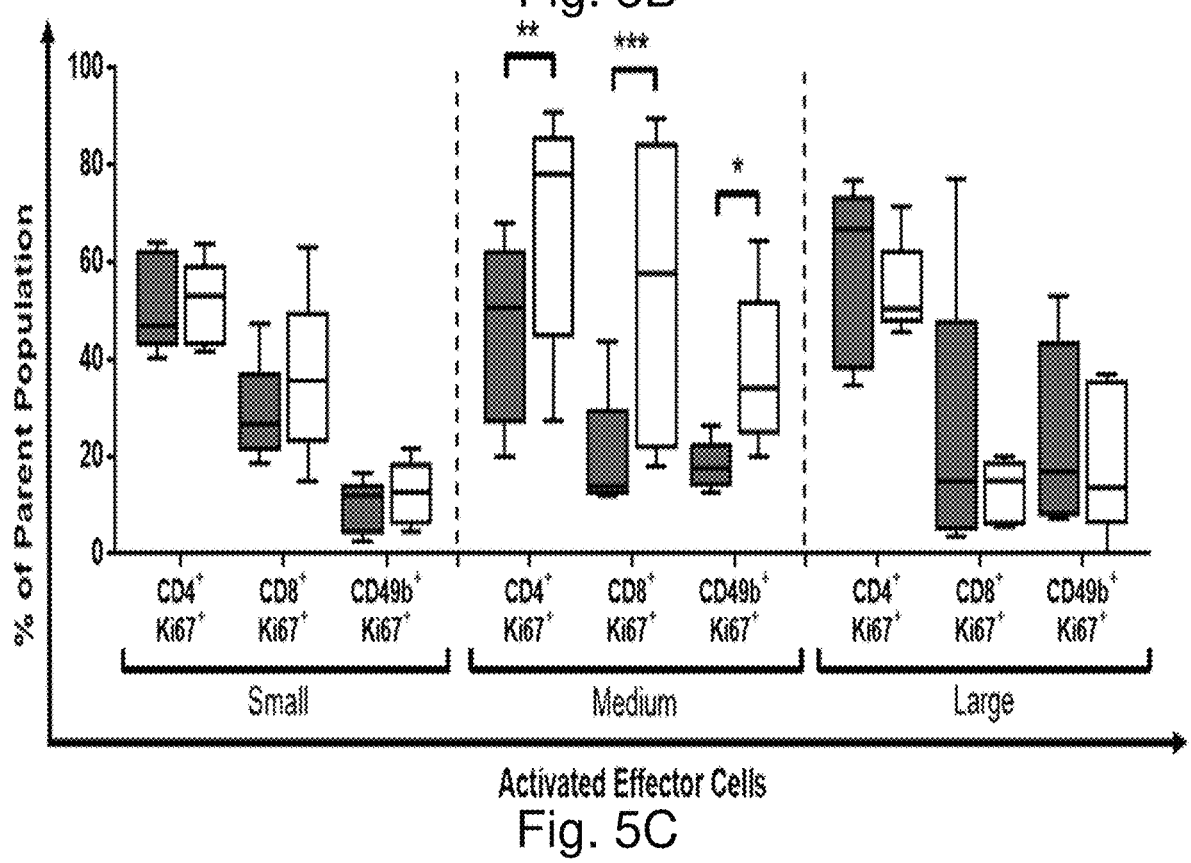

FIGS. 5A-5C show alterations in the tumor microenvironment in mice implanted with CD47$^{-/-}$ melanoma cells. Tumors were collected from CD47$^{+/-}$ B16F10 and CD47$^{-/-}$ 3BD9 engrafted mice (n=5 each group) at three stages of tumor development—small (200-300 mm$^3$), medium (500-600 mm$^3$), and large (800-900 mm$^3$). (FIG. 5A) PD-L1 expression on tumor cells, (FIG. 5B) infiltration of regulatory T cells (T-regs), and (FIG. 5C) activated (Ki67$^+$) effector cells (CD4$^+$ T cells, CD8$^+$ T cells, and NK cells) in the tumor microenvironment. *p<0.5, p<0.01, *p<0.001 by one-way ANOVA using GraphPad Prism.

TABLE 2

Antibodies used for immuno-phenotyping lymphocyte populations in TME and TDLNs

| No. | Marker | Antibody Clone | Fluorophore | Dilution | Concentration in Panel (µg/ml) |
|---|---|---|---|---|---|
| Panel T1 - Tumor Cells and Antigen Presenting Compartment - TME | | | | | |
| 1 | CD45 | 30-F11 | PerCP-Cy5.5 | 1:300 | 0.7 |
| 2 | CDIIb | MI/70 | Alexa Fluor 488 | 1:200 | 1 |
| 3 | Ly6C | HKI.4 | Brilliant Violet 785 | 1:300 | 0.7 |
| 4 | Ly6G | 1A8 | PE | 1:200 | 1 |
| 5 | CDIIc | N4 18 | Brilliant Violet 42 1 | 1:200 | 1 |
| 6 | CD47 | miap30 1 | Alexa Fluor 647 | 1:100 | 2 |
| 7 | PD-LI | 10F.9G2 | Brilliant Violet 605 | 1:100 | 2 |
| 8 | CDSO | 16-IOAI | Brilliant Violet 650 | 1:100 | 2 |
| 9 | MHC-11 | M5/114.15.2 | APC/Fire750 | 1:200 | 1 |
| Panel SLI - Antigen Presenting Comartment - TDLN | | | | | |
| 1 | CD45 | 30-FII | PerCP-Cy5.5 | 1:300 | 0.7 |
| 2 | CDIIb | MI/70 | Alexa Fluor 488 | 1:200 | 1 |
| 3 | Ly6C | HKI.4 | Brilliant Violet 785 | 1:300 | 0.7 |
| 4 | Ly6G | 1A8 | PE | 1:200 | 1 |
| 5 | CDIIc | N418 | Brilliant Violet 42 1 | 1:200 | 1 |
| 6 | CDSO | 16-IOAI | Brilliant Violet 650 | 1:100 | 2 |
| 7 | MHC-II | M5/114.15.2 | APC/Fire750 | 1:200 | 1 |
| 8 | CD206 | C068C2 | Alexa Fluor 647 | 1:100 | 2 |
| Panel P2 - Effector Cell Compartment - TME and TDLN | | | | | |
| 1 | CD45 | 30-FII | PerCP-Cy5.5 | 1:300 | 0.7 |
| 2 | CD8a | 53-6.7 | Brilliant Violet 510 | 1:100 | 2 |
| 3 | CD69 | HI.2 F3 | Brilliant Violet 650 | 1:100 | 2 |
| 4 | CD4 | GKI.5 | Brilliant Violet 785 | 1:200 | 1 |
| 5 | CD25 | 3C7 | APC | 1:100 | 2 |
| 6 | FoxP3 | FJK-16s | Alexa Fluor 488 | 1:100 | 2 |
| 7 | CD49b | CX5 | PE-CF594 | 1:100 | 2 |
| 8 | PD-1 | RMPI-14 | PE | 1:200 | 1 |
| 9 | Ki-67 | 16A8 | Brilliant Violet 421 | 1:200 | 1 |

The immuno-phenotyping of the tumor cells revealed a significant increase in cell surface PD-L1 expression as tumor progressed, in B16F10 engrafted mice, suggesting a gradual development of an immunosuppressive environment corresponding to the stage of tumor growth (FIG. 5A). The PDL-1 expressing tumor cells increased from approximately 20% at the early stage (200-300 mm$^3$) to around 45% when the tumor growth reached to a larger size (approx. 800-900 mm$^3$) in B16F10 implanted mice. In contrast, PD-L1 expression in CD47$^{-/-}$ 3BD9 engrafted mice remained at a low steady level as the tumor grew, suggesting suppression of tumor cell surface PD-L1 expression in these mice. Examining the T cell infiltration revealed an increase in resident CD4$^+$ CD25$^+$ FoxP3$^+$ regulatory T cells (T-regs) in the tumor compartment as tumors grew in both B16F10 and 3BD9 engrafted mice (FIG. 5B). The difference in T-reg infiltration is evident between B16F10 and 3BD9 engrafted mice when the tumors grew to a size of 500-600 mm$^3$. CD47$^{-/-}$ tumors exhibited higher T-regs infiltration in the tumor microenvironment. Interestingly, the T-regs infiltration were statistically at the same level when tumors grew larger in mice implanted with either CD47$^{+/+}$ or CD47$^{-/-}$ tumor cells. It seems that there is a phase of tumor growth when the host immune system responds to the tumors differently in CD47$^{+/+}$ and CD47$^{-/-}$ cancer cell engrafted mice.

The immuno-phenotyping of effector immune cells in lymph nodes confirmed this observation. A higher number of the Ki67$^+$ activated CD4$^+$ and CD8$^+$ T cells, as well as natural killer (NK) cells, were discovered in the CD47$^{-/-}$ tumor microenvironment (FIG. 5C) in both B16F10 and 3BD9 engrafted mice, the numbers of these immuno-activated cells in lymph nodes seemed to even out when the tumors were relatively small or very large, suggesting their escape from the immune system. A significantly high number of CD4$^+$ and CD8$^+$ T cells and NK cells were found in lymph nodes of 3BD9 engrafted mice when the tumors were at a medium size (500-600 mm$^3$) (p<0.001).

Immunization with Inactivated CD47$^{-/-}$ Tumor Cells Protects Mice from a Tumor Challenge.

Upon confirming the immune response of mice to CD47$^{-/-}$ cancer cells, it was determined whether inactivated CD47$^{-/-}$ cancer cells can be used as a vaccine to protect mice from a tumor challenge. First, 3BD9 cells were chemically inactivated using Mitomycin-C (MMC) which inhibits DNA synthesis, hence rendering the cell non-replicating. Mice were vaccinated with PBS (vehicle control), MMC-treated B16F10 (MMC-B16F10), and MMC-treated 3BD9 (MMC-3BD9), by following an immunization regime depicted in FIG. 6A.

Figure 6A:
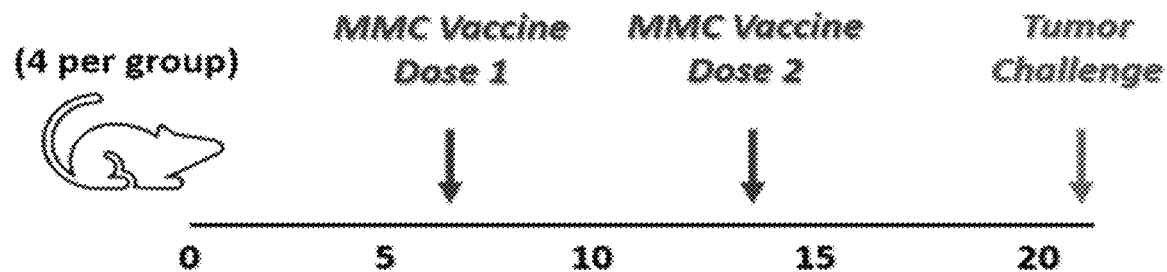
FIGS. 6A-6C show in vivo response to MMC treated melanoma cells.
Figure 6B:
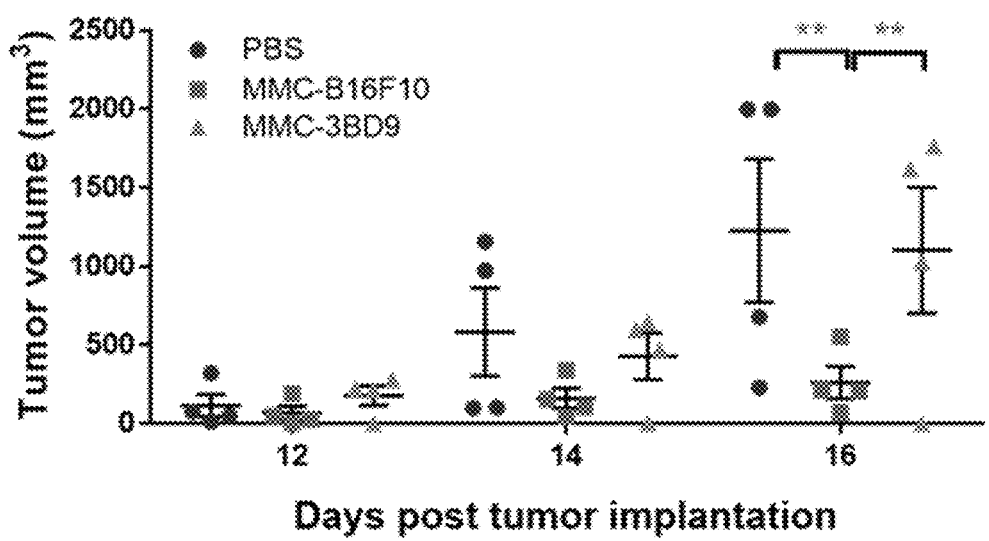
Figure 6C:
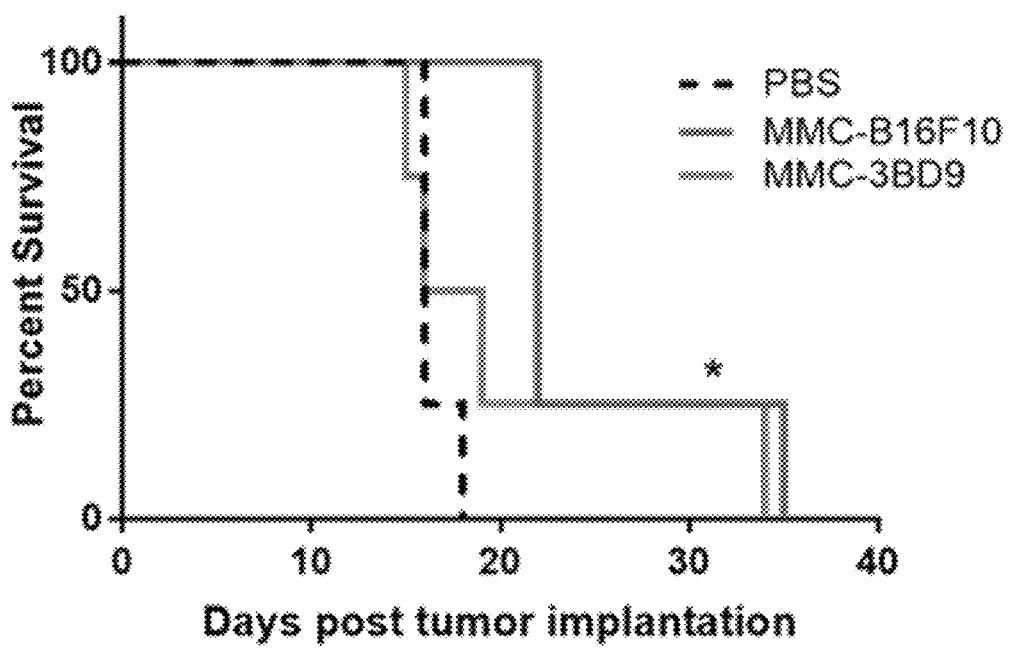

FIGS. 6A-6C show in vivo response to MMC treated melanoma cells. (FIG. 6A) The immunization regime where the red arrows mark the injection of either PBS (vehicle control) or MMC-inactivated melanoma cells (B16F10 or 3BD9). The blue arrow indicates a tumor challenge using live B16F10 cells. Two doses, separated by 7 days, of MMC-treated cells were injected into the left flanks of mice to vaccinate them. The tumor challenge was given 7 days after the 2$^{nd}$ dose of vaccines. (FIG. 6B) The development of tumors after B16F10 engrafting in MMC-B16F10, MMC-3BD9, and PBS vaccinated mice. **p<0.01 by unpaired t test. (FIG. 6C) Survival rate of vaccinated mice after tumor challenge. n=4 per group. *p<0.5 by Mantel-Cox test.

Immunogenicity in these vaccinated mice was determined after challenging the mice using B16F10 cells on day 7 post the second dose of vaccination. The MMC-3BD9 vaccinated mice exhibited a significantly delayed tumor growth by approximately 5 days (FIG. 6B). In both the MMC-B16F10 and MMC-3BD9 groups, the lifespan of tumor-bearing mice was doubled in comparison to the PBS vaccinated mice. MMC vaccinated mice survived for around 35 days, whereas PBS vaccinated mice only survived for 18 days. However, there was no significant difference in the survival rate of the mice within the B16F10 and 3BD9 groups, suggesting that CD47 does not play a role in this immunogenicity (FIG. 6C). MMC treatment makes cells inherently apoptotic (Terness et al. 2008; Scheffer et al. 2003; Roh et al. 2008; McKenna et al. 2012). CD47 is one of the most essential proteins in the clearance of apoptotic cells. The MMC treatment leads to the rearrangement of CD47 on the cell surface to form islands and helps cellular uptake by macrophages. Thus, the MMC treatment of B16F10 effectively elicited an immune response. These experimental results clearly suggested that MMC-treatment is inappropriate for testing the immunogenic capability of the 3BD9 cells against cancers.

The inactivation of 3BD9 using γ-irradiation (Roy et al. 2001) was then tested. Irradiation is one of the most commonly used methods for inactivating cells while maintaining their biological integrity Dranoff et al. 1993). Inactivated B16F10 and 3BD9 cells were prepared by γ-irradiating them using a Cs source at 35 Gy and used them to vaccinate mice before a tumor challenge. As controls, mice vaccinated with PBS and irradiated B16F10 cells were studied alongside. Flow cytometric analysis confirmed the expression of CD47 and the absence of CD47 on irradiated B16F10 and 3BD9 cells, respectively (FIG. 7B). This suggested that the expression of CD47 on cell surface was unaltered post irradiation.

Figure 7A:
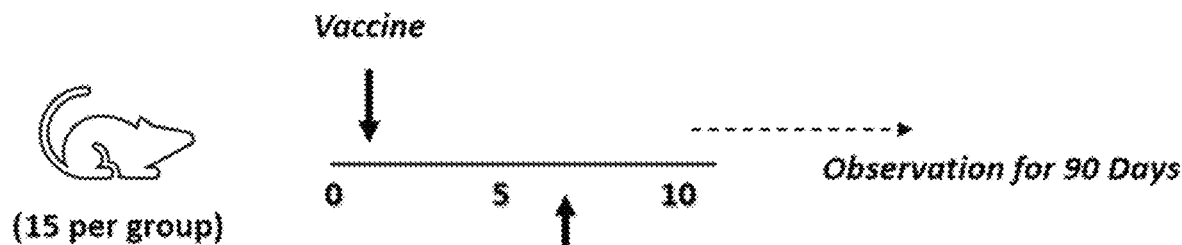
FIGS. 7A-7C show suppression of tumor growth in vaccinated mice.
Figure 7B:
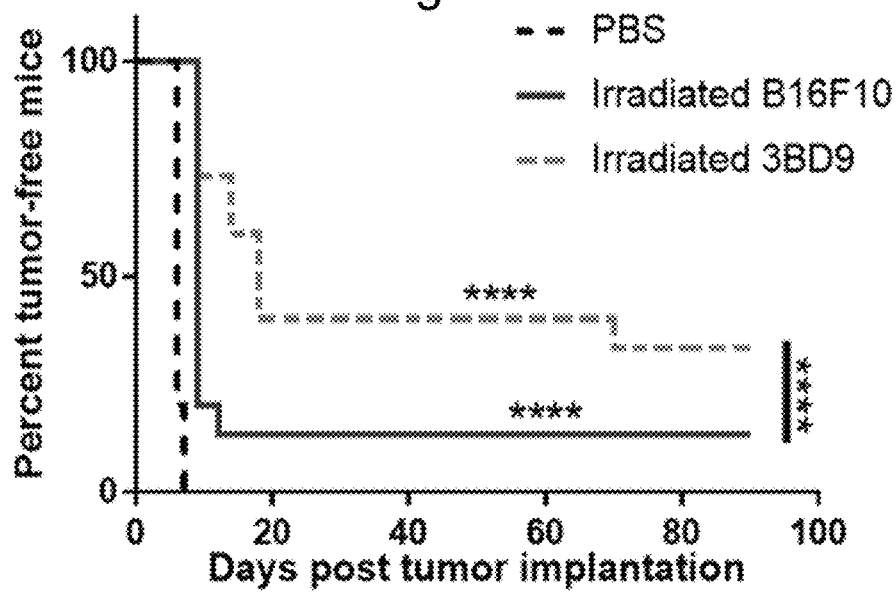

Mice (15 per group) were vaccinated subcutaneously with irradiated 3BD9 or B16F10 cells, on their left flanks and challenged with live B16F10 cells on the same flank 7 days later (FIG. 7A).

Figure 7C:
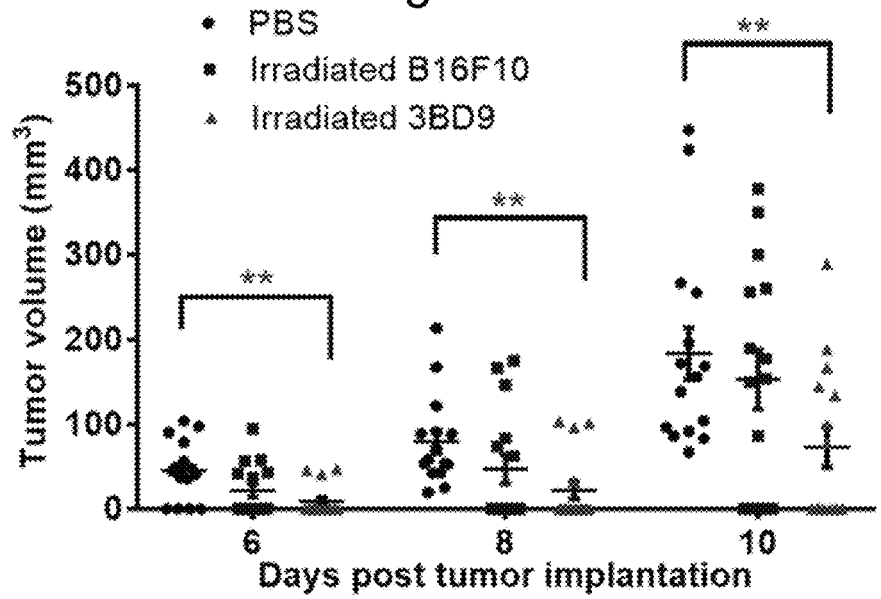

FIGS. 7A-7C show suppression of tumor growth in vaccinated mice. (FIG. 7A) The study regime: 15 mice per group were vaccinated with PBS, irradiated B16F10, or irradiated CD47$^{-/-}$ 3BD9 cells, and challenged with live B16F10 cells 7 days later. Mice were observed for 90-days post tumor implantation. (FIG. 7B) Tumor growth in mice from the three vaccination regimes. p<0.01 by unpaired t test. (FIG. 7C) Percentage of tumor free mice after vaccination. **p<0.0001 by the Mantel-Cox test. Symbol, Irr.: irradiation.

In the irradiated 3BD9 vaccinated group, 40% of the mice (6/15) were tumor-free until day 70 post tumor challenge, and 33% of the mice (5/15) were tumor-free until the end of the regime (90-days post tumor challenge). More significantly, 13% of these mice (2/15) were tumor free at the end of 90-days post tumor challenge (FIG. 7B). For those did develop tumor, a significant delay in tumor growth was observed (FIG. 7C). The average tumor size in irradiated 3BD9 vaccinated mice that developed tumor was around 60 mm$^3$, whereas it was close to 170 mm$^3$ in irradiated B16F10 vaccinated mice at day 10. 100% (15 mice) of PBS vaccinated mice developed tumors. These experimental data suggested a strong tumor-specific immune response to CD47 depleted tumor cell vaccines, and it was important to further understand the underlying mechanisms of these responses.

Vaccination with Irradiated CD47$^{-/-}$ Tumor Cells Confers Immunity to Mice by Upregulating Antigen Presentation and Increasing Effector Cell Activity To understand the underlying mechanisms that confer an anti-tumor immune response in the 3BD9 vaccinated mice, multi-parametric immune cell phenotyping was performed to characterize different immune cell subsets in the TME and in the TDLNs of mice using cell-specific protein markers shown in Table 3. A combination of various markers helped us identify specific subsets of cells, their lineages, and correlation with response to vaccines. A comprehensive list of cell types and subsets based on the markers chosen is available in Table 4. The immune mechanisms involved in mice that showed a complete response to vaccination by irradiated 3BD9 cells, i.e., those that did not develop a tumor 90-days post vaccination, were investigated. To that end the immune cell populations in the TDLNs of responders (CD47$^{-/-}$ 3BD9 R), and non-responders (CD47$^{-/-}$ 3BD9 NR) or those that developed delayed tumors after vaccination were compared.

Figure 8A:
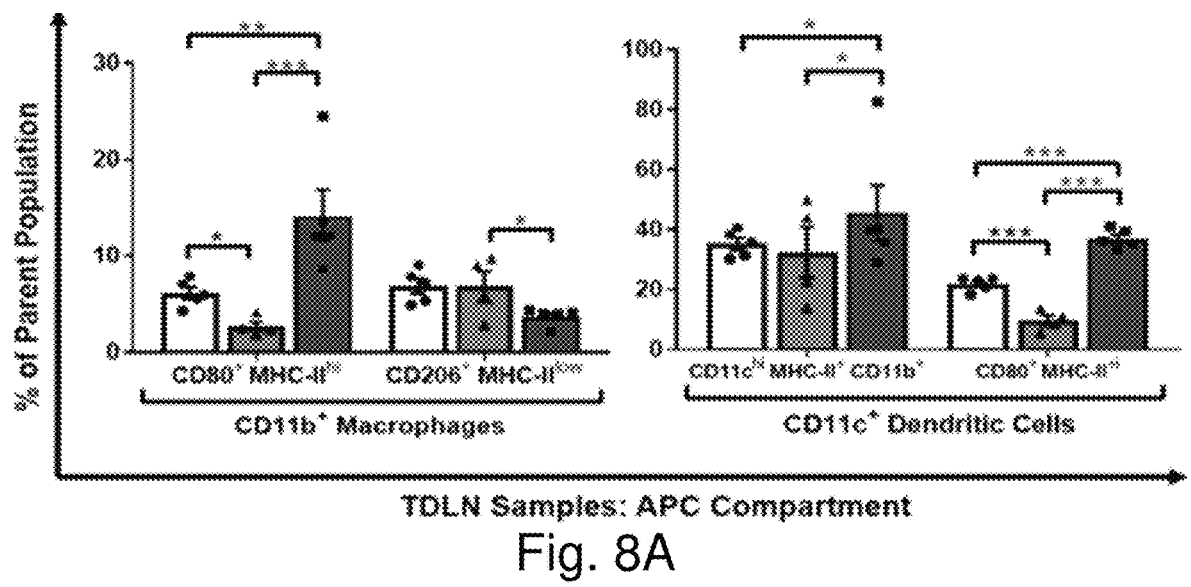
FIGS. 8A-8D show tumor-free vaccinated mice show more activated immune phenotypes in Tumor Draining Lymph Nodes (TDLNs).
Figure 8B:
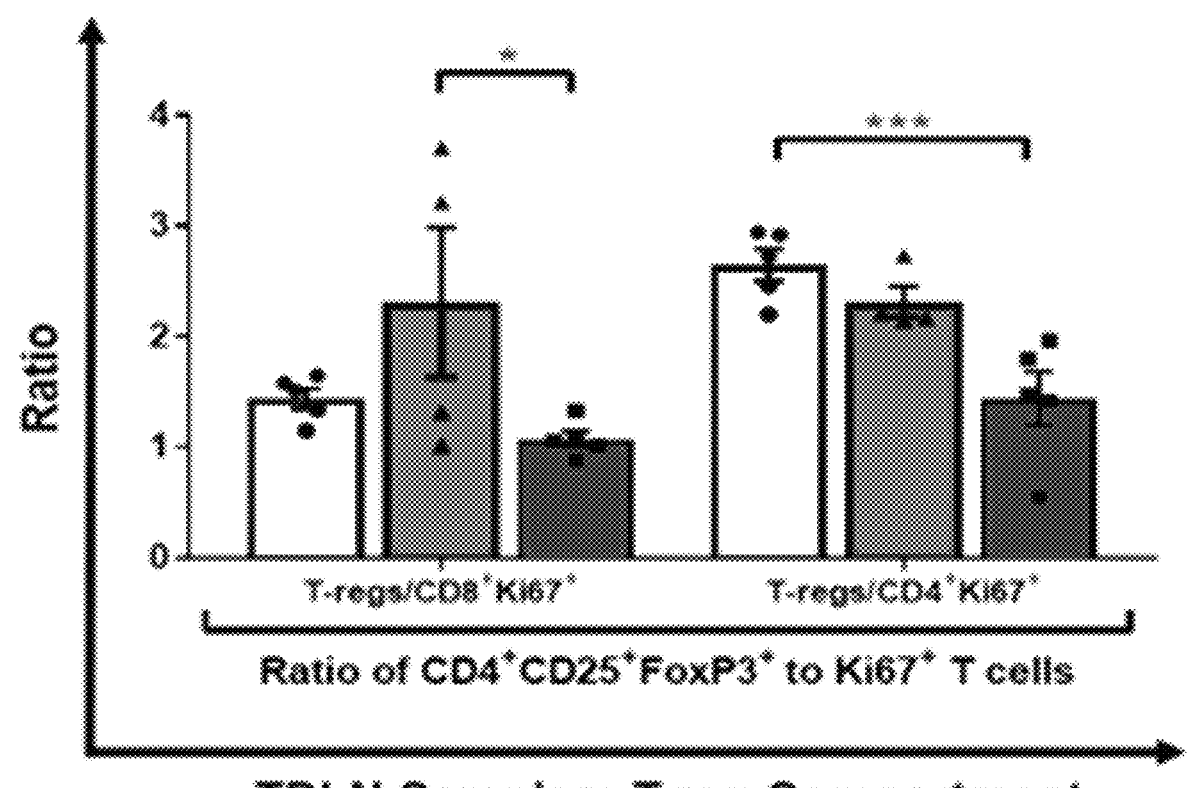
Figure 8C:
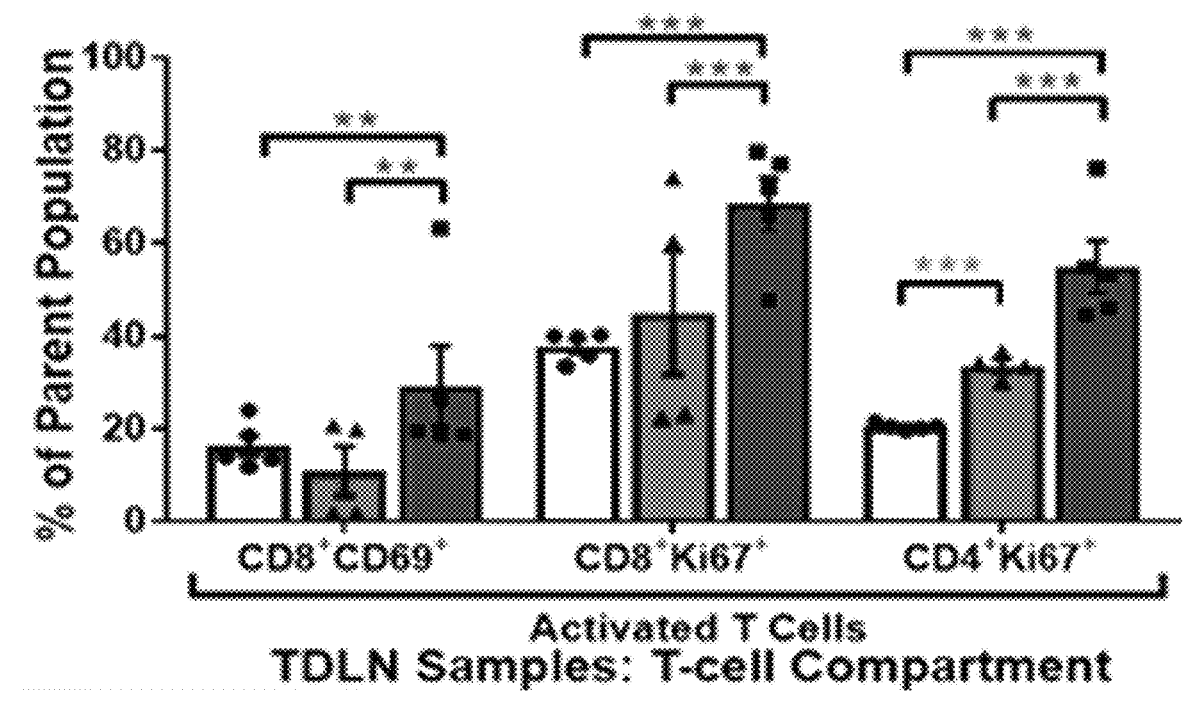
Figure 8D:
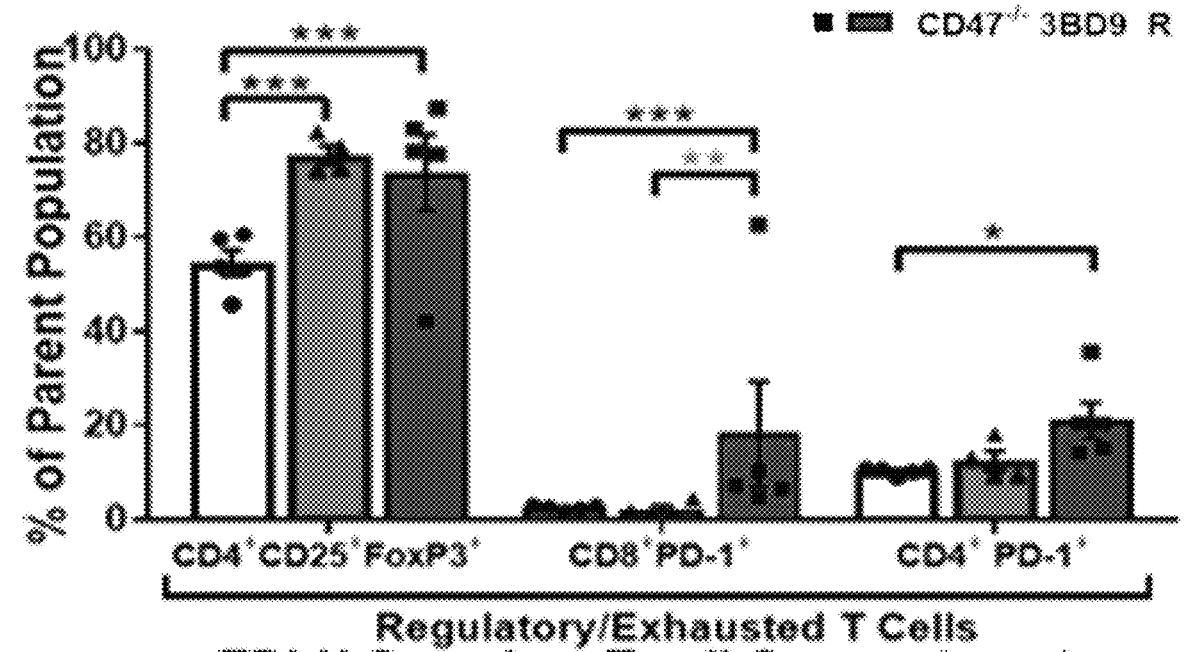

A significant increase in the M1-type anti-tumorigenic macrophages was observed, and a reduction in the M2-type pro-tumorigenic macrophages. M1 macrophage populations were five times higher and M2 macrophage populations were almost half the amount in the responders when compared to the non-responders. Additionally, the percentage of migratory DCs (Parajuli et al. 2010) and activated DCs that efficiently present antigens to the T cells, were significantly increased (FIG. 8A).

FIGS. 8A-8D show tumor-free vaccinated mice show more activated immune phenotypes in TDLNs. (FIG. 8A) Macrophage and dendritic cell subsets present in the antigen presenting cell (APC) compartment, (FIG. 8B) ratio of regulatory T cells (T-regs) and activated T cells (Ki67$^+$), (FIGS. 8C and 8D) CD8$^+$ and CD4$^+$ T cell subsets in the T-cell compartment of the tumor-draining lymph nodes (TDLNs). NR: non-responders (mice that grew tumors after vaccination); R—responders (tumor-free mice after vaccination). n=5 mice per cohort for PBS and R groups. n=4 for NR group. Immuno-phenotyping was performed by flow cytometry. Cell phenotypes are presented as a percentage of their parent cell population. *p<0.5, p<0.01, *p<0001 by the unpaired t test performed using GraphPad Prism.

Activated DC population were 6-7 times higher in the responders. These data suggest that the antigen presenting compartment is efficient in the TDLNs of the mice that responded to the 3BD9 vaccine. Moreover, the ratio of regulatory T cells (T-regs) to activated (Ki67$^+$) T cells was drastically reduced in the responders (FIG. 8B), further confirming the presence of a highly anti-tumorigenic immune response. Analysis of the specific T cell subsets showed that the activated effector cell percentages are much higher in the responders in comparison to the non-responders and the PBS vaccinated mice, leading to the hypothesis that the tumor rejection could be a result of this. It is, however, interesting to note that the T-reg and the exhausted T cell (PD-1+) populations were higher in the 3BD9 vaccinated groups that in the PBS vaccinated groups (FIGS. 8C and 8D), though the ratios were much less in comparison.

TABLE 3

Markers used for phenotypic characterization of immune and tumor cells.

| Marker | Cellular Location | Description |
|---|---|---|
| | Antigen Presenting Compartment/Tumor Compartment | |
| CD45 | Plasma Membrane | Pan leukocyte marker; to differentiate immune cells from other types of cells |
| CD11b | Plasma Membrane | Macrophage specific marker |
| Ly6C | Plasma Membrane | Monocyte marker; tumor-associated macrophage marker; part of the Gr1 complex with Ly6G |
| Ly6G | Plasma Membrane | Monocyte marker; tumor-neutrophilic lineage, part of the Gr1 complex with Ly6C |
| CD11c | Plasma Membrane | Dendritic cell specific marker |
| CD80 | Plasma Membrane | Antigen presenting cell (APC) specific activation marker; present in M1-type macrophages and activated DCs |
| CD206 | Plasma Membrane | M2-type macrophage marker |
| MHC-II | Plasma Membrane | Antigen presentation capability |
| PD-L1 | Plasma Membrane | Ligand for PD-1 on exhausted T-cells; present on tumor cells as a defense mechanism, and on APCs |
| CD47 | Plasma Membrane | "Don't eat me" signal on tumor cells; interacts with SIRP-α on macrophages to contain phagocytosis |
| | Effector Cell Compartment | |
| CD8a | Plasma Membrane | Cytotoxic T-cell (CTL) specific marker |
| CD69 | Plasma Membrane | CTL activation marker |
| CD4 | Plasma Membrane | Helper T-cell ($T_H$) specific marker |
| CD25 | Plasma Membrane | IL2RA protein for identification of CD4$^+$FoxP3$^+$ regulatory cells (T-regs) |
| FoxP3 | Nucleus | Transcription factor expressed by T-regs |
| CD49b | Plasma membrane | Natural Killer (NK) cell specific marker (only C57BL/6 mice) |
| PD-1 | Plasma Membrane | Programmed death protein expressed on the surface of exhausted T-cells; deactivation upon interaction with PD-L1 on tumor cells and APCs |
| Ki-67 | Nucleus | Proliferation marker expressed by activated effector cells (T cells, NK cells) |

Note:
The table lists cell-specific markers used in various combinations as part of two panels that identify specific characteristics of immune cells and tumor cells in the tumor microenvironment and in the tumor-draining lymph nodes.

TABLE 4

Phenotypic characterization of antigen presenting cells in immune infiltrates.

| Subset | Significance | Phenotype |
|---|---|---|
| Macrophage Subsets | Anti-tumorigenic; enhanced IL-2 production | CD11b$^+$ CD80$^+$ |
| M1-type Macrophages | Anti-tumorigenic; efficient antigen presentation | CD11$^+$ CD80$^+$ MHC-II$^{hi}$ |
| M2-type Macrophages | Pro-tumorigenic; suppressed antigen presentation | CD11b$^+$ CD206$^+$ MHC-II$^{low}$ |
| Suppressive Macrophages | T cell deactivation | CD11b$^+$ PD-L1$^+$ |
| Tumor-Associated Macrophage (TAM) Subsets | | |
| TAM-1 | Pro-tumorigenic; inefficient antigen presentation | CD11b$^+$ Ly6C$^{int}$ MHC-II$^{hi}$ |
| TAM-2 (MHC-II$^{hi}$ TAMs) | Pro-tumorigenic; normoxic conditions | CD11b$^+$ Ly6C$^{low}$ MHC-II$^{hi}$ |
| TAM-3 (MHC-II$^{low}$ TAMs) | Pro-tumorigenic; present in hypoxic conditions; suppressed antigen presentation | CD11b$^+$ Ly6C$^{low}$ MHC-II$^{low}$ |
| Dendritic Cell (DC) Subsets\ | | |
| Activated DCs | Anti-tumorigenic; enhanced IL-2 production; efficient antigen presentation | CD11c$^+$ MHC-II$^+$ CD80$^+$ |
| Migratory DCs | Present mostly in tumor-draining lymph nodes; signifies high DC activity | CD11c$^{hi}$ MHC-II$^+$ CD11b$^+$ |
| Regulatory DCs | May be pro-tumorigenic | CD11c$^+$ MHC-II$^+$ CD80$^+$ |
| Suppressive DCs | T cell deactivation | CD11c$^+$ PD-L1$^+$ |
| Myeloid-Derived Suppressor Cell (MDSC) Subsets | | |
| Poly-morphonuclear (PMN) MDSCs (granulocytic) | Pro-tumorigenic; from Ly6C$^{hi}$ monocytic precursors; differ in lineage; Ly6C$^{hi}$ forms | CD11b$^+$ Ly6C$^{low}$ Ly6G$^+$ |

TABLE 4-continued

Phenotypic characterization of antigen presenting cells in immune infiltrates.

| Subset | Significance | Phenotype |
|---|---|---|
| Monocytic (Mo) MDSCs Monocyte-derived (Mo-derived) MDSCs | more suppressive than $Ly6C^{low}$ forms | $CD11b^+$ $Ly6C^{hi}$ $Ly6G^+$ $CD11b^{hi}$ $Ly6G^+$ $MHC-II^+$ |
| Cytotoxic T Cell (CTL) Subsets - $CD8^+$ | | |
| Activated CTLs | Primed tumor-specific $CD8^+$ T cells | $CD8^+$ $CD69^+$ |
| Activated/Proliferating CTLs | Activated and proliferating $CD8^+$ T cells; produce granzymes, perforins, IFN-γ | $CD8^+$ $Ki67^+$ |
| Exhausted CTLs | Deactivated phenotype of $CD8^+$ T cells; incapable of cytotoxic killing | $CD8^+$ $PD-1^+$ |
| Helper T Cell ($T_H$) subsets $CD4^+$ | | |
| Regulatory T cells (T-regs) | Inhibit proliferation and activation of CTLs and $T_H$ cells | $CD4^+$ $CD25^+$ $FoxP3^+$ |
| Activated/Proliferating $T_H$ cells | Activated and proliferating $CD4^+$ T cells; produce IL-2, IFN-γ | $CD4^+$ $Ki67^+$ |
| Exhausted $T_H$ cells | Deactivated phenotype of $CD4^+$ T cells; incapable of cytokine release | $CD4^+$ $PD-1^+$ |
| Natural Killer (NK) Cell Subsets - $CD49^+$ | | |
| Activated Natural Killer Cells | Primed NK cells; produce granzymes; cytotoxic activity | $CD49b^+$ $Ki67^+$ |
| Ratios of Cell Types | | |
| Ratio of T-regs to $Ki67^+$ T cells | High ratio signifies a more suppressive environment; no T cell proliferation | $CD4^+$ $CD25^+$ $FoxP3^+$: $CD8^+$ $Ki67^+$ |
| Ratio of $PD-1^+$ to $Ki67^+$ T cells | High ratio signifies a more suppressive environment; exhausted T cells | $CD8^+$ $PD-1^+$: $CD8^+$ $Ki67^+$ $CD4^+$ $PD-1^+$: $CD4^+$ $Ki67^+$ |
| Ratio of $MHC-II^{hi}$ TAMs to $MHC-II^{low}$ TAMs | High ratio signifies a more normoxic condition and a less suppressive environment | $CD11b^+$ $LydC^{low}$: $MHC-II^{hi}$: CD11b+ $Ly6C^{low}$ $MHC-II^{low}$ |

Note:
The table lists all the phenotypic subsets used in this project to determine immune cell function associated with tumor rejection and escape. Categorization of these subsets is based on their lineage, function, and specific cell surface markers.

Comparison of tumor and lymphocyte populations in mice vaccinated with irradiated B16F10 and irradiated 3BD9 confirms the vital role of CD47

To elucidate the specific role of CD47 in this immunologic reaction, lymphocyte populations in the TME and in the TDLNs of irradiated B16F10 and 3BD9 vaccinated mice that developed tumors after a tumor challenge were compared. It was important to track the alteration in the immune phenotypes as the tumors grew to understand how the microenvironment and the specific immune responses evolve. To this end, cell types were characterized at three different stages of tumor growth—small (200-300 mm³), medium (500-600 mm³), and large (800-900 mm³). In the TME, activated and proliferated T and NK cells were examined, and found that the 3BD9 vaccinated mice had significantly higher percentages of $Ki67^+$ effector cells, especially in the small and medium sized tumors. In contrast, the B16F10 vaccinated mice lost their effector cell populations over time (FIG. 9A).

Figure 9A:
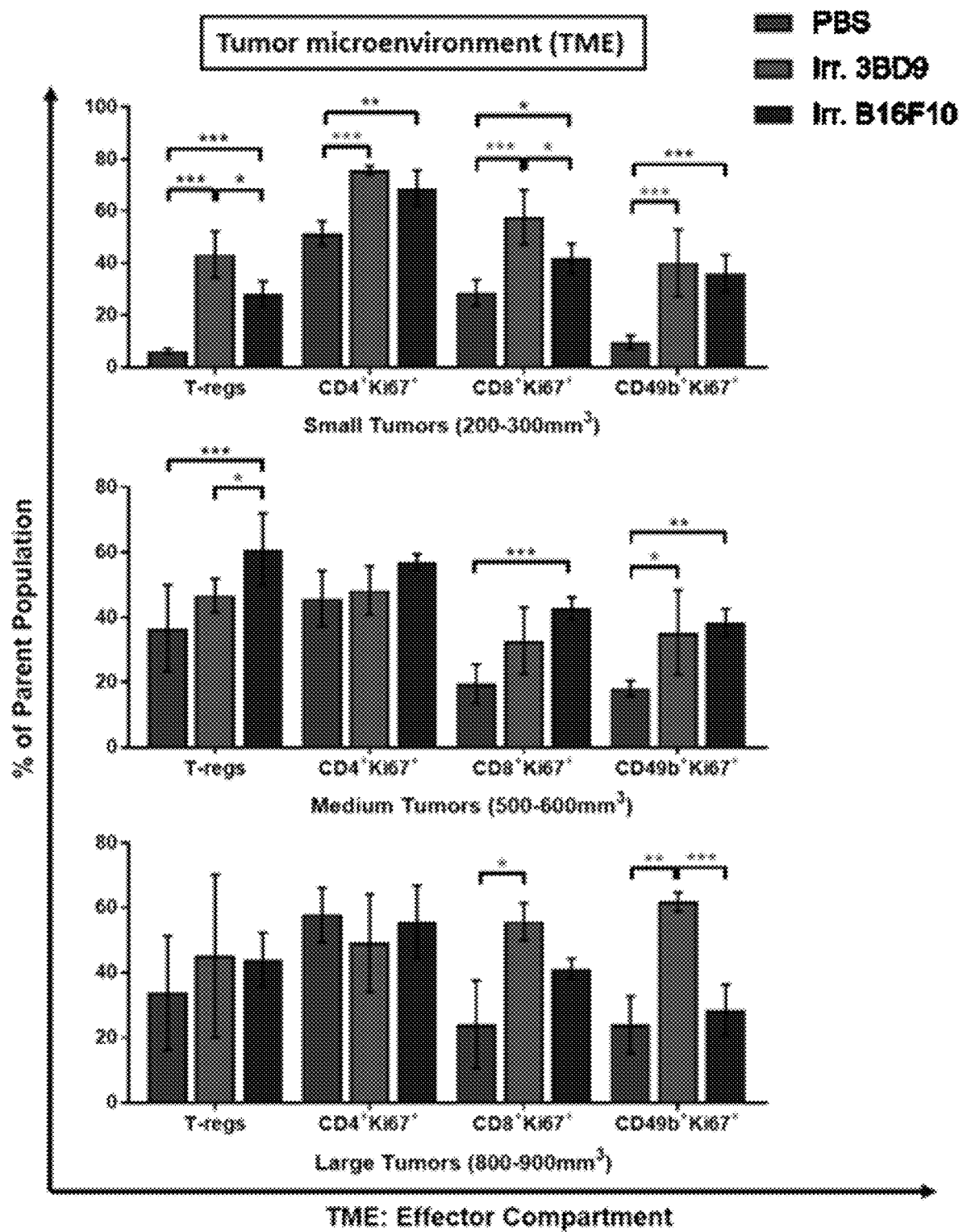
FIGS. 9A-9E show lymphocyte populations and loss of CD47 expression over time in B16F10 and 3BD9 vaccinated mice.
Figure 9B:
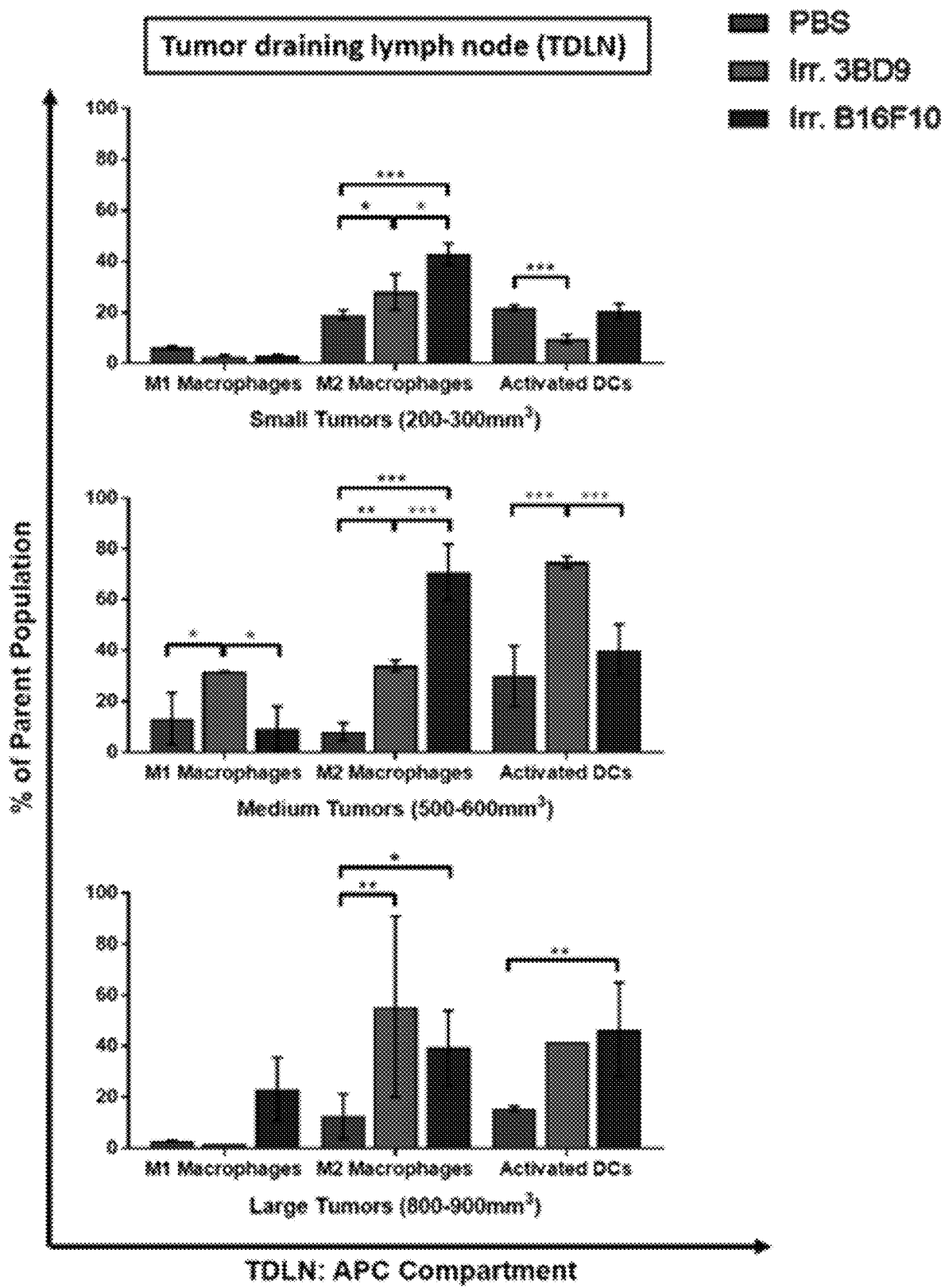
Figure 9C:
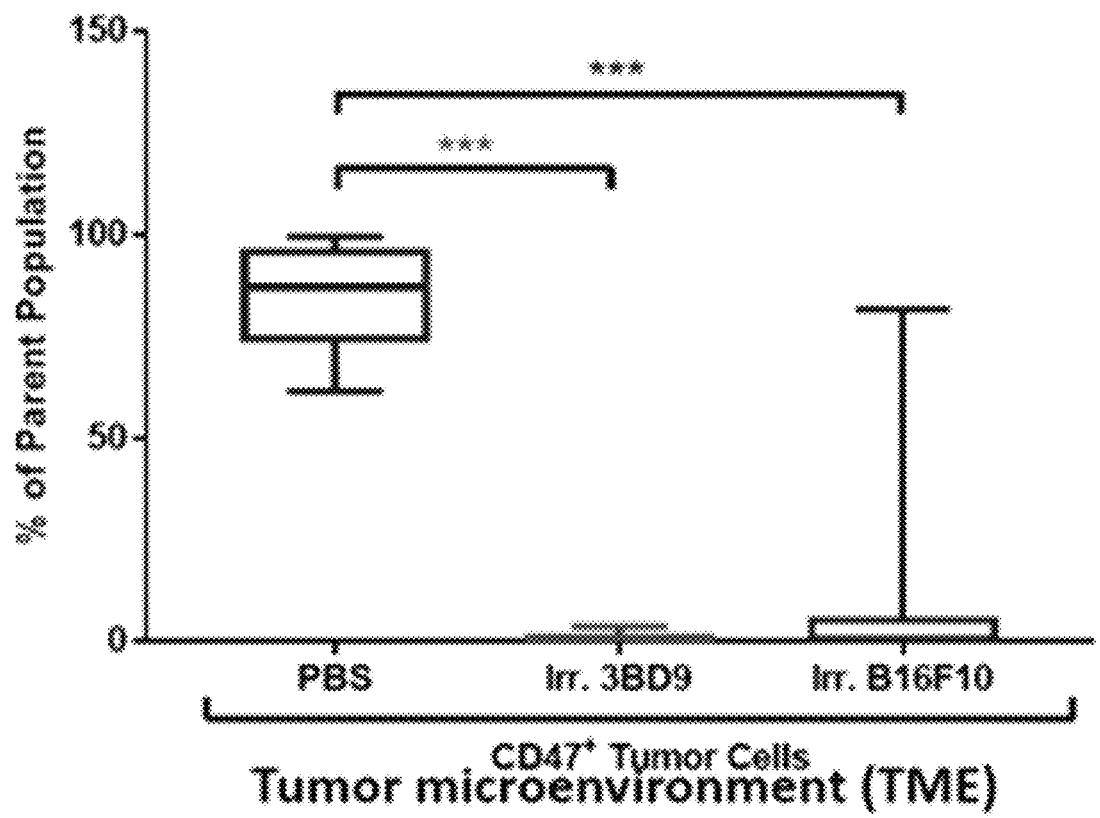
Figure 9D:
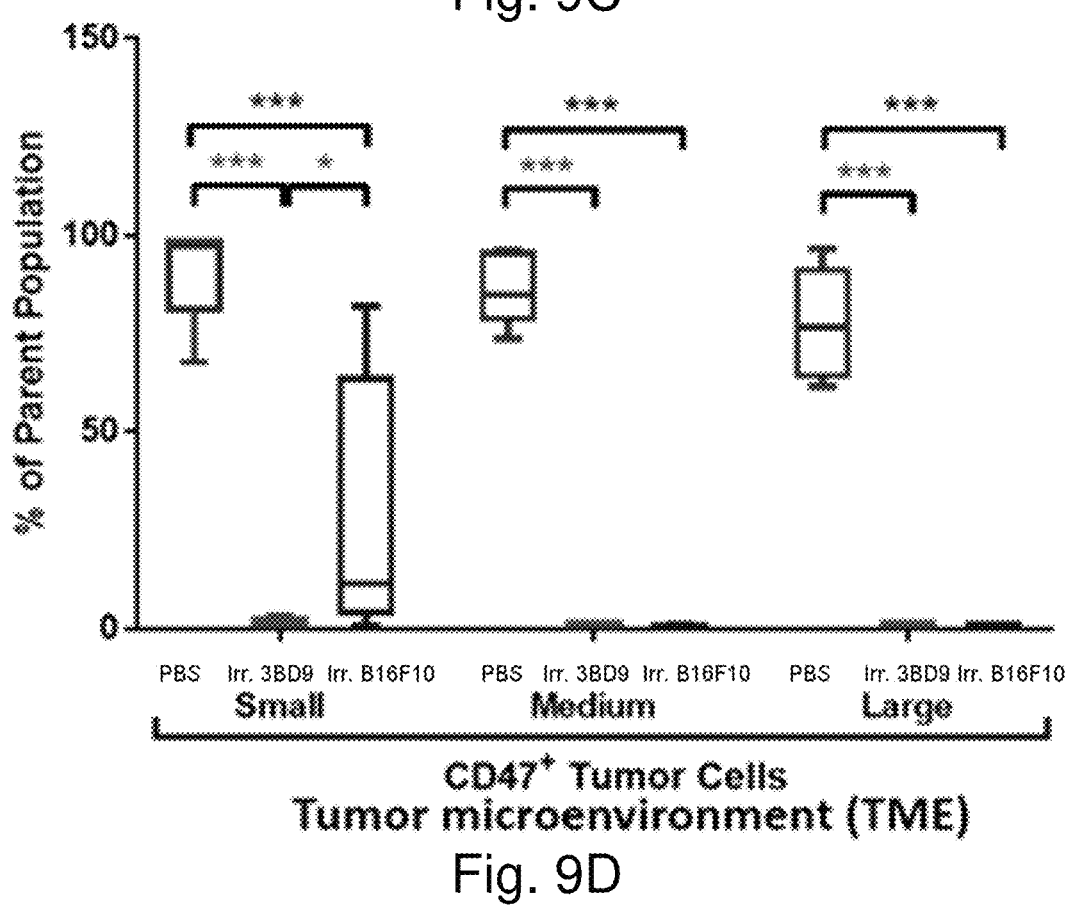
Figure 9E:
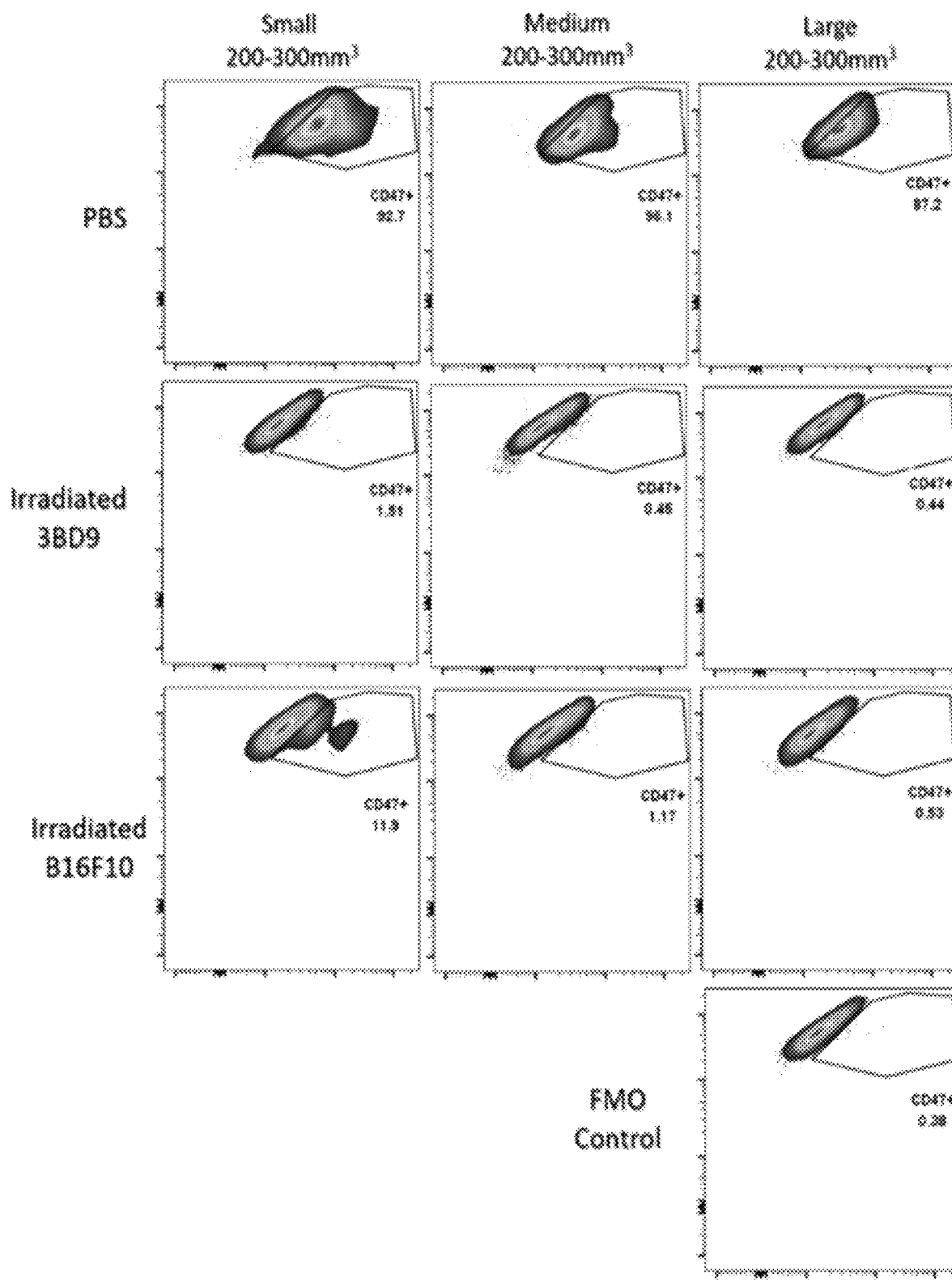

FIG. 9A09E show lymphocyte populations and loss of CD47 expression over time in B16F10 and 3BD9 vaccinated mice. (FIG. 9A) Regulatory T cells (T-regs), activated ($Ki67^+$) T cells and activated NK cells in the tumor microenvironment, and (FIG. 9B) macrophage (M1- and M2-type) and dendritic cell subsets in the tumor-draining lymph nodes of mice at different stages of tumor growth in the PBS, 3BD9, and B16F10 vaccinated groups. Comparison of CD47 expression on all tumors (FIG. 9C) at different stages of tumor growth (FIG. 9D) in the PBS, 3BD9, and B16F10 vaccinated mice with representative CD47 expression dot plots (FIG. 9E). In the PBS vaccination cohort, n=5 for all three stages of tumor growth. In the 3BD9 cohort, n=4 (small), n=3 (medium), n=2 (large) and in the B16F10 cohort n=4 (small), n=5 (medium), n=4 (large). Flow cytometric analysis was performed on FlowJo and cell phenotypes are presented as a percentage of the parent cell population. *$p<0.5$, $p<0.01$, *$p<0.001$ by unpaired t test performed on GraphPad Prism.

The specific effect of the absence of CD47 might be in improving the long-term survival of mice by increasing effector cell populations over time and delaying their exhaustion while keeping the suppressive cells to a minimum. The T-reg populations in the inactivated cell vaccinated mice were consistently observed to be higher than in the PBS vaccinated ones (FIG. 9A). This could be due to the abundance in T cell populations and cytokine release, driving the phenotypic change to a regulatory form. In the TDLNs, an increase in the levels of M1-type macrophages and a reduction in the M2-type macrophages in the small and medium sized tumors developed after irradiated 3BD9 vaccination were detected, which is one of the most expected responses to the lack of CD47 (FIG. 9B). PBS vaccinated mice initially showed a higher population of activated DCs, which reduced drastically over time, and the irradiated 3BD9 vaccinated mice showed much higher levels correlating with tumor progression (FIG. 9B), indicating high immune activity in the lymph nodes. These data correspond to the overall observation that the TME is "hot" and active in the 3BD9 vaccinated tumors, providing opportunities for further intervention to enhance this effect.

Another very remarkable observation pertaining specifically to the involvement of CD47 in the anti-tumor response, was in the non-TIL compartment of the tumors of vaccinated mice. All tumor implants were B16F10 cells, known to express CD47 on their surface. However, upon analysis of the CD45$^-$ (negative for the pan-leukocyte marker) tumor cells in the TME, CD47 was down regulated in 3BD9 vaccinated mice significantly (FIG. 9C). Breaking down this observation and analyzing at three stages of tumor growth, it was interesting to see that when the tumors are small, the B16F10 vaccinated tumors still have a significantly higher expression of CD47 when compared with the 3BD9 vaccinated tumors. However, as the tumor grows, even the B16F10 treated mice begin to lose their CD47 expression (FIG. 9D). Upon closer look, the stark difference in CD47 expression in 3BD9, B16F10 and PBS treated mice is evident in all the replicates analyzed at each stage of tumor growth (FIG. 9E). This observation also supports the corresponding TIL changes in the tumor microenvironment characterized in the above sections. It is worth considering that the tumors seem to evolve against an existing immune response according to the types of primed TILs that have been developing due to vaccination.

Investigating the TME and TDLNs of 3BD9 vaccinated mice reveals actively anti-tumorigenic conditions, with distinct TAM phenotypes.

Figure 10A:
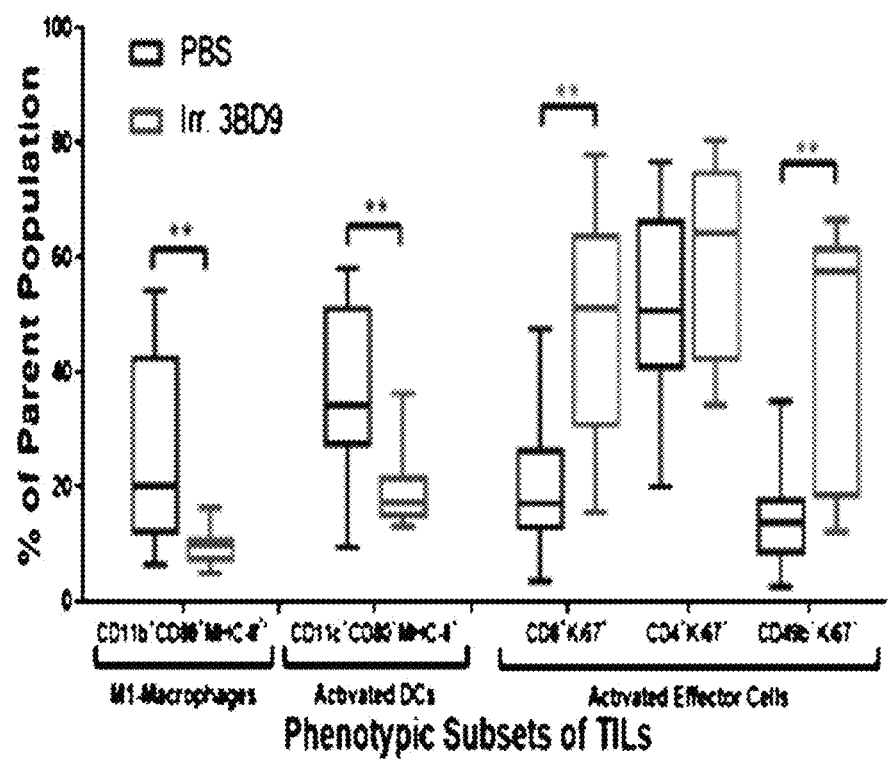
FIGS. 10A-10F show anti-tumorigenic tumor microenvironment in 3BD9 vaccinated mice with distinct suppressor cell phenotypes.
Figure 10B:
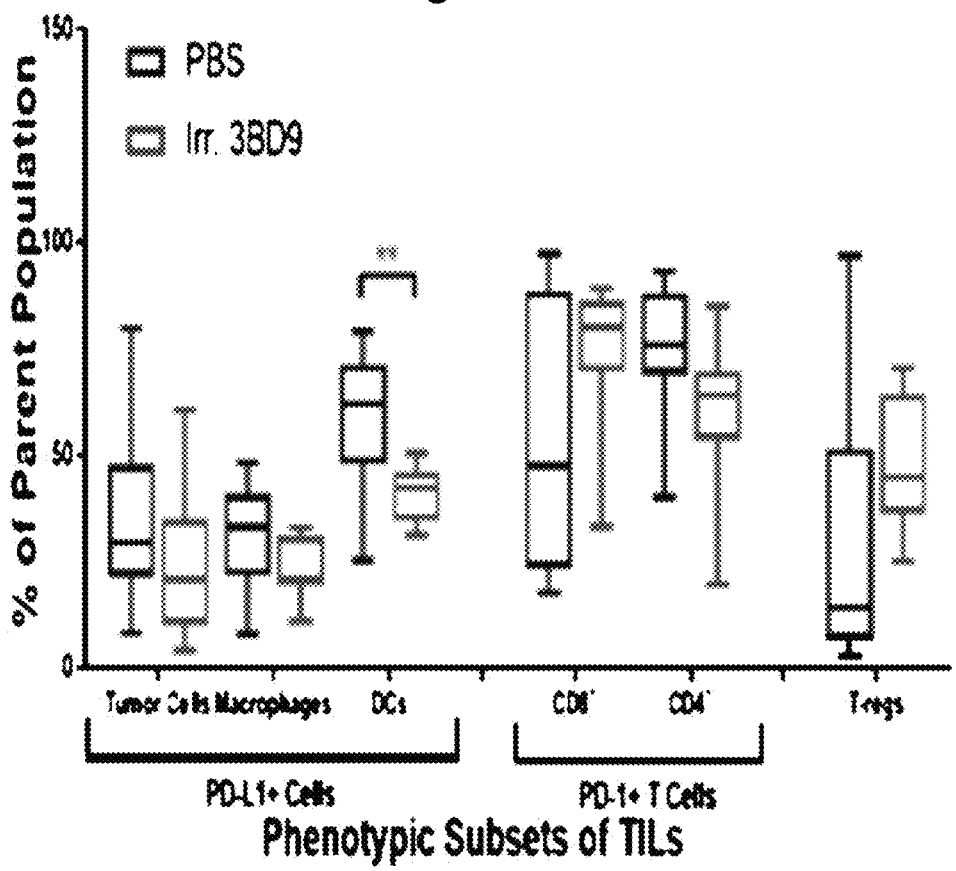
Figure 10C:
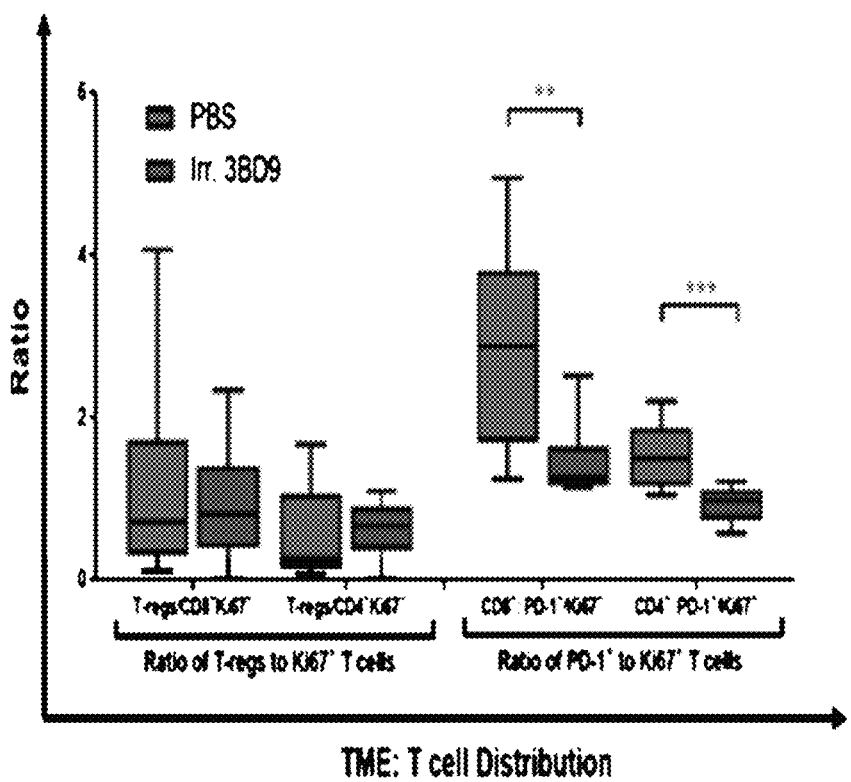

After determining the role of CD47 in eliciting an immune response in vaccinated mice, the immune activity in the tumor microenvironment and the draining lymph nodes of the mice vaccinated with irradiated 3BD9 cells was investigated. The populations of active antigen presenting cells and proliferating effector cells were investigated. More effector immune cell populations (Ki67$^+$ T cells and NK cells), but fewer antigen presenting cells in the TME of 3BD9 vaccinated mice as compared to those vaccinated with PBS were detected (FIG. 10A), suggesting an active immune cascade that ends in proliferation of effector cells in the 3BD9 vaccinated mice. To confirm this hypothesis, the antigen presenting cells were interrogated for the expression of the T cell-suppressive marker PD-L1 and found that both DCs and macrophages showed a higher level of PD-L1 expression in the PBS vaccinated mice in comparison with the 3BD9 vaccinated ones (FIG. 10B). There was no statistically significant difference in PD-1 expression on T cells, or in the percentage of T-reg populations between the two groups. However, the ratio of exhausted (PD-11 to activated (Ki67$^+$) T cells was drastically higher in the PBS vaccinated groups (FIG. 10C), further confirming the finding that the macrophages and dendritic cells in the TME of PBS vaccinated tumors are of a stagnant and suppressive phenotype, not leading to downstream immune cell activation.

FIGS. 10A-10F show anti-tumorigenic tumor microenvironment in 3BD9 vaccinated mice with distinct suppressor cell phenotypes. Multicolor flow cytometric analysis was performed to determine (FIG. 10A) infiltration of effector T, NK cells, macrophages, and DCs, (FIG. 10B) PD-L1 expression in tumor cells, infiltrating macrophages, and DCs, and (FIG. 10C) the distribution of regulatory and activated T cells in tumor microenvironment of 3BD9 vaccinated mice. Additional analysis was performed to characterize MDSC and TAM subsets (FIG. 10D) and the expression of lineage (Ly6G), activation (CD80), and T cell suppression (PD-L1) markers on the surface of MHC-II$^{hi}$ TAM and MHC-II$^{low}$ subsets (FIGS. 10E and 10F) in PBS and 3BD9 vaccinated mice at three stages of tumor growth—small (200-300 mm$^3$), medium (500-600 mm$^3$), and large (800-900 mm$^3$). n=15 mice for PBS, n=9 for irradiated 3BD9. In the PBS vaccination cohort, n=5 for all three stages of tumor growth. In the 3BD9 cohort, n=4 (small), n=3 (medium), and n=2 (large). Immune cell phenotypes are presented as a percentage of the parent cell population. p<0.01, *p<0.001 by unpaired t test performed on GraphPad Prism.

Figure 10D:
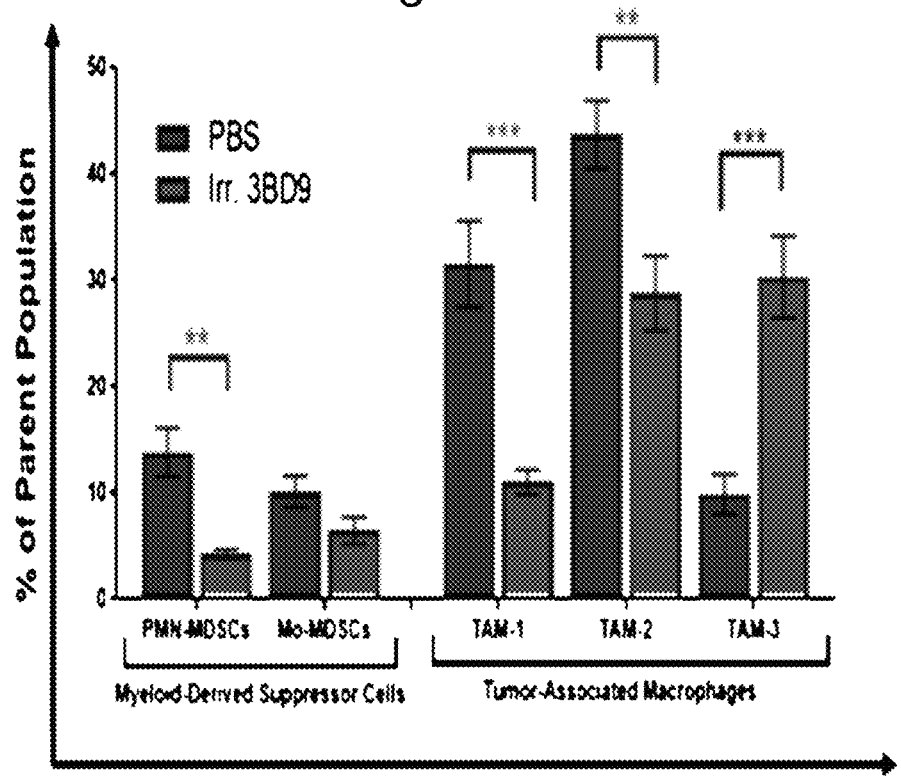

The suppressor cells—the tumor associated macrophages (TAMs) and the myeloid derived suppressor cells (MDSCs), were investigated in the tumor microenvironment. TAMs and MDSCs are responsible for a sizable portion of effector cell suppression (Bronte et al. 2016; Elliott et al. 2017; Italiani et al. 2014). This suppression is active and occurs both in the TME and in the TDLNs (Kumar et al. 2016; Movahedi et al. 2010). Phenotypic characterization of MDSCs and TAMs have been studied in previously. It has been emphasized that common characteristics of tumors that have been irreversible thus far like metastatic potential, downregulation of MHC genes, and overexpression of evasion markers, can be attributed to the specific APC phenotypes in the TME (Ostrand-Rosenberg et al. 2009; Richards et al. 2013). They are often distinguished by their cell surface marker expression (Table 4), and further studied based on mechanisms of action, T cell suppression potential, inhibitory cytokine production, and effect on other cell types. A very specific gating strategy was employed to characterize TAMs based on expression of the granulocytic lineage marker Ly6G, the monocytic marker Ly6C, and the antigen presentation complex MHC-II (FIGS. 11A and 11B). 3BD9 vaccinated tumors were found to have overall significantly less suppressive APCs in their TME—both the polymorphonuclear and the monocyte-derived MDSCs are lower (FIG. 10D). Event in the TAM compartment, the MHC-II$^{hi}$ TAMs (TAM-1 and TAM-2) are significantly lower in the 3BD9 vaccinated tumors (FIG. 10D). The MHC-II$^{low}$ TAMs (TAM-3), however, are significantly higher. These TAMs are usually found in hypoxic conditions, as opposed to their MHC-II$^{hi}$ counterparts (TAM-2), which are usually present in normoxic conditions (Movahedi et al. 2010). This could also explain the increased neo-vasculature observed near vaccinated tumors and could mean that vaccinated tumors are prone to increased necrosis due to low oxygen, hence their slower growth. The different TAMs also showed a high phenotypic variability, which was unprecedented, and also opens up many avenues for further exploration of this compartment.

Figure 11A:
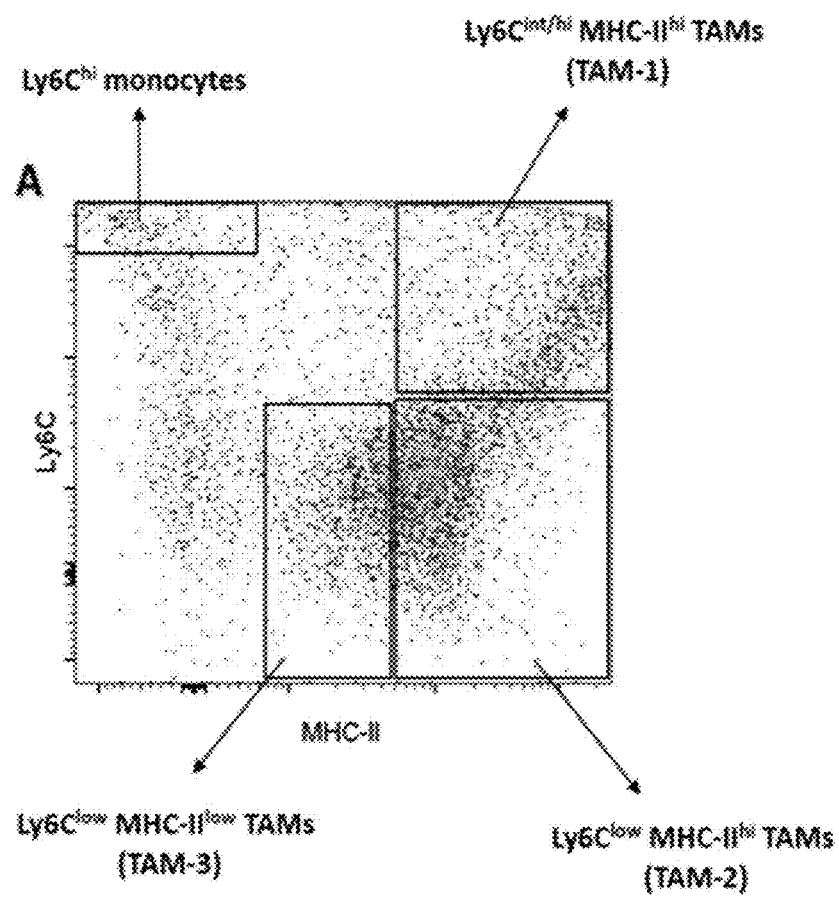
FIGS. 11A and 11B show a gating strategy for detecting tumor-associated macrophages (TAMs) in the TME.
Figure 11B:
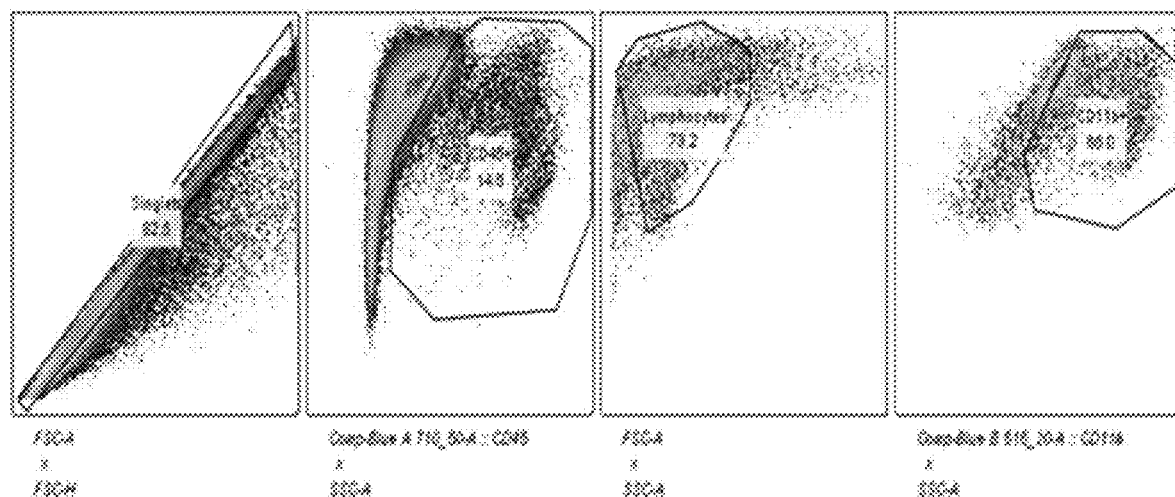

FIGS. 11A and 11B show a gating strategy for detecting tumor-associated macrophages (TAMs) in the TME. (FIG. 11A) A pseudo-color scatter plot of MHC-II expression against Ly6C expression by tumor infiltrating lymphocytes. Gates were drawn according to expression levels of the markers based on FMO controls. The populations were categorized based on cells expressing various levels of each marker on their cell surface. (FIG. 11B) A panel of four scatter plots showing the ancestry of back-gating of the cell population to arrive at the graph in (FIG. 11A). Cells were first gated based on their forward scatter (FSC) to filter out doublets and clumps. They were then gated for the expression of the pan-lymphocyte marker CD45 on their cell surface. The next gating was based on cell size, and the last step before categorizing cells as TAMs, was gating for the expression of the macrophage marker CD11 b.

Figure 10E:
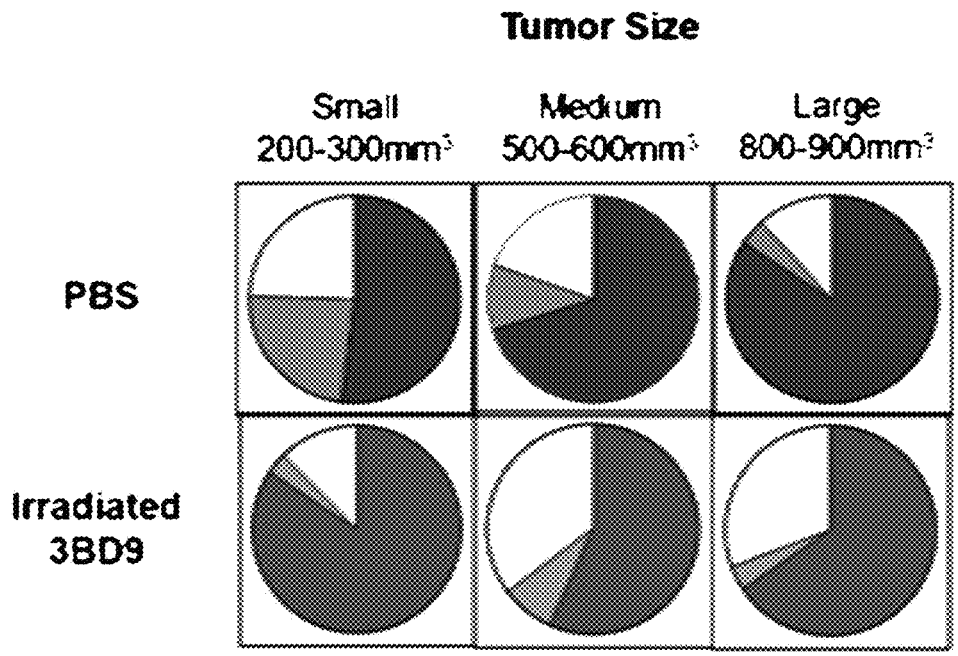
Figure 10F:
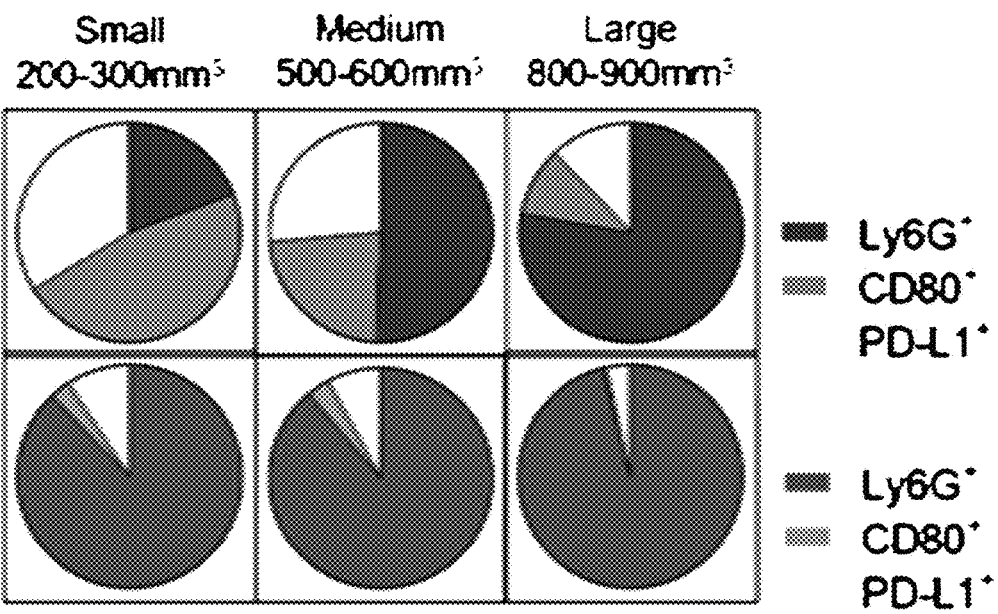

Tumors were harvested from mice at three stages of growth—small (200-300 mm$^3$), medium (500-600 mm$^3$), and large (800-900 mm$^3$). With increase in tumor size, the MHC-II$^{hi}$ TAMs in the TME of 3BD9 vaccinated tumors seemed to gradually lose Ly6G expression (FIG. 10E). Ly6G expression signifies a neutrophilic lineage, and hence renders the TME a more "inflammation-like" environment. This is important to note in the endeavor to change "cold" tumors into "hot" tumors. This is opposite to the phenotypes observed in the PBS vaccinated mice. These MHC-II$^{hi}$ TAMs in the TME also produced minimal T cell stimulatory surface antigens (CD80) in comparison to those on PBS vaccinated mice, which appeared to reduce over time as the tumor grew (FIG. 10E). In the case of the MHC-II$^{low}$ TAMs, the difference was more distinct. The TAMs in the 3BD9 vaccinated mice maintained a high level of Ly6G expression throughout the tumor growth phase. In contrast, Ly6G expression in the TAMs infiltrating tumors of the PBS vaccinated mice remained almost negligible in the early stages of tumor growth, but became more significant as tumor grows, (FIG. 10F). The latter TAMs also showed a significantly higher level of expression of CD80 in comparison to the MHC-II$^{low}$ TAMs in the 3BD9 vaccinated tumors (FIG. 10F). Expression of the suppressive PD-L1 on the TAM-2 subtype increased as tumor grew in the 3BD9 vaccinated group and was significantly higher than the PBS vaccinated group. The inverse is true for the TAM-3 subtypes. Using these data, the overall mechanism of immune response in the tumor microenvironment after vaccination with irradiated CD47$^{-/-}$ 3BD9 cells can be comprehensively understood (FIGS. 12 and 12B).

After scrutinizing the important immune cell populations in the TME, the draining lymph node was then analyzed to understand the immune activity in vaccinated mice. The TDLNs are T cell repertoires and act as hubs for immune cell activity. APCs of multiple phenotypes from the tumor drain into the nearest lymph nodes, and the environment there facilitates the interactions between APCs and the effector cells (T cells, B cells, NK cells). Profiling the immune cell phenotypes in the TDLNs provided an overview of the type of response that would lead to tumor rejection or escape. In contrast to the TME, TDLNs of the 3BD9 vaccinated mice have significantly high populations of activated APCs, and much lower suppressive populations of APCs. A high population of CD11b$^-$ effector and activated DCs and a low population of CD11b$^+$ regulatory DCs were detected in the 3BD9 vaccinated mice (FIG. 13A), suggesting an efficient T cell stimulating environment in the TDLNs.

Figure 12A:
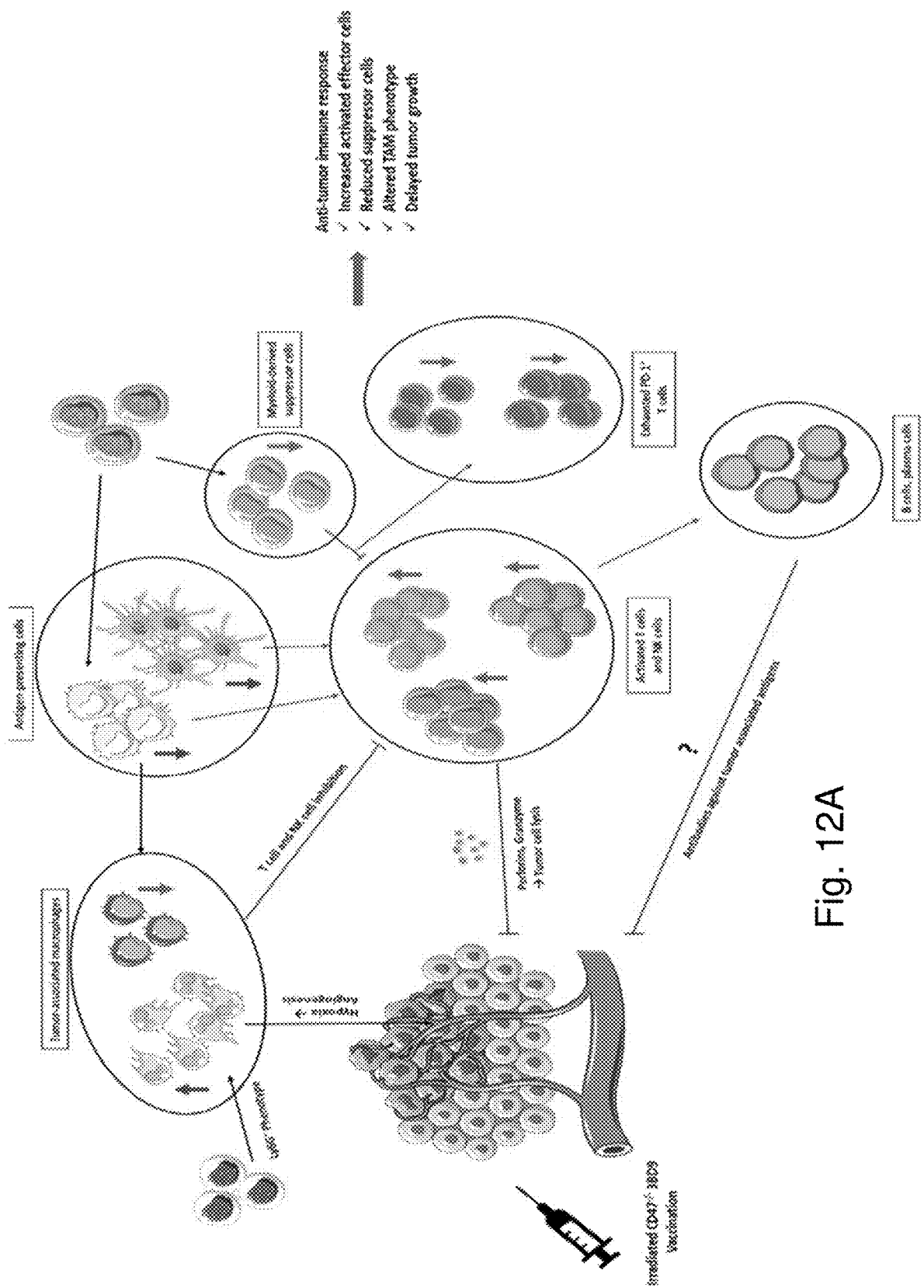
FIGS. 12A and 12B show immune response in the tumor microenvironment after vaccination with 3BD9 cells.
Figure 12B:

FIGS. 12A-12C show the immune response in the tumor microenvironment after vaccination with 3BD9 cells. The chart (FIG. 12B) depicts the immune activity as observed by analysis of the immune phenotypes infiltrating tumors post vaccination with CD47$^{-/-}$ 3BD9 cells. Green arrows and red arrows near cell subsets depict anti-tumorigenic and pro-tumorigenic cell types, respectively. Black arrows in the figure depict lineage, blue arrows depict activation, and red lines depict inhibition. Cell types are divided into sections based on their phenotypic characteristics. The antigen presenting cells subset shows activated M1-type macrophages and activated dendritic cells; the activated effector compartment includes Ki67$^+$ T cells and NK cells; the exhausted T cell compartment consists of PD-1$^+$ T cells; the tumor associated macrophage compartment includes the MHC$^{hi}$ TAMs (TAM-2) and MHC$^{low}$ TAMs (TAM-3); and the myeloid derived suppressor cells are shown in a separate section. (FIG. 12A).

Figure 13A:
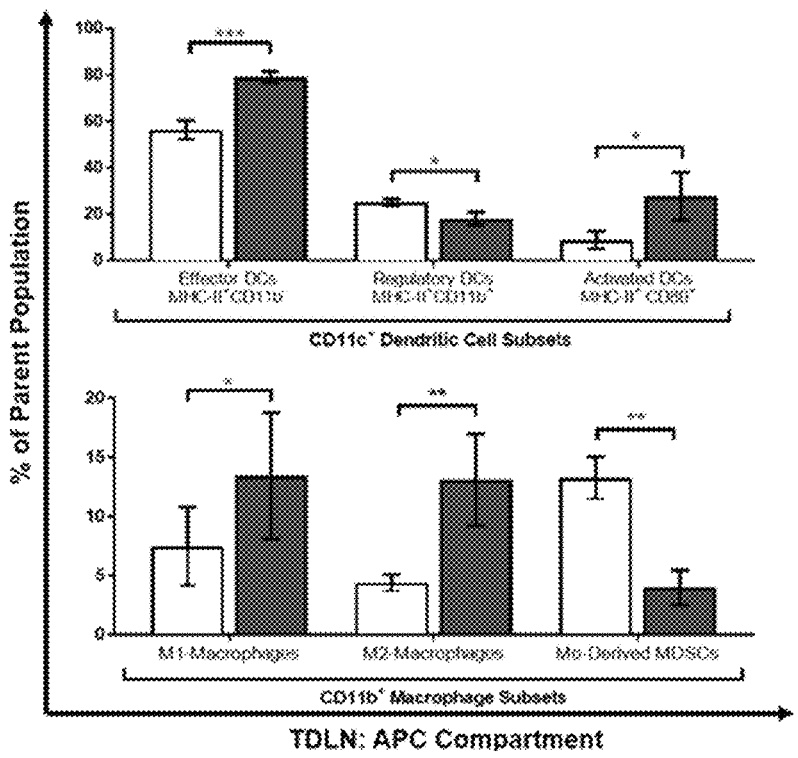
FIGS. 13A-13C show immune activity in Tumor Draining Lymph Nodes (TDLNs) of vaccinated mice.
Figure 13B:
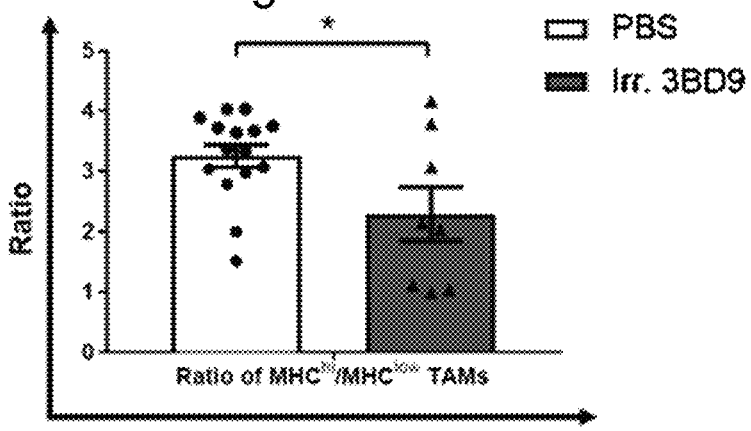
Figure 13C:
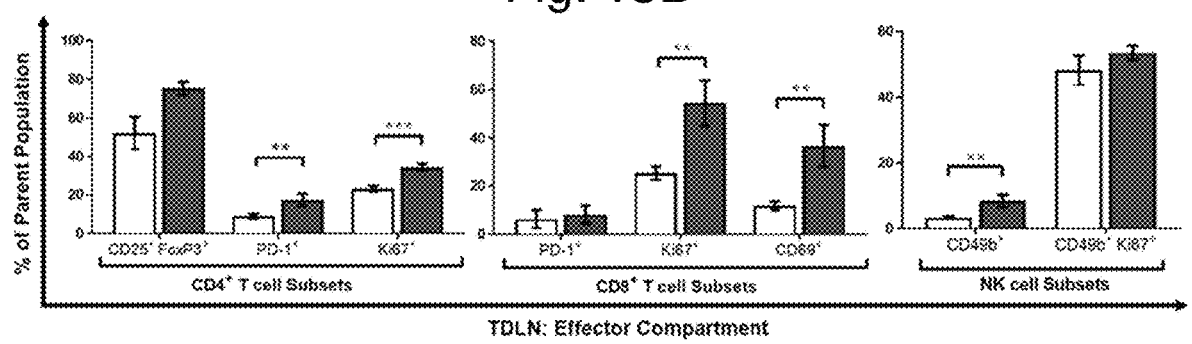

FIGS. 13A-13C show the immune activity in TDLNs of vaccinated mice. Multicolor flow cytometric phenotyping of (FIG. 13A) the dendritic cell and macrophage populations, (FIG. 13B) the ratio of MHC$^{hi}$/MHC$^{low}$ TAMs, and (FIG. 13C) the effector cell populations (CD4$^+$ T cells, CD8$^+$ T cells, and NK cells) in the TDLNs of PBS and 3BD9 vaccinated mice. In the PBS vaccination cohort, n=15. In the 3BD9 cohort, n=9. Immune cell phenotypes are presented as a percentage of the parent cell population. *p<0.5, p<0.01,*p<0.001 by unpaired t test performed on GraphPad Prism.

M1-polarized macrophages showed a slight increase, but it was interesting to note that the 3BD9 vaccinated mice had higher populations of M2 macrophages. Conversely, one of the most potent subsets of MDSCs, the monocyte-derived MDSCs (CD11b$^{hi}$ Ly6G$^-$ MHC-II$^+$), were significantly lower in the TDLNs of the CD47$^{-/-}$ 3BD9 vaccinated mice (FIG. 13A). Higher levels of MHC$^{low}$ TAMs were detected in the TME than MHC$^{hi}$ TAMs in the TDLNs of the 3BD9 vaccinated mice, and the ratio of MHC$^{hi}$/MHC$^{low}$ TAMs in these TDLNs was significantly lower (FIG. 13B). This may suggest, as mentioned above, that the migrating and antigen presenting macrophages are altering phenotypes to MHC$^{low}$ and expressing a defective phenotype due to tumors becoming more hypoxic. The next analysis was the effector cell populations in the TDLNs. The presence of significantly high populations of primed and proliferating T cell subsets was observed in the 3BD9 vaccinated lymph nodes (FIG. 13C). PD-1 expression on the CD4$^+$ T cells also seemed to be higher in these mice, which could be a correlation to the increase in the M2-type macrophages and inefficient antigen presentation and T cell suppression. There was also an increased number of natural killer cells in the TDLNs (FIG. 13C).

Vaccinated Mice Maintain Homogenous TIL Populations Throughout Tumor Growth Period.

Examining the macroscopic changes occurring the TME after vaccination was important to provide a baseline for developing combination therapies. The alterations to immune cells' infiltration into tumors after vaccination are not limited to the difference in phenotypes of TILs. The levels or amounts of the several types of TILs in the TME is also a crucial factor in the immune modulation potential of vaccines. Many anti-tumor therapies rely on the percentages of TILs in tumors, and tumors often show extreme heterogeneity in infiltrating lymphocytes at various stages of development. An important effect of vaccination before a tumor implant is the maintenance of stable TIL amounts throughout the development of a tumor. In particular, the percentage of suppressive phenotypes of all TILs remains constant at all stages of tumor growth in vaccinated mice, when compared to vehicle controls. Analyzing levels of TAMs and MDSCs (FIGS. 14A-B), as well as T-regs and PD-1$^+$ T cells (FIG. 14C) at three different stages of tumor growth, revealed that there is stability among these phenotypes in both the B16F10 and 3BD9 vaccinated tumors in comparison with the PBS vaccinated tumors. Since most immune checkpoint blockade therapies target these suppressive phenotypes, this is an important observation that could potentially alter dose escalation issues and minimize modulations in therapy.

Figure 14C:
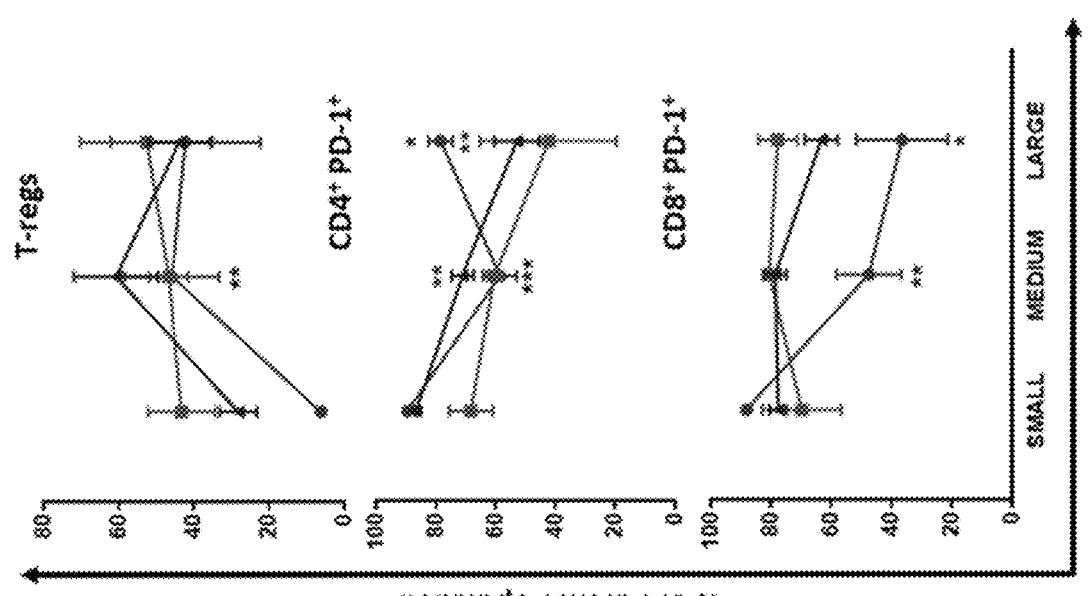
FIGS. 14A-14C show homogeneity of suppressive TIL populations in vaccinated mice within a Tumor Micro Environment (TME).
Figure 14B:
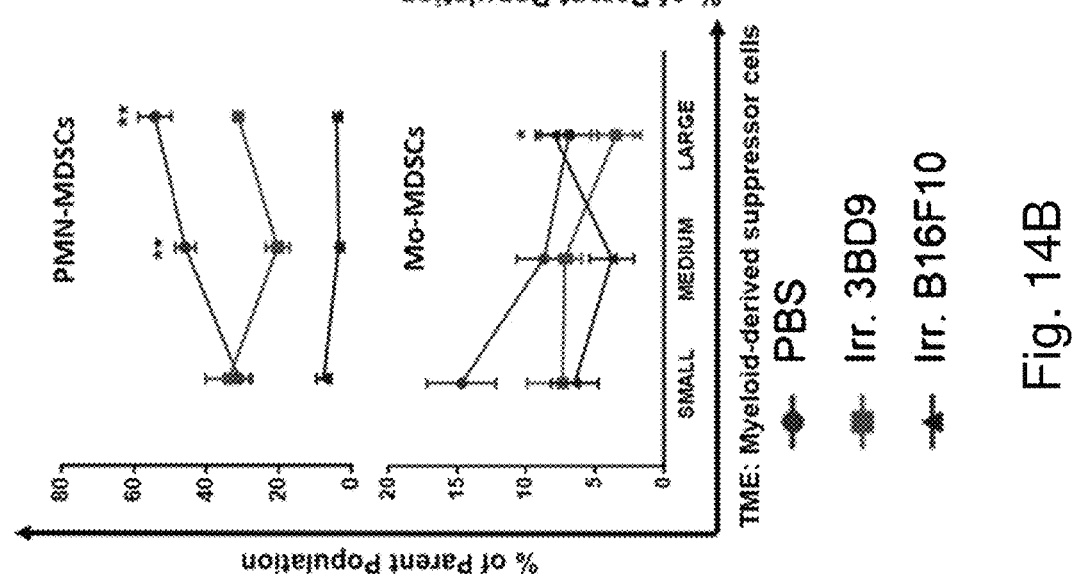
Figure 14A:
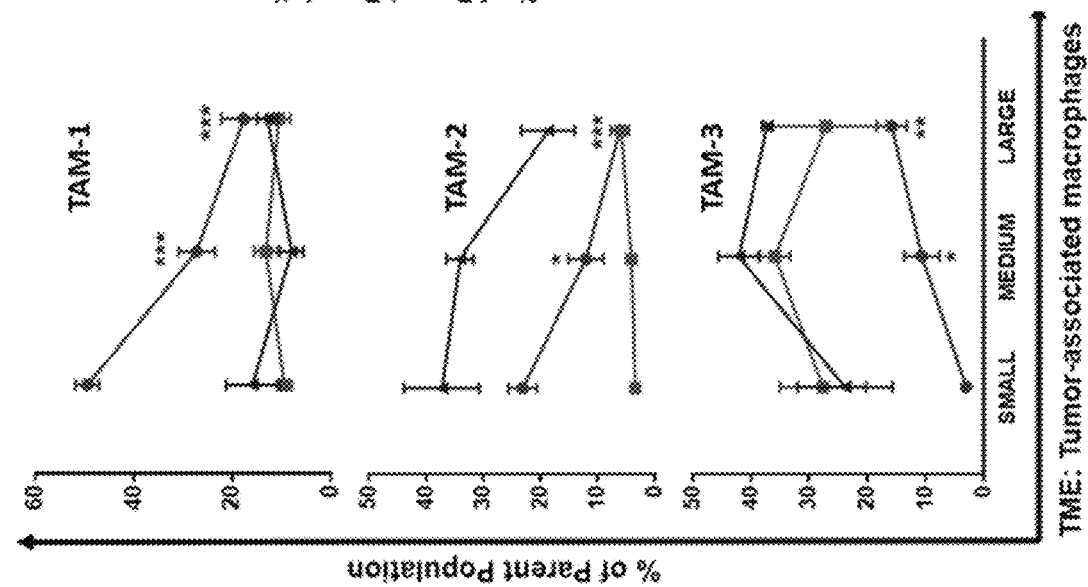

FIGS. 14A-14C show homogeneity of suppressive TIL populations in vaccinated mice. Tumors at different stages of growth were analyzed for suppressive TIL populations in PBS vaccinated (black lines), irradiated B61F10 vaccinated (blue lines), and irradiated 3BD9 vaccinated (pink lines) mice. (FIG. 14A) Tumor-associated macrophages (TAMs), (FIG. 14B) myeloid derived suppressor cells (MDSCs), and (FIG. 14C) T-regs (CD4$^+$CD25$^+$FoxP3$^+$) and PD-1$^+$ T-cells are shown. The quantification was done at three stages of tumor growth—small (200-300 mm$^3$), medium (500-600 mm³), and large (800-900 mm³). In the PBS vaccination cohort, n=5 for all three stages of tumor growth. In the CD47$^{-/-}$ 3BD9 cohort, n=4 (small), n=3 (medium), and n=2 (large). Immune cell phenotypes are presented as a percentage of the parent cell population. *p<0.5, p<0.01, *p<0.001 by unpaired t test performed on GraphPad Prism.

Preliminary Characterization of a STING Agonist as a Vaccine Adjuvant

The addition of adjuvants to vaccination regimes helps increase tumor specific immune cell infiltration to protect against an upcoming tumor challenge. To this end, addition of a STING pathway agonist—a cGAMP analog, 2'3'-c-di-AM(PS)2 (Rp,Rp)—was attempted as an adjuvant with irradiated whole-cell tumor vaccines following the immunization regime depicted in FIG. 15A. The adjuvant caused a significant delay in tumor growth (FIG. 15B) but did not enhance the overall effects of the CD47 depleted whole cell tumor vaccine. At the end of the 90-day observation regime, only 7% (1/15) of the mice were tumor free in the group that received the STING agonist, in comparison with the group that received only the irradiated 3BD9 vaccines without the adjuvant that had 33% (5/15) tumor-free mice (FIG. 15C).

Figure 15A:
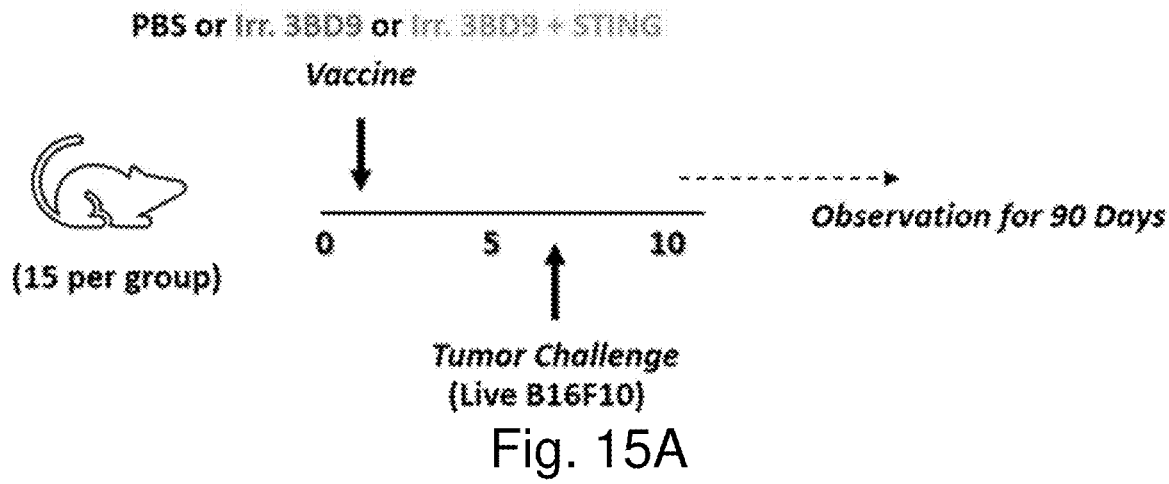
FIGS. 15A-15C show the effect of STING agonist on tumor growth and protection against tumor challenge.
Figure 15B:
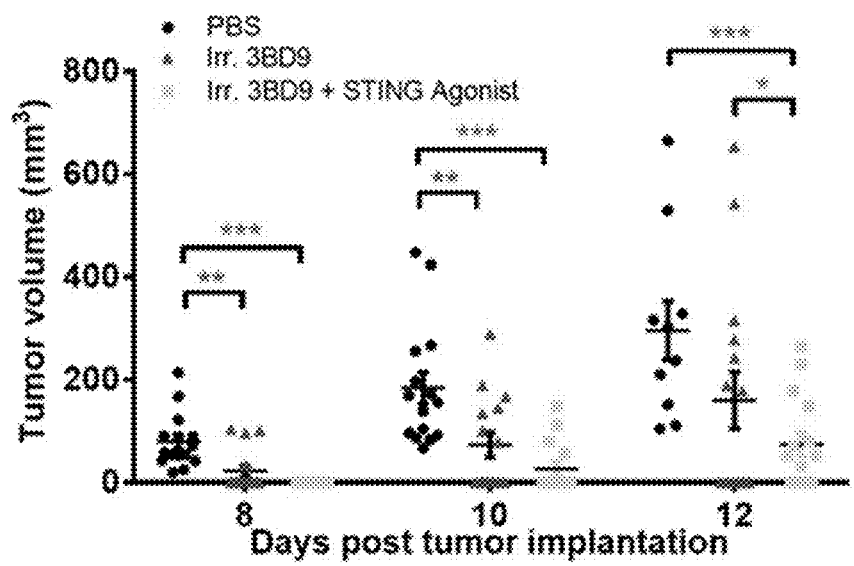
Figure 15C:
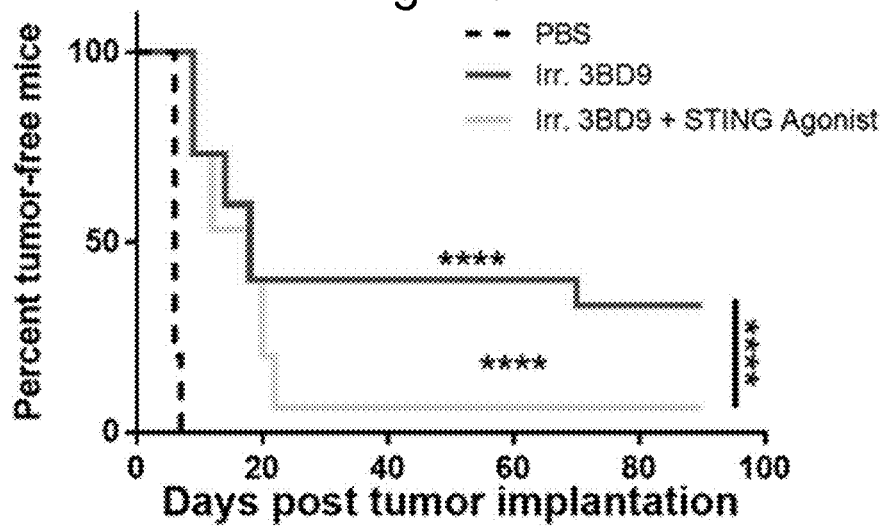

FIGS. 15A-15C show the effect of STING agonist on tumor growth and protection against tumor challenge. (FIG. 15A) The study regime: 15 mice per group were vaccinated with either vehicle (PBS), irradiated 3BD9, or irradiated 3BD9 with a STING agonist adjuvant. 7 days later, there were given a tumor challenge using live B16F10 cells. (FIG. 15B) Tumor growth in mice from the three vaccination regimes. p<0.01, *p<0.001 by unpaired t test. (FIG. 15C) Percentage of tumor free mice after vaccination. ****p<0.0001 by the Mantel-Cox test.

Modulations to the Anti-Tumor Immune Response by STING Agonist

Figure 16A:
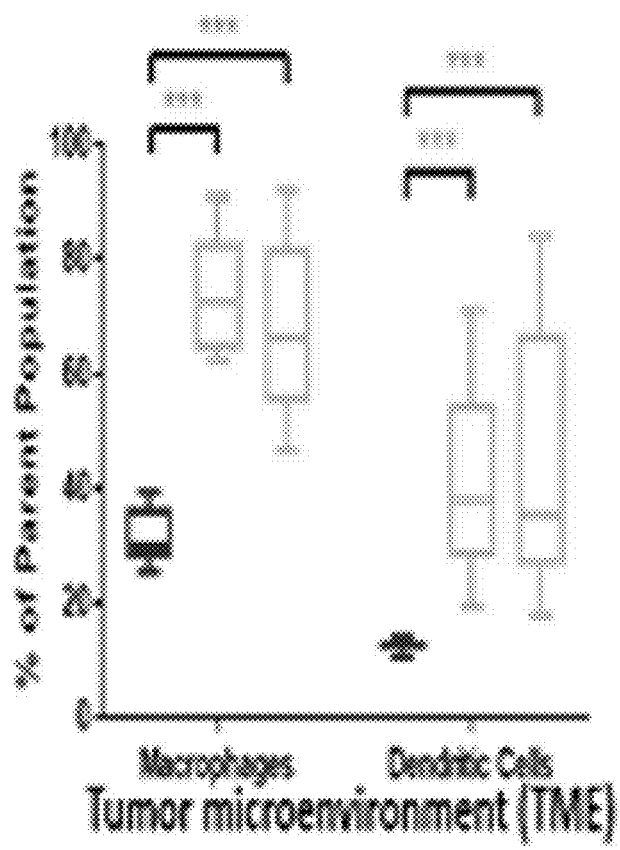
FIGS. 16A-16H show phenotypic changes in the TILs and tumor cells upon STING agonist vaccination.
Figure 16B:
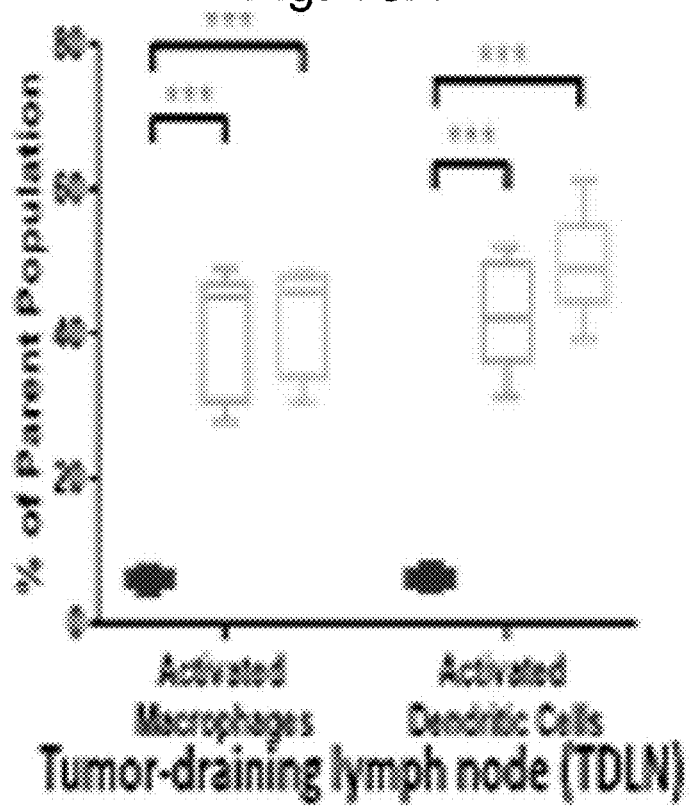
Figure 16C:
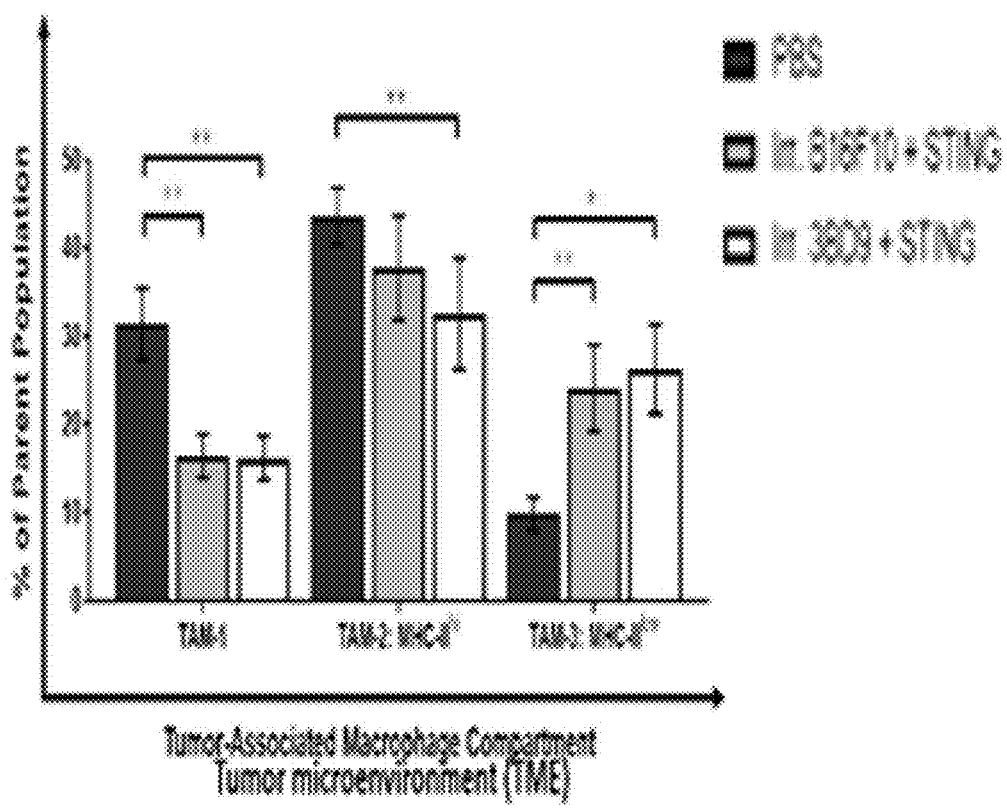
Figure 16D:
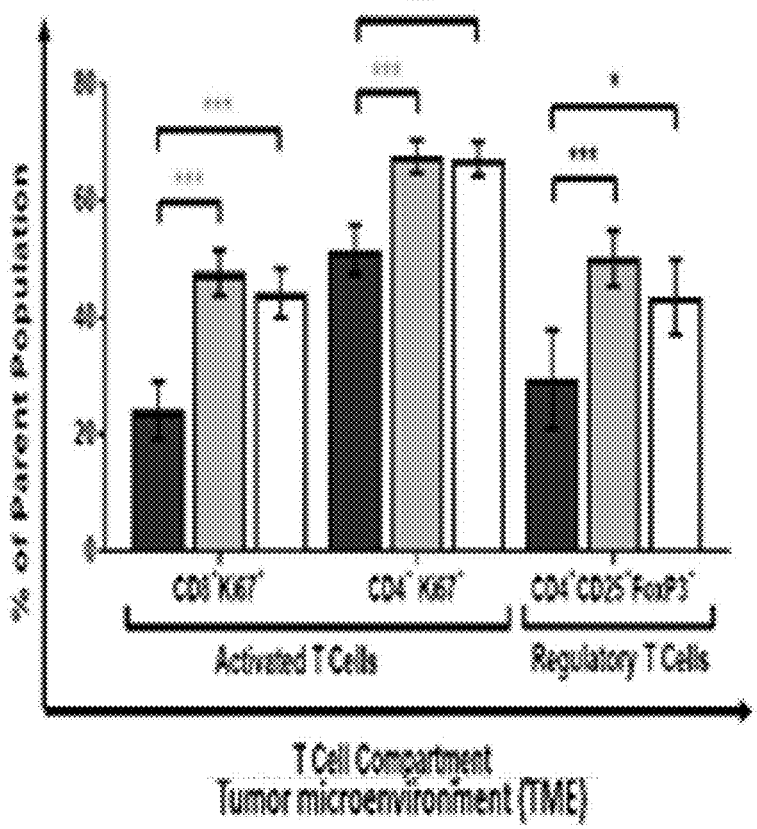

The STING agonist treatment in this study was a single subcutaneous dose of 10 µg per mouse along with the 0.5 million irradiated cells as part of the vaccination regime. It was sought to be determined whether the TIL phenotypes are altered by the addition of the adjuvant on the vaccinated groups. To study the immediate infiltration of the antigen presenting cells (DCs being the direct targets of the STING pathway agonist), this analysis was performed when the tumors were starting to grow and had reached a size of 200-300 mm³. As expected, there was a remarkable increase in the DCs infiltrating tumors and priming T cells in the TDLNs (FIGS. 16A and 16B). This enhancing effect of the STING agonist was observed on macrophages, which showed a significant increase in their activation and tumor infiltration. Otherwise, all through the various stages of tumor growth, the TILs of the 3BD9 groups vaccinated with a STING agonist behaved very similar to their non-adjuvant counterparts in that they showed an increase in the MHC$^{low}$ TAMs, and reduction in MHC$^{hi}$ TAMs (FIG. 16C). Furthermore, they also showed a significant increase in activated (Ki67$^{+}$) T cells as well as regulatory T cells in the effector cell compartment (FIG. 16D).

Figures 1A, 1B:
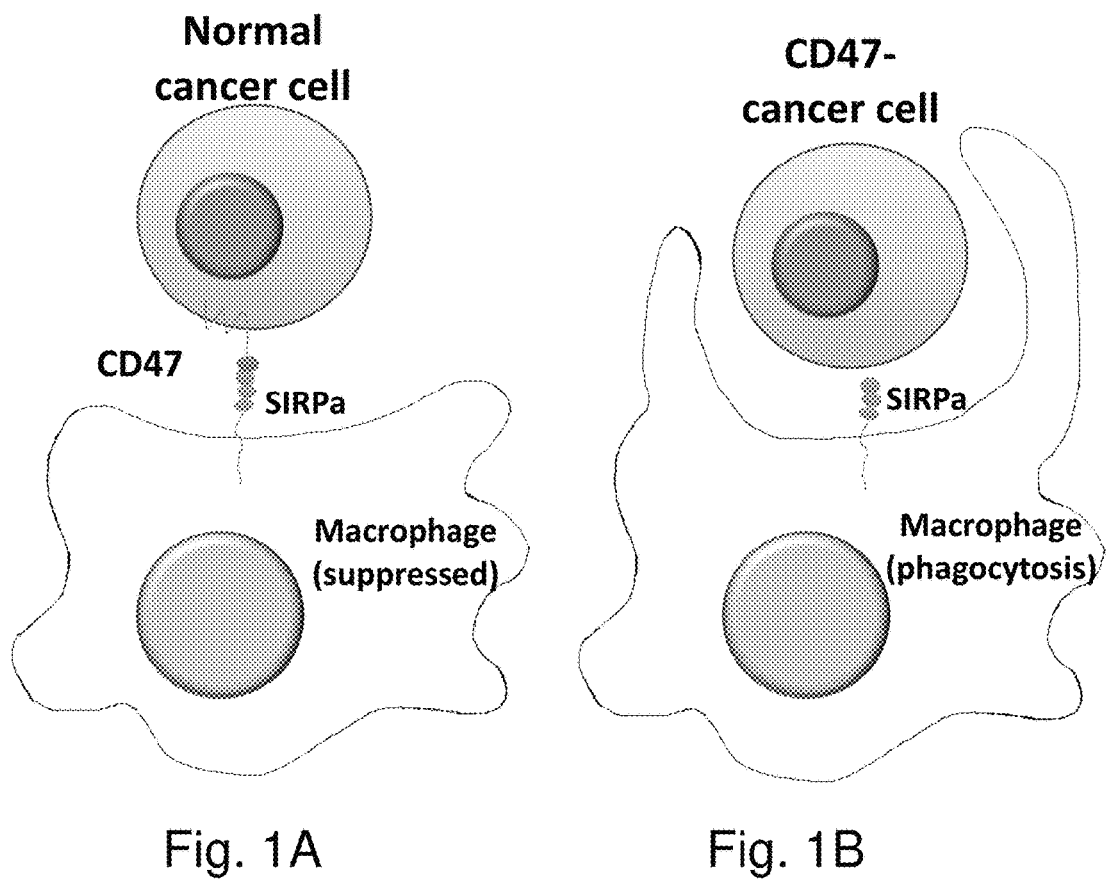
FIGS. 1A and 1B show schematic diagrams of the interaction of CD47$^{+/-}$ (normal) and CD47$^{-/-}$ (genome edited) cancer cells with macrophages.

FIGS. 16A-1H show phenotypic changes in the TILs and tumor cells upon STING agonist vaccination. Flow cytometric immuno-phenotyping analysis of the macrophage and dendritic cell subsets in the (FIG. 16A) tumor microenvironment and the (FIG. 16B) draining lymph nodes of small tumors (200-300 mm³; n=5 for all three cohorts), and (FIGS. 16C and 16D) the TAM and T cell compartments in the tumor microenvironment of the all mice vaccinated with PBS, irradiated B16F10 with STING agonist, and irradiated 3BD9 with STING agonist (PBS vaccination cohort, n=15. Both STING agonist cohorts n=14). Additional analysis of (FIG. 16E) PD-L1 and (FIG. 16F) CD47 expression on tumors, (FIG. 16G) PD-L1 expression on dendritic cells, and (FIG. 16H) the presence of activated (Ki67$^{+}$) NK cells in the tumor microenvironment was performed using multicolor flow cytometry for groups vaccinated with PBS, irradiated B16F10, irradiated B16F10 with STING agonist, irradiated 3BD9, and irradiated 3BD9 with STING agonist (PBS vaccination cohort, n=15. irradiated B16F10, n=13; irradiated 3BD9, n=9. Both STING agonist cohorts n=14). Immune cell phenotypes are presented as a percentage of the parent cell population. *p<0.5, p<0.01, *p<0.001 by unpaired t test performed on GraphPad Prism.

Figure 16E:
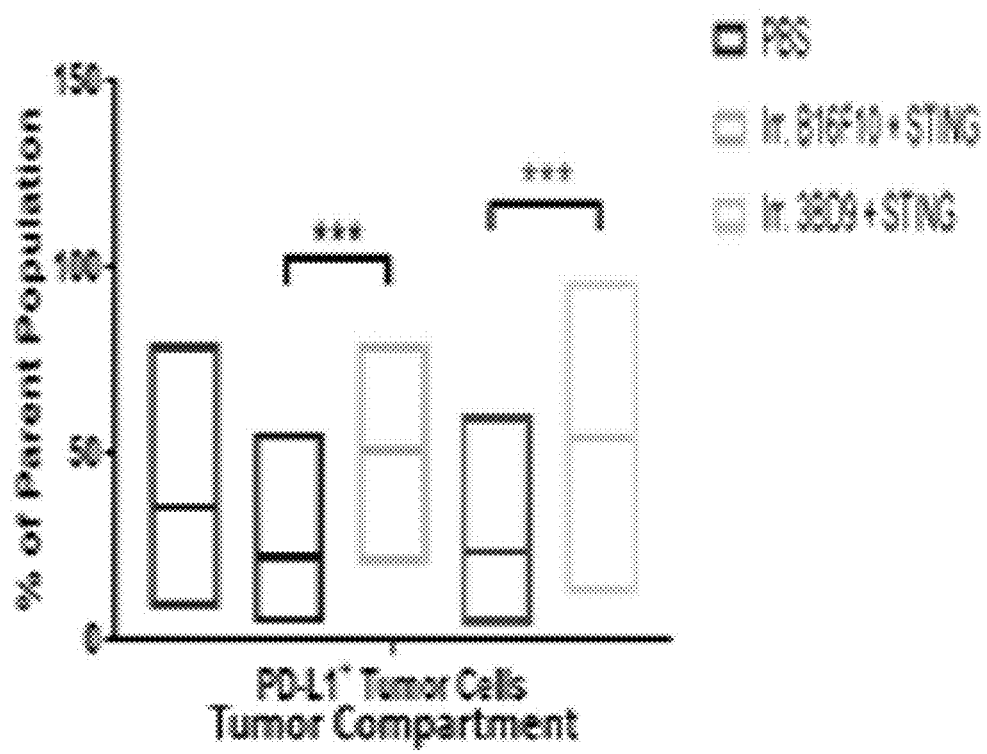
Figure 16F:
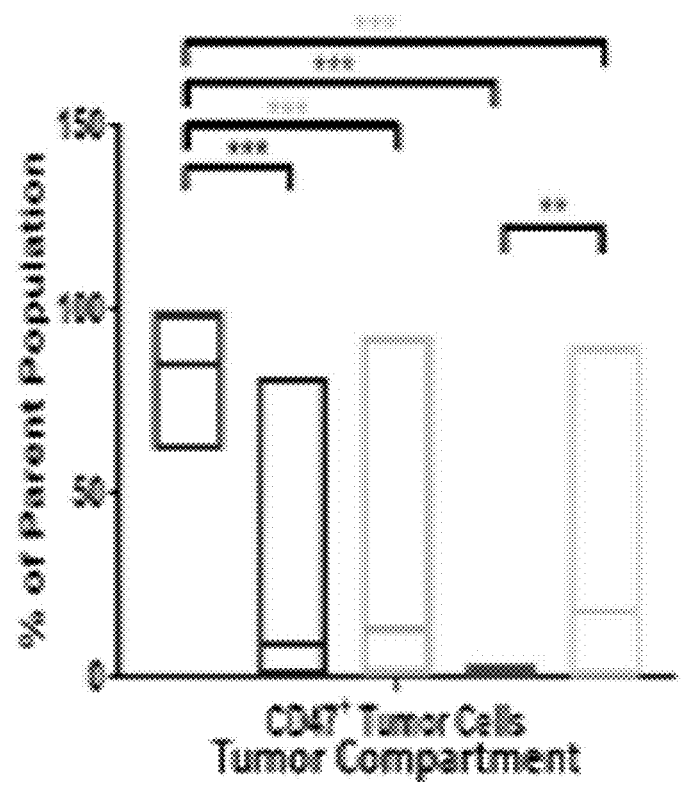
Figure 16G:
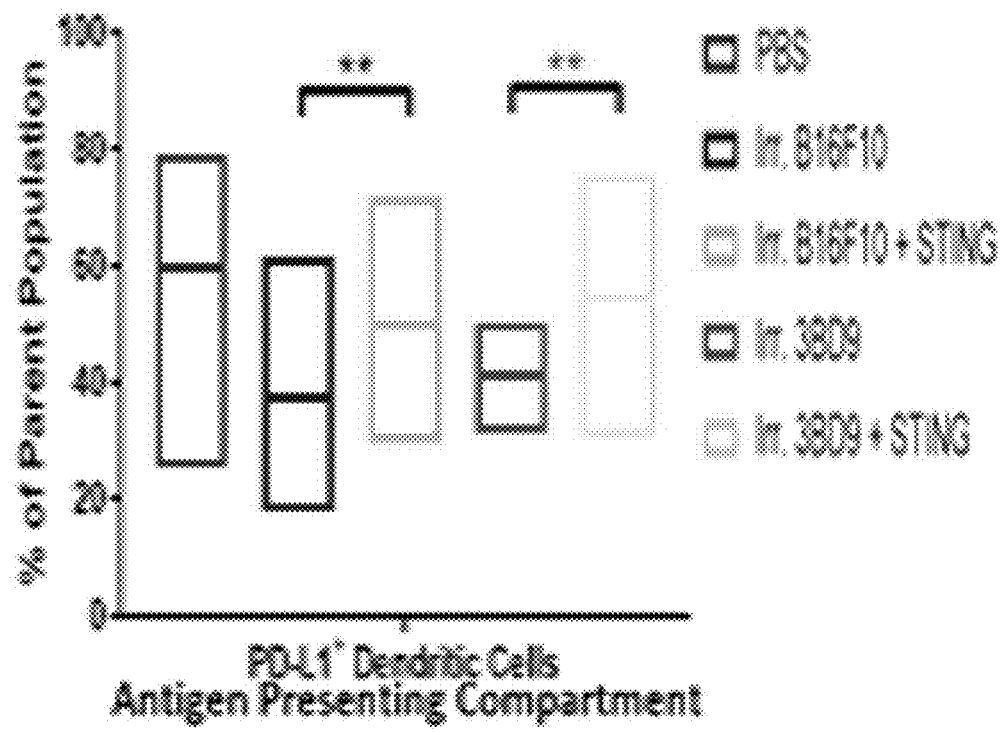
Figure 16H:
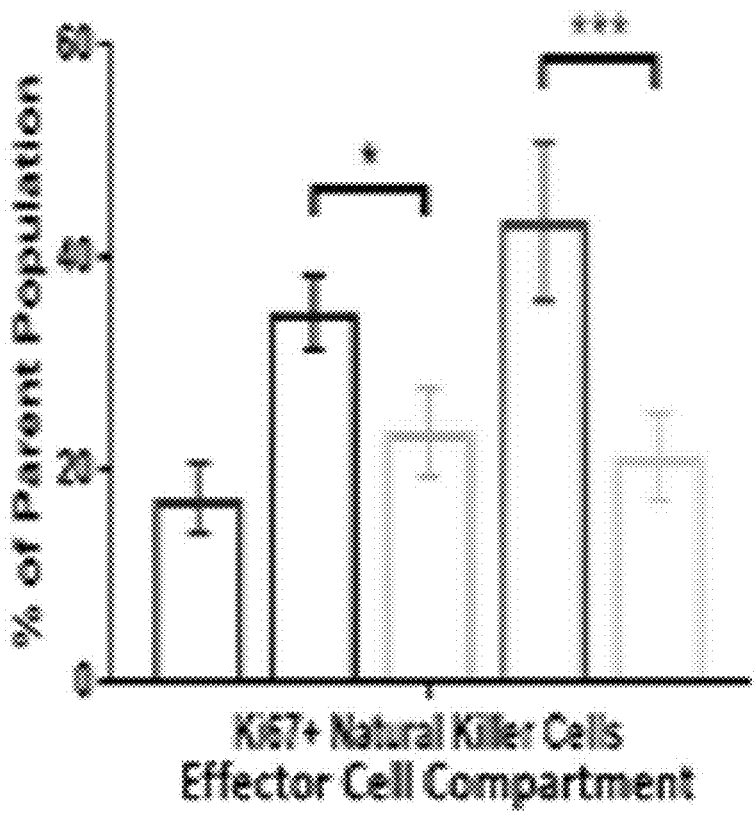

STING Agonist Increases Immune Evasion Marker Expression on Tumor Cells and Reduces NK Cell Activation Next, to understand the mechanisms due to which the STING agonist seemed to dampen the anti-tumor effect and sustained tumor rejection due to the 3BD9 vaccines, the cell types in the tumor microenvironment in mice vaccinated with B16F10 and 3BD9 were studied both with and without the STING agonist as an adjuvant. A significant increase in PD-L1 expression on tumor cells as well as dendritic cells in 3BD9 vaccinated mice was discovered, along with a STING agonist (Scarlett et al. 2012; Tran Janco et al. 2015) (FIGS. 16E, 16G and 16H). This effect almost seemed to be a reversal from the less suppressive phenotype in the 3BD9 vaccinated mice to the more suppressive phenotype of the vehicle vaccinated mice. In the groups vaccinated with irradiated 3BD9, the stark reduction in tumor cell surface CD47 expression also seemed to be reversed upon the inclusion of a STING agonist in the vaccine (FIG. 16F). These observations suggest that the overall increase in the activated antigen presenting cells, also simultaneously leads to the tumors building more defenses in response to the specific cytokines and tumor-specific immune attacks. An increase in PD-L1 expression on DCs is suggestive of gradual loss of antigen presenting and T cell activation capability (Benencia et al. 2012; Keirsse et al. 2017; Dudek et al. 2013). Similarly, with increase in Type I IFNs and activated macrophages, the tumors started producing more PD-L1 and CD47 to combat the response. Another interesting observation was the significant reduction in the activated NK cells in STING agonist groups (FIG. 16H). NK cells are one of the most potent anti-tumor effector cells, and this observation is essential in understanding the downregulation of tumor specific immune response upon addition of a STING adjuvant to the whole-cell tumor vaccines.

Figure 17:
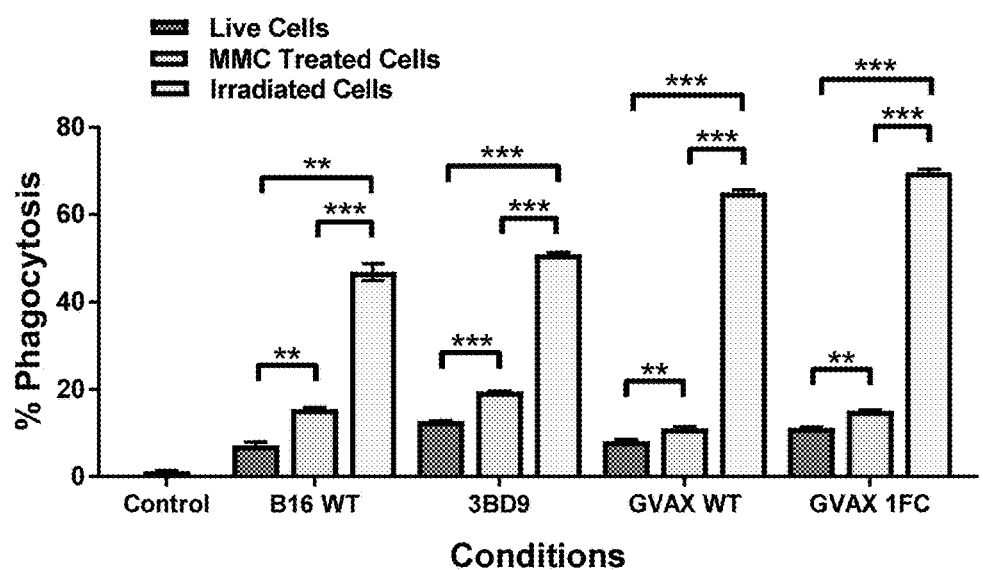
FIG. 17 shows a bar chart comparing live, mitomycin C-treated, and irradiated cells in a phagocytosis assay.

FIG. 17 shows in vitro phagocytosis of CFSE-stained live, MMC-treated, and gamma irradiated CD47$^{+/+}$ (WT) and CD47$^{-/-}$ cells by APC-F4/80-stained mouse bone marrow-derived macrophages. Phagocytosis was measured as a percentage of CFSE+F4/80+ macrophages and quantified by flow cytometry. The graph shows consolidated data from three independent experiments. Statistical analyses were performed on GraphPad Prism. p<0.01, *p<0.001.

Figure 18A:
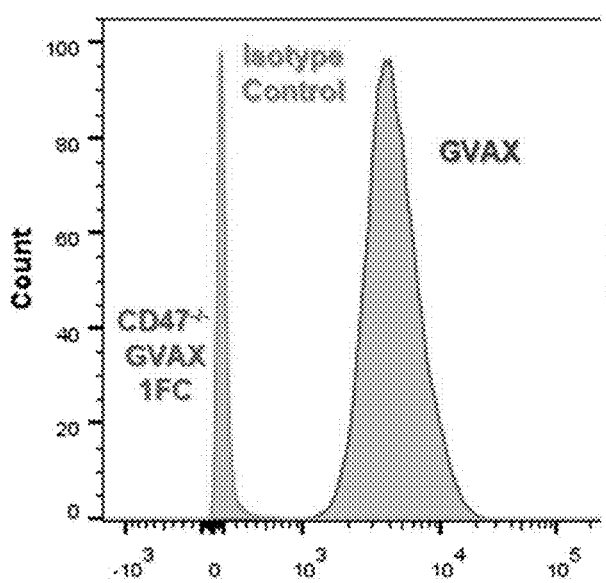
FIGS. 18A and 18B show depletion of cell surface CD47 by the CRISPR/Cas9 method
Figure 18B:
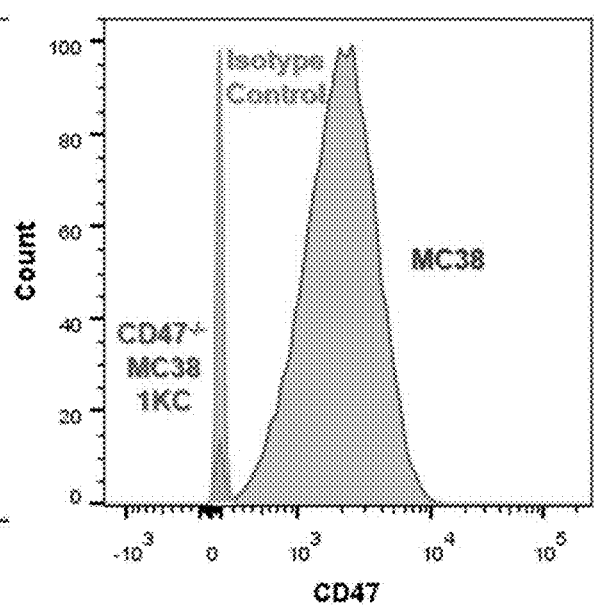

FIGS. 18A and 18B show depletion of cell surface CD47 by the CRISPR/Cas9 method. CRISPR components were transfected into GVAX and MC-38 cells by electroporation, and single cell clones were sorted out post CRISPR knock-out. Data shown on the histograms are for single cell clones GVAX-IFC (FIG. 18A), and MC38 IKC (FIG. 18B). Red peaks represent the CD47 expression on unedited WT cells (CD47$^{+/+}$)—positive control. Orange peaks represent the isotype control, and blue peaks represent the CD47-depleted samples, in each case. CD47 staining was performed using an Alexa Fluor 647-tagged rat anti-mouse CD47 antibody (clone miap301). Samples were run on the BD FACS Aria II flow cytometer and analysis was performed using the FlowJo software.

All these outcomes proved important for charting out the specifics of an anti-tumor response after vaccination with irradiated CD47$^{-/-}$ tumor cells, which is pictorially represented in FIGS. 12A, 12B, 19A, and 19B. Therapies targeting PD-1 expressing T cells, and the regulatory compartment of the T cells would be very effective in enhancing tumor rejection. Also, the use of cytokines like GM-CSF to selectively increase the M1-type macrophages (Italiani et al. 2014) and reduce the MHC$^{low}$ TAM populations (Movahedi et al. 2010) can be employed as adjunct therapies to CD47-based vaccination. The expression of CTLA-4, TIM-3 and LAG-3 usually corresponds to the expression of PD-1 on T cells (Anderson et al. 2016; Wherry et al. 2015; Yi et al. 2010) and these can be potential combinations with the CD47 target. (Kooreman et al. 2018).

CD47, an extensively explored immune evasion target, has always been studied in the context of active blockade using a therapeutic antibody treatment. This cell surface antigen has the potential to alter immune response dramatically, as it functions at one of the earliest and most crucial stages of an immune response cascade (Nilsson et al. 2009). The correct cocktail of factors in the body that harnesses cytokine release, macrophage activation, and the presence of tumor-specific antibodies can vividly enhance the already positive effects of CD47 as an immunotherapeutic target. In parallel, vaccinations, as a method of eliciting immune responses, are imperative in developing anti-tumor therapies. The use of inactivated non-replicating tumor cells as vaccines utilizes the immunogenic potential of whole tumor cells—it circumvents the extensive processing of neoantigens and intra-tumoral components to develop an effective vaccine concoction. Tumor cells lacking CD47 expression were hypothesized to elicit a strong immune response against tumors. These cells would aid the accumulation of anti-tumor effector cells that can protect the body from tumor development (preventive vaccines) or even eliminate tumors (therapeutic vaccines) from the body. Tumor cells lacking CD47 confer a lasting immune response, even in live formats. The prophylactic feasibilities of using inactivated CD47 depleted cancer cells was also demonstrated.

CD47$^{-/-}$ inactivated tumor cells can serve as a vaccine to confer a lasting immunity in mice, where 33% (5/15) vaccinated mice remained tumor-free at the end of 90-days post tumor challenge. The mechanisms underlying the action of these vaccines have been elucidated. Extensive profiling the tumor infiltrating lymphocytes and the cells in the draining lymph nodes, revealed remarkable differences in the immune response orchestrated by vaccination. In the mice that exhibited a complete response to vaccination and did not develop tumors for 90 days post a tumor challenge, a significant increase in M1-type and corresponding decrease in the M2-type macrophages were found. The activated effector T cells (CD4$^+$ and CD8$^+$) were significantly higher, as expected. However, there was also a remarkable increase in the number of regulatory T cells as well as PD-1 expression on T cells. Anti-tumor immunity is conferred by the large numbers of highly activated effector cells as well as the anti-tumorigenic macrophages stimulated by the vaccine. (Kooreman et al. 2018).

Enhancement in the populations of anti-tumorigenic macrophages and activated effector cell types in mice vaccinated with CD47$^{-/-}$ whole-cell vaccines in comparison with their CD47$^{+/+}$ counterparts confirmed the vital role played by CD47 in the efficacy of these vaccines. There was also unexpected extreme downregulation of cell surface CD47 by the tumor cells after vaccination with irradiated CD47$^{-/-}$ cells. The vaccinated tumors express almost no CD47, suggesting that the tumors might be reacting to the specific types of immune cell priming and response, which originated from cells that did not have cell surface CD47. This also suggests that the CD47 depletion from tumor cells had a very specialized effect on the anti-tumor immune response.

In the mice that showed delayed outgrowth of tumors after 3BD9 vaccination, there were significantly more effector cells infiltrating the tumor, which accounted for a delayed outgrowth. At the same time the activated antigen presenting cells (macrophages and DCs) were reduced in number, suggesting that multiple doses may prove more effective. It seemed that the regulatory T cell populations and the PD-1 expression on CD4$^+$ T cells were elevated, signifying the anti-tumor and suppressive function of these cells leading to eventual tumor escape in these mice. An increase in tumor infiltrating NK cells in the CD47$^{-/-}$ vaccinated mice was constantly observed. Other studies have shown the dependence of NK cell-associated cytotoxicity on CD47 expression (Kim et al. 2008; Soto-Pantoja et al. 2014), and the present experiments confirmed that the absence of CD47 leads to higher amounts of active NK cell populations, leading to tumor containment and sustained rejection. Presence of prominent levels of functionally activated NK cells keeps the immune response consistently anti-tumorigenic Guillerey et al. 2016; Lowry et al. 2017). Other principal factors in a suppressive environment are TAMs and MDSCs. The MHC-II$^{low}$ TAMs were significantly elevated, suggesting that the tumors became more hypoxic in the CD47$^{-/-}$ 3BD9 vaccinated mice. These TAMs were also found to express high levels of Ly6G, the neutrophil lineage marker. Aside from the MHC-II$^{low}$ TAMs, all other suppressor cells, including the PMN- and Mo-MDSCs, were highly downregulated in the TME of CD47$^{-/-}$ vaccinated tumors, proving that they have an overall anti-tumorigenic environment.

An important consideration in the design of therapeutic regimes for actively growing tumors is the intensity of immune activity in the tumors (Lehmann et al. 2017; Lee et al. 2012). Cold tumors, hence, are often hard to treat just by therapeutics, and this also one of the reasons solid tumors in the first place are harder to treat with immunotherapeutic agents than liquid or systemic tumors. The immune infiltration was found not only to increase, but also a consistent composition was maintained throughout the phases of tumor growth after vaccination. The extreme heterogeneity that is characteristic of melanoma tumors, is reversed upon vaccination, and tumors harvested at the three stages of growth show more homogeneity in TIL populations, especially in the suppressive subsets. These tumors also show a gradual increase in the effector cell compartment as tumor progresses, an effect opposite to the one seen in the tumors of mice vaccinated with inactivated B16F10 cells, which distinguishes the two types of vaccines and emphasizes the involvement of CD47 as a target in this regime.

The stimulator of interferon genes (STING) is a protein present on the endoplasmic reticulum of cells and is activated by a stream of preceding signaling mechanisms that involve the recognition of pathogen- or tumor-associated DNA by dendritic cells (DCs). One of the most crucial players in this pathway is the cyclic GMP-AMP (cGAMP) synthase (cGAS) that produces cyclic dinucleotides, commonly annotated as 2'3'-cGAMP that activated STING directly (Sokolowska et al. 2018; Li et al. 2016). The activation of STING leads to the production of Type-I interferons (IFNs): IFN-α and IFN-β. These IFNs act both as a self-stimulatory signal that helps in the maturation of DCs and a T cell proliferation signal that leads to the priming, maturation, and proliferation of CD8+ cytotoxic T cells (CTLs). STING agonists have been used in the recent years to mediate anti-tumor immunity in solid tumors (Curran et al. 2016; Bullock et al. 2017). Also, the use of adjuvants to vaccines has been names as one of the most crucial elements in the design of vaccines (Overwijk et al. 2017; Bullock et al. 2017). STING has also been shown previously to be involved in the CD47 blockade-based mechanism of anti-tumor activity (Liu et al. 2015). For the purpose of this study, 2'3'-c-di-AM(PS)2 (Rp,Rp) VacciGrade™, a cyclic dinucleotide cGAMP analog, that directly activates the STING protein, was used in the vaccine solution as an adjuvant to elicit a tumor-specific immune response.

The addition of a STING pathway agonist to therapeutic regimes is shown to increase the infiltration of dendritic cells into the TME and help the development of effective anti-tumor T cell responses. In this study, however, the addition of a STING pathway agonist as a vaccine adjuvant did delay the tumor development significantly, but also seemed to dampen the effect of the vaccine and cause an inferior prognosis. The addition of the adjuvant significantly increased not only dendritic cell infiltration into tumors but also macrophage infiltration. The most glaring reasons for the seemingly inverse effect of the STING agonist on vaccine efficacy are a drastic increase in PD-L1 expression on tumor cells and DCs, and a remarkable reduction of activated NK cells in these mice. Studies have found previously the very alarming role DCs seem to play in the TME and non-specific activation of the DC compartment could be leading to an unprecedented effect in combination with the CD47-based regime (Benencia et al. 2012; Keirsse et al. 2017; Dudek et al. 2013; Merad et al. 2013). Additionally, the STING agonist seemed to reverse the earlier observed CD47 reduction on tumor cells and showed a significantly higher expression in comparison with the $CD47^{-/-}$ cell vaccine regime without the adjuvant. This adjuvant study was a preliminary, single-dose study, and the effects observed would help design a better method of employing the anti-tumor capabilities of STING pathway stimulation.

The present findings point to the fact that as a certain type of immune cell population increases in percentage, the regulatory or suppressive phenotypes of that population also increase correspondingly. An increase in M2-type and TAM populations was observed as compared to the M1-type and the activated subsets when macrophage populations are enlarged. Similarly, elevated amounts of activated T cell populations were found after $CD47^{-/-}$ vaccination, but also correspondingly found elevated levels of regulatory subsets of these T cells. In the STING adjuvant-treated groups, there was extremely high infiltration of DCs, but the PD-L1 expression on these DCs also increase dramatically, leading to a suboptimal scenario.

Cell Culture. The B16F10 (mouse melanoma) cell line was obtained from ATCC. The cells were cultured using high glucose DMEM (Gibco, MD) supplemented with 10% v/v Fetal Bovine Serum (FBS) (Sigma-Aldrich, MO). Mouse bone marrow derived macrophages (BMDMs) were obtained by flushing out the bone marrows of untreated mice, and culturing for 7 days in RPMI 1640 (Gibco, MD) supplemented with 10% v/v FBS.

CD47 knockout using CRISPR. The spCas9(BB)-2A-GFP (PX458) plasmid (Addgene, MA) containing the gRNA sequence targeting CD47, and the Cas9 and an eGFP separated by a T2A sequence was transfected into the B16F10 cells using the Viafect transfection kit (Promega, WI). The successfully transfected single cells were sorted into 96-well plates using a BD FACS Aria II sorter. Single cells were expanded and tested for biallelic knockout of CD47 using PCR, T7E1 mismatch assay, and Sanger's sequencing. Absence of the protein expression in genome edited cells was reconfirmed by immunofluorescence microscopy and flow cytometric analysis. Rat anti-mouse CD47 antibody clone miap301 (BD Biosciences, NJ) was used as a primary antibody to determine the absence of CD47 expression in edited cells. This antibody was used at a final concentration of 10 μg/mL (1:50 dilution). Goat anti-rat IgG tagged with AlexaFluor-488 (2 mg/mL) (Sigma-Aldrich, MO) was used as a secondary antibody. This antibody was used at a final concentration of 10 μg/mL (1:200 dilution).

The required gRNA sequence (in the form of a ligated double stranded DNA, Invitrogen, CA) was cloned into the cloning site of the plasmid under a U6 promoter, using restriction digestion. The cloning site was flanked by restriction sites for Bbsl enzyme (New England Biolabs, MA). Two gRNAs were used, targeting Exons 1 and 2 of the cd47 gene. The distance between the cut sites for these gRNAs was approx. 12.9 kb. Confirmation of knockout was done using a PCR primer set (MA-FP/MC-RP) (Eurofins Genomics, KY) flanking the cut sites. The deletion of the 12 kb fragment was visually analyzed by PCR (BioRad, CA) and gel electrophoresis.

In vitro phagocytosis assay. Macrophages were extracted from bone marrows flushed out from the femurs of naïve mice, plated on 10 cm dishes. The growth medium was supplemented with 10 μg/ml GM-CSF. The cells were cultured for 7 days—the growth medium was replaced every 3 days. $5 \times 10^4$ macrophages were co-cultured with $1 \times 10^5$ Carboxyfluorescein (CFSE)-labeled B16F10 tumor cells in RPMI 1640 (Gibco, MD) for 2 hours at 37° C. and 5% $CO_2$ in the presence of 0.5 μg opsonizing antibodies, anti-CD47 miap301 (BD Biosciences, NJ) and anti-gp75 TA99 (BioXCell, NH). Macrophages were then stained with APC-tagged F4/80 (Biolegend, CA). Phagocytosis analysis was done on a BD FACS Aria II flow cytometer.

Vaccination and animal study. 7-week-old female C57BL/6 mice (Jackson Laboratory, ME) were housed in a pathogen-free facility in the vivarium of Binghamton University. All animal study procedures were approved by the Institutional Animal Care and Use Committee (IACUC) at Binghamton University.

$5 \times 10^5$ B16F10 cells were implanted on the left flank of 7-week-old female C57BL/6 mice to induce the tumor development. The tumors were measured using calipers every alternate day after tumor growth was observed.

To prepare whole cell vaccines, $CD47^{-/-}$ B16F10 cells (Referred to as $CD47^{-/-}$ 3BD9) and $CD47^{+/+}$ B16F10 cells (Referred to as B16 WT) were irradiated with 35Gy gamma irradiation using a Cs source (University of Rochester Medical Center).

Mice (15 animals per group) were vaccinated with $5 \times 10^5$ irradiated 3BD9 or B16 WT cells subcutaneously on the left flank and were challenged with $5 \times 10^5$ live B16F10 cells 7 days later. Two more cohorts of 15 mice each were vaccinated as mentioned above with 3BD9 and B16 WT along with 10 μg/mouse of a STING pathway agonist, 2'3'-c-di-AM(PS)2 (Rp,Rp) VacciGrade™ (InVivoGen).

Tumors and TDLNs at three different stages of tumor growth—small (200-300 $mm^3$), medium (500-600 $mm^3$), and large (800-900 $mm^3$)—were collected from 5 mice per group after euthanasia by $CO_2$ inhalation. For the mice that did not develop tumors, TDLNs alone were collected 90-days post tumor challenge. Organs were enzymatically digested and made into single cell suspensions for immunostaining.

Immunophenotyping. To determine the types of tumor infiltrating lymphocytes (TILs) and TDLN lymphocytes, single cell suspensions of the tumors and TDLNs were stained using two multicolor panels covering the APC compartment—macrophages ($M_\varphi$), dendritic cells (DCs), myeloid derived suppressor cells (MDSCs), and monocytes; and the effector cell compartment—cytotoxic T cells (CTLs), helper T cells ($T_H$ cells), memory cells, regulatory T cells (T-regs), natural killer (NK) cells, and activated effector cells. All pre-conjugated antibodies were purchased from Biolegend unless otherwise specified. Samples were run on LSR Fortessa flow cytometers (University of Rochester Medical Center Flow Core Facility) and analyzed using the FlowJo software v10 (TreeStar).

Statistical Analyses. All statistical analyses were performed on GraphPad Prism. The non-parametric Mantel-Cox test was used for survival and tumor-free mice data. For other correlative analyses either a one-way ANOVA or an unpaired t test was performed based on the number of groups being compared. The Shapiro-Wilk test was used to determine population distribution when necessary. 95% confidence interval was used in all analyses to accept or reject the null hypothesis.

Nucleofection of RNPs. For knocking out CD47 from GVAX cells (GM-CSF producing B16F10 cells), the ribonucleoprotein (RNP) method was used. gRNA (in the form of mRNA, Integrative DNA Technologies, IA)) was complexed with purified Cas9-3NLS protein in vitro (obtained from Integrative DNA Technologies, IA), and the mixture was added to GVAX cells and electroporated using the Neon Electroporation System (Invitrogen, CA). The cells were analyzed by flow cytometry (BD FACS Aria II) 6-9 days after electroporation, and $CD47^{-/-}$ cells were sorted for single cell colonies into 96-well plates using the BD FACS Aria II Cell Sorter. GVAX 1FC was chosen as the $CD47^{-/-}$ clone for further studies.

T7E1 mismatch assay. PCR products from CRISPR-edited cells were subjected thermal denaturation at 95° C. and cooled down at the rate of 0.1° C./min to 85° C., and then at the rate of 1° C./min to 25° C. Once cooled, 1U of the T7E1 enzyme (New England Biolabs, MA) was added to the mix and incubated at 37 C for 15 mins—the final volume of the mix was 20 µl. The reaction was stopped using 1.5 µl of 0.25M EDTA, and the digested were run on an agarose gel to check for indels in the cut site.

Immunofluorescence microscopy. Cells were plated on individual wells of a 6-well plate and maintained until they reached 70-80% confluency. The cells were washed with 1× D-PBS (Gibco, MD) once. Then they were fixed with 4% paraformaldehyde (PFA) at room temperature for 15 minutes, and washed twice with 1× D-PBS, followed by blocking with 0.5% BSA for 30 mins at room temperature. After blocking, the cells were incubated with primary antibody for 1 hour at 4° C. and washed once with 1×-DPBS. Secondary antibody was then added to the cells and incubated for 1 hour at 4° C. After another wash with 1×-DPBS, the cells were counterstained with a 1:1000 dilution of DAPI (Invitrogen, CA) at room temperature for 15 minutes. The cells were again washed twice with 1× D-PBS and viewed using a fluorescence microscope (Nikon, NY).

In vitro phagocytosis of GM-CSF producing B16F10 cells (GVAX). GVAX is a type of B16F10 mouse melanoma cell line that is genetically engineered to produce the cytokine granulocyte macrophage colony stimulating factor (GM-CSF). This cytokine is imperative in the growth, function, and maturation of myeloid derived granulocytes including macrophages and dendritic cells. The use of GVAX as a vaccination regime would mean the presence of GM-CSF as an innate adjuvant. Phagocytosis was performed with fresh BMDMs. $5\times10^4$ macrophages were co-cultured with $1\times10^5$ CFSE-labeled GVAX and B16F10 tumor cells for 2 hours at 37° C. and 5% $CO_2$ in the presence of 0.5 µg opsonizing antibodies, anti-CD47 miap301 (BD Biosciences) and anti-gp75 TA99 (BioXCell). Macrophages were then stained with APC-tagged F4/80. Phagocytosis analysis was done on a BD FACS Aria II flow cytometer.

Phenotyping tumor cells. gp75 profiling for use of TA99 antibody as opsonizing agent in in vitro phagocytosis assay. The B16 WT and $CD47^{-/-}$ 3BD9 cells were treated with purified anti-mouse TA99 primary antibody (BioXCell), and then with a rat anti-mouse Alexa Fluor 488-tagged secondary antibody (Sigma). As a negative control, the same cells were treated with only the secondary antibody. Cells were analyzed by flow cytometry on the BD FACS Aria II.

CD47 profiling of irradiated cells for use as vaccines in vivo. The gamma irradiated cells used as vaccines—B16 WI and $CD47^{-/-}$ 3BD9 cells were stained for cell surface CD47 expression using an Alexa Fluor 647-tagged anti-CD47 antibody, clone miap301 (Biolegend), and analyzed on the BD FACS Aria II. Isotype control for the CD47 antibody, a rat IgG-k Alexa Fluor 647 (Biolegend), was used as a negative control.

Comparison of $CD47^{-/-}$ and WT melanoma tumor growth in vivo. Tumor implants. $5\times10^5$ B16F10 tumor cells ($CD47^{-/-}$ and WT) were implanted subcutaneously into the left flanks of 7-week-old female C57BL/6 mice. Tumor growth was observed every alternate day and tumors were measured using a Vernier caliper. Two separate experiments with 4 mice per group were performed to compare the tumor growth pattern. Another cohort of 15 mice per group was used to study tumor infiltrating lymphocytes and TDLN immunophenotypes at three different stages of tumor growth—small (200-300 $mm^3$ tumors), medium (500-600 $mm^3$ tumors), and large (800-900 $mm^3$ tumors).

Organ Preparation and Immuno-Phenotyping.

Tumors. Tumors were harvested at the three stages mentioned above, stored and transported in media containing RPMI 1640 (Gibco), 2% FBS (Sigma), and 1× Pen-Strep antibiotic (Gibco) on ice. Tumors were then digested using 1 mg/ml Collagenase and 10 mg/ml DNase (Sigma) at 37° C. for one 20-minute cycle with intermittent high-speed vortexing, and another 20-minute cycle with intermittent vigorous pipetting. Homogenized suspensions were filtered using a 70 µm filter and suspended in FACS Buffer (1× PBS, 2% FBS, 2 mM EDTA (Gibco), and 25 mM HEPES (Gibco)) until use.

Lymph nodes. TDLNs were harvested from mice along with the tumors and transported separately in media containing RPMI 1640 (Gibco), 2% FBS (Sigma), and 1× Pen-Strep antibiotic (Gibco) on ice. TDLNs were cut into small pieces using a sharp scalpel and 26G needle (BD Biosciences). Fragments were placed in 2 ml warm Digest Buffer containing 1 mg/ml Collagenase and 10 mg/ml DNase and digested at 37° C. for 30 minutes with intermittent high-speed vortexing. Fragments were filtered using a 70 µm filter and suspended in FACS Buffer until use.

Immunostaining. Approximately 2-4 million cells from tumors and 0.5-1 million cells from TDLNs were transferred to non-treated U-bottom 96-well plates (Costar). Two multicolor panels were used for tumors and TDLNs—Panel T1 for tumors and Panel SL1 for TDLNs (containing all the antibodies for phenotyping the APC compartment, and tumor antigens), and Panel P2 for both (containing an antibody cocktail for phenotyping the effector cell compartment). All the antibodies used in this experiment were titrated using mouse melanoma tumors and the dilutions were optimized for use in the multi-color panels. CD16/CD32 Fc Block (Biolegend, CA) was used to block immune cell receptors along with the antibody cocktails. Cells were stained for extracellular antigens in FACS Buffer for 30 minutes on ice, and then fixed and permeabilized using the Transcription Factor Buffer Set (BD Biosciences) for 30 minutes at 4° C. The intracellular antigen staining was performed using the Perm/Wash Buffer from the set for 30 minutes at 4° C. Stained cells were stored in the dark at 4° C. in FACS Buffer until analysis by flow cytometry. Multi-color compensation was performed by staining polymer beads from the AbC Antibody Compensation Kit (Invitrogen) with the appropriate amounts of all antibodies used in the staining panels.

What is claimed is:

1. A vaccine, comprising:
a non-apoptotic senescent or mitosis-arrested irradiated cell which expresses a target antigen,
wherein the cell has been genetically edited to:
express a serpin protease inhibitor;
knockout CD47;
knockout PD-L1; and
genomically integrate a gene encoding GM-CSF.

2. The vaccine according to claim 1, wherein the target antigen is a tumor-associated neoantigen.

3. The vaccine according to claim 1, in a kit further comprising:
a therapy selectively targeting at least one of PD-1 producing cells, CTLA-4 producing cells, LAG-3 producing cells, CD47 producing cells, and PD-L1 producing cells.

4. The vaccine according to claim 1, wherein the non-apoptotic senescent or mitosis-arrested irradiated cell has been CRISPR edited to knockout CD47 expression.

5. The vaccine according to claim 4, wherein the non-apoptotic senescent or mitosis-arrested irradiated cell is a genetically engineered senescent or mitosis-arrested cultured cell having at least one restriction endonuclease recognition site.

6. The vaccine according to claim 5, wherein the non-apoptotic senescent or mitosis-arrested irradiated cell is derived from a neoplastic cell which expresses the target antigen.

7. The vaccine according to claim 6, wherein the neoplastic cell is a melanoma cell.

8. A method for preparing a vaccine, comprising:
isolating a live cell which expresses at least one target antigen;
genetically editing the live cell to:
knockout expression of CD47,
knockout expression of PD-L1,
genomically integrate a gene encoding GM-CSF, and
express a serpin protease inhibitor,
while preserving expression of the at least one target antigen;
expanding the genetically edited live cell by cell culture; and
modifying the cultured live cell by irradiation to ensure that it remains alive and non-apoptotic, but is incapable of proliferating after in vivo administration to a human patient.

9. The method according to claim 8, further comprising obtaining the live cell from a human suffering from a neoplasia, wherein the live cell is a neoplastic cell, and readministering the modified cultured live cell to the human.

10. The method according to claim 9, further comprising administering an immunostimulatory therapy selectively targeting cells producing at least one of CTLA-4, LAG-3, and CD47.

11. The method according to claim 8, wherein the knockout of CD47 comprises knockout of CD47 by CRISPR-Cas9 gene editing.

12. A vaccine, comprising:
a non-apoptotic senescent or mitosis-arrested irradiated cell derived from a neoplastic cell which expresses a neoantigen;
wherein the cell has been genetically edited to:
express a serpin protease inhibitor;
genomically integrate a gene encoding GM-CSF;
knockout CD-47; and
knockout PD-L1;
and wherein the cell has been expanded before being made senescent or mitosis-arrested by irradiation; and
a formulation adapted for administration to a patient.

13. The vaccine according to claim 1, wherein CD47 is knocked out by a frameshift mutation of a gene producing CD47.

14. The method according to claim 8, wherein the genetic editing to knockout CD47 comprises causing a frameshift mutation of a gene producing CD47 to knock out CD47.

15. The vaccine according to claim 12, wherein CD47 is knocked out by a frameshift mutation of a gene producing CD47.

* * * * *

```
                        SEQUENCE LISTING

<160> NUMBER OF SEQ ID NOS: 7

<210> SEQ ID NO 1
<211> LENGTH: 37
<212> TYPE: DNA
<213> ORGANISM: Artificial Sequence
<220> FEATURE:
<223> OTHER INFORMATION: Exon 1 of cd47 gene

<400> SEQUENCE: 1
atgtggccct tggcggcggc gctgttgctg ggctcct                            37

<210> SEQ ID NO 2
<211> LENGTH: 39
<212> TYPE: DNA
<213> ORGANISM: Artificial Sequence
<220> FEATURE:
<223> OTHER INFORMATION: Exon 2 of cd47 gene

<400> SEQUENCE: 2
cccttcgatc gtccgtaatg tggaggcgca aagcaccga                          39

<210> SEQ ID NO 3
<211> LENGTH: 33
<212> TYPE: DNA
<213> ORGANISM: Artificial Sequence
<220> FEATURE:
<223> OTHER INFORMATION: 12 kb fragment from the cd47 gene

<400> SEQUENCE: 3
atgtggccct tgtgtggagg cgcaaagcac cga                                33

<210> SEQ ID NO 4
<211> LENGTH: 20
<212> TYPE: RNA
<213> ORGANISM: Artificial Sequence
<220> FEATURE:
<223> OTHER INFORMATION: Guide M1 RNA for Exon 1 of cd47

<400> SEQUENCE: 4
aaccgccgcc gcgacaacga                                               20

<210> SEQ ID NO 5
<211> LENGTH: 20
<212> TYPE: DNA
<213> ORGANISM: Artificial Sequence
<220> FEATURE:
<223> OTHER INFORMATION: Guide M3 RNA for cd47 Exon 2

<400> SEQUENCE: 5
tgctttgcgc ctccacatta                                               20

<210> SEQ ID NO 6
<211> LENGTH: 18
<212> TYPE: DNA
```

```
<213> ORGANISM: Artificial Sequence
<220> FEATURE:
<223> OTHER INFORMATION: Forward primer, upstream of Guide M1 targeted
      cd47 gene

<400> SEQUENCE: 6
agccagaggg aaggagtt                                                        18

<210> SEQ ID NO 7
<211> LENGTH: 18
<212> TYPE: DNA
<213> ORGANISM: Artificial Sequence
<220> FEATURE:
<223> OTHER INFORMATION: Reverse primer, downstream of Guide M3 targeted
      cd47 gene (with MA-FP, amplicon length: 12,986 bp in intact, and
      473 bp in a deleted cd47 gene)

<400> SEQUENCE: 7
ccacttgccc aagaagag                                                        18
```